US009834575B2

(12) United States Patent
White et al.

(10) Patent No.: US 9,834,575 B2
(45) Date of Patent: Dec. 5, 2017

(54) CANCER THERAPY

(71) Applicant: TriAct Therapeutics, Inc., San Francisco, CA (US)

(72) Inventors: Thomas F. White, San Francisco, CA (US); Steven Smith, San Jose, CA (US)

(73) Assignee: TRIACT THERAPEUTICS, INC., San Francisco, CA (US)

( * ) Notice: Subject to any disclaimer, the term of this patent is extended or adjusted under 35 U.S.C. 154(b) by 84 days.

(21) Appl. No.: 14/191,331

(22) Filed: Feb. 26, 2014

(65) Prior Publication Data

US 2014/0249099 A1 Sep. 4, 2014

Related U.S. Application Data

(60) Provisional application No. 61/769,623, filed on Feb. 26, 2013.

(51) Int. Cl.
| | |
|---|---|
| A61K 31/7012 | (2006.01) |
| A61K 31/7034 | (2006.01) |
| C07H 15/20 | (2006.01) |
| C07F 9/12 | (2006.01) |
| A61K 31/662 | (2006.01) |
| A61K 45/06 | (2006.01) |
| A61K 31/517 | (2006.01) |
| A61K 31/5377 | (2006.01) |
| A61K 31/661 | (2006.01) |
| C07H 15/203 | (2006.01) |

(52) U.S. Cl.
CPC ........... *C07H 15/20* (2013.01); *A61K 31/517* (2013.01); *A61K 31/5377* (2013.01); *A61K 31/661* (2013.01); *A61K 31/662* (2013.01); *A61K 31/7012* (2013.01); *A61K 31/7034* (2013.01); *A61K 45/06* (2013.01); *C07F 9/12* (2013.01); *C07H 15/203* (2013.01)

(58) Field of Classification Search
None
See application file for complete search history.

(56) References Cited

U.S. PATENT DOCUMENTS

| | | |
|---|---|---|
| 2,644,822 A | 7/1953 | Pearl et al. |
| 4,659,695 A | 4/1987 | Labrie |
| 4,683,202 A | 7/1987 | Mullis |
| 4,843,155 A | 6/1989 | Chomczynski |
| 4,868,103 A | 9/1989 | Stavrianopoulos et al. |
| 4,946,778 A | 8/1990 | Ladner et al. |
| 5,008,294 A | 4/1991 | Neiss et al. |
| 5,541,232 A | 7/1996 | Howell et al. |
| 5,624,803 A | 4/1997 | Noonberg et al. |
| 5,631,169 A | 5/1997 | Lakowicz et al. |
| 5,650,415 A | 7/1997 | Tang et al. |
| 5,656,643 A | 8/1997 | Spada et al. |
| 5,747,498 A | 5/1998 | Schnur et al. |
| 5,789,427 A | 8/1998 | Chen et al. |
| 5,854,033 A | 12/1998 | Lizardi |
| 5,861,268 A | 1/1999 | Tang et al. |
| 5,981,732 A | 11/1999 | Cowsert |
| 6,046,321 A | 4/2000 | Cowsert |
| 6,107,091 A | 8/2000 | Cowsert |
| 6,180,603 B1 | 1/2001 | Frey, II |
| 6,191,169 B1 | 2/2001 | Nadler et al. |
| 6,291,524 B1 | 9/2001 | Huang et al. |
| 6,331,526 B1 | 12/2001 | Baserga et al. |
| 6,337,338 B1 | 1/2002 | Kozlowski et al. |
| 6,365,354 B1 | 4/2002 | Bennett et al. |
| 6,410,323 B1 | 6/2002 | Roberts et al. |
| 6,417,234 B1 | 7/2002 | Huang et al. |
| 6,437,105 B1 | 8/2002 | Priebe et al. |
| 6,506,559 B1 | 1/2003 | Fire et al. |
| 6,566,131 B1 | 5/2003 | Cowsert |
| 6,566,135 B1 | 5/2003 | Watt |
| 6,573,099 B2 | 6/2003 | Graham |
| 6,960,474 B2 | 11/2005 | Salvati et al. |
| 7,081,454 B2 | 7/2006 | Wittman et al. |
| 7,189,716 B2 | 3/2007 | Beaulieu et al. |
| 7,232,826 B2 | 6/2007 | Velaparthi et al. |
| 7,741,357 B1 | 6/2010 | Huang et al. |
| 8,710,104 B2 | 4/2014 | White et al. |
| 9,314,437 B2* | 4/2016 | Chaturvedi ............ A61K 31/05 |
| 9,381,246 B2 | 7/2016 | White et al. |
| 2004/0005593 A1 | 1/2004 | Lorens |
| 2004/0018191 A1 | 1/2004 | Wang et al. |
| 2004/0175756 A1 | 9/2004 | Kolkman et al. |
| 2004/0209930 A1 | 10/2004 | Carboni et al. |

(Continued)

FOREIGN PATENT DOCUMENTS

| | | |
|---|---|---|
| DE | 19629652 | 1/1998 |
| EP | 520722 | 12/1992 |

(Continued)

OTHER PUBLICATIONS

Lambert et al., Toxicon, vol. 40, 2002, 1701-1708.*
PCT/US2014/018762 International Preliminary Report on Patentability dated Sep. 11, 2015.
U.S. Appl. No. 14/261,810, filed Apr. 25, 2014.
U.S. Appl. No. 14/261,810 Office Action dated Dec. 3, 2015.
U.S. Appl. No. 14/481,837 Office Action dated Jul. 8, 2015.
"Protein kinase inhibitor," Wikipedia, The Free Encyclopedia http://en.wikipedia.org/wiki/Protein_kinase_inhibitor (downloaded Jan. 30, 2010).
Agrawal et al., "Overview of tyrosine kinase inhibitors in clinical breast cancer" Endocrine Related Cancer (Mar. 2005) 12:S135-S144.
Albert et al., "Pteridine Studies,. Part XXXIX. Pteridines Unsubstituted in the 4-Position; a New Synthesis from Pyrazines, via 3,4-Dihydropteridines," J. Chem. Soc. 11:1540-1547 (1970).

(Continued)

*Primary Examiner* — Traviss C McIntosh, III
(74) *Attorney, Agent, or Firm* — Wilson Sonsini Goodrich & Rosati

(57) ABSTRACT

The present application relates to compositions and methods for treating a proliferative disorder by administering to a subject a pharmaceutical composition of a dual kinase inhibitor metabolite. Catecholic butane metabolites can serve as dual kinase inhibitors for purposes of methods described herein.

23 Claims, 27 Drawing Sheets

(56) References Cited

U.S. PATENT DOCUMENTS

| | | |
|---|---|---|
| 2005/0037421 A1 | 2/2005 | Honda et al. |
| 2005/0048512 A1 | 3/2005 | Kolkman et al. |
| 2005/0048647 A1 | 3/2005 | Taira et al. |
| 2005/0053973 A1 | 3/2005 | Kolkman et al. |
| 2005/0060771 A1 | 3/2005 | Farmer |
| 2005/0089932 A1 | 4/2005 | Kolkman et al. |
| 2005/0136063 A1 | 6/2005 | Wang et al. |
| 2005/0164301 A1 | 7/2005 | Kolkman et al. |
| 2005/0221384 A1 | 10/2005 | Kolkman et al. |
| 2006/0141029 A1 | 6/2006 | Heller et al. |
| 2006/0151574 A1 | 7/2006 | Herget et al. |
| 2007/0065858 A1 | 3/2007 | Haley |
| 2007/0099847 A1 | 5/2007 | Goldfine et al. |
| 2008/0096967 A1 | 4/2008 | Lopez et al. |
| 2008/0113874 A1 | 5/2008 | Bunn |
| 2008/0207532 A1 | 8/2008 | Huang et al. |
| 2009/0306070 A1 | 12/2009 | Heller et al. |
| 2010/0256232 A1 | 10/2010 | White et al. |
| 2010/0256323 A1 | 10/2010 | Athey et al. |
| 2014/0235714 A1 | 8/2014 | White et al. |
| 2015/0071919 A1 | 3/2015 | White et al. |

FOREIGN PATENT DOCUMENTS

| | | |
|---|---|---|
| EP | 566226 | 10/1993 |
| EP | 682027 | 11/1995 |
| EP | 787772 | 8/1997 |
| EP | 837063 | 4/1998 |
| EP | 0404097 | 6/2009 |
| EP | 2961412 A1 | 1/2016 |
| JP | 2-49731 A | 3/1990 |
| JP | 07-133280 | 5/1995 |
| JP | 7-238037 A | 9/1995 |
| JP | 8-337510 A | 12/1996 |
| JP | 2007523187 A | 8/2007 |
| JP | 2011510949 A | 4/2011 |
| JP | 2011522814 A | 8/2011 |
| WO | WO-88-01509 | 3/1988 |
| WO | WO-92-20642 A1 | 11/1992 |
| WO | WO-93-11161 A1 | 6/1993 |
| WO | WO-95-09847 A1 | 4/1995 |
| WO | WO-95-19774 A1 | 7/1995 |
| WO | WO-95-19970 A1 | 7/1995 |
| WO | WO-96-30347 A1 | 10/1996 |
| WO | WO-96-31510 A1 | 10/1996 |
| WO | WO-96-33980 A1 | 10/1996 |
| WO | WO-96-37201 | 11/1996 |
| WO | WO-97-02266 A1 | 1/1997 |
| WO | WO-97-13771 A1 | 4/1997 |
| WO | WO-97-19065 A1 | 5/1997 |
| WO | WO-97-27199 A1 | 7/1997 |
| WO | WO-97-28161 A1 | 8/1997 |
| WO | WO-97-30034 A1 | 8/1997 |
| WO | WO-97-30044 A1 | 8/1997 |
| WO | WO-97-32880 A1 | 9/1997 |
| WO | WO-97-32881 A1 | 9/1997 |
| WO | WO-97-34895 A1 | 9/1997 |
| WO | WO-97-38983 A1 | 10/1997 |
| WO | WO-97-38994 A1 | 10/1997 |
| WO | WO-97-49688 A1 | 12/1997 |
| WO | WO-98-02434 A1 | 1/1998 |
| WO | WO-98-02437 A1 | 1/1998 |
| WO | WO-98-02438 A1 | 1/1998 |
| WO | WO-98-07726 A1 | 2/1998 |
| WO | WO-98-14449 A1 | 4/1998 |
| WO | WO-98-14451 A1 | 4/1998 |
| WO | WO-98-17662 A1 | 4/1998 |
| WO | WO-98-33787 A1 | 8/1998 |
| WO | WO-99-07701 A1 | 2/1999 |
| WO | WO-99-32619 A1 | 7/1999 |
| WO | WO-99-35132 A1 | 7/1999 |
| WO | WO-99-35146 A1 | 7/1999 |
| WO | WO-00-17203 A1 | 3/2000 |
| WO | WO-00-35455 | 6/2000 |
| WO | WO-00-35455 A1 | 6/2000 |
| WO | WO-00-71129 A1 | 11/2000 |
| WO | WO-01-36646 A1 | 5/2001 |
| WO | WO-01-68836 A2 | 9/2001 |
| WO | WO-02-092599 | 11/2002 |
| WO | WO-02-092599 A1 | 11/2002 |
| WO | WO-02-102804 | 12/2002 |
| WO | WO-02-102804 A1 | 12/2002 |
| WO | WO-02-102805 A1 | 12/2002 |
| WO | WO-03-018021 A1 | 3/2003 |
| WO | WO-03-018022 | 3/2003 |
| WO | WO-03-018022 A1 | 3/2003 |
| WO | WO-03-024967 | 3/2003 |
| WO | WO-03-024967 A2 | 3/2003 |
| WO | WO-03-035614 A2 | 5/2003 |
| WO | WO-03-035615 A2 | 5/2003 |
| WO | WO-03-035616 | 5/2003 |
| WO | WO-03-035616 A2 | 5/2003 |
| WO | WO-03-035619 A1 | 5/2003 |
| WO | WO-03-048133 A1 | 6/2003 |
| WO | WO-03-068265 A1 | 8/2003 |
| WO | WO-2004-030625 | 4/2004 |
| WO | WO-2005-037836 A2 | 4/2005 |
| WO | WO-2005-082415 | 9/2005 |
| WO | WO-2005082353 A2 | 9/2005 |
| WO | WO-2006-041902 A2 | 4/2006 |
| WO | WO-2006-138729 | 12/2006 |
| WO | WO-2008-089388 A2 | 7/2008 |
| WO | WO-2009095418 A1 | 8/2009 |
| WO | WO-2009-108857 | 9/2009 |
| WO | WO-2009150405 A1 | 12/2009 |
| WO | WO-2010/054264 | 5/2010 |
| WO | WO2010/054264 * | 5/2010 |
| WO | WO 2014/134202 A1 | 9/2014 |
| WO | WO-2015035410 A1 | 3/2015 |

OTHER PUBLICATIONS

Avrameas, "Peroxidase labelled antibody and Fab conjugates with enhanced intracellular penetration," Immunochemistry 8:1175-1179 (1975).
Barany, "Genetic disease detection and DNA amplification using cloned thermostable ligase," PNAS USA 88:189-193 (1991).
Baserga, "The IGF-1 Receptor in Cancer Research," Exp. Cell. Res. 253:1-6 (1999).
Baserga, R The insulin-like growth factor I receptor: a key to tumor growth? Cancer Res 55 (1995).
Berge et al., J. Pharm. Sci. 66:1-19 (1977).
Bird et al., Science 242:423-426 (1988).
Blum et al., "Development of New Insulin-like Growth Factor-1 Receptor Kinase Inhibitors Using Catechol Mimics" The Journal of Biological Chemistry, 278(42):40442-40454 (2003).
Blum et al., "Substrate Competitive Inhibitors of IGF-1 Receptor Kinase" Biochemistry, 39:15705-15712 (2000).
Boston-Howes et al., "Nordihydroguaiaretic acid increases glutamate uptake in vitro and in vivo: Therapeutic implications for amyotrophic lateral sclerosis," Exp. Neurol. 213(1):229-237 (2008).
Brem, H. and Gabikian, P. "Biodegradable polymer implants to treat brain tumors," J. Controlled Release 74:63-67 (2001).
Brummelkamp et al., "A System for Stable Expression of Short Interfering RNAs in Mammalian Cells," Science 296:550-553 (2002).
Burfeind, P, RNA to the type I insulin-like growth factor receptor suppresses tumor growth and prevents invasion by prostate cancer cells in vivo. Proc Natl Acad Sci USA 93:14:7263-8 (1996).
CA 2,742,986 Office action dated Oct. 25, 2013.
CA 2,742,986 Office action dated Sep. 11, 2012.
Camirand and Pollak, "Co-targeting IGF-1R and c-kit: synergistic inhibition of proliferation and induction of apoptosis in H209 small cell lung cancer cells," Brit. J. Cancer 90:1825-1829 (2004).
Camp et al. Clin Cancer Res 11:397-405, (2005).
Chang et al., "Nonreceptor Tyrosine Kinases in Prostate Cancer" Neoplasia, 9(2):90-100 (Feb. 2007).
Chang et al., "Experimentally-induced prostatic hyperplasia in young beagles: a model to evaluate the chemotherapeutic effects of gossypol," Res Comm Mol Path Pharmacol 92(3):341-360 (1996).
CN200980126999.1 Decision of Rejection dated Jul. 7, 2014.

(56) References Cited

OTHER PUBLICATIONS

Cole et al., "The EBV-Hybridoma Technique and Its Application to Human Lung Cancer," Monoclonal Antibodies and Cancer Therapy, Alan R. Liss Inc. 1985, pp. 77-96.
Cote et al., "Generation of human monoclonal antibodies reactive with cellular antigens," PNAS USA 80:2026-2030 (1983).
Diaz et al., "Management of Androgen-Independent Prostate Cancer" Cancer Control, 11(6):364-373 (Nov./ Dec. 2004).
Doctor's Guide, Sep. 28, 1998, pp. 1-3.
Domin et al., "Preferential inhibition of platelet-derived growth factor-stimulated DNA synthesis and protein tyrosine phosphorylation by nordihydroguaiaretic acid," J. Biol. Chem. 269(11):8260-8267 (1994).
Earashi et al., "Effects of Eicosanoid Synthesis Inhibitors on the in vitro Growth and Prostaglandin E and Leukotriene B. Secretion of a Human Breast Cancer Cell Line" Oncology, 52:150-155 (1995).
Elbashir et al., "Duplexes of 21-nucleotide RNAs mediate RNA interference in cultured mammalian cells," Nature 411:494-498 (2001).
Eli. Ketoconazole binds to the human androgen receptor. Horm. Metabol. Res. 24(8): 367-370 (1992).
Engvall, "Enzyme-linked immunosorbent assay (ELISA) Quantitative assay of immunoglobulin G," Immunochemistry 8:871-874 (1971).
Fleming, "Pharmacokinetics of the Carmustine Implant," Clin. Pharmacokinet. 41:403-419 (2002).
Fu et al., "New polymeric carriers for controlled drug delivery following inhalation or injection," Biomaterials 23:4425-4433 (2002).
Garcia-Echeverria et al., "In vivo antitumor activity of NVP-AEW541-A novel, potent, and selective inhibitor of the IGF-1R kinase," Cancer Cell 5:231-239 (2004).
Gavezzotti, "Are Crystal Structures Predictable'?", Accounts of Chemical Research, vol. 27, pp. 309-314 (1994).
Gendreau, et al. "Inhibition of the T790M Gatekeeper Mutant of the Epidermal Growth Factor Receptor by EXEL-7647." Clin Cancer Res 13:3713-3723 (2007).
Goldstein et al., Biological Efficacy of a Chimeric Antibody to the Epidermal Growth Factor Receptor in a Human Tumor Xenograft Model,: Clin. Cancer Res. 1:1311-1318 (1995).
Greco et al., "The Search for Syngergy: A Critical Review from a Response Surface Perspective" Pharmacological Reviews 47(2):331-385 (1995).
Guatelli et al., "Isothermal, in vitro amplification of nucleic acids by a multienzyme reaction modeled after retroviral replication," PNAS USA 87:1874-1878 (1990).
Gura, Trisha, "Cancerl Models: Systems for Identifying New Drugs Are Often Faulty" Science (Nov. 1997) 278(5340):1041-42.
Hage, "Recent advances in chromatographic and electgrophoretic methods for the study of drug-protein interactions," Chromatogr. B. Biomed Sci. Appl. 699(1-2):499-525 (1997).
Hannon, "RNA interference," Nature 418:244-251 (2002).
Heegaard, "Capillary electrophoresis for the study of affinity interactions," J. Mol. Recognit. WInter 11(1-6):141-148 (1998).
Holliger et al., "Diabodies: Small bivalent and bispecific antibody fragments," PNAS USA 90:6444-6448 (1993).
Huang et al. Nordihydroguaiaretic acid-induced Ca2+ handling and cytotoxicity in human prostate cancer cells. Life Sciences, 75:2341-2351 (2004).
Huang et al., "Epidermal Growth Factor Receptor Blockade with C225 Modulates Proliferation, Apoptosis, and Radiosensitivity in Squamous Cell Carcinomas of the Head and Neck," Cancer Res. 15:59(8):1935-1940 (1999).
Huse et al., Science 246:1275-1281 (1989).
Huston et al., PNAS USA 85:5879-5883 (1988).
Ibrahim and Yee, "Insulin-Like Growth Factor-1 and Breast Cancer Therapy," Clin. Cancer Res. 11:944s-950s (2005).
Ishikawa et al., "Enzyme-Labeling of Antibodies and Their Fragments for Enzyme Immunoassay and Immunohistochemical Staining," J. Immunoassay 4(3):209-327 (1983).
Jablonski, "The Preparation of Bacterial Luciferase Conjugates for Immunoassay and Application to Rubella Antibody Detection," Anal. Biochem. 148:199-206 (1985).
Jones et al., Nature 321:522-525 (1986).
Kisielewska et al., "The effect of tyrosine kinase inhibitors, tyrphostins: AG1024 and SU1498, on autocrine growth of prostate cancer cells (DU145)" Folia Histochemica et Cytobiologica, 46(2):185-91 (2008).
Kohler and Milstein, Nature 256:495-497 (1975).
Kozbor et al., "The production of monoclonal antibodies from human lymphocytes," Immunol. Today 4:72-79 (1983).
Kwoh et al., "Transcription-based amplification system and detection of amplified human immunodeficiency virus type 1 with a bead-based sandwich hybridization format," PNAS USA 86:1173-1177 (1989).
Larsson et al., "Role of insulin-like growth factor 2 receptor signalling in cancer," Brit. J. Cancer 92:2097-2101 (2005).
Lee et al., "Expression of small interfering RNAs targeted against HIV-1 rev transcripts in human cells," Nat. Biotech. 20:500-505 (2002).
Lizardi et al., "Exponential amplification of recombinant-RNA hybridization probes," Biotechnology 6:1197-1202 (1988).
McManus and Sharp, "Gene silencing in mammals by small interfering RNAs," Nature Reviews Genetics 3:737-747 (2002).
Meyer et al., "Nordihydroguaiaretic Acid Inhibits Insulin-Like Growth Factor Signaling Growth, and Survival in Human Neuroblastoma Cells" Journal of Cellular Biology, 102(6):1529-1541 (Dec. 2007).
Mitsiades et al., "Inhibition of the insulin-like growth factor receptor-1 tyrosine kinase activity as a therapeutic strategy for multiple myeloma, other hematologic malignancies, and solid tumors," Cancer Cell 5:221-230 (2004).
Miyagishi et al., "Y6 promoter-driven siRNAs with four uridine 3' overhangs efficiently suppress targeted gene expression in mamalian cells," Nat. Biotech. 20:497-500 (2002).
Modjtahedi et al., "The human EGF receptor as a target for cancer therapy: six new rat mAbs against the receptor on the breast carcinoma MDA-MB 468," Br. J. Cancer 67:247-253 (1993).
Morgillo, et al. Implication of the insulin-like growth factor-IR pathway in the resistance of non-small cell lung cancer cells to treatment with gefitinib. Clin Cancer Res. 13(9):2795-2803 (2007).
Muyldermans et al., "Sequence and structure of VH domain from naturally occurring camel heavy chain immunoglobulins lacking light chains," Protein Engineering 7(9):1129-1133 (1994).
MX/a/2011/004824 office action dated Sep. 28, 2012.
Nickerson, T, In vivo progression of LAPC-9 and LNCaP prostate cancer models to androgen independence is associated with increased expression of insulin-like growth factor I (IGF-I) and IGF-I receptor (IGF-IR) 1. Cancer Res 61(16):6276-80 (2001).
Nicolini et al. Oral low-dose cyclophosphamide in metastatic hormone refractory prostate cancer (MHRPC). Biomedicine & Pharmacotherapy, 58:447-450 (2004).
Nieto,M, Prostate cancer: Re-focusing on androgen receptor signaling. Int J Biochem Cell Biol 39(9):1562-8 (2007).
Osborne et al., "Inhibition of Breast Cancer Cell Growth in Vitro by a Tyrosine Kinase Inhibitor," Cancer Res. 52:3636-3641 (1992).
Osbourn et al., Nat. Biotech. 16:778 (1998).
Paddison et al., "Short hairpin RNAs (shRNAs) induce sequence-specific silencing in mammalian cells," Genes Dev. 16:948-958 (2002).
Pao, et al., "Acquired Resistance of Lung Adenocarcinomas to Gefitinib or Erlotinib Is Associated with a Second Mutation in the EGFR Kinase Domain." PLoS Med 2(3): e73; pp. 1-10. doi:10.1371/journal.pmed.0020073.
Parrizas et al., "Specific Inhibition of Insulin-Like Growth Factor-1 and Insulin Receptor Tyrosine Kinase Activity and Biological Function by Tyrphostins," Endocrinology 138:1427-1433 (1997).
Paul et al., "Effective expression of small interfering RNA in human cells," Nat. Biotech. 20:505-508 (2002).
PCT/US09/63646 IPRP dated May 10, 2011.
PCT/US09/63646 Search Report dated Feb. 19, 2010.
PCT/US09/63646 Written Opinion dated Jul. 5, 2011.

(56) References Cited

OTHER PUBLICATIONS

PCT/US2014/018762 International Search Report and Written Opinion dated Aug. 5, 2014.
Pirtskhalaishvilli et al. The treatment of prostate cancer: an overview of current options. Cancer Practice, vol. 9, No. 6, Nov./Dec. 2001.
Pluckthun in Handbook of Experimental Pharmacology vol. 113, Rosenburg and Moore eds., Springer-Verlag, NY, pp. 269-315 (1994).
Pollak, M. Insulin-like growth factors and prostate cancer 115. Epidemiol Rev 23(1):59-66 (2001).
Presta, Curr. Op. Struct. Biol. 2:593-596 (1992).
Reichmann et al., "Reshaping human antibodies for therapy," Nature 332:323-329 (1988).
Rheinwald et al., "Epidermal growth factor and the multiplication of cultured human epidermal keratinocytes," Nature 265:421-424 (1977).
Rivas, "New developments in the study of biomolecular associations via sedimentation equilibrium," Trends Biochem. Sci. 18(8):284-287 (1993).
Robertson et al., "Overview of tyrosine kinase inhibitors in clinical breast cancer," Endocrine-Related Cancer 12:S135-S144 (2005).
Robins et al., "Synthesis and anticancer activity of nordihydroguaiaretic acid (NDGA) and analogues," Anti-Cancer Drug Design 16:261-270 (2001).
Rodeck et al., "EGF-R dependent regulation of keratinocyte survival," J. Cell Science 110:113-121 (1997).
Rowe et al., "Nordihydroguaiaretic acid, a cytotoxic insulin-like growth factor-I receptor/HER2 inhibitor in trastuzumab-resistant breast cancer," Mol. Cancer Therapeutics 7(7):1900-1908 (2008).
Rozengurt et al., "Preferential Inhibition of Platelet-derived Growth Factor-stimulated DNA Synthesis and Protein Tyrosine Phosphorylation by Nordihydroguaiaretic Acid," J. Biol. Chem. 269(11):8260-8267 (1994).
Ryan et al. "A pilot dose-escalation study of the effects of nordihydroguareacetic acid on hormone and prostate specific antigen levels in patients with relapsed prostate cancer" BJU International, 101(4):436-439 (Feb. 2008).
Ryan et al., "Androgen-independent prostate cancer: target evolution and disease dynamics" Drug Discovery Today: Disease Mechanisms, Elsevier, 1(2):223-228 (Nov. 1, 2004).
Ryan et al., "Inhibitory Effects of Nordihydroguaiaretic Acid (NDGA) on the IGF-1 Receptor and Androgen Dependent Growth of LAPC-4-Prostate Cancer Cells" The Prostate, 68:1232-1240 (2008).
Seufferlein et al., "Mechanisms of nordiydroguaiaretic acid-induced growth inhibition and apoptosis in human cancer cells," Br. J. Cancer 86:1188-1196 (2002).
Sharifi et al. Leuprolide acetate (30 mg depot every four months) in the treatment of advanced prostate cancer. Urology, 51: 271-276 (1998).
Sherwood et al., "Selective inhibition of heregulin-dependent tyrosin phosphorylation and cellular signaling through erbB2, erbB3 and erbB4 by PD 158780 and a new irreversible inhibitor, PD 183805," Proc. Am. Assoc. Cancer Res. 40:723 (1999).
Silverman et al., "Corrigendum : Multivalent avimer proteins evolved by exon shuffling of a family of human receptor domains," Nat. Biotech.. 24:220 (2006).
Silverman et al., "Multivalent avimer proteins evolved by exon shuffling of a family of human receptor domains," Nat. Biotech. 23:1493-1494 (2005).
Sjolander, "Integrated Fluid Handling System for Biomolecular Interaction Analysis," Anal. Chem. 63:2338-2345 (1991).
Szabo et al., "Surface plasmon resonance and its use in biomolecular interaction analysis (BIA)," Curr. Op. Struct. Biol. 5:699-705 (1995).
Taichman et al. The evolving biology and treatment of prostate cancer. The Journal of Clinical Investigation. vol. 117, No. 9, 2351-2361, Sep. 2007.
Teramoto et al., "Inhibitory Effect of Anti-Epidermal Growth Factor Receptor Antibody on a Human Gastric Cancer," Cancer 77:639-645 (1996).
Therasse et al., J. Natl. Cancer Inst. 92(3):205-216 (2000).
Traxler, "Use of a Pharmacophore Model for the Design of EGFR Tyrosine Kinase Inhibitors: Isoflavones and 3-Phenyl-4(1H)-quinolones," J. Med. Chem. 42:1018-1026 (1999).
Tuschl et al., "Targeted mRNA degradation by double-stranded RNA in vitro," Genes Dev. 13(24):3191-3197 (1999).
Tuschl et al., "Expanding small RNA interference," Nat. Biotech. 20:446-448 (2002).
TW 098137952 Office action dated Jun. 4, 2012.
U.S. Appl. No. 11/552,686 Office Action dated Jul. 20, 2011.
U.S. Appl. No. 11/552,686 Office action dated May 29, 2009.
U.S. Appl. No. 11/552,686 Office action dated Nov. 24, 2008.
U.S. Appl. No. 11/552,686 Office action dated Nov. 4, 2009.
U.S. Appl. No. 12/434,071 Office action dated Aug. 15, 2013.
U.S. Appl. No. 12/434,071 Office action dated Aug. 9, 2012.
U.S. Appl. No. 12/434,071 Office action dated Jan. 29, 2013.
U.S. Appl. No. 12/434,071 Office action dated Jul. 14, 2011.
U.S. Appl. No. 12/434,071 Office action dated Nov. 8, 2011.
U.S. Appl. No. 12/614,283 Office action dated Jan. 10, 2013.
U.S. Appl. No. 12/614,283 Office action dated Jul. 3, 2013.
U.S. Appl. No. 12/614,283 Office action dated May 2, 2012.
Vaughan et al., "Human antibodies by design," Nature Biotech. 16:535-539 (1998).
Vippagunta et al, "Crystalline Solids", Advanced Drug Delivery Reviews, vol. 48, pp. 3-26 (2001).
Ward et al., Nature 341:544-546 (1989).
Wilkinson et al. An evaluation of intermediate dose ketoconazole in hormone refractory prostate cancer. European Urology, 45:581-585 (2004).
Woodburn et al., "ZD1839, an epidermal growth factor tyrosine kinase inhibitor selected for clinical development," Proc. Am. Assoc. Cancer Res. 38:633 (1997).
Yang, et al., "Eradication of Established Tumors by a Fully Human Monoclonal Antibody to the Epidermal Growth Factor Receptor without Concomitant Chemotherapy," Cancer Res. 59:1236-1243 (1999).
Fleming et al., Synergistic inhibition of ErbB signaling by combined treatment with seliciclib and ErbB-Trageting agents. Clinical Cancer Research, 14(13): 4326-4335 (2008).
Gerber et al., ALK inhibition for non-small cell lung cancer: From discovery to therapy in record time. Cancer Cell, 18(6): 548-551 (2010).
Merck Manual, p. 800-803 (1992).
Neoptolimos et al., Adjuvant therapy in pancreatic cancer: historical and current perspectives, Annals of Oncology, 14:675-692 (2003).
Ortiz-Ferron et al., Roscovitine sensitizes breast cancer cells to Trail-induced apoptosis through a pleiotropic mechanism. Cell Research, 18:664-676 (2008).
PCT/US09/002781 IPRP dated Nov. 9, 2010.
PCT/US09/002781 ISR dated Sep. 29, 2009.
PCT/US09/002781 WO dated Sep. 29, 2009.
PCT/US2014/054832 ISR and WO dated Dec. 22, 2014.
Sharma et al., In the clinic: ongoing clinical trials evaluating c-MET inhibiting drugs. Therapeutic Advances in Medical Oncology, 3(1): 537-550 (2011).
U.S. Appl. No. 13/399,031 Office Action dated Jul. 25, 2012.
PCT/US2014/054832 International Preliminary Report on Patentability dated Mar. 24, 2016.
U.S. Appl. No. 14/261,810 Office Action dated Aug. 29, 2016.
Japanese Patent Application No. 2015-559304 Office Action dated Dec. 19, 2016.

* cited by examiner

CANCER THERAPY

CROSS-REFERENCE

This application claims the benefit of U.S. Provisional Application No. 61/769,623, filed Feb. 26, 2013, which is incorporated herein by reference in its entirety.

BACKGROUND OF THE INVENTION

Proliferative diseases are a serious threat to modern society. Cancerous growths, including malignant cancerous growth, pose serious challenges for modern medicine due to their unique characteristics. Their characteristics include uncontrollable cell proliferation resulting in, for example, unregulated growth of malignant tissue, an ability to invade local and even remote tissues, lack of differentiation, lack of detectable symptoms and most significantly, the lack of effective therapy and prevention.

Cancer can develop in any tissue of any organ at any age. The etiology of cancer is not clearly defined but mechanisms such as genetic susceptibility, chromosome breakage disorders, viruses, environmental factors and immunologic disorders have all been linked to a malignant cell growth and transformation. Cancer encompasses a large category of medical conditions, affecting millions of individuals worldwide. Cancer cells can arise in almost any organ and/or tissue of the body. Cancer develops when cells in a part of the body begin to grow or differentiate out of control. All cancer types begin with the out-of-control growth of abnormal cells.

Currently, some of the main treatments available are surgery, radiation therapy, and chemotherapy. Surgery is often a drastic measure and can have serious consequences. For example, all treatments for ovarian cancer may result in infertility. Some treatments for cervical cancer and bladder cancer may cause infertility and/or sexual dysfunction. Surgical procedures to treat pancreatic cancer may result in partial or total removal of the pancreas can itself carry significant risks, causing serious adverse effects to the patient. Breast cancer surgery invariably involves removal of part of or the entire breast. Some surgical procedures for prostate cancer carry the risk of urinary incontinence and impotence. The procedures for lung cancer patients often have significant post-operative pain as the ribs must be cut through to access and remove the cancerous lung tissue. In addition, patients who have both lung cancer and another lung disease, such as emphysema or chronic bronchitis, typically experience an increase in their shortness of breath following the surgery.

Worldwide, more than 10 million people are diagnosed with cancer every year and it is estimated that this number will grow to 15 million new cases every year by 2020. Cancer causes six million deaths every year or 12% of the deaths worldwide.

SUMMARY OF THE INVENTION

The embodiments disclosed herein relate generally to compositions for treatment of diseases using a catecholic butane metabolite or a derivative thereof. Some specific embodiments relate to the use of the catecholic butane metabolite or a salt, solvate, isomer, tautomer, analog, or prodrug thereof in treating a proliferative disease. In one embodiment, the compositions are for treatment of patients who have been treated with, and become resistant to, compounds or compositions targeted to EGFR, including but not limited to erlotinib (TARCEVA®), gefitinib (IRESSA®) and cetuximab (ERBITUX®).

Provided herein is a composition, comprising a therapeutically effective amount of a metabolite of nordihydroguaiaretic acid (NDGA) and one or more excipients.

In one embodiment, the metabolite is NDGA glucuronide, NDGA sulfonate, tetraglycinyl NDGA, tetra-dimethylglycinyl NDGA, tri-O-methyl NDGA, NDGA tetrapivalate, NDGA tetrapropionate, o-quinone metabolite of NDGA, or a prodrug or salt thereof.

In another embodiment, the metabolite is metabolite having a formula of any one of formulas IV-LXVII, or a phosphate ester thereof, where the formulas are provided in Table 1. R groups refer to those shown in the formula illustrated in FIG. 29.

In another embodiment, the metabolite is metabolite having a formula of any one of formulas LXXII-CXXXV, or a phosphate ester thereof, where the formulas are provided in Table 3. R groups refer to those shown in the formula illustrated in FIG. 29.

In other embodiments, a phosphate ester has a structure of any one of formulas LXVIII-LXXI as provided in Table 2. R groups refer to those shown in the formula illustrated in FIG. 29. In one embodiment, a phosphate prodrug of NDGA exhibits improved solubility, and improved oral absorption.

In still other embodiments, a phosphate ester has a structure of any one of formulas CXXXVI-CXXXVII as provided in Table 4. R groups refer to those shown in the formula illustrated in FIG. 29. In one embodiment, a phosphate prodrug of NDGA exhibits improved solubility, and improved oral absorption.

In one embodiment, the composition comprises from about 5 mg/kg to about 375 mg/kg per dose of said metabolite of NDGA.

In another embodiment, the composition is formulated for administration to a patient in an amount of from about 50 mg per day to about 2,500 mg per day.

In yet another embodiment, the composition is formulated for administration to a patient in an amount of from about 1,500 mg per day to about 2,500 mg per day.

In one embodiment, the composition is formulated for a route of administration selected from the group consisting of intranasal administration; oral administration; inhalation administration; subcutaneous administration; transdermal administration; intra-arterial administration, with or without occlusion; intracranial administration; intraventricular administration; intravenous administration; buccal administration; intraperitoneal administration; intraocular administration; intramuscular administration; implantation administration; and central venous administration.

Provided herein are methods for treating a disease comprising administering an effective amount of one pharmaceutical compound capable of inhibiting the tyrosine kinase activity of both insulin-like growth factor-1 receptor (IGF-1R) and epidermal growth factor receptor (EGFR) (i.e., a dual kinase inhibitor), wherein the pharmaceutical compound is a catecholic butane metabolite.

Also provided herein are methods for treating a disease in a subject that has developed resistance to one or more tyrosine kinase inhibitors, for example, one or more EGF-R inhibitors and/or one or more IGF-1R inhibitors, comprising administering an effective amount of a pharmaceutical compound capable of inhibiting the tyrosine kinase activity of both IGF-1R and EGFR (i.e., a single compound that is a dual kinase inhibitor), wherein the pharmaceutical compound is a catecholic butane metabolite.

Diseases to be treated using the methods provided herein are proliferative diseases. A proliferative disease includes, but is not limited to, a malignant, pre-malignant or benign cancer. Cancers to be treated using the disclosed methods include, for example, a solid tumor, a lymphoma or a leukemia. In one embodiment, a cancer can be, for example, a brain tumor (e.g., a malignant, pre-malignant or benign brain tumor such as, for example, a glioblastoma, an astrocytoma, a meningioma, a medulloblastoma or a peripheral neuroectodermal tumor), a carcinoma (e.g., gall bladder carcinoma, bronchial carcinoma, basal cell carcinoma, adenocarcinoma, squamous cell carcinoma, small cell carcinoma, large cell undifferentiated carcinoma, adenomas, cystadenoma, etc.), a basalioma, a teratoma, a retinoblastoma, a choroidea melanoma, a seminoma, a sarcoma (e.g., Ewing sarcoma, rhabdomyosarcoma, craniopharyngeoma, osteosarcoma, chondrosarcoma, myosarcoma, liposarcoma, fibrosarcoma, leimyosarcoma, Askin's tumor, lymphosarcoma, neurosarcoma, Kaposi's sarcoma, dermatofibrosarcoma, angiosarcoma, etc.), a plasmocytoma, a head and neck tumor (e.g., oral, laryngeal, nasopharyngeal, esophageal, etc.), a liver tumor, a kidney tumor, a renal cell tumor, a squamous cell carcinoma, a uterine tumor, a bone tumor, a prostate tumor, a breast tumor including, but not limited to a breast tumor that is Her2− and/or ER− and/or PR−, a bladder tumor, a pancreatic tumor, an endometrium tumor, a squamous cell carcinoma, a stomach tumor, gliomas, a colorectal tumor, a testicular tumor, a colon tumor, a rectal tumor, an ovarian tumor, a cervical tumor, an eye tumor, a central nervous system tumor (e.g., primary CNS lymphomas, spinal axis tumors, brain stem gliomas, pituitary adenomas, etc.), a thyroid tumor, a lung tumor (e.g., non-small cell lung cancer (NSCLC) or small cell lung cancer), a leukemia or a lymphoma (e.g., cutaneous T-cell lymphomas (CTCL), non-cutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma, etc.), a multiple myeloma, a skin tumor (e.g., basal cell carcinomas, squamous cell carcinomas, melanomas such as malignant melanomas, cutaneous melanomas or intraocular melanomas, Dermatofibrosarcoma protuberans, Merkel cell carcinoma or Kaposi's sarcoma), a gynecologic tumor (e.g., uterine sarcomas, carcinoma of the fallopian tubes, carcinoma of the endometrium, carcinoma of the cervix, carcinoma of the vagina, carcinoma of the vulva, etc.), Hodgkin's disease, a cancer of the small intestine, a cancer of the endocrine system (e.g., a cancer of the thyroid, parathyroid or adrenal glands, etc.), a mesothelioma, a cancer of the urethra, a cancer of the penis, tumors related to Gorlin's syndrome (e.g., medulloblastomas, meningioma, etc.), a tumor of unknown origin; or metastases of any thereto.

In another embodiment, the cancer is a lung tumor, a breast tumor, a colon tumor, a colorectal tumor, a head and neck tumor, a liver tumor, a prostate tumor, a glioma, a glioblastoma multiforme, a ovarian tumor or a thyroid tumor; or metastases of any thereto.

In yet another embodiment, the cancer is an endometrial tumor, bladder tumor, multiple myeloma, melanoma, renal tumor, sarcoma, cervical tumor, leukemia, and neuroblastoma.

Tumors as provided herein may be primary tumors or metastases.

Provided herein are methods for treating a malignant, pre-malignant or benign cancer, comprising administering an effective amount of a pharmaceutical compound capable of inhibiting the tyrosine kinase activity of both IGF-1R and EGFR (i.e., a single compound that is a dual kinase inhibitor), wherein the pharmaceutical compound is a catecholic butane metabolite.

Cancers to be treated using the disclosed methods include, for example, a solid tumor, a lymphoma or a leukemia. In one embodiment, a cancer can be, for example, a brain tumor (e.g., a malignant, pre-malignant or benign brain tumor such as, for example, a glioblastoma, an astrocytoma, a meningioma, a medulloblastoma or a peripheral neuroectodermal tumor), a carcinoma (e.g., gall bladder carcinoma, bronchial carcinoma, basal cell carcinoma, adenocarcinoma, squamous cell carcinoma, small cell carcinoma, large cell undifferentiated carcinoma, adenomas, cystadenoma, etc.), a basalioma, a teratoma, a retinoblastoma, a seminoma, a sarcoma (e.g., Ewing sarcoma, rhabdomyosarcoma, craniopharyngeoma, osteosarcoma, chondrosarcoma, myosarcoma, liposarcoma, fibrosarcoma, leimyosarcoma, Askin's tumor, lymphosarcoma, neurosarcoma, Kaposi's sarcoma, dermatofibrosarcoma, angiosarcoma, etc.), a plasmocytoma, a head and neck tumor (e.g., oral, laryngeal, nasopharyngeal, esophageal, etc.), a liver tumor, a kidney tumor, a renal cell tumor, a squamous cell carcinoma, a uterine tumor, a bone tumor, a prostate tumor, a breast tumor including, but not limited to a breast tumor that is Her2− and/or ER− and/or PR−, a bladder tumor, a pancreatic tumor, an endometrium tumor, a squamous cell carcinoma, a stomach tumor, gliomas, a colorectal tumor, a testicular tumor, a colon tumor, a rectal tumor, an ovarian tumor, a cervical tumor, an eye tumor, a central nervous system tumor (e.g., primary CNS lymphomas, spinal axis tumors, brain stem gliomas, pituitary adenomas, etc.), a thyroid tumor, a lung tumor (e.g., non-small cell lung cancer (NSCLC) or small cell lung cancer), a leukemia or a lymphoma (e.g., cutaneous T-cell lymphomas (CTCL), non-cutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma, etc.), a multiple myeloma, a skin tumor (e.g., basal cell carcinomas, squamous cell carcinomas, melanomas such as malignant melanomas, choroidea melanomas, cutaneous melanomas or intraocular melanomas, Dermatofibrosarcoma protuberans, Merkel cell carcinoma or Kaposi's sarcoma), a gynecologic tumor (e.g., uterine sarcomas, carcinoma of the fallopian tubes, carcinoma of the endometrium, carcinoma of the cervix, carcinoma of the vagina, carcinoma of the vulva, etc.), Hodgkin's disease, a cancer of the small intestine, a cancer of the endocrine system (e.g., a cancer of the thyroid, parathyroid or adrenal glands, etc.), a mesothelioma, a cancer of the urethra, a cancer of the penis, tumors related to Gorlin's syndrome (e.g., medulloblastomas, meningioma, etc.), a tumor of unknown origin; or metastases of any thereto.

In another embodiment, the cancer is a lung tumor, a breast tumor, a colon tumor, a colorectal tumor, a head and neck tumor, a liver tumor, a prostate tumor, a glioma, glioblastoma multiforme, a ovarian tumor or a thyroid tumor; or metastases of any thereto.

In yet another embodiment, the cancer is an endometrial tumor, bladder tumor, multiple myeloma, melanoma, renal tumor, sarcoma, cervical tumor, leukemia, and neuroblastoma.

Tumors, as provided herein, may be primary tumors or metastases. Cancers may also be epithelial based cancers. In one embodiment, cells of tumors may express EGFR. In another embodiment, cells of tumors may express IGF-1R. In yet another embodiment, cells of tumors may express EGFR and IGF-1R.

Provided herein are methods for treating a disorder of the skin, comprising administering an effective amount of a pharmaceutical compound capable of inhibiting the tyrosine kinase activity of both IGF-1R and EGFR (i.e., a single compound that is a dual kinase inhibitor), wherein the pharmaceutical compound is a catecholic butane metabolite.

In one aspect, a pharmaceutical composition to be administered to a subject is a catecholic butane metabolite.

In one embodiment of the compositions and methods described here, a catecholic butane metabolite may have the structure of Formula II:

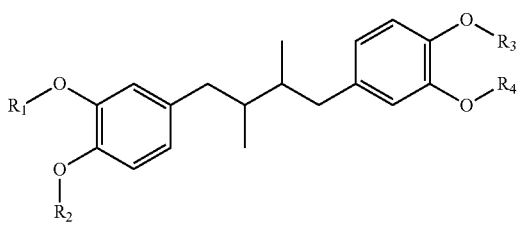

wherein at least one of $R_1$, $R_2$, $R_3$ or $R_4$ is $CH_3$, a glucuronide or a sulfate.

In another embodiment of the methods described herein, a catecholic butane metabolite may have the structure of Formula III:

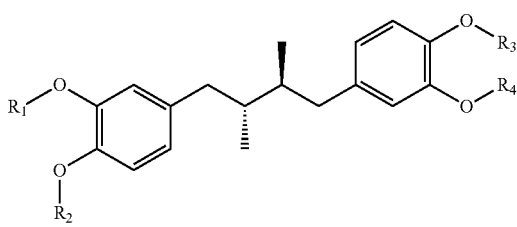

wherein at least one of $R_1$, $R_2$, $R_3$ or $R_4$ is $CH_3$, a glucuronide or a sulfate.

In another embodiment of the methods described herein, a catecholic butane metabolite may have the structure of any one of formulas IV-LXVII, wherein the formulas are provided in Table 1. R groups refer to those shown in the formula illustrated in FIG. 29. In another embodiment, catecholic butane metabolite may additionally include a phosphate ester. In some embodiments, $R_1$, $R_2$, $R_3$ and $R_4$ may include an H, a $CH_3$, a glucuronide, a sulfate or a phosphate ester. In yet other embodiments, compounds including H at each of $R_1$, $R_2$, $R_3$ and $R_4$ is not included.

In yet another embodiment of the methods provided herein, a phosphate ester of a catecholic butane metabolite may have the structure of any one of formulas LXVIII-LXXI, wherein the formulas are provided in Table 2. R groups refer to those shown in the formula illustrated in FIG. 29. In one embodiment, a phosphate prodrug of NDGA exhibits improved solubility, and improved oral absorption.

In yet another embodiment of the methods described herein, a catecholic butane metabolite may have the structure of any one of formulas IV-LXVII, wherein the formulas are provided in Table 1. R groups refer to those shown in the formula illustrated in FIG. 29. In another embodiment, a catecholic butane metabolite may additionally include a phosphate ester. In some embodiments, $R_1$, $R_2$, $R_3$ and $R_4$ may include an H, a $CH_3$, a glucuronide, a sulfate or a phosphate ester. In yet other embodiments, compounds including H at each of $R_1$, $R_2$, $R_3$ and $R_4$ is not included. In another embodiment of the methods provided herein, a phosphate ester of a catecholic butane metabolite may have the structure of any one of formulas LXVIII-LXXI, wherein the formulas are provided in Table 2. R groups refer to those shown in the formula illustrated in FIG. 29. In one embodiment, a phosphate prodrug of NDGA exhibits improved solubility, and improved oral absorption.

In another embodiment of the methods described herein, a catecholic butane metabolite may have the structure of any one of formulas LXXII-CXXXV, wherein the formulas are provided in Table 3. R groups refer to those shown in the formula illustrated in FIG. 29. In another embodiment, a catecholic butane metabolite may additionally include a phosphate ester. In some embodiments, $R_1$, $R_2$, $R_3$ and $R_4$ may include an H, a $CH_3$, a glucuronide, a sulfate or a phosphate ester. In yet other embodiments, compounds including H at each of $R_1$, $R_2$, $R_3$ and $R_4$ is not included.

In yet another embodiment of the methods provided herein, a phosphate ester of a catecholic butane metabolite may have the structure of any one of formulas CXXXVI-CXXXVII, wherein the formulas are provided in Table 4. R groups refer to those shown in the formula illustrated in FIG. 29. In one embodiment, a phosphate prodrug of NDGA exhibits improved solubility, and improved oral absorption. In yet another embodiment of the methods described herein, a catecholic butane metabolite may have the structure of any one of formulas LXXII-CXXXV, wherein the formulas are provided in Table 3. R groups refer to those shown in the formula illustrated in FIG. 29. In another embodiment, a catecholic butane metabolite may additionally include a phosphate ester. In some embodiments, $R_1$, $R_2$, $R_3$ and $R_4$ may include an H, a $CH_3$, a glucuronide, a sulfate or a phosphate ester. In yet other embodiments, compounds including H at each of $R_1$, $R_2$, $R_3$ and $R_4$ is not included. In another embodiment of the methods provided herein, a phosphate ester of a catecholic butane metabolite may have the structure of any one of formulas CXXXVI-CXXXVII, wherein the formulas are provided in Table 4. R groups refer to those shown in the formula illustrated in FIG. 29. In one embodiment, a phosphate prodrug of NDGA exhibits improved solubility, and improved oral absorption.

Pharmaceutical compositions of the present embodiments may be formulated for any route of administration such as, for example, intranasal administration; oral administration; inhalation administration; subcutaneous administration; transdermal administration; intra-arterial administration, with or without occlusion; intracranial administration; intraventricular administration; intravenous administration; buccal administration; intraperitoneal administration; intraocular administration; intramuscular administration; implantation administration; and central venous administration. In one embodiment, the catecholic butane metabolite is formulated for oral administration. In another embodiment, the catecholic butane metabolite is formulated for intravenous administration.

Doses of catecholic butane metabolites may be determined using empirical means. By way of example only, catecholic butane metabolites may be administered in an amount of from about 5 mg/kg to about 375 mg/kg per dose; from about 5 mg/kg to about 250 mg/kg per dose; from about 5 mg/kg to about 200 mg/kg per dose; from about 5 mg/kg to about 150 mg/kg per dose; from about 5 mg/kg to about 100 mg/kg per dose; from about 5 mg/kg to about 75 mg/kg per dose; or from about 5 mg/kg to about 50 mg/kg per dose.

Alternatively, catecholic butane metabolites may be administered in an amount of from about 1,500 mg per day to about 2,500 mg per day; from about 1,800 mg per day to about 2,300 mg per day; or about 2,000 mg per day. In one embodiment, a catecholic butane metabolite may be contacted with target cells in a concentration in a range of about 1 µM to about 300 µM. In another embodiment, a catecholic butane metabolite may be contacted with target cells in a concentration in a range of about 1 µM to about 10 µM.

In one embodiment, a pharmaceutical composition may be administered more frequently than once every 6 days for a period of time, or more frequently than once every 2 days for a period of time. In one embodiment, a pharmaceutical composition is administered daily for four weeks. In another embodiment, a pharmaceutical composition is administered three times daily for three weeks with a one week hiatus prior to starting a new cycle. In another embodiment, a pharmaceutical composition is administered daily for one week followed by a one week hiatus. In another embodiment, a pharmaceutical composition is administered daily for two weeks followed by a two week hiatus. In another embodiment, a pharmaceutical composition is administered one time or two times daily continuously or with a one week hiatus prior to starting a new cycle. In yet another embodiment, a pharmaceutical composition is administered one time per week or two times per week.

In any of such methods provided herein, a subject being administered a catecholic butane metabolite may be further administered one or more additional anti cancer agents or treatment regimens. Anti-cancer agents include, but are not limited to, DNA damaging agents, topoisomerase inhibitors and mitotic inhibitors. In some embodiments, the one or more anti-cancer agents to be administered may be an EGFR inhibitor, an IGF-1R inhibitor, or both.

In one aspect of the methods described herein, a patient being administered a catecholic butane metabolite may be further treated by administering an EGFR inhibitor, an IGF-1R inhibitor, or both.

In one embodiment, the subject to be treated may be resistant to treatment with one or more tyrosine kinase inhibitors, for example, an EGFR inhibitor alone, an IGF-1R inhibitor alone, or an EGFR inhibitor and an IGF-1R inhibitor.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

(1) NL: 3.00E5
m/z = 301.1430-301.1460 F: FTMS − p ESI
Full ms [150.00-900.00] MS
12triap3_20sept_negsa_04
(2) NL: 3.00E5
m/z = 301.1430-301.1460 F: FTMS − p ESI
Full ms [150.00-900.00] MS
12triap3_20sept_negsa_05
(3) NL: 3.00E5
m/z = 301.1430-301.1460 F: FTMS − p ESI
Full ms [150.00-900.00] MS
12triap3_20sept_negsa_06
(4) NL: 3.00E5
m/z = 301.1430-301.1460 F: FTMS − p ESI
Full ms [150.00-900.00] MS
12triap3_20sept_negsa_08
(5) NL: 3.00E5
m/z = 301.1430-301.1460 F: FTMS − p ESI
Full ms [150.00-900.00] MS
12triap3_20sept_negsa_10
(6) NL: 3.00E5
m/z = 301.1430-301.1460 F: FTMS − p ESI
Full ms [150.00-900.00] MS
12triap3_20sept_negsa_11

Figure 2:
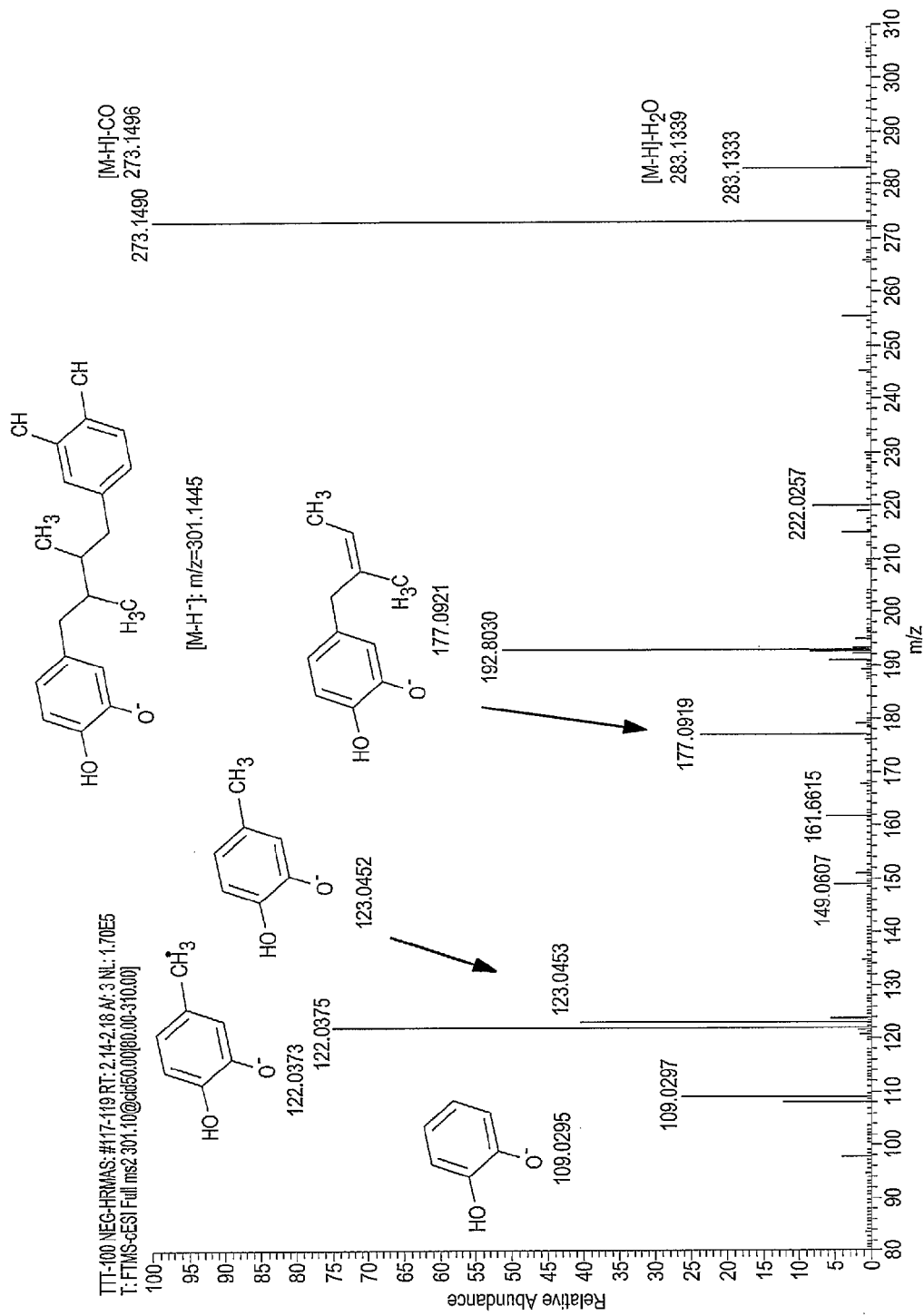

FIG. 2 shows MS/MS spectra of the parent compound (a direct infusion experiment) and the elaborated fragmentation pathway. $MS^2$ spectrum of NDGA (negative mode) and elaborated fragmentation pathway. Small text at the top of the figure is as follows: NDGA NEG-HRMAS2 #117-119 RT:2.14-2.18 AV:3 NL:1.70E5 T:FTMS-c ESI Full ms2 301.10@cid50.00 [80.00-310.00].

Figure 3:
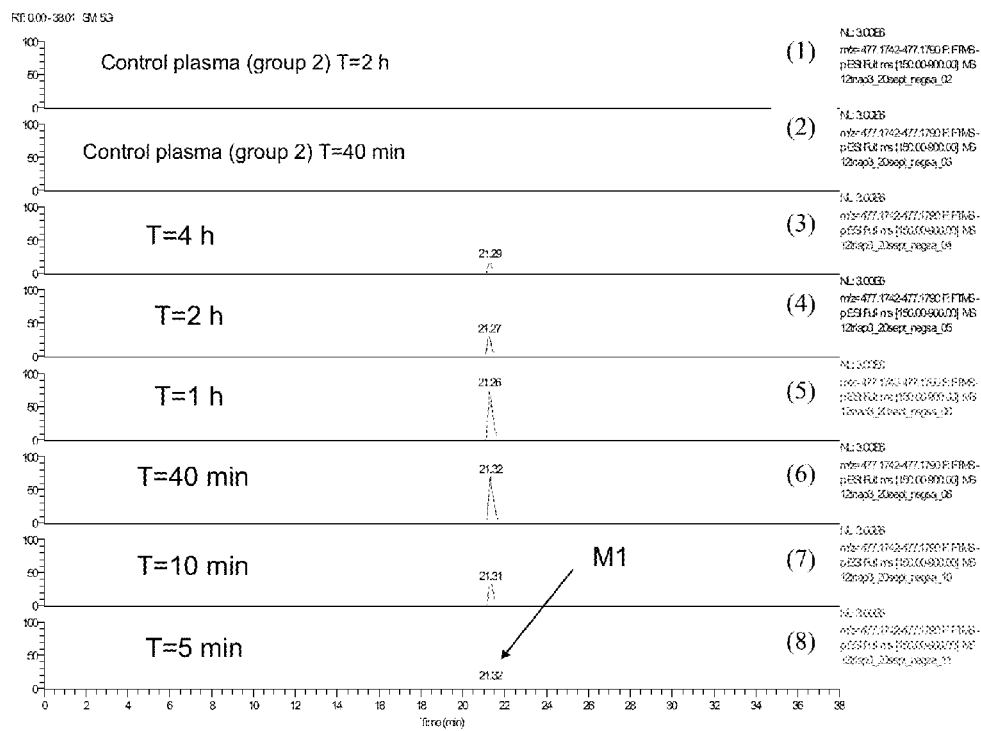

FIG. 3 shows XIC detection of the peak of metabolite M1 across data points in plasma of dosed animals and the lack thereof in control plasma samples. XIC (m/z=477.1759) traces of the peak of putative metabolite M1 (glucuronidation) in plasma samples (normalized scale). XIC (m/z=477.1759) traces of the peak of putative metabolite M1 (glucuronidation) in plasma samples (normalized scale); x-axis: time in minutes.

(1) NL: 3.00E6
m/z = 477.1742-477.1790 F: FTMS − p ESI
Full ms [150.00-900.00] MS
12triap3_20sept_negsa_02
(2) NL: 3.00E6
m/z = 477.1742-477.1790 F: FTMS − p ESI
Full ms [150.00-900.00] MS
12triap3_20sept_negsa_03

(3) NL: 3.00E6
m/z = 477.1742-477.1790 F: FTMS − p ESI
Full ms [150.00-900.00] MS
12triap3_20sept_negsa_04
(4) NL: 3.00E6
m/z = 477.1742-477.1790 F: FTMS − p ESI
Full ms [150.00-900.00] MS
12triap3_20sept_negsa_05
(5) NL: 3.00E6
m/z = 477.1742-477.1790 F: FTMS − p ESI
Full ms [150.00-900.00] MS
12triap3_20sept_negsa_06
(6) NL: 3.00E6
m/z = 477.1742-477.1790 F: FTMS − p ESI
Full ms[150.00-900.00] MS
12triap3_20sept_negsa_08
(7) NL: 3.00E6
m/z = 477.1742-477.1790 F: FTMS − p ESI
Full ms [150.00-900.00] MS
12triap3_20sept_negsa_10
(8) NL: 3.00E6
m/z = 477.1742-477.1790 F: FTMS − p ESI
Full ms [150.00-900.00] MS
12triap3_20sept_negsa_11

Figure 4:
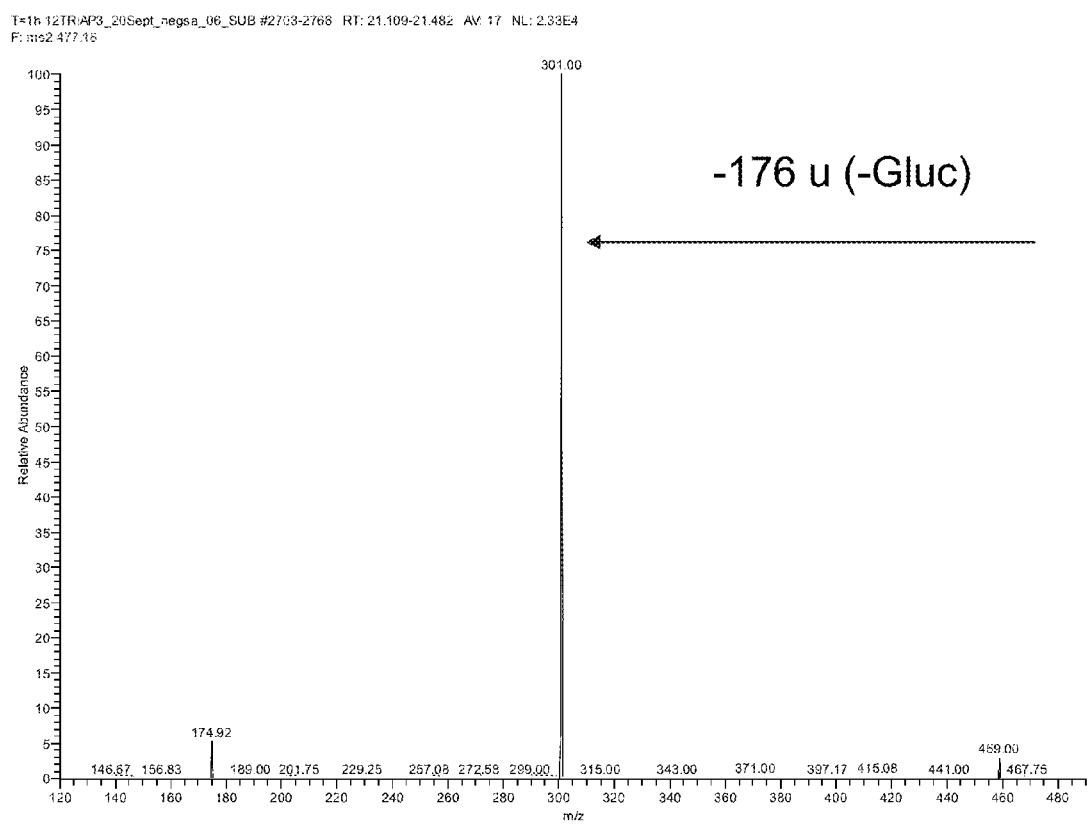

FIG. 4. MS$^2$ spectrum of putative metabolite M1. Based on the results of the accurate mass measurement, metabolite M1 corresponds to the product of direct glucuronidation of the parent compound. MS/MS data confirms the structure assignment. The spectrum shows the characteristic neutral loss of 176 u, typical for glucuronides. The exact site of glucuronidation cannot be established using LC-MS(n) methodology. Small text at the top of the figure is as follows: T=1 h 12TRIAP3_20Sept_negsa_06_SUB #2703-2766 RT:21.109-21.482 AV:17 NL:2.33E4 F:ms2 477.18.

Figure 5:
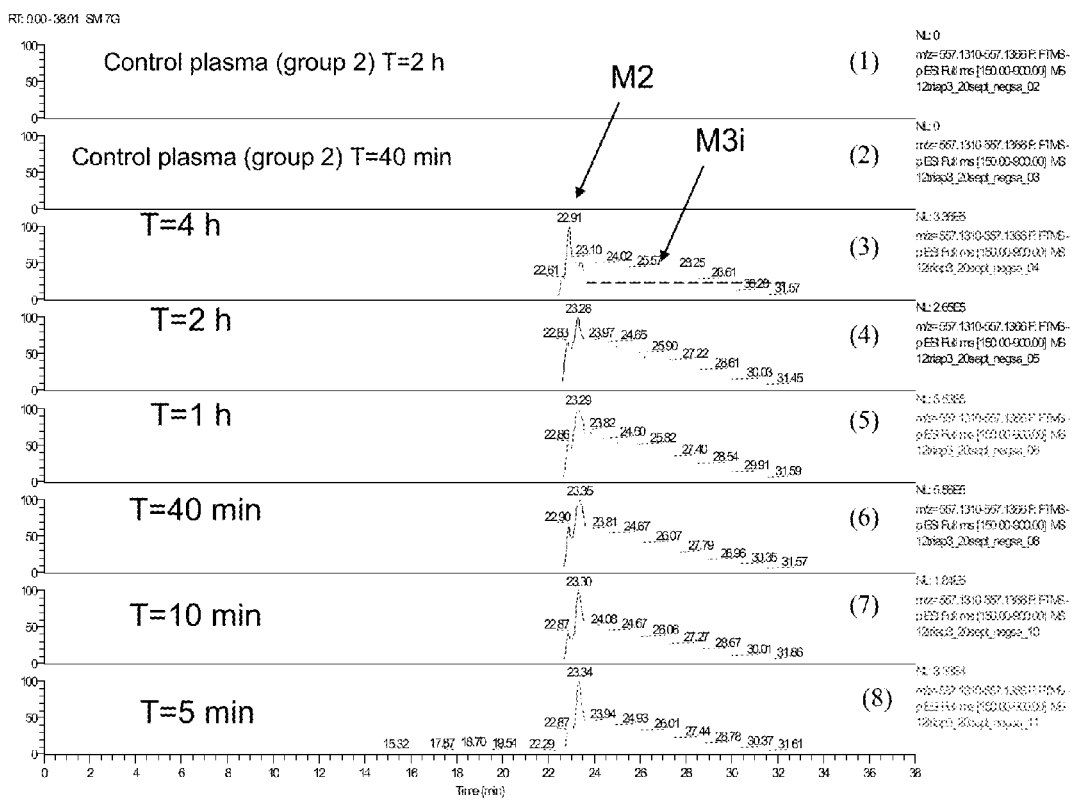

FIG. 5. XIC (m/z=557.1338) traces of the peaks of putative metabolites M2 and M3i (net gain of 255.9893) in plasma samples. FIG. 5 shows XIC detection of the pool of putative metabolites M2 and M3i across data points in the plasma of dosed animals, and the lack thereof in control plasma samples. The "hill-like" appearance of the peaks of M3i could be either due to the presence of multiple isomers (most likely), or tautomerization/isomerization during chromatography and/or column overload (less likely). The formal gain of 255.9893 u implies the occurrence of complex conjugative metabolism. The putative metabolites M2 and M3i could be rationalized as the net results of mono-glucuronidation (+176.0321) plus sulfation (+79.9568), resulting in conjugates at m/z=(301.1445+176.0321+79.9568)=557.1334 u. Such conjugates typically show extremely facile loss of sulfate or/and glucuronic moieties during ionization in positive mode, and indeed sample analysis using positive mode (LC method I) did not lead to the detection of the peaks at "nominal" m/z=559.2 (protonated M2 and M3i). Instead, "hill-like" peaks of the parent were detected as seen in FIG. 6.

(1) NL: 0
m/z = 557.1310-557.1366 F: FTMS − p ESI
Full ms [150.00-900.00] MS
12triap3_20sept_negsa_02
(2) NL: 0
m/z = 557.1310-557.1366 F: FTMS − p ESI
Full ms [150.00-900.00] MS
12triap3_20sept_negsa_03
(3) NL: 3.36E5
m/z = 557.1310-557.1366 F: FTMS − p ESI
Full ms [150.00-900.00] MS
12triap3_20sept_negsa_04
(4) NL: 2.65E5
m/z = 557.1310-557.1366 F: FTMS − p ESI
Full ms [150.00-900.00] MS
12triap3_20sept_negsa_05
(5) NL: 5.53E5
m/z = 557.1310-557.1366 F: FTMS − p ESI
Full ms [150.00-900.00] MS
12triap3_20sept_negsa_06
(6) NL: 5.56E5
m/z = 557.1310-557.1366 F: FTMS − p ESI
Full ms [150.00-900.00] MS
12triap3_20sept_negsa_08
(7) NL: 1.84E5
m/z = 557.1310-557.1366 F: FTMS − p ESI
Full ms [150.00-900.00] MS
12triap3_20sept_negsa_10
(8) NL: 3.38E4
m/z = 557.1310-557.1366 F: FTMS − p ESI
Full ms [150.00-900.00] MS
12triap3_20sept_negsa_11

Figure 6:
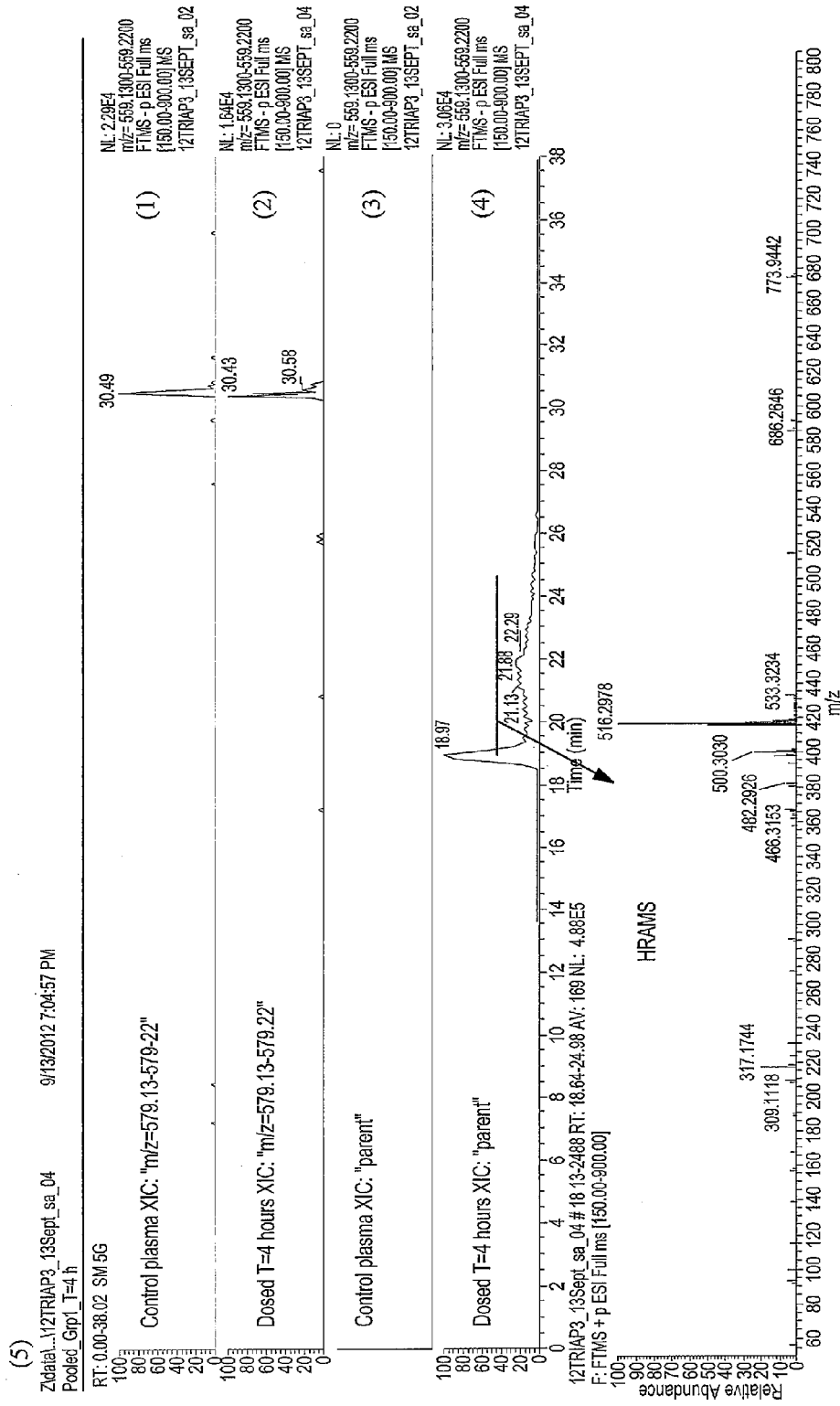

FIG. 6. XIC traces of the parent compound, lack of signal at m/z=559 u and recorded HRAMS spectrum in positive ionization mode. Peak at RT=18.97 is an artifact due SID of metabolite M1; a "true" peak of the parent compound (eluting later) was not detectable at that level due to its extremely poor ionization in positive mode. The appearance of the artifact —"hill-like" peak of the parent compound is in agreement with the expected instability of M2 and M3i during ionization in positive mode.

(1) NL: 2.29E4
m/z = 559.1300-559.2200 F: FTMS + p ESI Full ms [150.00-900.00] MS 12TRIAP3_13Sept_sa_02
(2) NL: 1.84E4
m/z = 559.1300-559.2200 F: FTMS + p ESI Full ms [150.00-900.00] MS 12TRIAP3_13Sept_sa_04
(3) NL: 0
m/z = 303.1572-303.1602 F: FTMS + p ESI Full ms [150.00-900.00] MS 12TRIAP3_13Sept_sa_02
(4) NL: 3.06E4
m/z = 303.1572-303.1602 F: FTMS + p ESI Full ms [150.00-900.00] MS 12TRIAP3_13Sept_sa_04
(5) 0412TRIAP3_13Sept_sa_04 #1813-2488 RT:18.64-24.98 AV:169 NL:4.88E5 F:FTMS + p ESI Full ms [150.00-900.00]

Figure 7:
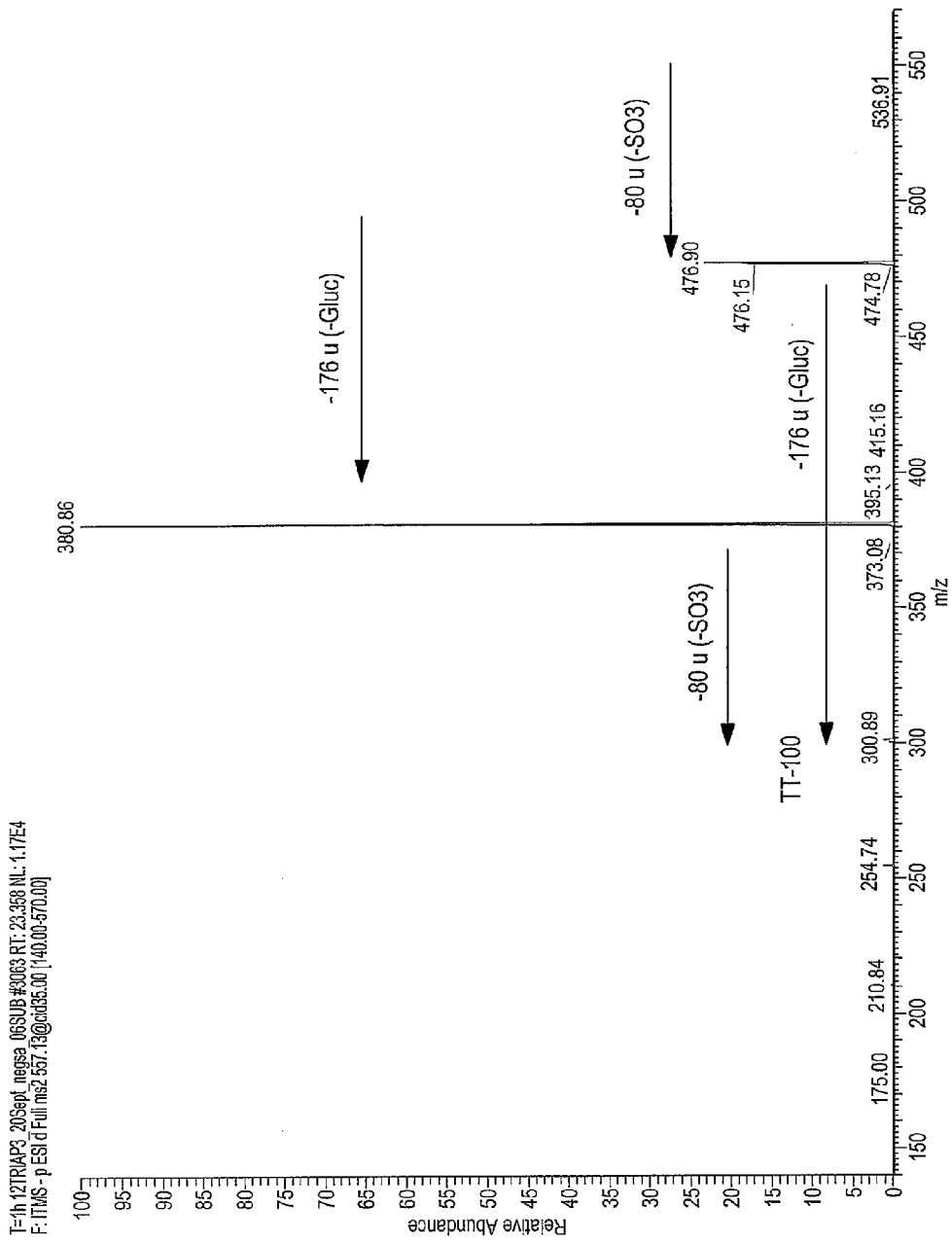

FIG. 7. MS$^2$ spectrum of metabolite M2. The MS$^2$ spectrum shows consequent neutral losses of 176 u (loss of glucuronic moiety) and 80 u (loss of SO$_3$), confirming the structure assignment. The exact sites of conjugation cannot be established using LC-MS(n) methodology. Small text at top of the figure is as follows: T=1 h 12TRIAP3_20Sept_negsa_06_SUB #3063 RT:23.358 NL:1.17E4 F:ITMS-p ESI d Full ms2 557.13@cid35.00 [140.00-570.00].

Figure 8:
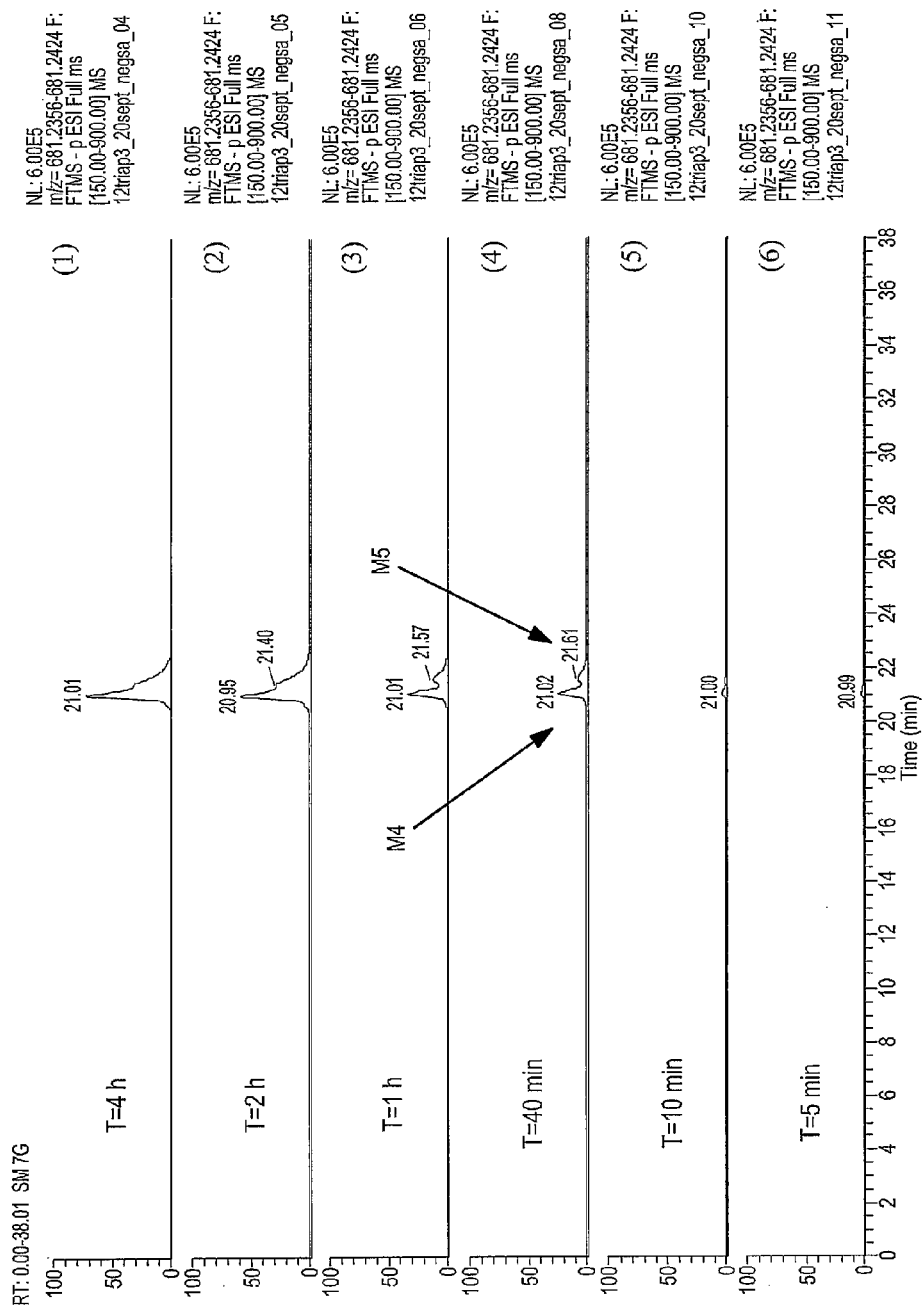

FIG. 8. XIC (m/z=681.2390) traces of the peaks of putative metabolites M4 and M5 (net gain of 380.0945) in plasma samples (normalized scale). FIG. 8 shows detection of putative metabolites M4 and M5 in plasma of dosed animals (not detected in control plasma samples; representative traces of control plasma samples are not shown). The formal gain of 380.0945 u implies the occurrence of complex conjugative metabolism. Based on the results of accurate mass measurements, there appears to be a net result of bis-methylation and bis-glucuronidation (shift of 380.0956). The recorded MS$^2$ spectrum is in agreement with the proposed structure as seen in FIG. 9.

(1) NL: 6.00E5
m/z = 681.2356-681.2424 F: FTMS – p ESI
Full ms [150.00-900.00] MS
12triap3_20sept_negsa_04
(2) NL: 6.00E5
m/z = 681.2356-681.2424 F: FTMS – p ESI
Full ms [150.00-900.00] MS
12triap3_20sept_negsa_05
(3) NL: 6.00E5
m/z = 681.2356-681.2424 F: FTMS – p ESI
Full ms [150.00-900.00] MS
12triap3_20sept_negsa_06
(4) NL: 6.00E5
m/z = 681.2356-681.2424 F: FTMS – p ESI
Full ms [150.00-900.00] MS
12triap3_20sept_negsa_08
(5) NL: 6.00E5
m/z = 681.2356-681.2424 F: FTMS – p ESI
Full ms [150.00-900.00] MS
12triap3_20sept_negsa_10
(6) NL: 6.00E5
m/z = 681.2356-681.2424 F: FTMS – p ESI
Full ms [150.00-900.00] MS
12triap3_20sept_negsa_11

Figure 9:
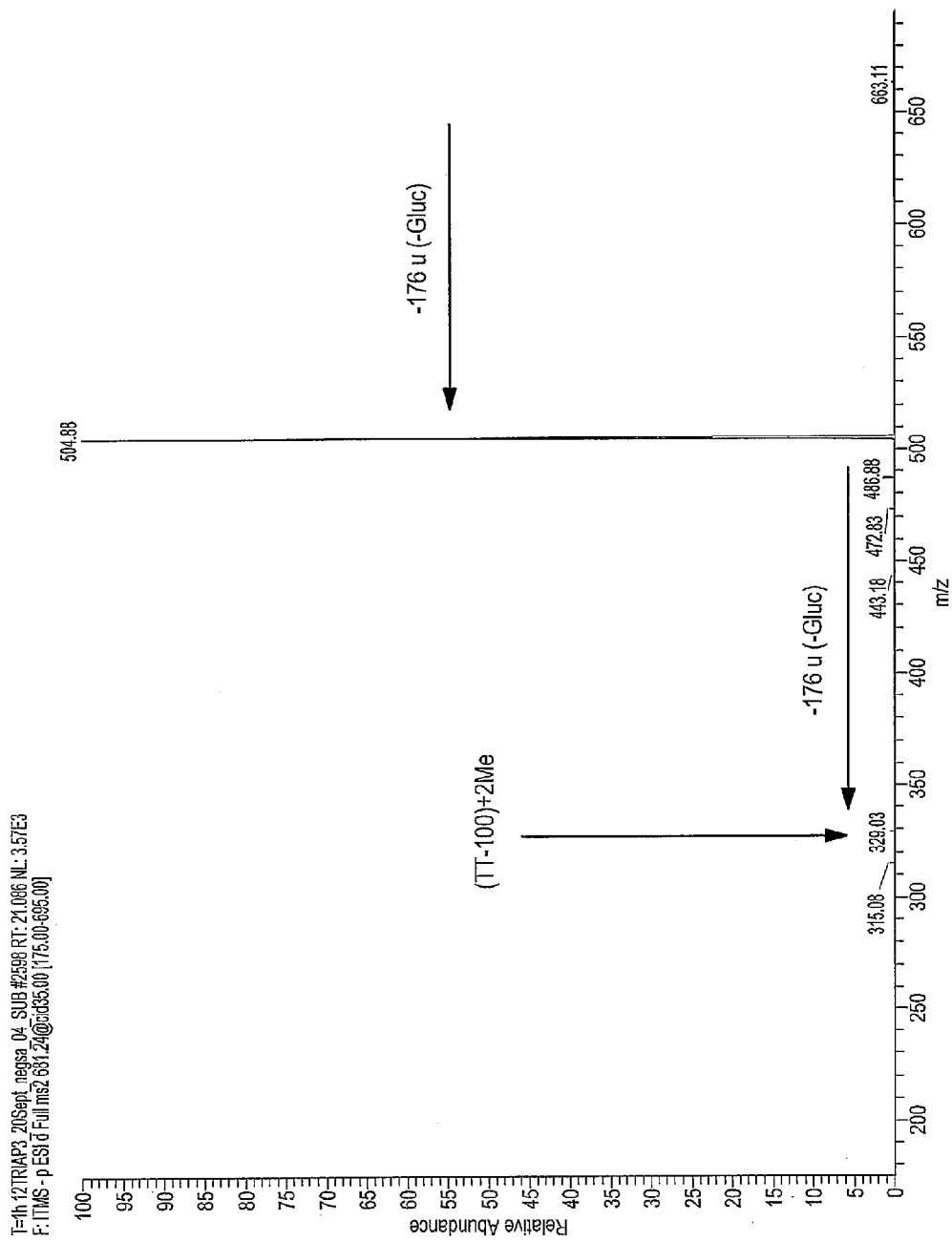

FIG. 9. $MS^2$ spectrum of metabolite M5. The $MS^2$ spectrum shows consequent neutral losses of 176 u (loss of glucuronic moiety); moreover, the product ion at m/z=329 corresponds to bis-methylated NDGA (based on HRAMS results). Exact sites of conjugation cannot be established using LC-MS(n) methodology. It appears that metabolites M4 and M5 are late-forming metabolites and could be long-circulating metabolites in vivo. Small text at the top of the figure is as follows: T=4 h 12TRIAP3_20Sept_negsa_04_SUB #2598 RT:21.086 NL:3.57E3 F:ITMS-p ESI d Full ms2 681.24@cid35.00 [175.00-695.00].

Figure 10:
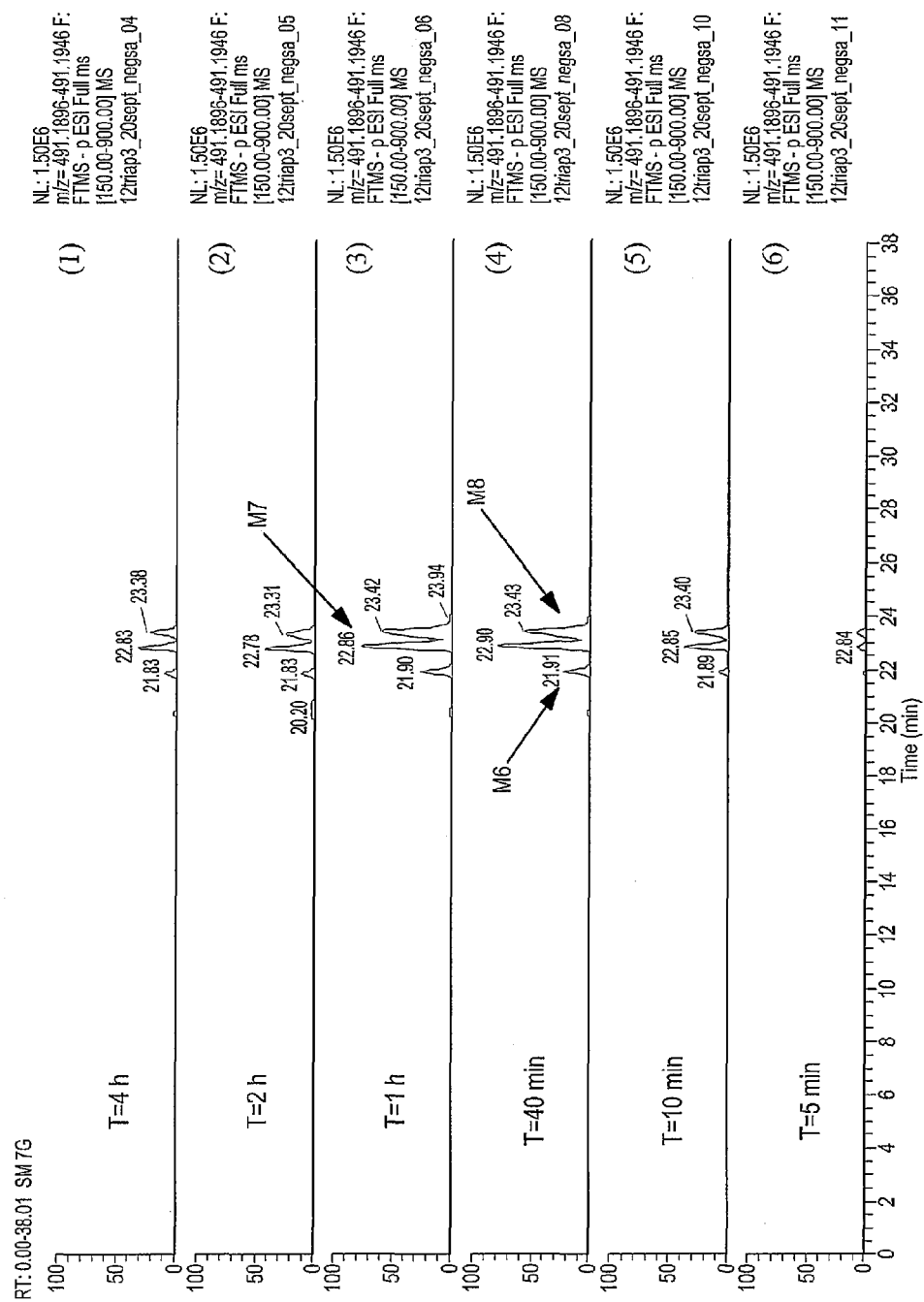

FIG. 10. XIC (m/z=491.1921) traces of the peaks of putative metabolites M6-M8 (190.0481) in plasma samples (normalized scale). FIG. 10 shows detection of putative metabolites M6-M8 in plasma of dosed animals (not detected in control plasma samples; representative traces of control plasma samples are not shown).

(1) NL: 1.50E6
m/z = 491.1896-491.1946 F: FTMS – p
ESI Full ms [150.00-900.00] MS
12triap3_20sept_negsa_04
(2) NL: 1.50E6
m/z = 491.1896-491.1946 F: FTMS – p
ESI Full ms [150.00-900.00] MS
12triap3_20sept_negsa_05
(3) NL: 1.50E6
m/z = 491.1896-491.1946 F: FTMS – p
ESI Full ms [150.00-900.00] MS
12triap3_20sept_negsa_06
(4) NL: 1.50E6
m/z = 491.1896-491.1946 F: FTMS – p
ESI Full ms [150.00-900.00] MS
12triap3_20sept_negsa_08
(5) NL: 1.50E6
m/z = 491.1896-491.1946 F: FTMS – p
ESI Full ms [150.00-900.00] MS
12triap3_20sept_negsa_10
(6) NL: 1.50E6
m/z = 491.1896-491.1946 F: FTMS – p
ESI Full ms [150.00-900.00] MS
12triap3_20sept_negsa_11

Figure 11:
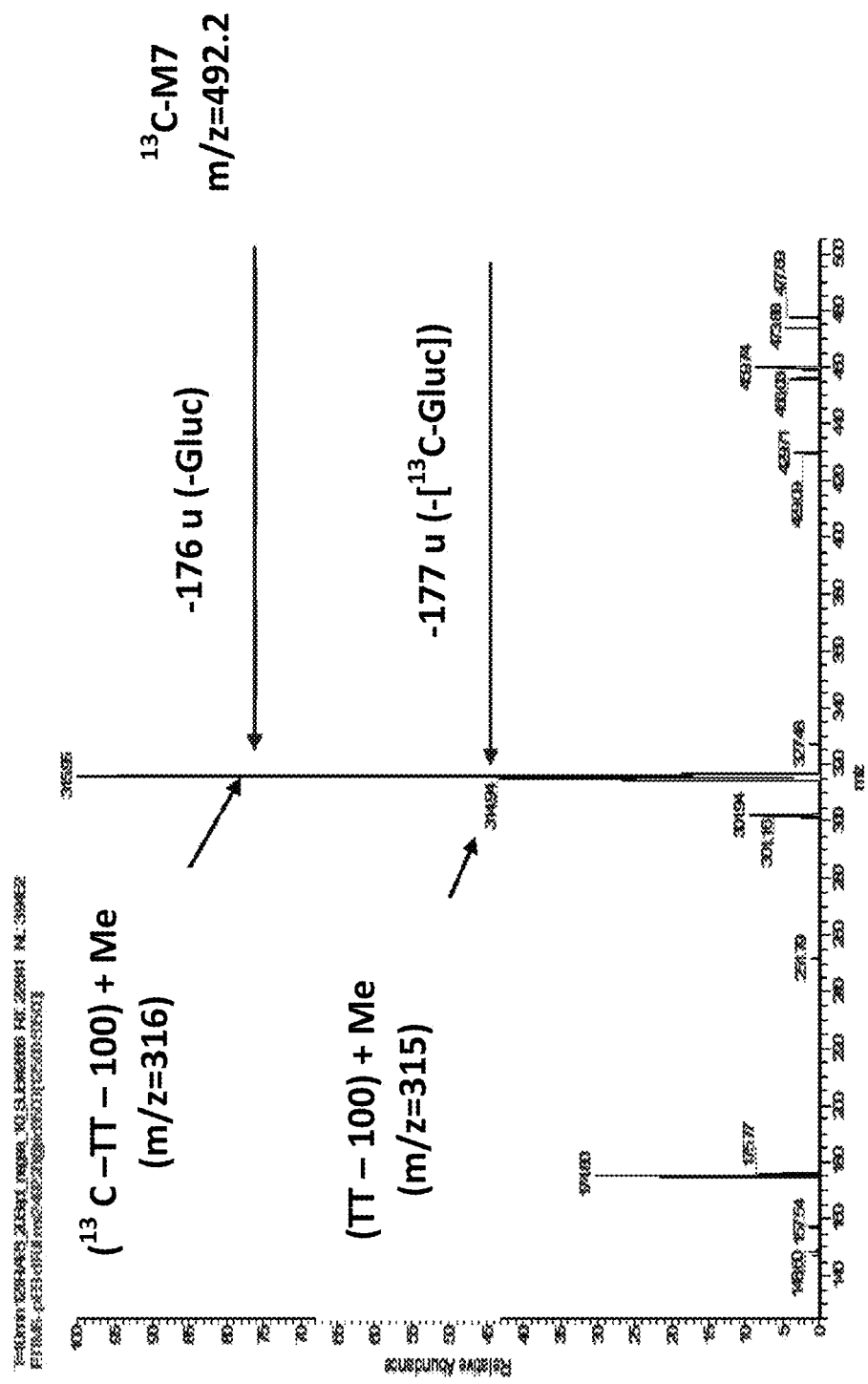

FIG. 11. $MS^2$ spectrum of metabolite M7. The formal gain of 190.0481 u implies occurrence of complex conjugative metabolism. Based on the results of accurate mass measurements, they correspond to the net result of methylation and glucuronidation (shift of 190.0478). Recorded $MS^2$ spectrum of metabolite M7 is in agreement with the proposed structure. The ion with nominal m/z=491.2, corresponding to the protonated molecular ion of M7, happened to be on the exclusion list generated for the plasma matrix. As a result, no $MS^2$ spectra using targeted ion with m/z=491.2 were acquired. However, the DDA triggered $MS^2$ data acquisition on the 13 C isotopomer of M7 (m/z=492.2), the spectrum of which is shown above. The $MS^2$ spectrum fully supports the structure assignment and shows fine isotopic pattern matching that theoretically expected for this isotopomer. The exact sites of conjugation cannot be established using LC-MS(n) methodology. Small text at the top of the figure is as follows: T=10 min 12TRIAP3_20Sept_negsa_10_SUB #2866 RT:22.841 NL:3.94E2F:ITMS-p ESI d Full ms2 492.20@cid35.00 [125.00-505.00].

Figure 12:
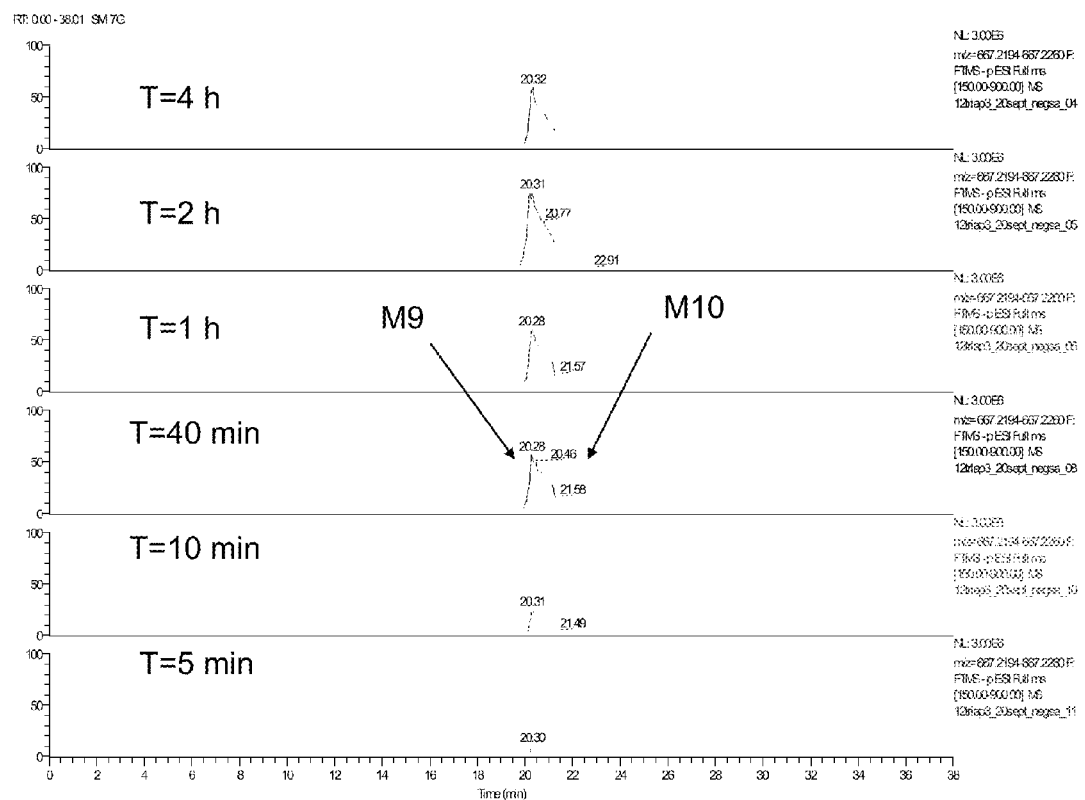

FIG. 12. XIC (m/z=667.2227) traces of the peaks of putative metabolites M9 and M10 (net gain of 366.0782) in plasma samples (normalized scale). FIG. 12 shows detection of putative metabolites M9 and M10 in plasma of dosed animals (not detected in control plasma samples; representative traces of control plasma samples are not shown). The "hill-like" appearance implies the possible presence of multiple isomers and/or tautomerization during separation. The formal gain of 366.0782 u implies occurrence of complex conjugative metabolism. Based on the results of accurate mass measurements, they correspond to the net result of methylation and bis-glucuronidation (shift of 366.0799). The recorded $MS^2$ spectrum of metabolite M9 is in agreement with the proposed structure of FIG. 13.

(1) NL: 3.00E6
m/z = 667.2194-667.2260 F: FTMS – p
ESI Full ms [150.00-900.00] MS
12triap3_20sept_negsa_04
(2) NL: 3.00E6
m/z = 667.2194-667.2260 F: FTMS – p
ESI Full ms [150.00-900.00] MS
12triap3_20sept_negsa_05
(3) NL: 3.00E6
m/z = 667.2194-667.2260 F: FTMS – p
ESI Full ms [150.00-900.00] MS
12triap3_20sept_negsa_06
(4) NL: 3.00E6
m/z = 667.2194-667.2260 F: FTMS – p
ESI Full ms [150.00-900.00] MS
12triap3_20sept_negsa_08
(5) NL: 3.00E6
m/z = 667.2194-667.2260 F: FTMS – p
ESI Full ms [150.00-900.00] MS
12triap3_20sept_negsa_10
(6) NL: 3.00E6
m/z = 667.2194-667.2260 F: FTMS – p
ESI Full ms [150.00-900.00] MS
12triap3_20sept_negsa_11

Figure 13:
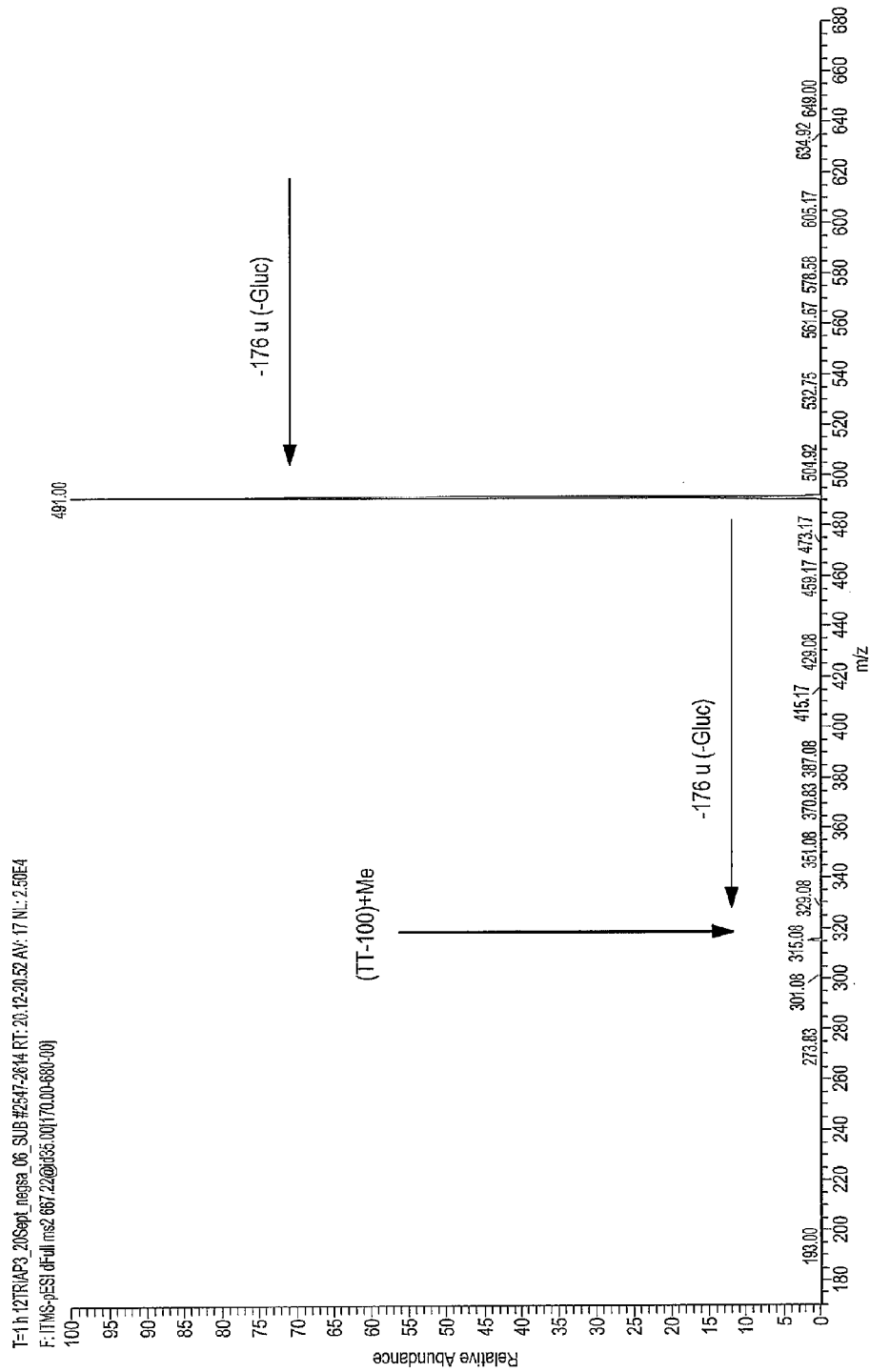

FIG. 13. $MS^2$ spectrum of metabolite M9. The $MS^2$ spectrum shows consequent neutral loss of 176 u (loss of glucuronic moiety); moreover, the product ion at m/z=315 corresponds to methylated NDGA (based on HRAMS results). Exact sites of conjugation cannot be established using LC-MS(n) methodology. It appears that metabolites M9 and M10 could be long-circulating metabolites in vivo. Small text at the top of the figure is T=1 h 12TRIAP3_20Sept_negsa_06_SUB #2547-2614 RT:20.12-20.52 AV:17 NL:2.50E4F:ITMS-p ESI d Full ms2 667.22@cid35.00 [170.00-680.00].

Figure 14:
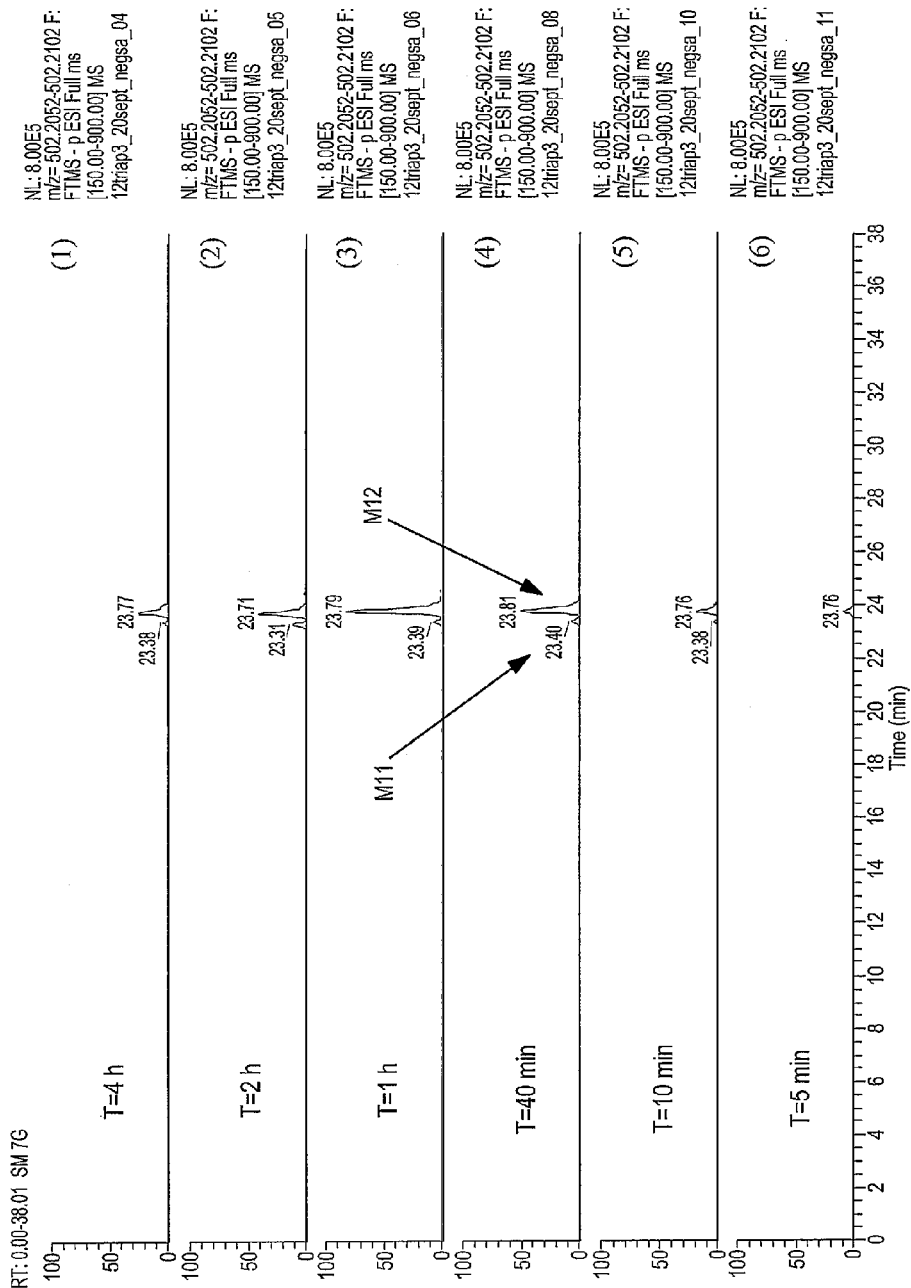
Figure 15:
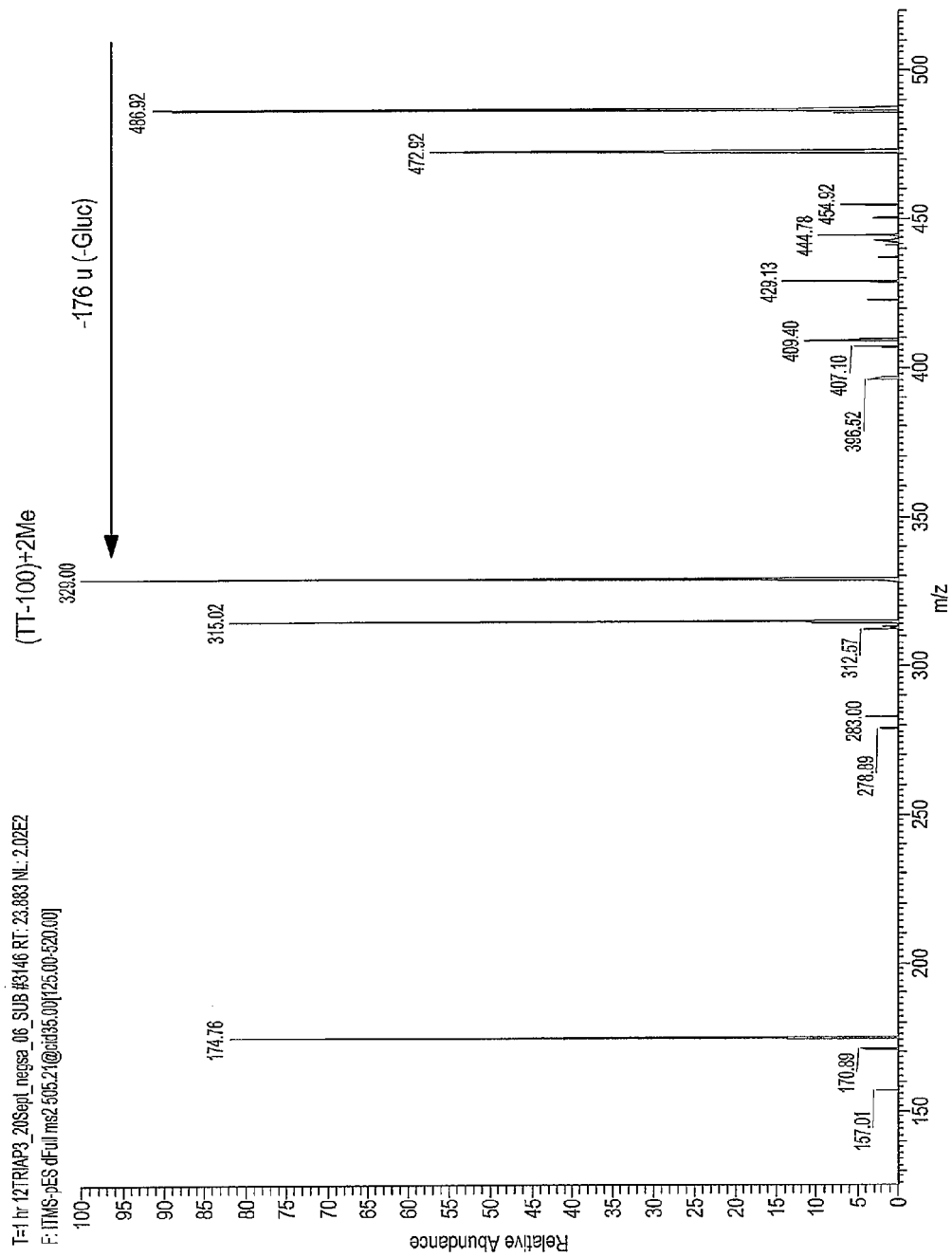

FIG. 14. XIC (m/z=505.2077) traces of the peaks of putative metabolites M11 and M12 (net gain of 204.0632) in plasma samples (normalized scale). FIG. 14 shows detection of putative metabolites M11 and M12 in plasma of dosed animals (not detected in control plasma samples; representative traces of control plasma samples are not shown). The formal gain of 204.0632 u implies occurrence of complex conjugative metabolism. Based on the results of accurate mass measurements they could be the net result of bis-methylation and glucuronidation (shift of 204.0622). The recorded $MS^2$ spectrum of metabolite M12 is in agreement with the proposed structure (FIG. 15).

---

(1) NL: 8.00E5
m/z = 505.2052-505.2102 F: FTMS − p ESI
Full ms [150.00-900.00] MS
12triap3_20sept_negsa_04
(2) NL: 8.00E5
m/z = 505.2052-505.2102 F: FTMS − p ESI
Full ms [150.00-900.00] MS
12triap3_20sept_negsa_05
(3) NL: 8.00E5
m/z = 505.2052-505.2102 F: FTMS − p ESI
Full ms [150.00-900.00] MS
12triap3_20sept_negsa_06
(4) NL: 8.00E5
m/z = 505.2052-505.2102 F: FTMS − p ESI
Full ms [150.00-900.00] MS
12triap3_20sept_negsa_08
(5) NL: 8.00E5
m/z = 505.2052-505.2102 F: FTMS − p ESI
Full ms [150.00-900.00] MS
12triap3_20sept_negsa_10
(6) NL: 8.00E5
m/z = 505.2052-505.2102 F: FTMS − p ESI
Full ms [150.00-900.00] MS
12triap3_20sept_negsa_11

---

FIG. 15. $MS^2$ spectrum of metabolite M12. The $MS^2$ spectrum shows neutral loss of 176 u (loss of glucuronic moiety); moreover, the product ion at m/z=329 corresponds to methylated NDGA (based on HRAMS results). The exact sites of conjugation cannot be established using LC-MS(n) methodology.

Figure 16:
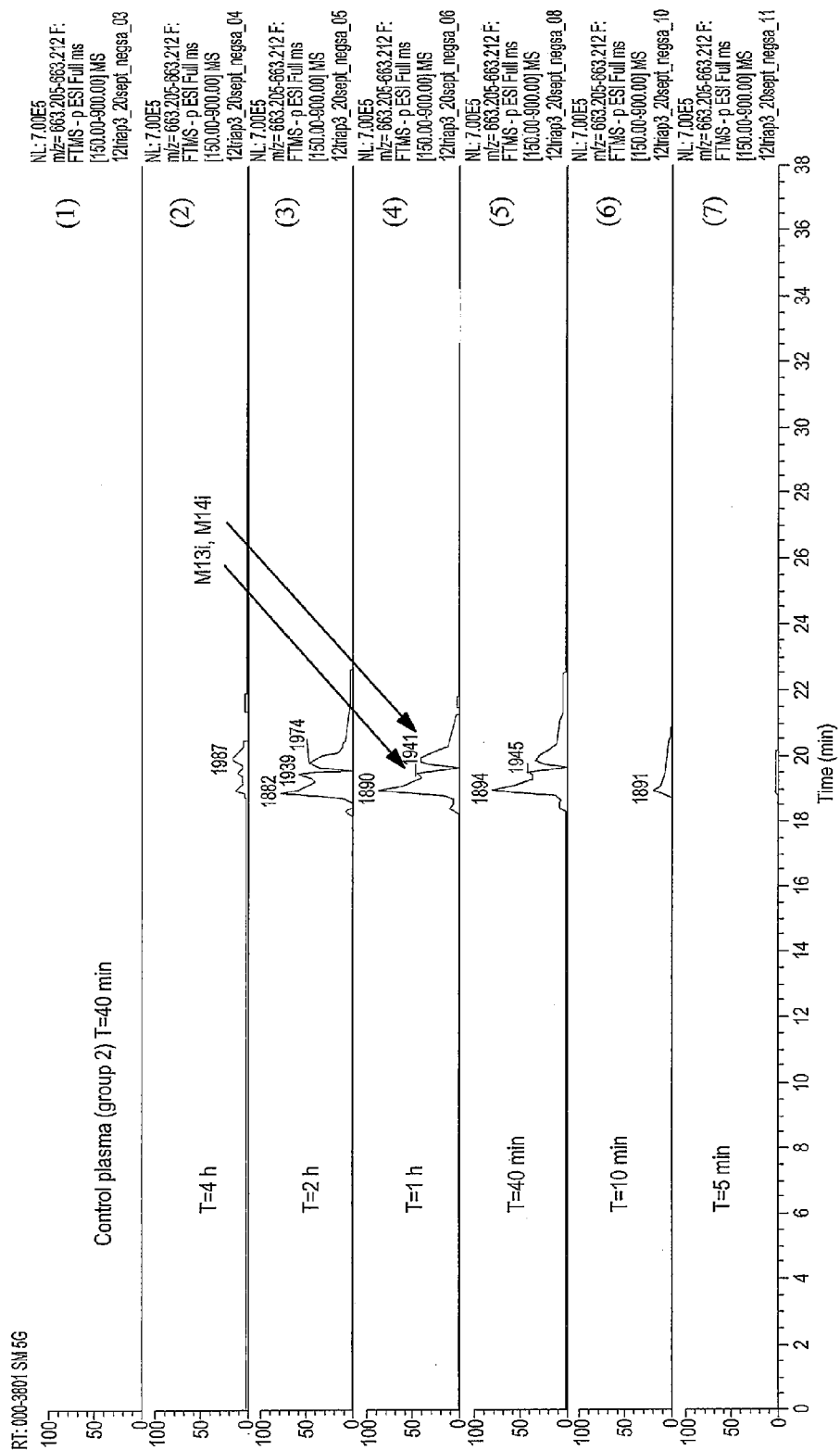
Figure 17:
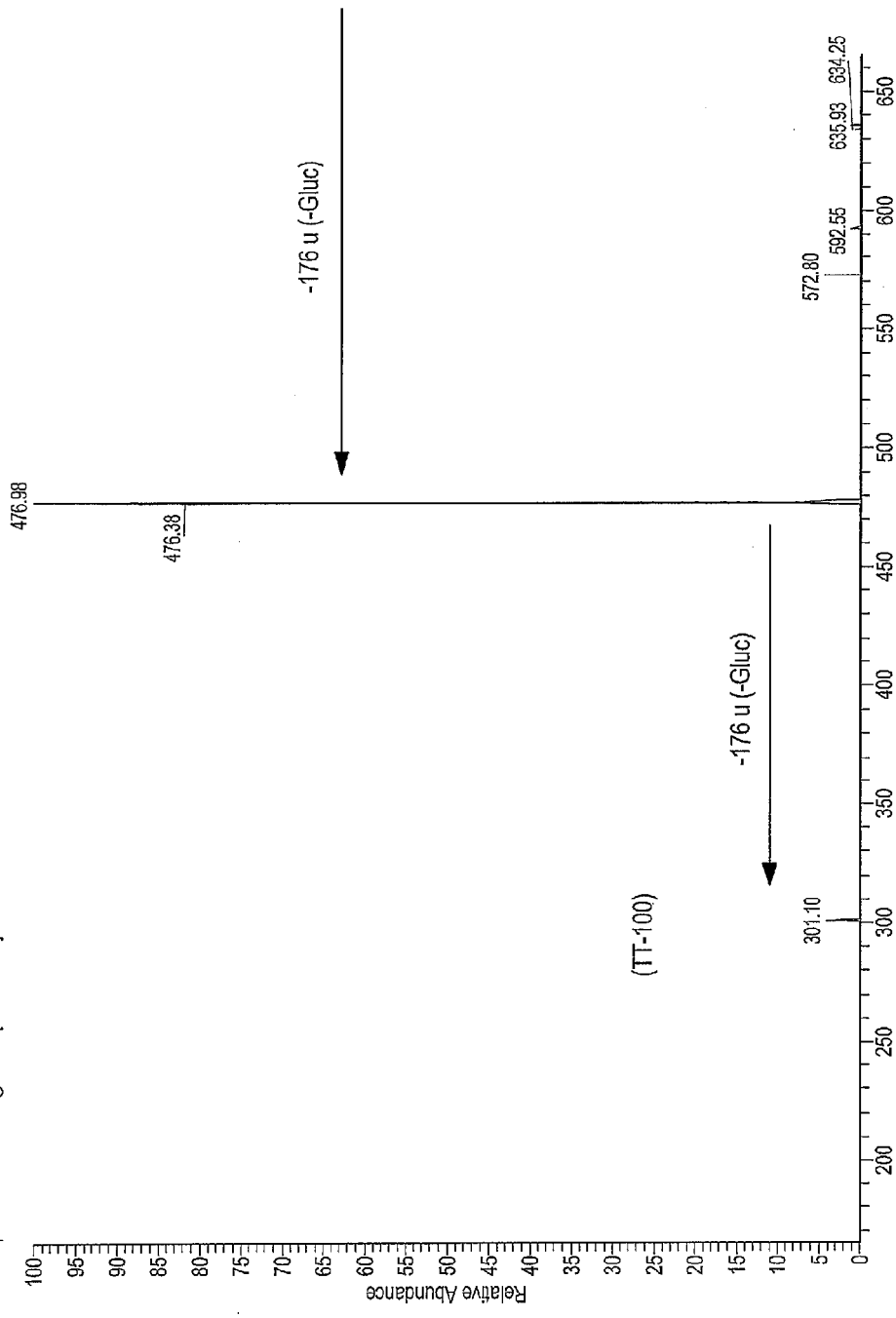

FIG. 16. XIC (m/z=653.2087) traces of the peaks of a pool of isobaric putative metabolites M13i and M14i (net gain of 352.0642) in plasma samples. FIG. 16 shows detection of a pool of putative isobaric metabolites M13i and M14i in plasma of dosed animals and the lack thereof in control plasma samples. The "hill-like" appearance of the peaks of M13i and M14i could be either due to the presence of multiple isomers (most likely), or tuatomerization/isomerization during chromatography and/or column overload (less likely). The formal gain of 352.2087 u implies the occurrence of complex conjugative metabolism. Based on the results of accurate mass measurements, they correspond to the net result of bis-glucuronidation (shift of 352.0642). The recorded $MS^2$ spectrum of metabolite M13i is in agreement with the proposed structure (FIG. 17). Small text at the top of the figure is as follows: T=1 h 12TRIAP3_20Sept_negsa_06_SUB #3146 RT:23.883 NL:2.02E2F:ITMS-p ESI d Full ms2 505.21@cid35.00 [125.00-520.00].

---

(1) NL: 7.00E5
m/z = 653.2054-653.2120 F: FTMS − p ESI
Full ms [150.00-900.00] MS
12triap3_20sept_negsa_03
(2) NL: 7.00E5
m/z = 653.2054-653.2120 F: FTMS − p ESI
Full ms [150.00-900.00] MS
12triap3_20sept_negsa_04
(3) NL: 7.00E5
m/z = 653.2054-653.2120 F: FTMS − p ESI
Full ms [150.00-900.00] MS
12triap3_20sept_negsa_05
(4) NL: 7.00E5
m/z = 653.2054-653.2120 F: FTMS − p ESI
Full ms [150.00-900.00] MS
12triap3_20sept_negsa_06
(5) NL: 7.00E5
m/z = 653.2054-653.2120 F: FTMS − p ESI
Full ms [150.00-900.00] MS
12triap3_20sept_negsa_08
(6) NL: 7.00E5
m/z = 653.2054-653.2120 F: FTMS − p ESI
Full ms [150.00-900.00] MS
12triap3_20sept_negsa_10
(7) NL: 7.00E5
m/z = 653.2054-653.2120 F: FTMS − p ESI
Full ms [150.00-900.00] MS
12triap3_20sept_negsa_11

---

FIG. 17. $MS^2$ spectrum of metabolite M13i. The $MS^2$ spectrum shows consequent neutral loss of 176 u (loss of glucuronic moiety), leading to the aglycone, NDGA with m/z=301. The exact site of conjugation cannot be established using LC-MS(n) methodology. Besides these reported "fourteen" putative metabolites, a number of other unique peaks, which could be putative metabolites, were detected in the plasma of dosed animals. Comprehensive elaboration of their nature was beyond the scope of the current study protocol (covering the ten most abundant metabolites). A representative Total Ion Current chromatogram and survey MS spectrum showing other plausible metabolites are shown in Appendix III. Small text at top of the figure is as follows: T=4 h 12TRIAP3_20Sept_negsa_04_SUB #2256 RT:18.916 NL:6.17E2F:ITMS-p ESI d Full ms2 653.21@cid35.00 [165.00-665.00].

Figure 18:
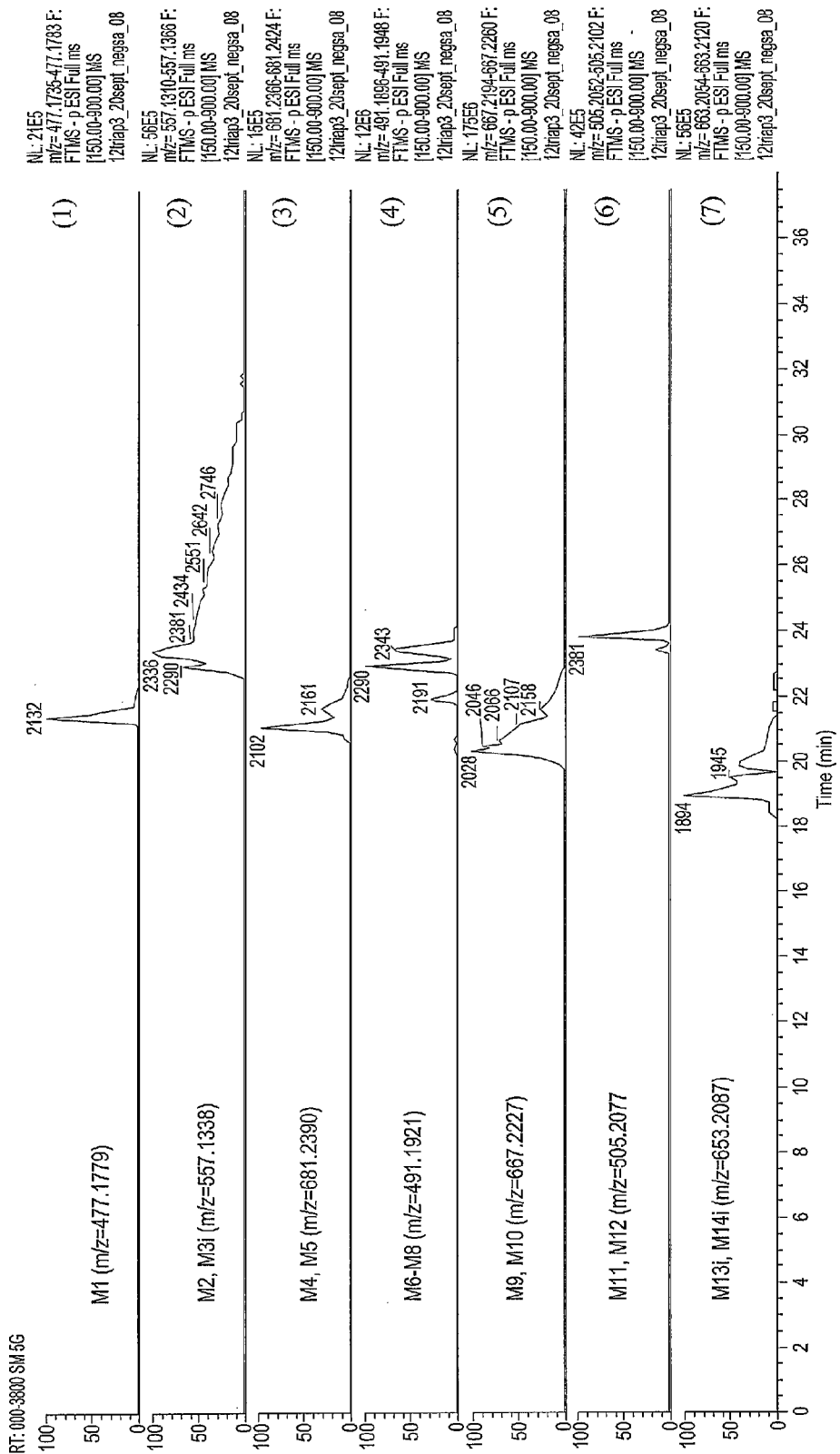

FIG. 18. Elution profiles of the detected putative metabolites in dosed plasma sample. FIG. 18 shows the elution profiles of the detected putative metabolites in dosed plasma sample (T=1 hr). The elution profiles of metabolites show lack of "co-elution" between reported metabolites, confirming that they are not artifacts due to in source-induced dissociation of "true" metabolites (for example, hypothetical loss of a single glucuronic moiety from M13i/M14i metabolites could generate an artifact isobaric to "true" metabolite M1).

---

(1) NL: 2.11E6
m/z = 477.1735-477.1783 F: FTMS − p
ESI Full ms [150.00-900.00] MS
12triap3_20sept_negsa_08
(2) NL: 5.64E5
m/z = 557.1310-557.1366 F: FTMS − p
ESI Full ms [150.00-900.00] MS
12triap3_20sept_negsa_08
(3) NL: 1.52E5
m/z = 681.2356-681.2424 F: FTMS − p
ESI Full ms [150.00-900.00] MS
12triap3_20sept_negsa_08
(4) NL: 1.25E6
m/z = 491.1896-491.1946 F: FTMS − p
ESI Full ms [150.00-900.00] MS
12triap3_20sept_negsa_08
(5) NL: 1.75E6
m/z = 667.2194-667.2260 F: FTMS − p
ESI Full ms [150.00-900.00] MS
12triap3_20sept_negsa_08

-continued (6) NL: 4.21E5
m/z = 505.2052-505.2102 F: FTMS − p
ESI Full ms [150.00-900.00] MS
12triap3_20sept_negsa_08
(7) NL: 5.63E5
m/z = 653.2054-653.2120 F: FTMS − p
ESI Full ms [150.00-900.00]
MS 12triap3_20sept_negsa_08

Figure 19:
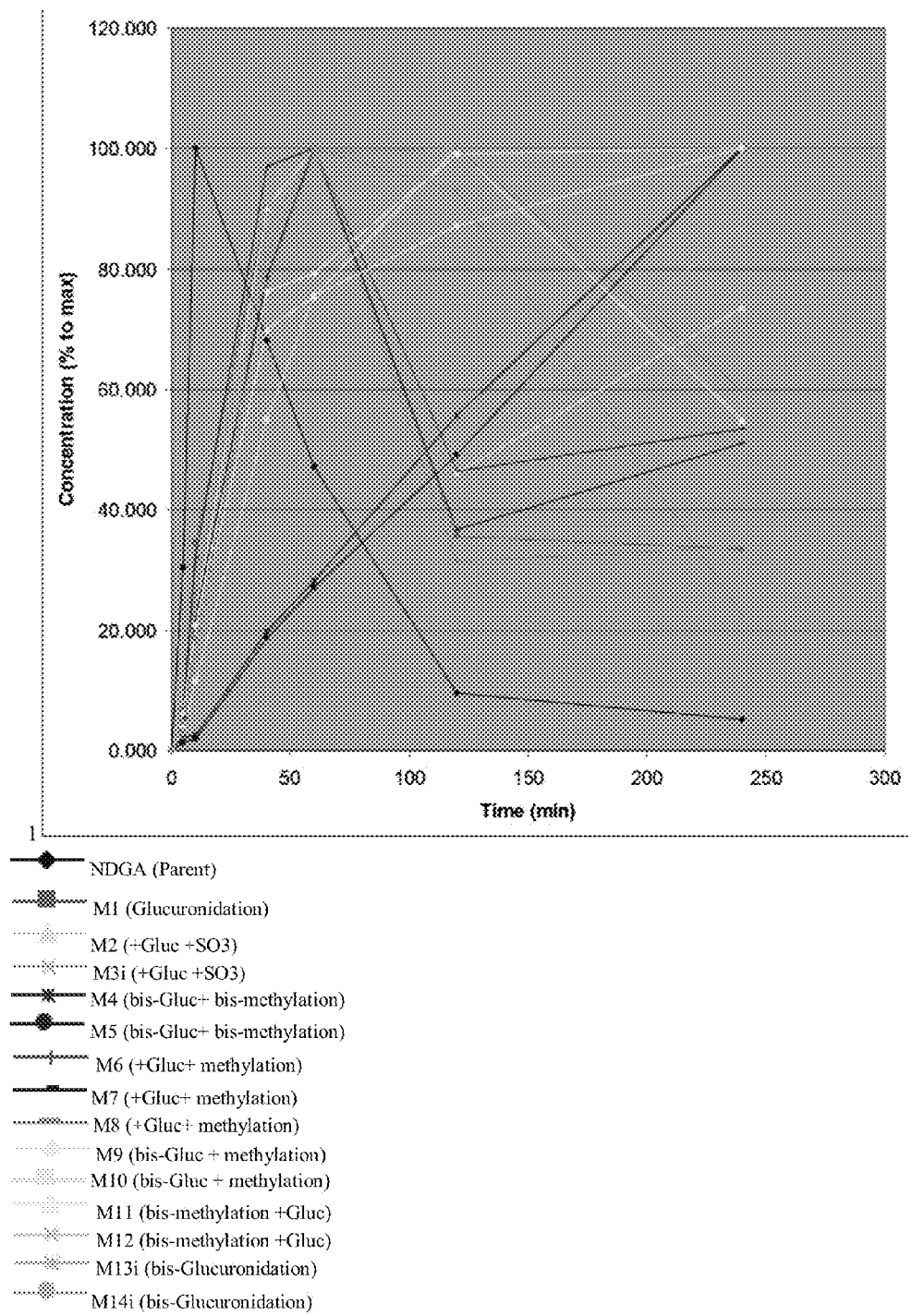

FIG. 19. Normalized levels of metabolites and test compound (highest concentration of each compound is 100%) in plasma samples. Based on profiles of concentration vs. time, the metabolites could be divided into three groups—"first-formed," mirroring the concentration of the parent test compound; "later-formed," whose concentration increased over the investigated time interval; and plausible subjects of enterohepatic recyling, leading to a "saw-like" pattern.

Figure 20:
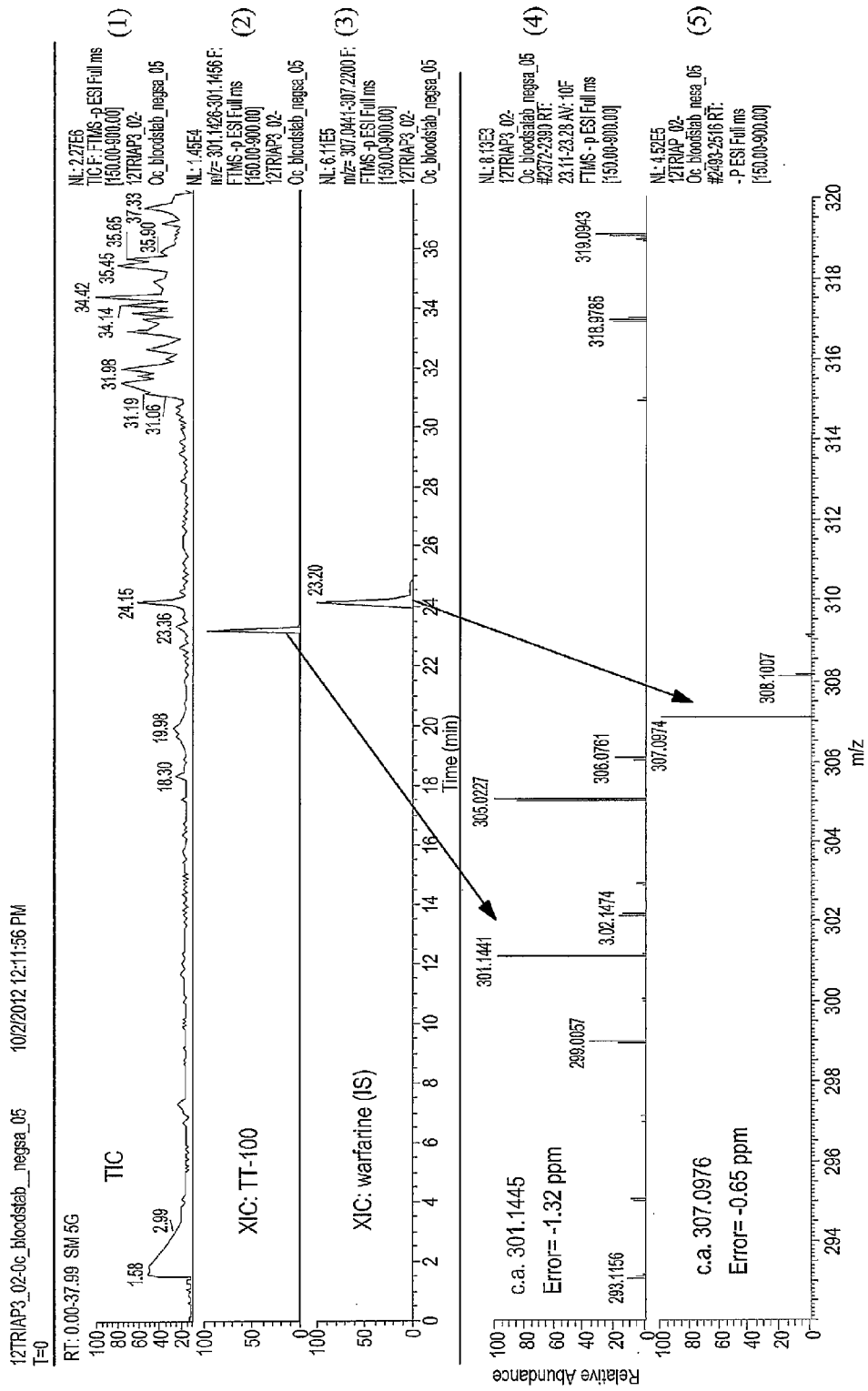

FIG. 20. Detection of NDGA in extract of whole blood (t=0 minute sample). The data confirms the MS accuracy of the Orbitrap and a sufficiently high signal of the internal standard. No putative metabolites were detected upon incubation in whole blood in vitro.

(1) NL: 2.27E6
TIC F: FTMS − p ESI Full ms [150.00-900.00] MS 12TRIAP3_02-Oc_bloodstab_negsa_05
(2) NL: 1.45E4
m/z = 301.1426-301.1456 F: FTMS − p ESI Full ms [150.00-900.00] MS 12TRIAP3_02-Oc_bloodstab_negsa_05
(3) NL: 6.11E5
m/z = 307.0441-307.2200 F: FTMS − p ESI Full ms [150.00-900.00] MS 12TRIAP3_02-Oc_bloodstab_negsa_05
(4) NL: 8.13E3
12TRIAP3_02-Oc_bloodstab_negsa_05
2373-2390 RT: 23.11-23.28 AV: 10 F: FTMS − p ESI Full ms [150.00-900.00]
(5) NL: 4.52E5
12TRIAP3_02-Oc_bloodstab_negsa_05
2493-2516 RT: 24.12-24.25 AV: 6 F: FTMS − p ESI Full ms [150.00-900.00]

Figure 21:
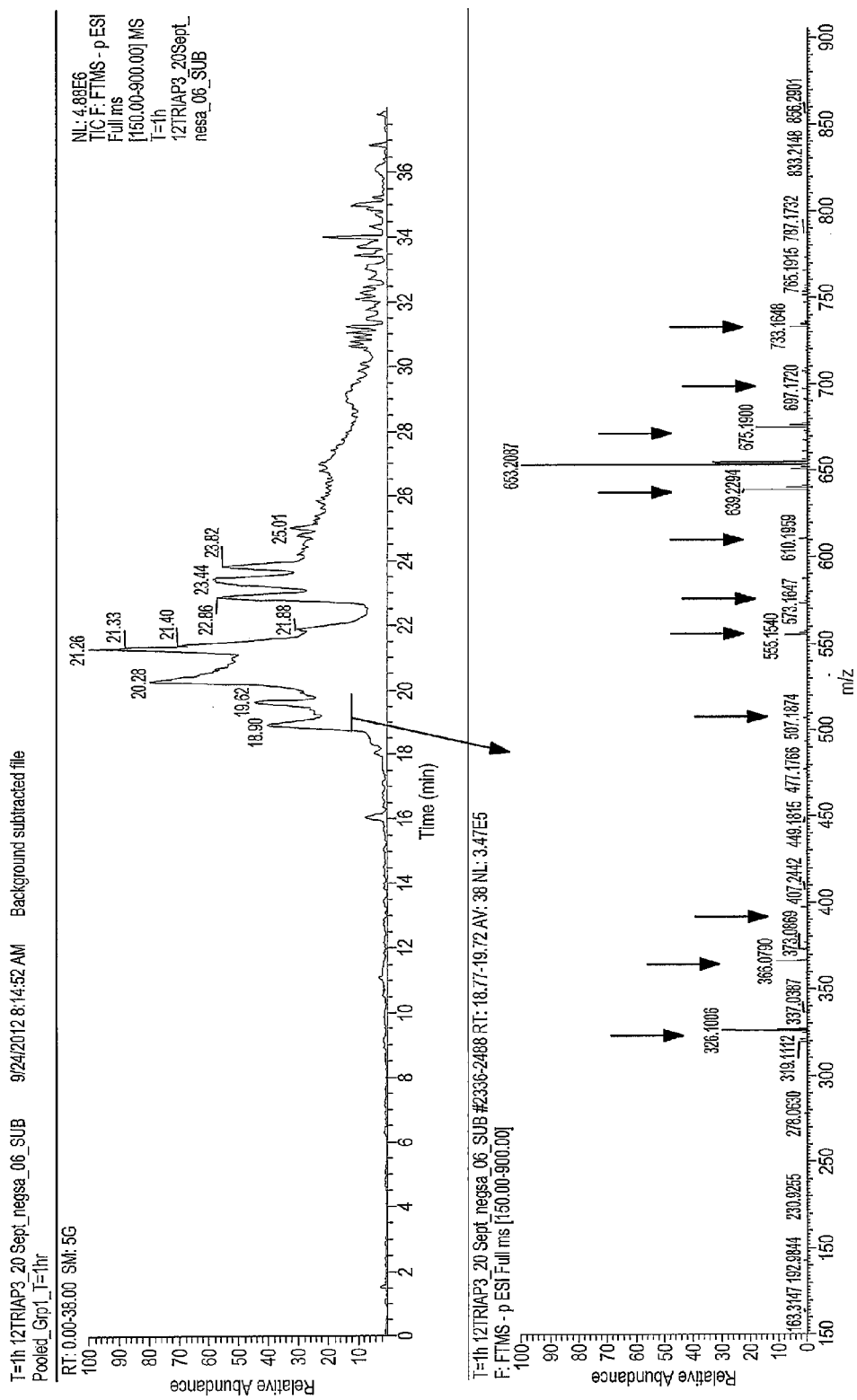

FIG. 21. The Total Ion Current (TIC) trace of the "SUB" file (T=1 hour) is shown in the upper pane in each case; the lower pane shows the HRAMS spectrum for a different retention time interval (indicated by the blue line). The plausible peaks of additional putative metabolites are indicated by red arrows.

Figure 22:
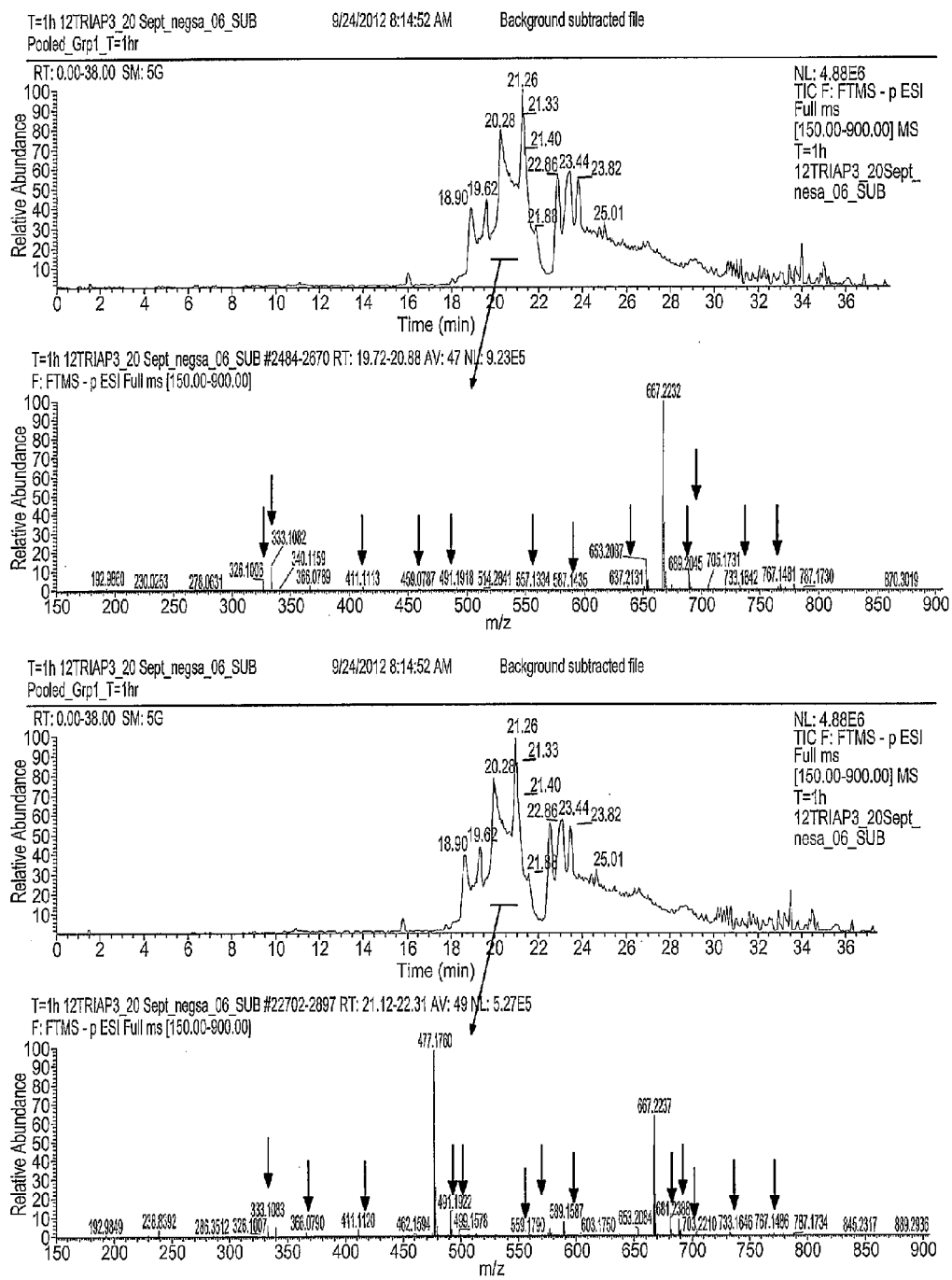

FIG. 22. The Total Ion Current (TIC) trace of the "SUB" file (T=1 hour) is shown in the upper pane in each case; the lower pane shows the HRAMS spectrum for a different retention time interval (indicated by the blue line). The plausible peaks of additional putative metabolites are indicated by red arrows.

Figure 23:
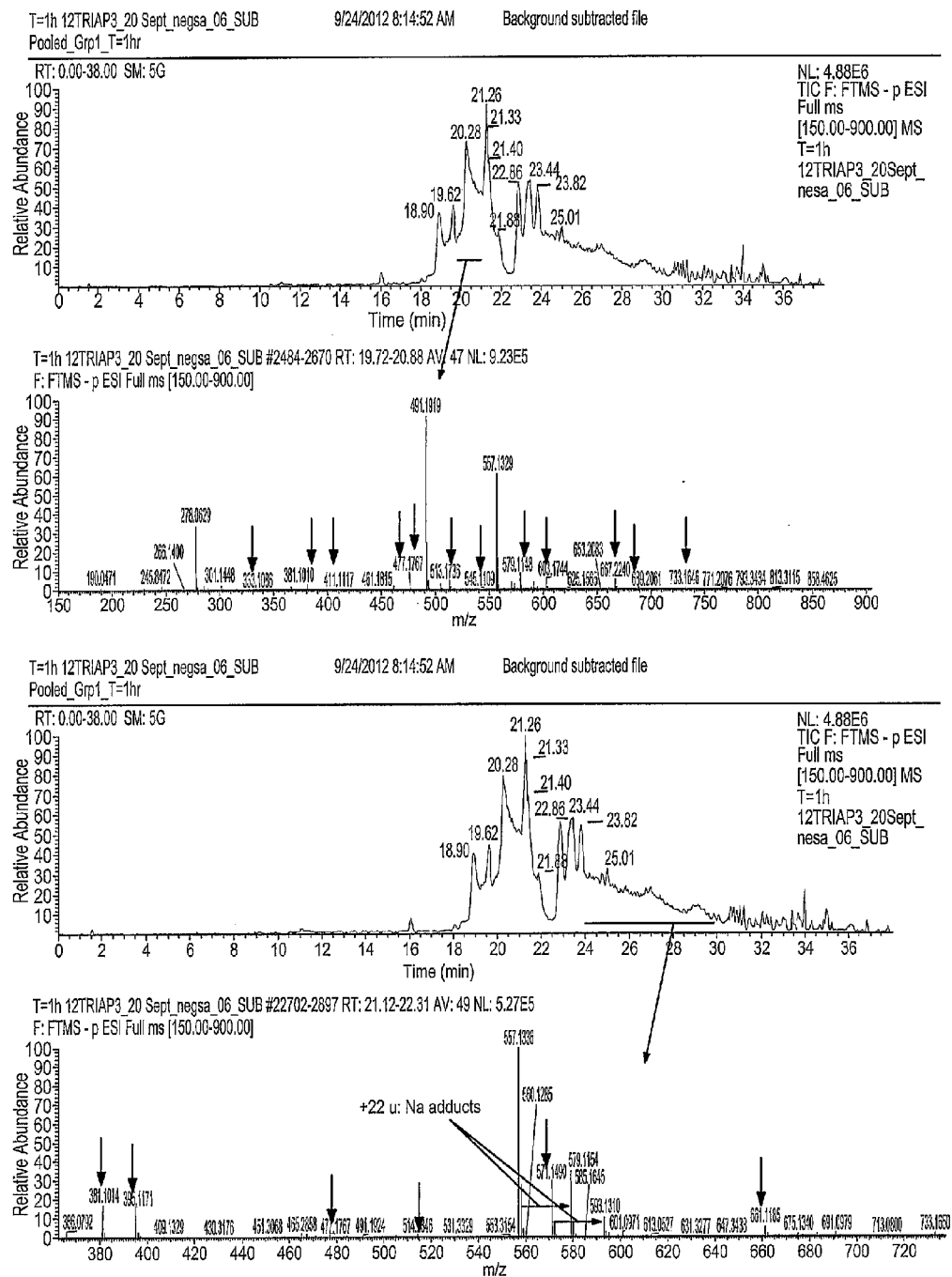

FIG. 23. The Total Ion Current (TIC) trace of the "SUB" file (T=1 hour) is shown in the upper pane in each case; the lower pane shows the HRAMS spectrum for a different retention time interval (indicated by the blue line). The plausible peaks of additional putative metabolites are indicated by red arrows.

Figure 24:
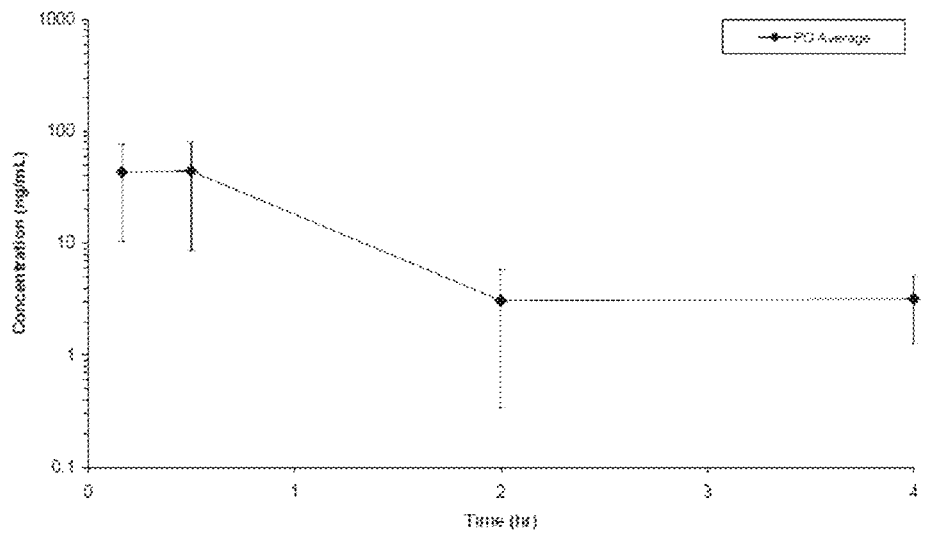

FIG. 24 shows average Plasma Concentration of NDGA Versus Time Following Oral Administration in Male CD-1 Mice at 100 mg/kg from 0.5% MC in DI water Formulation.

Figure 25:
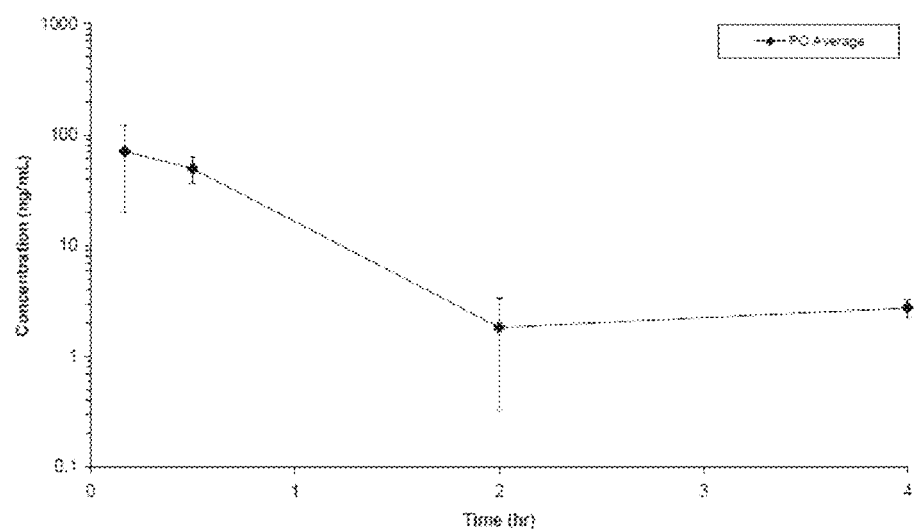

FIG. 25 shows average Plasma Concentration of NDGA Versus Time Following Oral Administration in Male CD-1 Mice at 100 mg/kg from 0.5% NaCMC in DI water Formulation.

Figure 26:
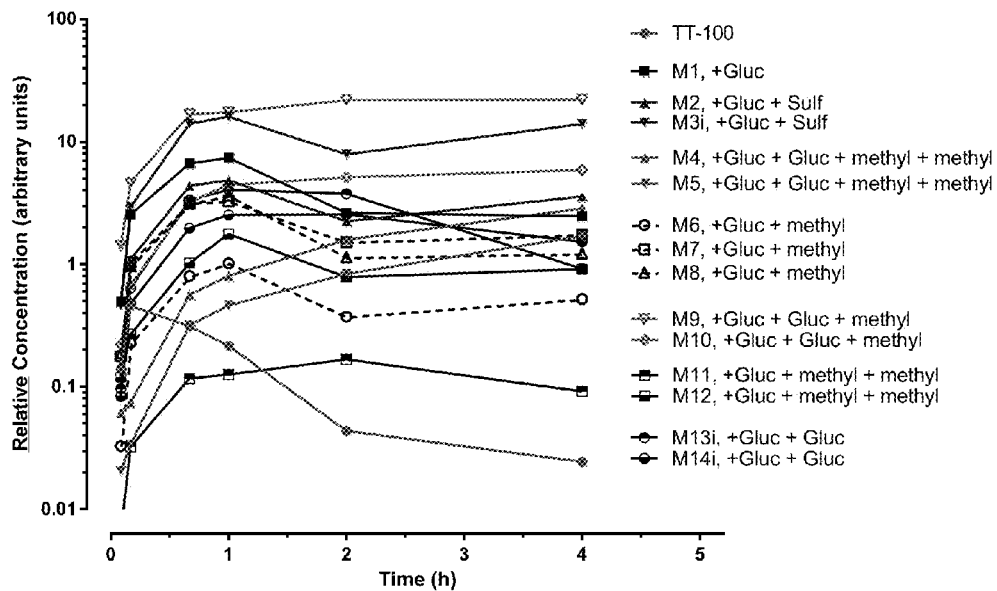

FIG. 26 shows metabolite profiles after a 300-mg/kg PO dose of NDGA to mice.

Figure 27:
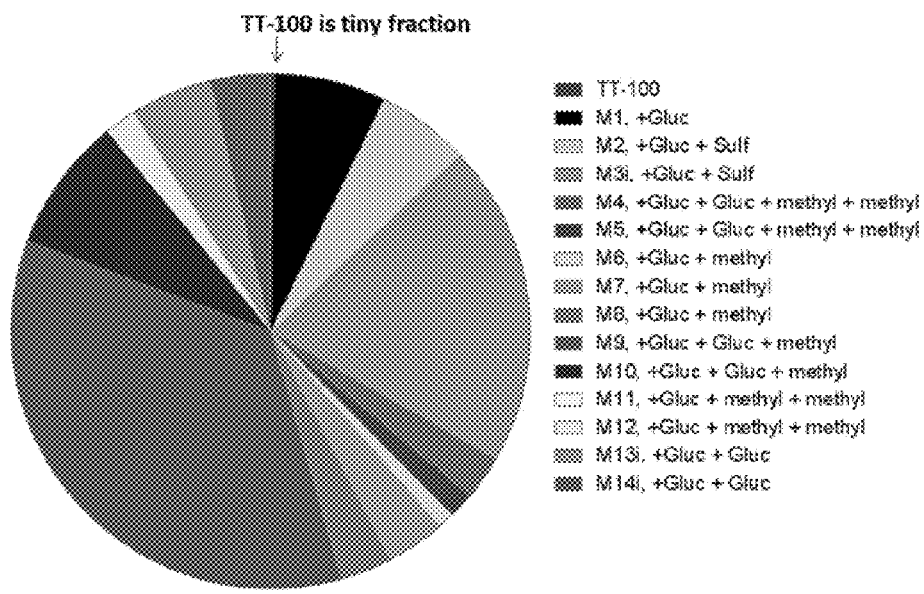

FIG. 27 shows plasma metabolite approximate AUC after a 300-mg/kg PO dose of NDGA to mice.

Figure 28:
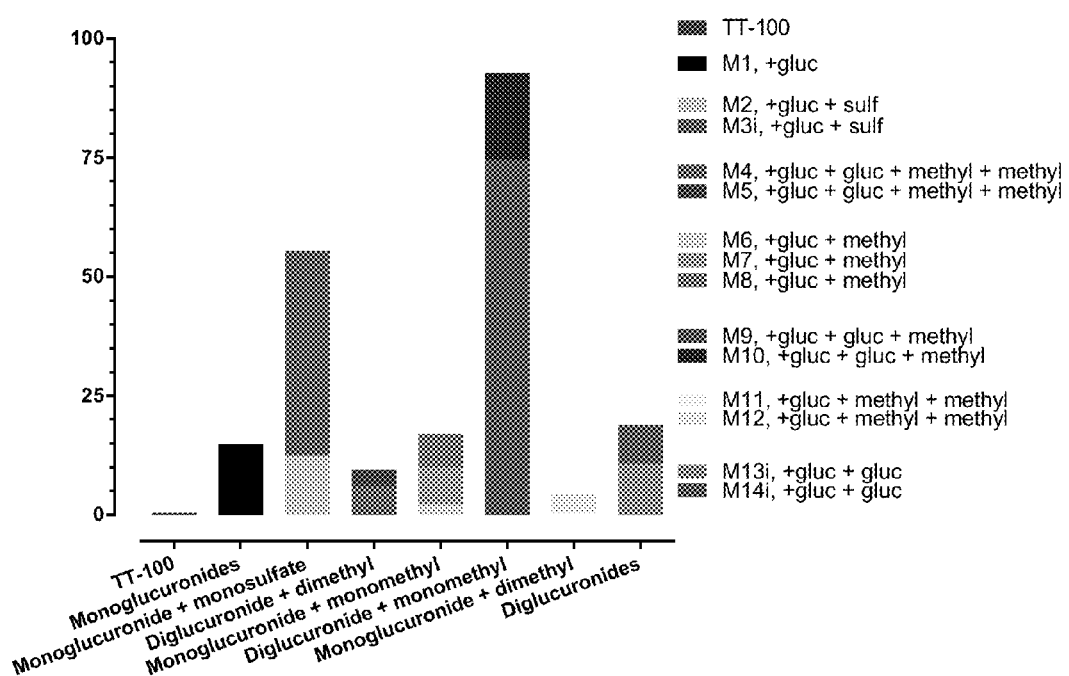

FIG. 28 shows plasma metabolite approximate AUC after a 300-mg/kg PO dose of NDGA to mice grouped by type of metabolites.

Figure 29:
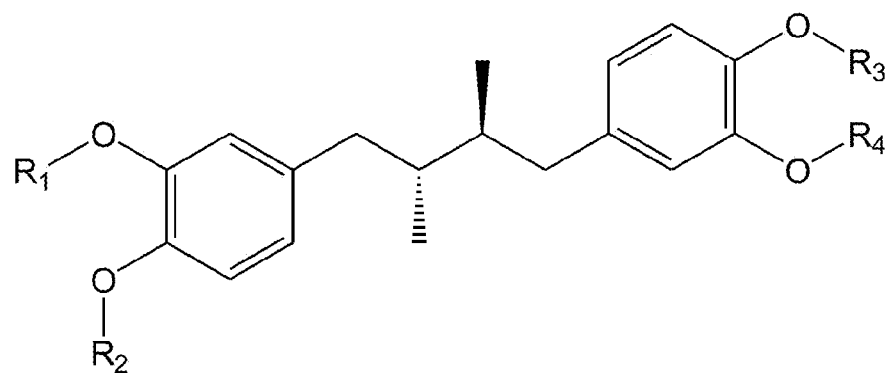

FIG. 29 is a representative graph of a metabolite provided herein.

Figure 30:
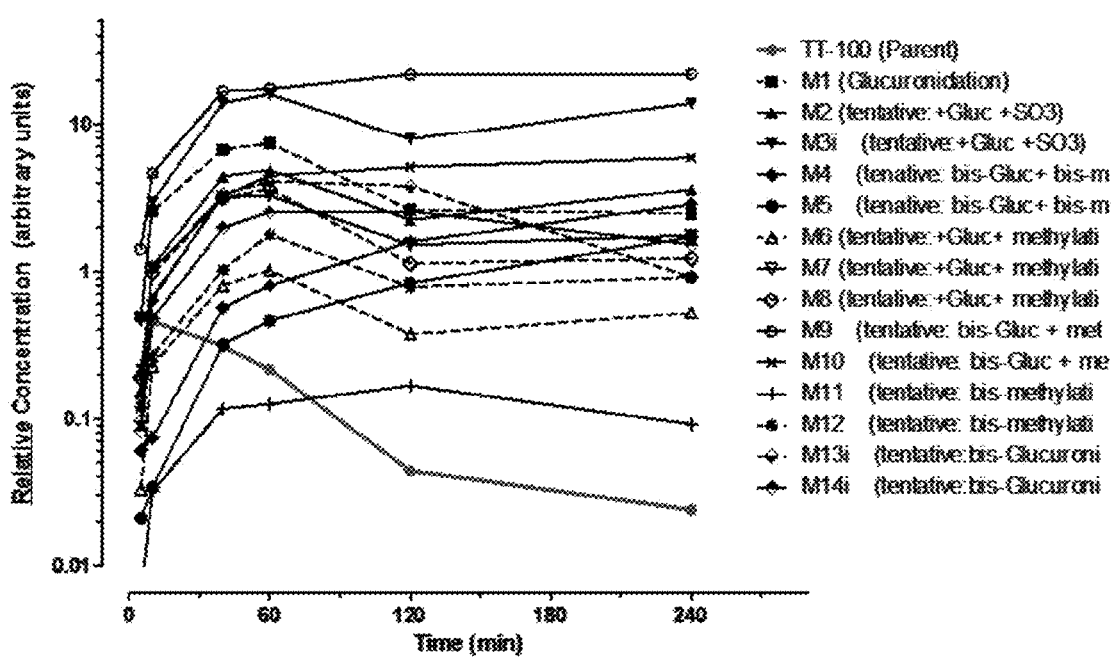

FIG. 30. Normalized levels of metabolites and test compound (highest concentration of each compound is 100%) in plasma samples.

DETAILED DESCRIPTION OF THE INVENTION

Diseases to be treated using the methods provided herein are proliferative diseases.

A proliferative disease includes, but is not limited to, a malignant, pre-malignant or benign cancer. Cancers to be treated using the disclosed methods include, for example, a solid tumor, a lymphoma or a leukemia. In one embodiment, a cancer can be, for example, a brain tumor (e.g., a malignant, pre-malignant or benign brain tumor such as, for example, a glioblastoma, an astrocytoma, a meningioma, a medulloblastoma or a peripheral neuroectodermal tumor), a carcinoma (e.g., gall bladder carcinoma, bronchial carcinoma, basal cell carcinoma, adenocarcinoma, squamous cell carcinoma, small cell carcinoma, large cell undifferentiated carcinoma, adenomas, cystadenoma, etc.), a basalioma, a teratoma, a retinoblastoma, a choroidea melanoma, a seminoma, a sarcoma (e.g., Ewing sarcoma, rhabdomyosarcoma, craniopharyngeoma, osteosarcoma, chondrosarcoma, myosarcoma, liposarcoma, fibrosarcoma, leimyosarcoma, Askin's tumor, lymphosarcoma, neurosarcoma, Kaposi's sarcoma, dermatofibrosarcoma, angiosarcoma, etc.), a plasmocytoma, a head and neck tumor (e.g., oral, laryngeal, nasopharyngeal, esophageal, etc.), a liver tumor, a kidney tumor, a renal cell tumor, a squamous cell carcinoma, a uterine tumor, a bone tumor, a prostate tumor, a breast tumor including, but not limited to a breast tumor that is Her2− and/or ER− and/or PR−, a bladder tumor, a pancreatic tumor, an endometrium tumor, a squamous cell carcinoma, a stomach tumor, gliomas, a colorectal tumor, a testicular tumor, a colon tumor, a rectal tumor, an ovarian tumor, a cervical tumor, an eye tumor, a central nervous system tumor (e.g., primary CNS lymphomas, spinal axis tumors, brain stem gliomas, pituitary adenomas, etc.), a thyroid tumor, a lung tumor (e.g., non-small cell lung cancer (NSCLC) or small cell lung cancer), a leukemia or a lymphoma (e.g., cutaneous T-cell lymphomas (CTCL), non-cutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma, etc.), a multiple myeloma, a skin tumor (e.g., basal cell carcinomas, squamous cell carcinomas, melanomas such as malignant melanomas, cutaneous melanomas or intraocular melanomas, Dermatofibrosarcoma protuberans, Merkel cell carcinoma or Kaposi's sarcoma), a gynecologic tumor (e.g., uterine sarcomas, carcinoma of the fallopian tubes, carcinoma of the endometrium, carcinoma of the cervix, carcinoma of the vagina, carcinoma of the vulva, etc.), Hodgkin's disease, a cancer of the small intestine, a cancer of the endocrine system (e.g., a cancer of the thyroid, parathyroid or adrenal glands, etc.), a mesothelioma, a cancer of the urethra, a cancer of the penis, tumors related to Gorlin's syndrome (e.g., medulloblastomas, meningioma, etc.), a tumor of unknown origin; or metastases of any thereto.

In another embodiment, the cancer is a lung tumor, a breast tumor, a colon tumor, a colorectal tumor, a head and neck tumor, a liver tumor, a prostate tumor, a glioma, glioblastoma multiforme, a ovarian tumor or a thyroid tumor; or metastases of any thereto.

In yet another embodiment, the cancer is an endometrial tumor, bladder tumor, multiple myeloma, melanoma, renal tumor, sarcoma, cervical tumor, leukemia, and neuroblastoma.

Tumors, as provided herein, may be primary tumors or metastases.

In one aspect, a pharmaceutical composition to be administered to a subject in any of the methods described herein is a catecholic butane metabolite.

In one embodiment of the methods described herein, a catecholic butane may have the structure of formula I:

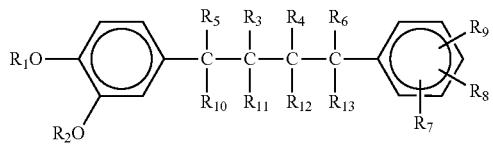

wherein $R_1$ and $R_2$ are independently H, lower alkyl, or lower acyl; $R_3$, $R_4$, $R_5$, $R_6$, $R_{10}$, $R_{11}$, $R_{12}$ and $R_{13}$ are independently H or lower alkyl; and $R_7$, $R_8$ and $R_9$ are independently H, hydroxy, lower alkoxy or lower acyloxy. Also included are pharmaceutically acceptable salts, pharmaceutically acceptable solvates, tautomers, metabolites, and prodrugs of formula I.

In another embodiment of the methods described herein, a catecholic butane may have the structure of formula I:

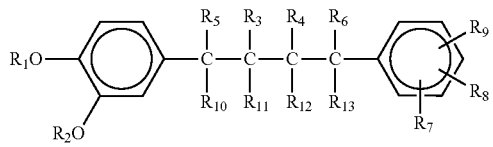

wherein $R_5$, $R_{10}$, $R_6$, and $R_{13}$ are independently H;
when $R_3$ is H, $R_{11}$ is lower alkyl; or when $R_3$ is lower alkyl, $R_{11}$ is H;
when $R_4$ is H, $R_{12}$ is lower alkyl; or when $R_4$ is lower alkyl, $R_{12}$ is H;
two of $R_7$, $R_8$, and $R_9$ are hydroxy, the other is H, and one of the hydroxy groups is in the 3-position and the other hydroxy group is in the 4-position relative to the alkylene substituent. Also included are pharmaceutically acceptable salts, pharmaceutically acceptable solvates, tautomers, metabolites, and prodrugs of formula II.

Non-limiting examples of catecholic butanes for use in the present methods include, for example, NDGA, tetraglycinyl NDGA; tetra-dimethylglycinyl NDGA or a salt thereof and tri-O-methyl NDGA; nordihydroguaiaretic acid tetrapivalate; nordihydroguaiaretic acid tetrapropionate and all optical configurations thereof.

Non-limiting examples of catecholic butanes for use in the present methods also include, for example, 1,4-bis(3,4-dihydroxphenyl)-2,3-dimethylbutane; 1,4-bis(3,4-dihydroxyphenyl)butane; 1,4-bis(3,4-dimethoxyphenyl)-2,3-dimethylbutane; 1,4-bis(3,4-diethoxyphenyl)-2,3-dimethylbutane; 1,4-bis(3,4-dipropoxyphenyl)-2,3-dimethylbutane; 1-(3,4-dihydroxyphenyl)-4-(3,4,5-trihydroxyphenyl) butane; 1,4-bis(3,4-diacetoxyphenyl)-2,3-dimethylbutane; 1,4-bis(3,4-dipropionyloxyphenyl)-2,3-dimethylbutane; 1,4-bis(3,4-dibutyroyloxyphenyl)-2,3-dimethylbutane; 1,4-bis(3,4-divaleroyloxyphenyl)-2,3-dimethylbutane; 1,4-bis(3,4-dipivaloyloxyphenyl)-2,3-dimethylbutane; 1,4-bis(3,4-dineopentylcarboxylphenyl)-2,3-dimethylbutane; or 1-(3,4-dihydroxyphenyl)-4-phenylbutane; 1-(3,4-dihydroxyphenyl)-4-(2,5-dihydroxyphenyl) butane, and d-, l-, racemic mixture of d- and l-, and meso-isomers thereof.

In one embodiment, the catecholic butane is nordihydroguaiaretic acid (NDGA).

In one embodiment of the compositions and methods described here, a catecholic butane metabolite may have the structure of Formula II:

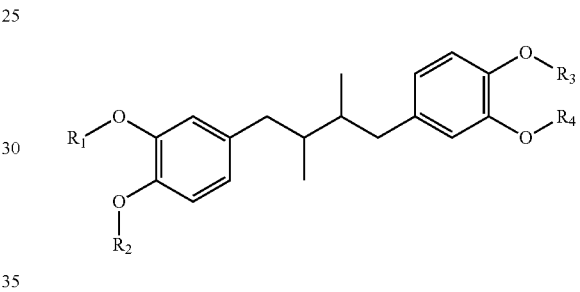

wherein at least one of $R_1$, $R_2$, $R_3$ or $R_4$ is $CH_3$, a glucuronide or a sulfate.

In one embodiment, a catecholic butane metabolite has a structure of Formula III:

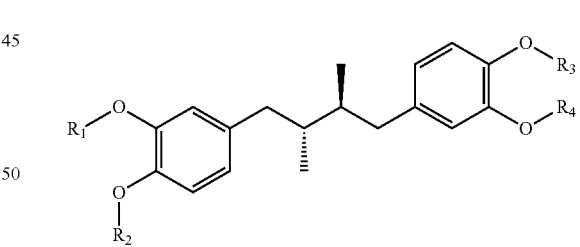

wherein at least one of $R_1$, $R_2$, $R_3$ or $R_4$ is $CH_3$, a glucuronide or a sulfate.

In another embodiment of the methods described herein, a catecholic butane metabolite may have the structure of any one of formulas IV-LXVII, wherein the formulas are provided in Table 1. R groups refer to those shown in the formula illustrated in FIG. 29. In another embodiment, a catecholic butane metabolite may additionally include a phosphate ester. In some embodiments, $R_1$, $R_2$, $R_3$ and $R_4$ may include an H, a $CH_3$, a glucuronide, a sulfate or a phosphate ester. In still other embodiments, compounds including H at each of $R_1$, $R_2$, $R_3$ and $R_4$ is not included.

TABLE 1

| Formula No. | Name | R1 | R2 | R3 | R4 | Structure |
|---|---|---|---|---|---|---|
| IV | M1 | G | H | H | H | Structure |
| V | M1 | H | G | H | H | Structure |
| VI | M1 | H | H | G | H | Structure |
| VII | M1 | H | H | H | G | Structure |
| VIII | M2 and M3i | G | S | H | H | Structure |

TABLE 1-continued

| Formula No. | Name | R1 | R2 | R3 | R4 | Structure |
|---|---|---|---|---|---|---|
| IX | M2 and M3i | G | H | S | H | Structure |
| X | M2 and M3i | G | H | H | S | Structure |
| XI | M2 and M3i | S | G | H | H | Structure |
| XII | M2 and M3i | H | G | S | H | Structure |
| XIII | M2 and M3i | H | G | H | S | Structure |

TABLE 1-continued

| Formula No. | Name | R1 | R2 | R3 | R4 | Structure |
|---|---|---|---|---|---|---|
| XIV | M2 and M3i | S | H | G | H | Structure |
| XV | M2 and M3i | H | S | G | H | Structure |
| XVI | M2 and M3i | H | H | G | S | Structure |
| XVII | M2 and M3i | S | H | H | G | Structure |
| XVIII | M2 and M3i | H | S | H | G | Structure |

TABLE 1-continued

| Formula No. | Name | R1 | R2 | R3 | R4 | Structure |
|---|---|---|---|---|---|---|
| XIX | M2 and M3i | H | H | S | G | Structure |
| XX | M4 and M5 | G | G | M | M | Structure |
| XXI | M4 and M5 | G | M | G | M | Structure |
| XXII | M4 and M5 | G | M | M | G | Structure |

TABLE 1-continued

| Formula No. | Name | R1 | R2 | R3 | R4 | Structure |
|---|---|---|---|---|---|---|
| XXIII | M4 and M5 | M | M | G | G | Structure |
| XXIV | M4 and M5 | M | G | M | G | Structure |
| XXV | M4 and M5 | M | G | G | M | Structure |
| XXVI | M6, M7, M8 | G | M | H | H | Structure |

TABLE 1-continued

| Formula No. | Name | R1 | R2 | R3 | R4 | Structure |
|---|---|---|---|---|---|---|
| XXVII | M6, M7, M8 | G | H | M | H | Structure |
| XXVIII | M6, M7, M8 | G | H | H | M | Structure |
| XXIX | M6, M7, M8 | M | G | H | H | Structure |
| XXX | M6, M7, M8 | H | G | M | H | Structure |
| XXXI | M6, M7, M8 | H | G | H | M | Structure |

TABLE 1-continued

| Formula No. | Name | R1 | R2 | R3 | R4 | Structure |
|---|---|---|---|---|---|---|
| XXXII | M6, M7, M8 | M | H | G | H | Structure |
| XXXIII | M6, M7, M8 | H | M | G | H | Structure |
| XXXIV | M6, M7, M8 | H | H | G | M | Structure |
| XXXV | M6, M7, M8 | M | H | H | G | Structure |
| XXXVI | M6, M7, M8 | H | M | H | G | Structure |
| XXXVII | M6, M7, M8 | H | H | M | G | Structure |

TABLE 1-continued
| Formula No. | Name | R1 | R2 | R3 | R4 | Structure |
|---|---|---|---|---|---|---|
| XXXVIII | M9 and M10 | H | M | G | G | Structure |
| XXXIX | M9 and M10 | H | G | M | G | Structure |
| XXXX | M9 and M10 | H | G | G | M | Structure |
| XXXXI | M9 and M10 | M | H | G | G | Structure |
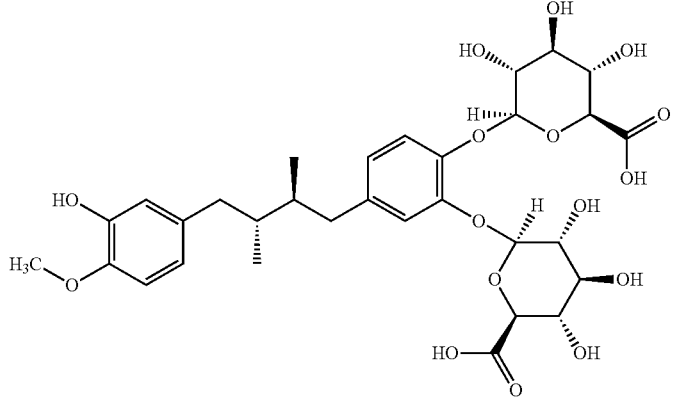 [SMILES: COc1ccc(C[C@@H](C)[C@@H](C)Cc2ccc(O[C@@H]3O[C@H](C(=O)O)[C@@H](O)[C@H](O)[C@H]3O)c(O[C@@H]3O[C@H](C(=O)O)[C@@H](O)[C@H](O)[C@H]3O)c2)cc1O]
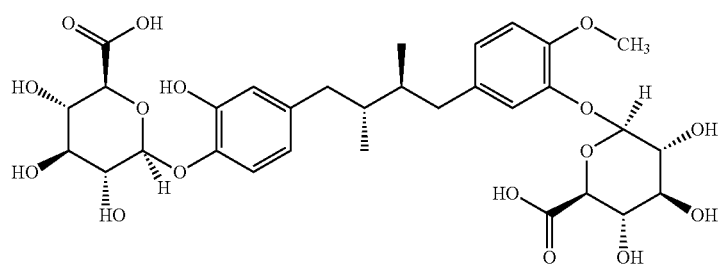 [SMILES: COc1ccc(C[C@H](C)[C@H](C)Cc2ccc(O[C@@H]3O[C@H](C(=O)O)[C@@H](O)[C@H](O)[C@H]3O)c(O)c2)cc1O[C@@H]1O[C@H](C(=O)O)[C@@H](O)[C@H](O)[C@H]1O]
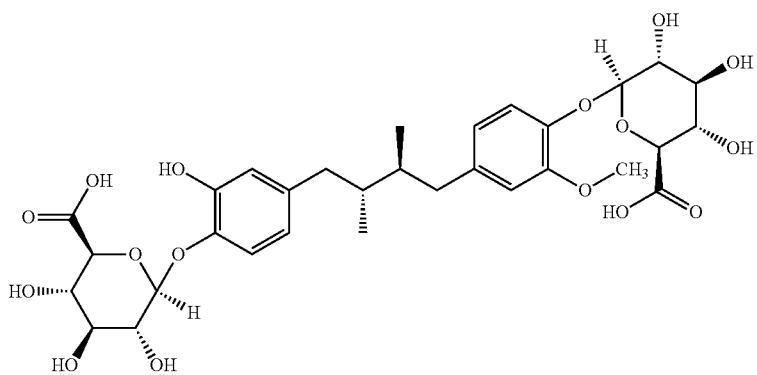 [SMILES: COc1cc(C[C@H](C)[C@H](C)Cc2ccc(O[C@@H]3O[C@H](C(=O)O)[C@@H](O)[C@H](O)[C@H]3O)c(O)c2)ccc1O[C@@H]1O[C@H](C(=O)O)[C@@H](O)[C@H](O)[C@H]1O]
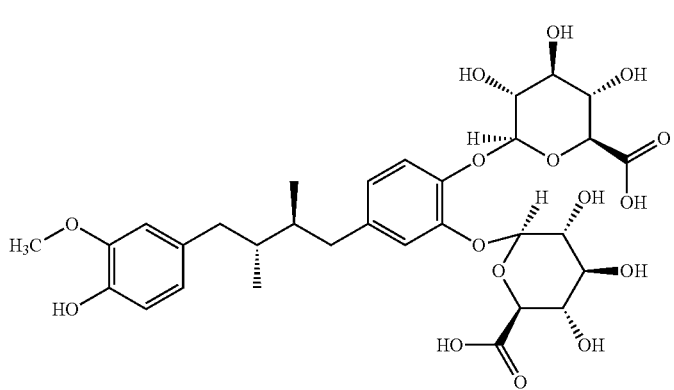 [SMILES: COc1cc(C[C@@H](C)[C@@H](C)Cc2ccc(O[C@@H]3O[C@H](C(=O)O)[C@@H](O)[C@H](O)[C@H]3O)c(O[C@@H]3O[C@H](C(=O)O)[C@@H](O)[C@H](O)[C@H]3O)c2)ccc1O]

TABLE 1-continued
| Formula No. | Name | R1 | R2 | R3 | R4 | Structure |
|---|---|---|---|---|---|---|
| XXXXII | M9 and M10 | G | H | M | G | Structure |
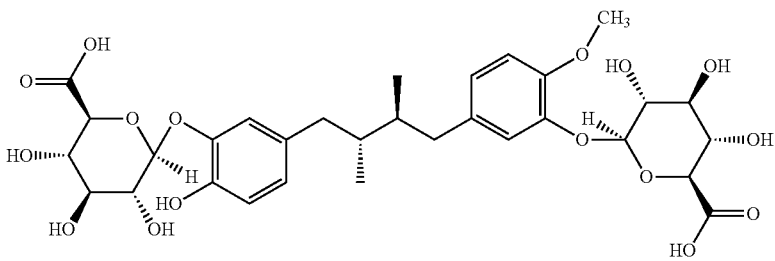 [SMILES: COc1ccc(C[C@H](C)[C@H](C)Cc2ccc(O)c(O[C@@H]3O[C@H](C(=O)O)[C@@H](O)[C@H](O)[C@H]3O)c2)cc1O[C@@H]1O[C@H](C(=O)O)[C@@H](O)[C@H](O)[C@H]1O]
| XXXXIII | M9 and M10 | G | H | G | M | Structure |
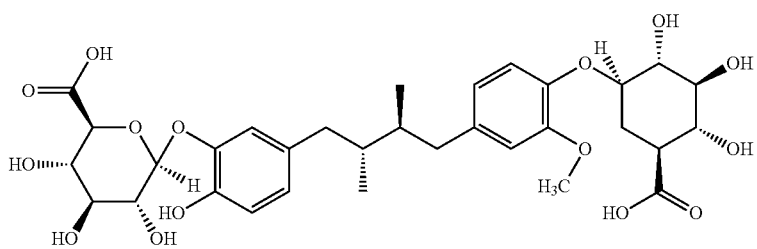 [SMILES: COc1cc(C[C@H](C)[C@H](C)Cc2ccc(O)c(O[C@@H]3O[C@H](C(=O)O)[C@@H](O)[C@H](O)[C@H]3O)c2)ccc1O[C@@H]1C[C@H](C(=O)O)[C@@H](O)[C@H](O)[C@H]1O]
| XXXXIV | M9 and M10 | M | G | H | G | Structure |
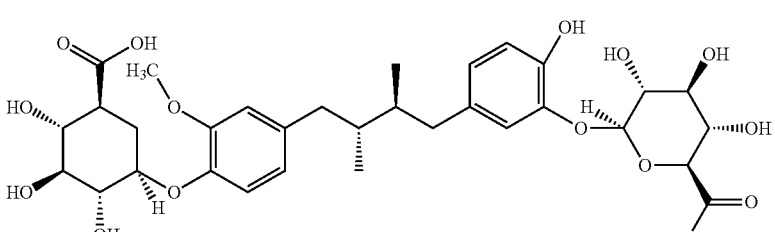
| XXXXV | M9 and M10 | G | M | H | G | Structure |
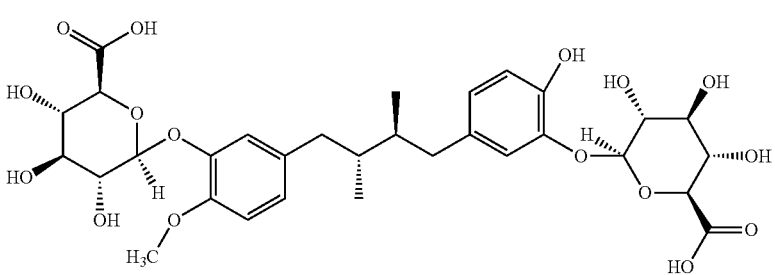 [SMILES: COc1ccc(C[C@@H](C)[C@@H](C)Cc2ccc(O)c(O[C@@H]3O[C@H](C(=O)O)[C@@H](O)[C@H](O)[C@H]3O)c2)cc1O[C@@H]1O[C@H](C(=O)O)[C@@H](O)[C@H](O)[C@H]1O]

TABLE 1-continued
| Formula No. | Name | R1 | R2 | R3 | R4 | Structure |
|---|---|---|---|---|---|---|
| XXXXVI | M9 and M10 | G | G | H | M | Structure |
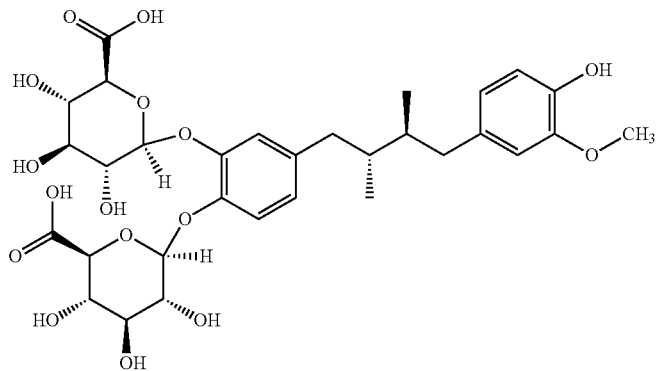 [SMILES: COc1cc(C[C@H](C)[C@H](C)Cc2ccc(O[C@@H]3O[C@H](C(=O)O)[C@@H](O)[C@H](O)[C@H]3O)c(O[C@@H]3O[C@H](C(=O)O)[C@@H](O)[C@H](O)[C@H]3O)c2)ccc1O]
| XXXXVII | M9 and M10 | M | G | G | H | Structure |
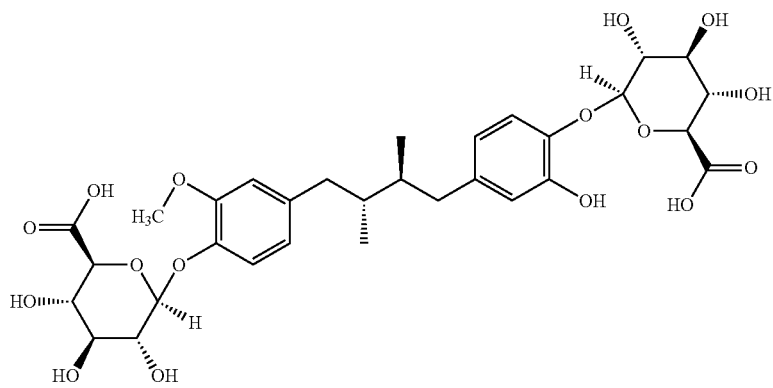 [SMILES: COc1cc(C[C@@H](C)[C@@H](C)Cc2ccc(O[C@@H]3O[C@H](C(=O)O)[C@@H](O)[C@H](O)[C@H]3O)c(O)c2)ccc1O[C@@H]1O[C@H](C(=O)O)[C@@H](O)[C@H](O)[C@H]1O]
| XXXXVIII | M9 and M10 | G | M | G | H | Structure |
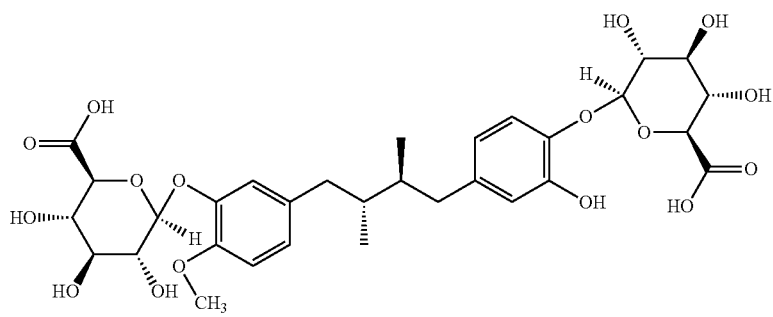 [SMILES: COc1ccc(C[C@@H](C)[C@@H](C)Cc2ccc(O[C@@H]3O[C@H](C(=O)O)[C@@H](O)[C@H](O)[C@H]3O)c(O)c2)cc1O[C@@H]1O[C@H](C(=O)O)[C@@H](O)[C@H](O)[C@H]1O]

TABLE 1-continued

| Formula No. | Name | R1 | R2 | R3 | R4 | Structure |
|---|---|---|---|---|---|---|
| XXXXIX | M9 and M10 | G | G | M | H | Structure |
| L | M11 and M12 | H | G | M | M | Structure |
| LI | M11 and M12 | H | M | G | M | Structure |
| LII | M11 and M12 | H | M | M | G | Structure |

TABLE 1-continued

| Formula No. | Name | R1 | R2 | R3 | R4 | Structure |
|---|---|---|---|---|---|---|
| LIII | M11 and M12 | G | H | M | M | Structure |
| LIV | M11 and M12 | M | H | G | M | Structure |
| LV | M11 and M12 | M | H | M | G | Structure |
| LVI | M11 and M12 | G | M | H | M | Structure |
| LVII | M11 and M12 | M | G | H | M | Structure |

TABLE 1-continued

| Formula No. | Name | R1 | R2 | R3 | R4 | Structure |
|---|---|---|---|---|---|---|
| LVIII | M11 and M12 | M | M | H | G | Structure |
| LIX | M11 and M12 | G | M | M | H | Structure |
| LX | M11 and M12 | M | G | M | H | Structure |
| LXI | M11 and M12 | M | M | G | H | Structure |
| LXII | M13i and M14i | G | G | H | H | Structure |

TABLE 1-continued
| Formula No. | Name | R1 | R2 | R3 | R4 | Structure |
|---|---|---|---|---|---|---|
| LXIII | M13i and M14i | G | H | G | H | Structure |
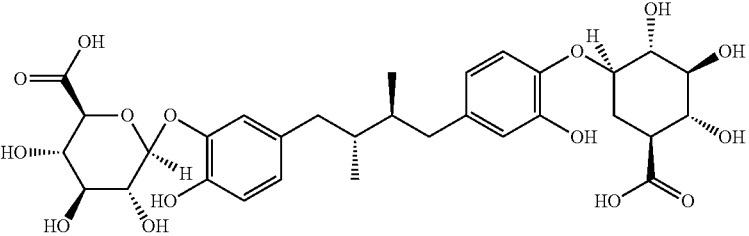 [SMILES: C[C@H](Cc1ccc(O)c(O[C@@H]2O[C@H](C(=O)O)[C@@H](O)[C@H](O)[C@H]2O)c1)[C@@H](C)Cc1ccc(O[C@@H]2C[C@H](C(=O)O)[C@@H](O)[C@H](O)[C@H]2O)c(O)c1]
| LXIV | M13i and M14i | G | H | H | G | Structure |
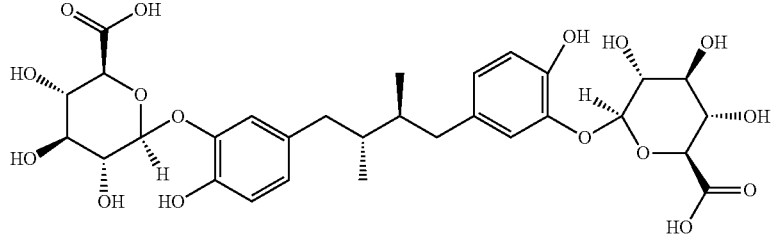 [SMILES: C[C@H](Cc1ccc(O)c(O[C@@H]2O[C@H](C(=O)O)[C@@H](O)[C@H](O)[C@H]2O)c1)[C@@H](C)Cc1ccc(O)c(O[C@@H]2O[C@H](C(=O)O)[C@@H](O)[C@H](O)[C@H]2O)c1]
| LXV | M13i and M14i | H | G | G | H | Structure |
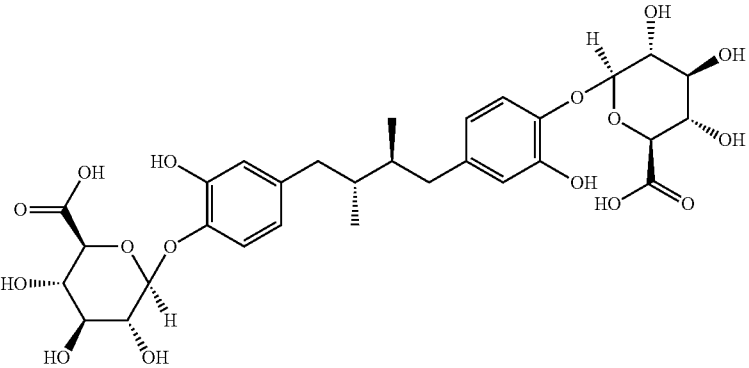 [SMILES: C[C@H](Cc1ccc(O[C@@H]2O[C@H](C(=O)O)[C@@H](O)[C@H](O)[C@H]2O)c(O)c1)[C@@H](C)Cc1ccc(O[C@@H]2O[C@H](C(=O)O)[C@@H](O)[C@H](O)[C@H]2O)c(O)c1]
| LXVI | M13i and M14i | H | G | H | G | Structure |
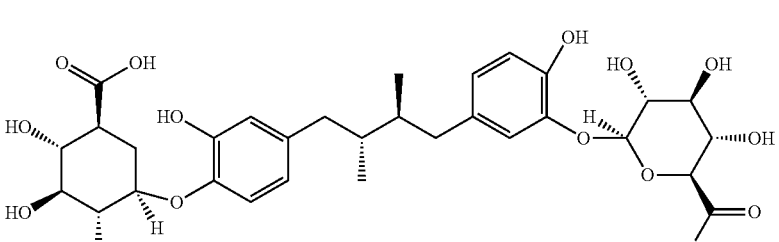

TABLE 1-continued

| Formula No. | Name | R1 | R2 | R3 | R4 | Structure |
|---|---|---|---|---|---|---|
| LXVII | M13i and M14i | H | H | G | G | Structure |

G = glucuronic acid, S = sulfate and M = methyl

In another embodiment of the methods provided herein, a phosphate ester of a catecholic butane metabolite may have the structure of any one of formulas LXVIII-LXXI, wherein the formulas are provided in Table 2. R groups refer to those shown in the formula illustrated in FIG. 29.

TABLE 2

| Formula # | Structure |
|---|---|
| LXVIII | 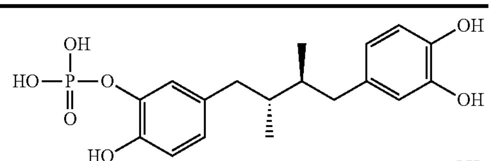 |
| LXIX | 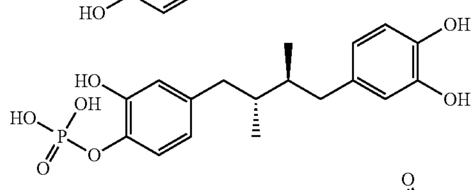 |
| LXX | 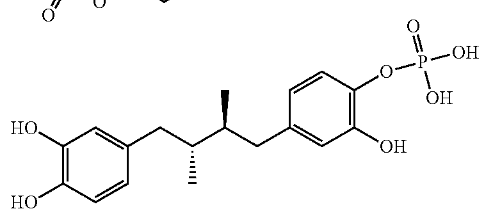 |

TABLE 2-continued

| Formula # | Structure |
|---|---|
| LXXI | 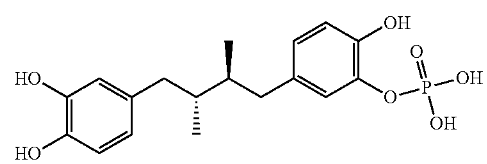 [SMILES: C[C@H](Cc1ccc(O)c(O)c1)[C@@H](C)Cc1ccc(O)c(OP(=O)(O)O)c1] |

In yet another embodiment of the methods described herein, a catecholic butane metabolite may have the structure of any one of formulas LXXII-CXXXV, wherein the formulas are provided in Table 1. R groups refer to those shown in the formula illustrated in FIG. 29. In another embodiment, a catecholic butane metabolite may additionally include a phosphate ester. In some embodiments, $R_1$, $R_2$, $R_3$ and $R_4$ may include an H, a $CH_3$, a glucuronide, a sulfate or a phosphate ester. In still other embodiments, compounds including H at each of $R_1$, $R_2$, $R_3$ and $R_4$ is not included.

TABLE 3

| Formula No. | Name | R1 | R2 | R3 | R4 | Structure |
|---|---|---|---|---|---|---|
| LXXII | | M1 | G | H | H | H | Structure |

TABLE 3-continued

| Formula No. | Name | R1 | R2 | R3 | R4 | Structure |
|---|---|---|---|---|---|---|
| LXXIII | M1 | H | G | H | H | Structure |
| LXXIV | M1 | H | H | G | H | Structure |
| LXXV | M1 | H | H | H | G | Structure |
| LXXVI | M2 and M3i | G | S | H | H | Structure |
| LXXVII | M2 and M3i | G | H | S | H | Structure |

TABLE 3-continued

| Formula No. | Name | R1 | R2 | R3 | R4 | Structure |
|---|---|---|---|---|---|---|
| LXXVIII | M2 and M3i | G | H | H | S | Structure |
| LXXIX | M2 and M3i | S | G | H | H | Structure |
| LXXX | M2 and M3i | H | G | S | H | Structure |
| LXXXI | M2 and M3i | H | G | H | S | Structure |
| LXXXII | M2 and M3i | S | H | G | H | Structure |

TABLE 3-continued
| Formula No. | Name | R1 | R2 | R3 | R4 | Structure |
|---|---|---|---|---|---|---|
| LXXXIII | M2 and M3i | H | S | G | H | Structure |
| LXXXIV | M2 and M3i | H | H | G | S | Structure |
| LXXXV | M2 and M3i | S | H | H | G | Structure |
| LXXXVI | M2 and M3i | H | S | H | G | Structure |
| LXXXVII | M2 and M3i | H | H | S | G | Structure |
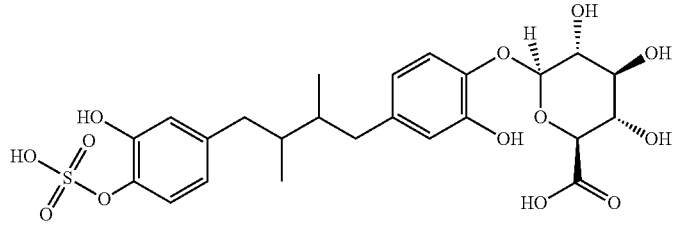 [SMILES: CC(Cc1ccc(O[C@@H]2O[C@H](C(=O)O)[C@@H](O)[C@H](O)[C@H]2O)c(O)c1)C(C)Cc1ccc(OS(=O)(=O)O)c(O)c1]
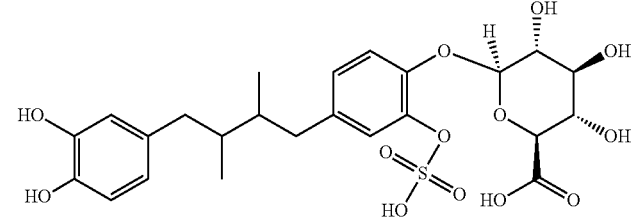 [SMILES: CC(Cc1ccc(O)c(O)c1)C(C)Cc1ccc(O[C@@H]2O[C@H](C(=O)O)[C@@H](O)[C@H](O)[C@H]2O)c(OS(=O)(=O)O)c1]
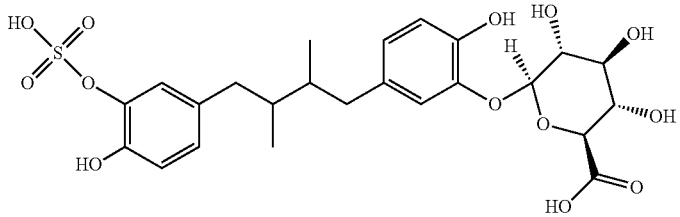 [SMILES: CC(Cc1ccc(O)c(O[C@@H]2O[C@H](C(=O)O)[C@@H](O)[C@H](O)[C@H]2O)c1)C(C)Cc1ccc(O)c(OS(=O)(=O)O)c1]
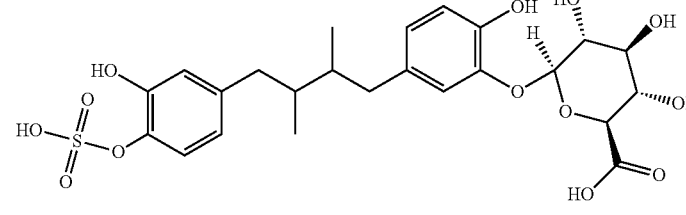
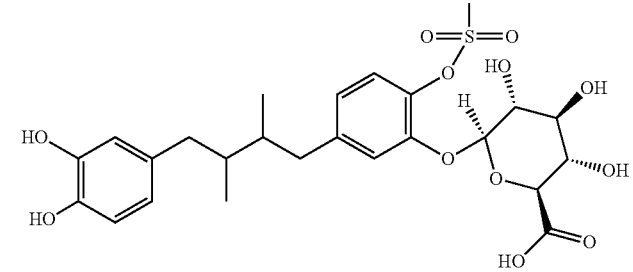

TABLE 3-continued
| Formula No. | Name | R1 | R2 | R3 | R4 | Structure |
|---|---|---|---|---|---|---|
| LXXXVIII | M4 and M5 | G | G | M | M | Structure |
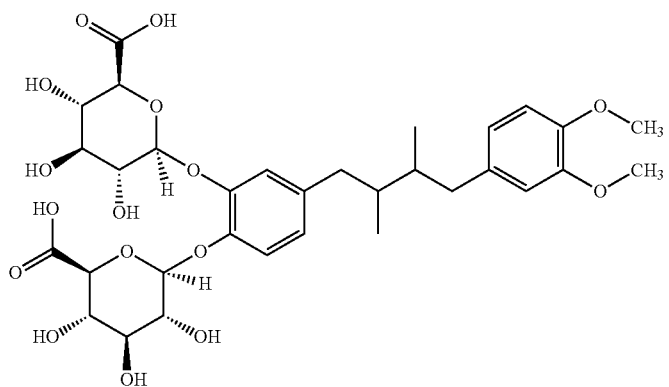 [SMILES: COc1ccc(CC(C)C(C)Cc2ccc(O[C@@H]3O[C@H](C(=O)O)[C@@H](O)[C@H](O)[C@H]3O)c(O[C@@H]3O[C@H](C(=O)O)[C@@H](O)[C@H](O)[C@H]3O)c2)cc1OC]
| | | | | | | |
|---|---|---|---|---|---|---|
| LXXXIX | M4 and M5 | G | M | G | M | Structure |
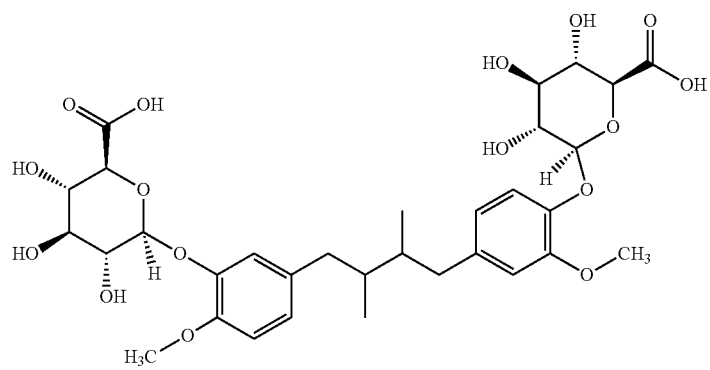 [SMILES: COc1cc(CC(C)C(C)Cc2ccc(OC)c(O[C@@H]3O[C@H](C(=O)O)[C@@H](O)[C@H](O)[C@H]3O)c2)ccc1O[C@@H]1O[C@H](C(=O)O)[C@@H](O)[C@H](O)[C@H]1O]
| | | | | | | |
|---|---|---|---|---|---|---|
| XC | M4 and M5 | G | M | M | G | Structure |
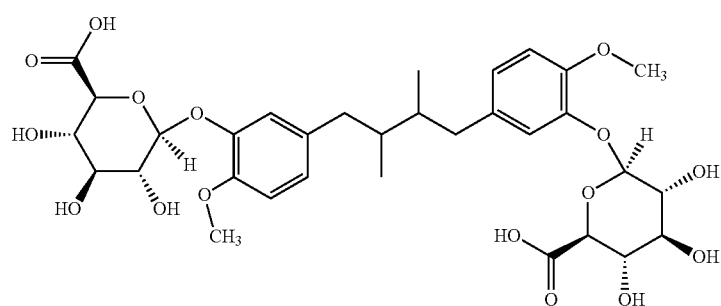 [SMILES: COc1ccc(CC(C)C(C)Cc2ccc(OC)c(O[C@@H]3O[C@H](C(=O)O)[C@@H](O)[C@H](O)[C@H]3O)c2)cc1O[C@@H]1O[C@H](C(=O)O)[C@@H](O)[C@H](O)[C@H]1O]

TABLE 3-continued

| Formula No. | Name | R1 | R2 | R3 | R4 | Structure |
|---|---|---|---|---|---|---|
| XCI | M4 and M5 | M | M | G | G | Structure |
| XCII | M4 and M5 | M | G | M | G | Structure |
| XCIII | M4 and M5 | M | G | G | M | Structure |
| XCIV | M6, M7, M8 | G | M | H | H | Structure |

TABLE 3-continued

| Formula No. | Name | R1 | R2 | R3 | R4 | Structure |
|---|---|---|---|---|---|---|
| XCV | M6, M7, M8 | G | H | M | H | Structure |
| XCVI | M6, M7, M8 | G | H | H | M | Structure |
| XCVII | M6, M7, M8 | M | G | H | H | Structure |
| XCVIII | M6, M7, M8 | H | G | M | H | Structure |
| XCIX | M6, M7, M8 | H | G | H | M | Structure |

TABLE 3-continued

| Formula No. | Name | R1 | R2 | R3 | R4 | Structure |
|---|---|---|---|---|---|---|
| C | M6, M7, M8 | M | H | G | H | Structure |
| CI | M6, M7, M8 | H | M | G | H | Structure |
| CII | M6, M7, M8 | H | H | G | M | Structure |
| CIII | M6, M7, M8 | M | H | H | G | Structure |
| CIV | M6, M7, M8 | H | M | H | G | Structure |

TABLE 3-continued

| Formula No. | Name | R1 | R2 | R3 | R4 | Structure |
|---|---|---|---|---|---|---|
| CV | M6, M7, M8 | H | H | M | G | Structure |
| CVI | M9 and M10 | H | M | G | G | Structure |
| CVII | M9 and M10 | H | G | M | G | Structure |
| CVIII | M9 and M10 | H | G | G | M | Structure |

TABLE 3-continued
| Formula No. | Name | R1 | R2 | R3 | R4 | Structure |
|---|---|---|---|---|---|---|
| CIX | M9 and M10 | M | H | G | G | Structure |
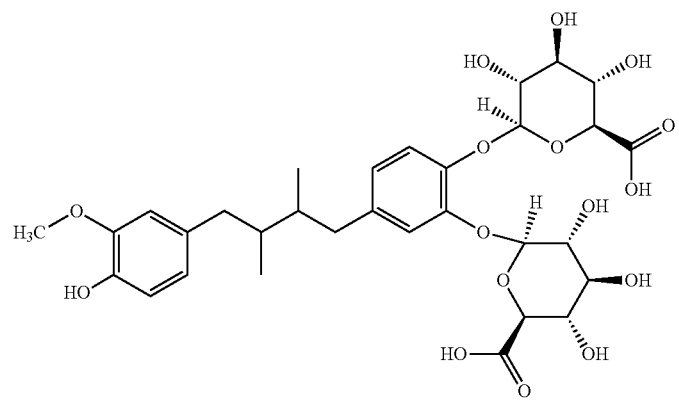 [SMILES: COc1cc(CC(C)C(C)Cc2ccc(O[C@@H]3O[C@H](C(=O)O)[C@@H](O)[C@H](O)[C@H]3O)c(O[C@@H]3O[C@H](C(=O)O)[C@@H](O)[C@H](O)[C@H]3O)c2)ccc1O]
| CX | M9 and M10 | G | H | M | G | Structure |
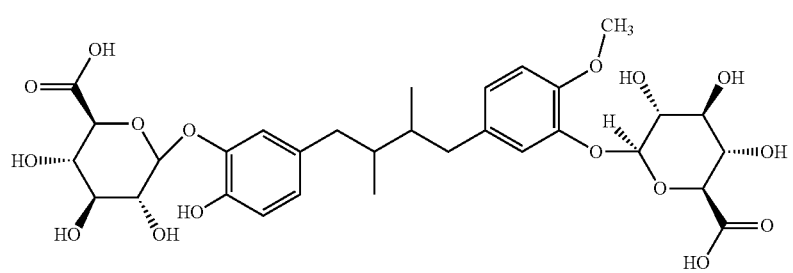 [SMILES: COc1ccc(CC(C)C(C)Cc2ccc(O)c(OC3O[C@H](C(=O)O)[C@@H](O)[C@H](O)[C@H]3O)c2)cc1O[C@@H]1O[C@H](C(=O)O)[C@@H](O)[C@H](O)[C@H]1O]
| CXI | M9 and M10 | G | H | G | M | Structure |
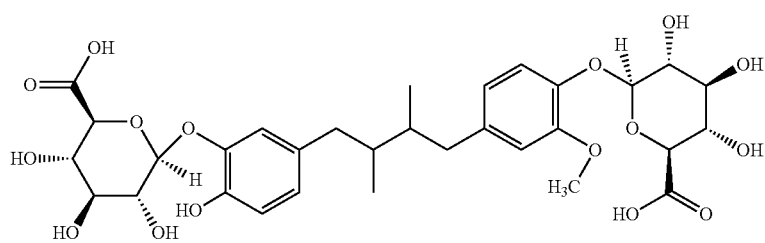 [SMILES: COc1cc(CC(C)C(C)Cc2ccc(O)c(O[C@@H]3O[C@H](C(=O)O)[C@@H](O)[C@H](O)[C@H]3O)c2)ccc1O[C@@H]1O[C@H](C(=O)O)[C@@H](O)[C@H](O)[C@H]1O]
| CXII | M9 and M10 | M | G | H | G | Structure |
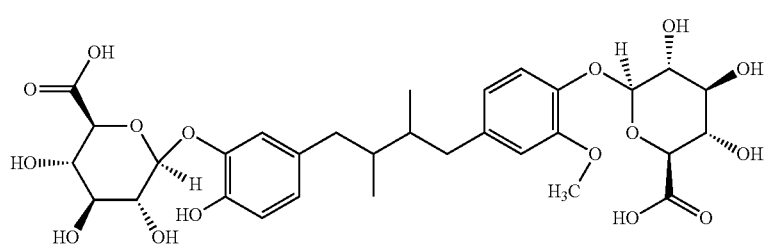 [SMILES: COc1cc(CC(C)C(C)Cc2ccc(O)c(O[C@@H]3O[C@H](C(=O)O)[C@@H](O)[C@H](O)[C@H]3O)c2)ccc1O[C@@H]1O[C@H](C(=O)O)[C@@H](O)[C@H](O)[C@H]1O]

TABLE 3-continued

| Formula No. | Name | R1 | R2 | R3 | R4 | Structure |
|---|---|---|---|---|---|---|
| CXIII | M9 and M10 | G | M | H | G | Structure |
| CXIV | M9 and M10 | G | G | H | M | Structure |
| CXV | M9 and M10 | M | G | G | H | Structure |
| CXVI | M9 and M10 | G | M | G | H | Structure |

TABLE 3-continued

| Formula No. | Name | R1 | R2 | R3 | R4 | Structure |
|---|---|---|---|---|---|---|
| CXVII | M9 and M10 | G | G | M | H | Structure |
| CXVIII | M11 and M12 | H | G | M | M | Structure |
| CXIX | M11 and M12 | H | M | G | M | Structure |
| CXX | M11 and M12 | H | M | M | G | Structure |
| CXXI | M11 and M12 | G | H | M | M | Structure |

TABLE 3-continued
| Formula No. | Name | R1 | R2 | R3 | R4 | Structure |
|---|---|---|---|---|---|---|
| CXXII | M11 and M12 | M | H | G | M | Structure |
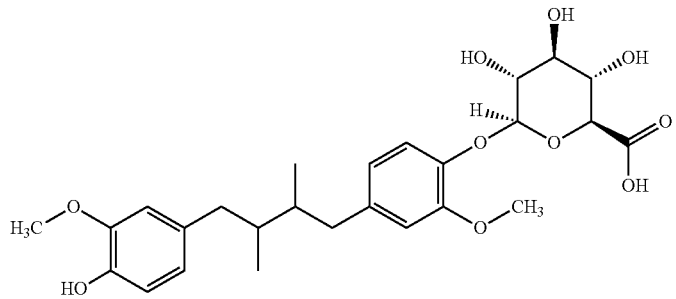 [SMILES: COc1cc(CC(C)C(C)Cc2ccc(O[C@@H]3O[C@H](C(=O)O)[C@@H](O)[C@H](O)[C@H]3O)c(OC)c2)ccc1O]
| CXXIII | M11 and M12 | M | H | M | G | Structure |
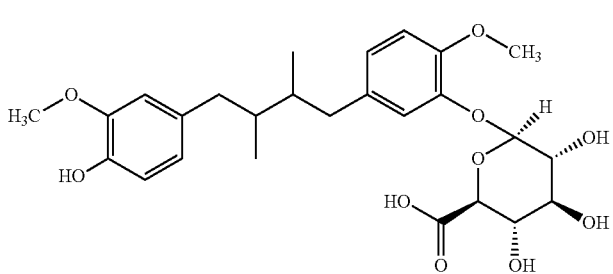 [SMILES: COc1cc(CC(C)C(C)Cc2ccc(OC)c(O[C@@H]3O[C@H](C(=O)O)[C@@H](O)[C@H](O)[C@H]3O)c2)ccc1O]
| CXXIV | M11 and M12 | G | M | H | M | Structure |
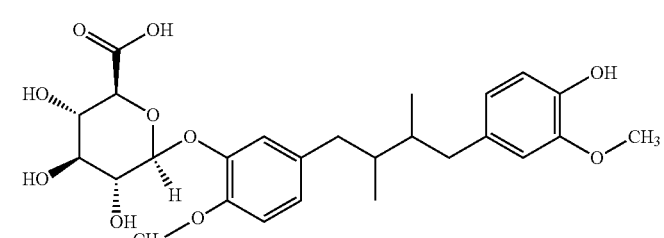
| CXXV | M11 and M12 | M | G | H | M | Structure |
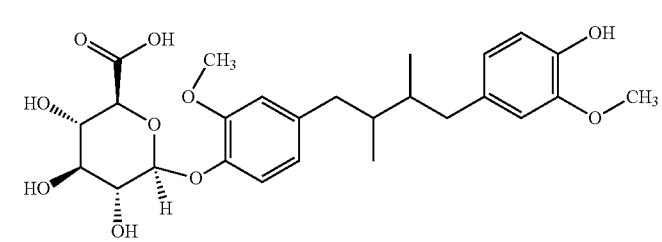 [SMILES: COc1cc(CC(C)C(C)Cc2ccc(O[C@@H]3O[C@H](C(=O)O)[C@@H](O)[C@H](O)[C@H]3O)c(OC)c2)ccc1O]
| CXXVI | M11 and M12 | M | M | H | G | Structure |
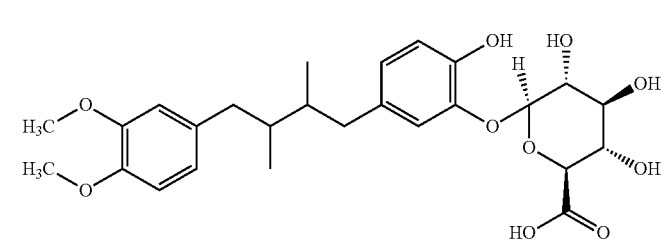 [SMILES: COc1ccc(CC(C)C(C)Cc2ccc(O)c(O[C@@H]3O[C@H](C(=O)O)[C@@H](O)[C@H](O)[C@H]3O)c2)cc1OC]

TABLE 3-continued

| Formula No. | Name | R1 | R2 | R3 | R4 | Structure |
|---|---|---|---|---|---|---|
| CXXVII | M11 and M12 | G | M | M | H | Structure |
| CXXVIII | M11 and M12 | M | G | M | H | Structure |
| CXXIX | M11 and M12 | M | M | G | H | Structure |
| CXXX | M13i and M14i | G | G | H | H | Structure |
| CXXXI | M13i and M14i | G | H | G | H | Structure |

TABLE 3-continued

| Formula No. | Name | R1 | R2 | R3 | R4 | Structure |
|---|---|---|---|---|---|---|
| CXXXII | M13i and M14i | G | H | H | G | Structure |
| CXXXIII | M13i and M14i | H | G | G | H | Structure |
| CXXXIV | M13i and M14i | H | G | H | G | Structure |
| CXXXV | M13i and M14i | H | H | G | G | Structure |

In another embodiment of the methods provided herein, a phosphate ester of a catecholic butane metabolite may have the structure of any one of formulas CXXXXVI-CXXXXVII, wherein the formulas are provided in Table 4. R groups refer to those shown in the formula illustrated in FIG. 29.

TABLE 4

| Formula # | Structure |
|---|---|
| CXXXVI | 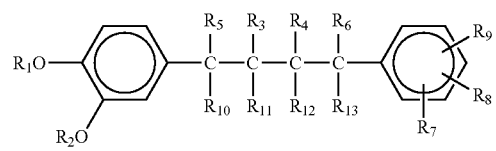 |
| CXXXVII | 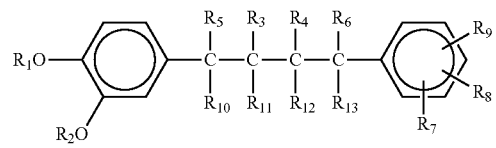 |

In one embodiment, a phosphate prodrug of NDGA exhibits improved solubility, and improved oral absorption, including a phosphate prodrug of the Formulas of IV-LXVII or LXXII-CXXXV.

Pharmaceutical compositions of the present embodiments may be formulated for any route of administration such as, for example, intranasal administration; oral administration; inhalation administration; subcutaneous administration; transdermal administration; intra-arterial administration, with or without occlusion; intracranial administration; intraventricular administration; intravenous administration; buccal administration; intraperitoneal administration; intraocular administration; intramuscular administration; implantation administration; and central venous administration. In one embodiment, the catecholic butane metabolite is formulated for oral administration. In another embodiment, the catecholic butane metabolite is formulated for intravenous administration.

Doses of catecholic butane metabolites may be determined using empirical means. By way of example only, catecholic butane metabolites may be administered in an amount of about 5 mg/kg to about 375 mg/kg per dose; about 5 mg/kg to about 250 mg/kg per dose; about 5 mg/kg to about 200 mg/kg per dose; about 5 mg/kg to about 150 mg/kg per dose; about 5 mg/kg to about 100 mg/kg per dose; about 5 mg/kg to about 75 mg/kg per dose; or about 5 mg/kg to about 50 mg/kg per dose. Alternatively, catecholic butane metabolites may be administered in an amount of from about 1,500 mg per day to about 2,500 mg per day; from about 1,800 mg per day to about 2,300 mg per day; or about 2,000 mg per day. In one embodiment, a catecholic butane metabolite may be contacted with target cells in a concentration in a range of about 1 µM to about 30 µM. In another embodiment, a catecholic butane metabolite may be contacted with target cells in a concentration in a range of about 1 µM to about 10 µM.

In one embodiment, a pharmaceutical composition may be administered more frequently than once every 6 days for a period of time, or more frequently than once every 2 days for a period of time. In one embodiment, a pharmaceutical composition is administered daily for four weeks. In another embodiment, a pharmaceutical composition is administered three times daily for three weeks with a one week hiatus prior to starting a new cycle. In another embodiment, a pharmaceutical composition is administered daily for one week followed by a one week hiatus. In another embodiment, a pharmaceutical composition is administered daily for two weeks followed by a two week hiatus. In another embodiment, a pharmaceutical composition is administered one time or two times daily continuously or with a one week hiatus prior to starting a new cycle. In yet another embodiment, a pharmaceutical composition is administered one time per week or two times per week.

Catecholic Butanes and Metabolites Thereof

As used herein, the term "catecholic butane metabolite" refers to metabolites of compounds that are dual kinase inhibitors of both EGFR and IGF-1R (i.e., a single compound that is a dual kinase inhibitor).

In one embodiment, a catecholic butane may have the structure of formula I:

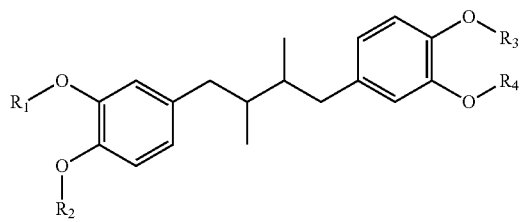

wherein $R_1$ and $R_2$ are independently H, lower alkyl, or lower acyl; $R_3$, $R_4$, $R_5$, $R_6$, $R_{10}$, $R_{11}$, $R_{12}$ and $R_{13}$ are independently H or lower alkyl; and $R_7$, $R_8$ and $R_9$ are independently H, hydroxy, lower alkoxy or lower acyloxy. Also included are pharmaceutically acceptable salts, pharmaceutically acceptable solvates, tautomers, metabolites, and prodrugs of Formula I.

In another embodiment, a catecholic butane may have the structure of Formula I:

wherein $R_5$, $R_{10}$, $R_6$, and $R_{13}$ are independently H;
when $R_3$ is H, $R_{11}$ is lower alkyl; or when $R_3$ is lower alkyl, $R_{11}$ is H;
when $R_4$ is H, $R_{12}$ is lower alkyl; or when $R_4$ is lower alkyl, $R_{12}$ is H;
two of $R_7$, $R_8$, and $R_9$ are hydroxy, the other is H, and one of the hydroxy groups is in the 3-position and the other hydroxy group is in the 4-position relative to the alkylene substituent. Also included are pharmaceutically acceptable salts, pharmaceutically acceptable solvates, tautomers, metabolites, and prodrugs of Formula I.

In one embodiment of the compositions and methods described here, a catecholic butane metabolite may have the structure of Formula II:

wherein at least one of $R_1$, $R_2$, $R_3$ or $R_4$ is $CH_3$, a glucuronide or a sulfate.

As used herein, lower alkyl is intended to generally mean $C_1$-$C_6$ alkyl, and preferably $R_3$ and $R_4$ are $C_1$-$C_3$ alkyl. As used herein, lower alkyl also represents, inter alia, methyl, ethyl, n-propyl, isopropyl, n-butyl, iso-butyl, tert-butyl, n-pentyl, isopentyl, n-hexyl, and the like.

As used herein, lower acyl is intended to generally mean [$C_1$-$C_6$] acyl, with [$C_2$-$C_6$] acyl being preferred. As used herein, lower acyl also represents groups having the general formula RCO—, e.g., acetyl ($CH_3CO$—), propionyl ($CH_3CH_2CO$—), butyryl (CH $CH_2CH_2CO$—), and the like.

Catecholic butanes may be directed to both the phenolic compounds and the conventional esters and ethers thereof. When the catecholic butane compound is, for example, a substituted phenyl, the corresponding groups are acetoxy ($CH_3CO_2$—), propionyloxy ($CH_3CH_2CO_2$—), and butyroyloxy ($CH_3CH_2CH_2CO_2$—).

Compounds may be in the form of a single optical isomer or a mixture of such isomers, e.g., a racemic mixture, or diastereoisomers.

In one embodiment, the catecholic butane is nordihydroguaiaretic acid (NDGA) or a derivative thereof. NDGA is a phenolic compound that was identified as a major component of a tea made from resinous extracts of the creosote bush *Larrea divaricatta*.

In one embodiment, a catecholic butane metabolite has a structure of Formula III:

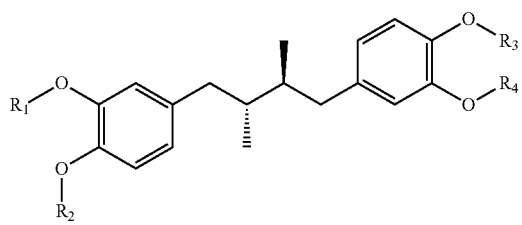

wherein at least one of $R_1$, $R_2$, $R_3$ or $R_4$ is $CH_3$, a glucuronide or a sulfate.

In another embodiment of the methods described herein, a catecholic butane metabolite may have the structure of any one of formulas IV-LXVII, wherein the formulas are provided in Table 1. R groups refer to those shown in the formula illustrated in FIG. 29. In another embodiment, a catecholic butane metabolite may additionally include a phosphate ester. In some embodiments, $R_1$, $R_2$, $R_3$ and $R_4$ may include a H, a $CH_3$, a glucuronide, a sulfate or a phosphate ester. In another embodiment of the methods provided herein, a phosphate ester of a catecholic butane metabolite may have the structure of any one of formulas LXVIII-LXXI, wherein the formulas are provided in Table 2.

In another embodiment of the methods described herein, a catecholic butane metabolite may have the structure of any one of formulas LXXII-CXXXV, wherein the formulas are provided in Table 3. R groups refer to those shown in the formula illustrated in FIG. 29. In another embodiment, a catecholic butane metabolite may additionally include a phosphate ester. In some embodiments, $R_1$, $R_2$, $R_3$ and $R_4$ may include a H, a $CH_3$, a glucuronide, a sulfate or a phosphate ester. In another embodiment of the methods provided herein, a phosphate ester of a catecholic butane metabolite may have the structure of any one of formulas CXXXXVI-CXXXXVII, wherein the formulas are provided in Table 4.

R groups refer to those shown in the formula illustrated in FIG. 29. In one embodiment, a phosphate prodrug of NDGA exhibits improved solubility, and improved oral absorption.

Non-limiting examples of catecholic butane metabolies for use in the present methods include, but are not limited to, a catecholic butane metabolite having a structure of any one of Formulas IV-LXVII, or a phosphate ester thereof, where the formulas are provided in Table 1. R groups refer to those shown in the formula illustrated in FIG. 29. In one embodiment, a phosphate ester of a metabolite described herein has a structure of any one of Formulas LXVIII-LXXI, wherein the formulas are provided in Table 2. R groups refer to those shown in the formula illustrated in FIG. 29.

Yet other non-limiting examples of catecholic butane metabolies for use in the present methods include, but are not limited to, a catecholic butane metabolite having a structure of any one of Formulas LXXII-CXXXV, or a phosphate ester thereof, where the formulas are provided in Table 3. R groups refer to those shown in the formula illustrated in FIG. 29. In one embodiment, a phosphate ester of a metabolite described herein has a structure of any one of Formulas CXXXXVI-CXXXXIX, wherein the formulas are provided in Table 4. R groups refer to those shown in the formula illustrated in FIG. 29.

Other non-limiting examples of catecholic butane metabolites for use in the present methods include, but are not limited to, metabolites of NDGA, tetraglycinyl NDGA; tetra-dimethylglycinyl NDGA or a salt thereof; or tri-O-methyl NDGA; nordihydroguaiaretic acid tetrapivalate; nordihydroguaiaretic acid tetrapropionate and all optical configurations thereof.

Non-limiting examples of catecholic butanes for use in the present methods include, for example, 1,4-bis(3,4-dihydroxphenyl)-2,3-dimethylbutane; 1,4-bis(3,4-dihydroxyphenyl)butane; 1,4-bis(3,4-dimethoxyphenyl)-2,3-dimethylbutane; 1,4-bis(3,4-diethoxyphenyl)-2,3-dimethylbutane; 1,4-bis(3,4-dipropoxyphenyl)-2,3-dimethylbutane; 1-(3,4-dihydroxyphenyl)-4-(3,4,5-trihydroxyphenyl) butane; 1,4-bis(3,4-diacetoxyphenyl)-2,3-dimethylbutane; 1,4-bis(3,4-dipropionyloxyphenyl)-2,3-dimethylbutane; 1,4-bis(3,4-dibutyroyloxyphenyl)-2,3-dimethylbutane; 1,4-bis(3,4-divaleroyloxyphenyl)-2,3-dimethylbutane; 1,4-bis(3,4-dipivaloyloxyphenyl)-2,3-dimethylbutane; 1,4-bis(3,4-dineopentylcarboxylphenyl)-2,3-dimethylbutane; or 1-(3,4-dihydroxyphenyl)-4-phenylbutane; and 1-(3,4-dihydroxyphenyl)-4-(2,5-dihydroxyphenyl) butane.

Non-limiting examples of catecholic butanes for use in the present methods also include, for example, 1,4-bis(3,4-dihydroxphenyl)-2,3-dimethylbutane; 1,4-bis(3,4-dihydroxyphenyl)butane; 1,4-bis(3,4-dimethoxyphenyl)-2,3-dimethylbutane; 1,4-bis(3,4-diethoxyphenyl)-2,3-dimethylbutane; 1,4-bis(3,4-dipropoxyphenyl)-2,3-dimethylbutane; 1-(3,4-dihydroxyphenyl)-4-(3,4,5-trihydroxyphenyl) butane; 1,4-bis(3,4-diacetoxyphenyl)-2,3-dimethylbutane; 1,4-bis(3,4-dipropionyloxyphenyl)-2,3-dimethylbutane; 1,4-bis(3,4-dibutyroyloxyphenyl)-2,3-dimethylbutane; 1,4-bis(3,4-divaleroyloxyphenyl)-2,3-dimethylbutane; 1,4-bis(3,4-dipivaloyloxyphenyl)-2,3-dimethylbutane; 1,4-bis(3,4-dineopentylcarboxylphenyl)-2,3-dimethylbutane; or 1-(3,4-dihydroxyphenyl)-4-phenylbutane; and 1-(3,4-dihydroxyphenyl)-4-(2,5-dihydroxyphenyl) butane and the d-, l-, racemic mixture of d- and l-, and meso-isomers thereof.

Other catecholic butanes described in the art are contemplated for use herein. Catecholic butanes described in, for example, U.S. Pat. No. 5,008,294; 6,291,524; or U.S. Pat. No. 6,417,234; U.S. Published Application Nos.

20080207532, 20080096967, 20060151574, 20060141029 and 20070099847 are incorporated herein by reference.

Definition of standard chemistry terms may be found in reference works, including Carey and Sundberg "Advanced Organic Chemistry 4th Ed." Vols. A (2000) and B (2001), Plenum Press, New York. Unless otherwise indicated, conventional methods of mass spectroscopy (MS), nuclear magnetic resonance (NMR), high phase liquid chromatography (HPLC), infrared (IR) UV/Vis spectroscopy, and pharmacology, or HPLC-MS within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

The compounds presented herein may exist as tautomers. Tautomers are compounds that are interconvertible by migration of a hydrogen atom, accompanied by a switch of a single bond and adjacent double bond. In solutions where tautomerization is possible, a chemical equilibrium of the tautomers will exist. The exact ratio of the tautomers depends on several factors, including temperature, solvent, and pH. Some examples of tautomeric pairs include:

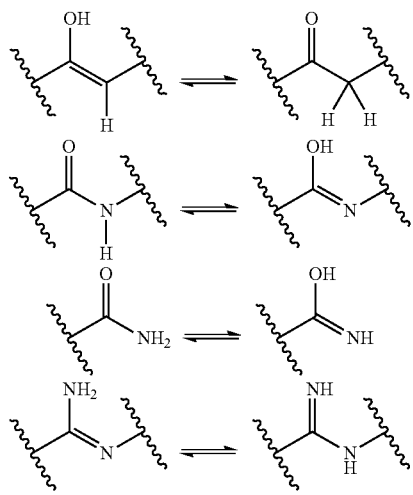

The term "pharmaceutically acceptable derivative or prodrug" as used herein, refers to any pharmaceutically acceptable salt, ester, salt of an ester or other derivative of a compound, which, upon administration to a recipient, is capable of providing (either directly or indirectly) a pharmaceutically active metabolite or residue thereof. Particularly favored derivatives or prodrugs are those that increase the bioavailability of the compounds when such compounds are administered to a patient (e.g., by allowing orally administered compound to be more readily absorbed into blood) or which enhance delivery of the parent compound to a biological compartment (e.g., the brain or lymphatic system).

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds, or by separately reacting a purified compound in its free base form with a suitable organic or inorganic acid, and isolating the salt thus formed. Examples of pharmaceutically acceptable salts include those salts prepared by reaction of the compound with a mineral or organic acid or an inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate, metaphosphate, methanesulfonate, methoxybenzoate, methylbenzoate, monohydrogen phosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds described herein and their pharmaceutically acceptable acid addition salts. See, for example, Berge et al., J. Pharm. Sci. 1977, 66, 1-19. Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, N+(C1-4 alkyl)$_4$, and the like. Representative organic amines useful for the formation of base addition salts include ethylamine, diethylamine, ethylenediamine, ethanolamine, diethanolamine, piperazine and the like. It should be understood that compounds also include the quaternization of any basic nitrogen-containing groups they may contain. Water or oil-soluble or dispersible products may be obtained by such quaternization. See, for example, Berge et al., supra.

Catecholic butanes metabolites can also exist in various polymorphic states, all of which are herein contemplated, and which can also be useful for treating disorders. For example, polymorphs of catecholic butane metabolites may be administered in embodiments of the methods described herein. Catecholic butane metabolites include, for example, all crystalline forms (known as polymorphs). Polymorphs include the different crystal packing arrangements of the same elemental composition of the compound. Polymorphs can have different X-ray diffraction patterns, infrared spectra, melting points, density, hardness, crystal shape, optical and electrical properties, stability, solvates and solubility. Various factors such as the recrystallization solvent, rate of crystallization, and storage temperature can cause a single crystal form to dominate. The various polymorphs can be administered as pharmaceutical compositions.

In pharmaceutical dosage forms, active agents may be administered in the form of their pharmaceutically acceptable salts, or they may also be used alone or in appropriate association, as well as in combination, with other pharmaceutically active compounds. The following methods and excipients are merely exemplary and are in no way limiting. Methods of preparing various pharmaceutical compositions with a specific amount of active compound are known or will be apparent to those skilled in this art. For examples, see Remington's Pharmaceutical Sciences, Mack Publishing Company, Ester, Pa., 18th Edition (1990).

The pharmaceutically acceptable excipients, such as vehicles, adjuvants, carriers or diluents, are conventional in the art. Suitable excipient vehicles are, for example, water, saline, dextrose, glycerol, ethanol, or the like, and combinations thereof. In addition, if desired, the vehicle may contain minor amounts of auxiliary substances such as pH adjusting and buffering agents, tonicity adjusting agents, stabilizers, wetting agents or emulsifying agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The active agents can be formulated into preparations for injection by dissolving, suspending or emulsifying them in an aqueous or non-aqueous solvent, such as vegetable or other similar oils, including corn oil, castor oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents can be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose, saccharin or aspartame.

Pharmaceutical preparations can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. The formulations can be presented in unit-dose or multi-dose containers, for example sealed ampoules and vials, and can be stored in powder form or in a freeze-dried (lyophilized) condition requiring only the addition of the sterile liquid carrier, for example, saline or sterile pyrogen-free water, immediately prior to use. Extemporaneous injection solutions and suspensions can be prepared from sterile powders, granules and tablets of the kind previously described.

Formulations for parenteral administration include aqueous and non-aqueous (oily) sterile injection solutions of the active compounds which can contain antioxidants, buffers, biocide, bacteriostats and solutes which render the formulation isotonic with the blood of the intended recipient; and aqueous and non-aqueous sterile suspensions which can include suspending agents and thickening agents. Examples of suitable isotonic vehicles for use in such formulations include Sodium Chloride Injection, Ringer's Solution, or Lactated Ringer's Injection. Suitable lipophilic solvents or vehicles include fatty oils such as sesame oil, or synthetic fatty acid esters, such as ethyl oleate or triglycerides, or liposomes or other microparticulate systems can be used to target the compound to blood components or one or more organs. The concentration of the active ingredient in the solution can vary widely. Typically, the concentration of the active ingredient in the solution is from about 1 ng/ml to about 10 µg/ml, for example from about 10 ng/ml to about 1 µg/ml. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions Pharmaceutical preparations can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions can take the form of tablets, lozenges, pastilles, or gels formulated in conventional manner. Such compositions can comprise the active ingredient in a flavored basis such as sucrose and acacia or tragacanth.

Pharmaceutical preparations can be administered topically, that is by non-systemic administration. This includes the application of the compositions externally to the epidermis or the buccal cavity and the instillation of such compound into the ear, eye and nose, such that the compound does not significantly enter the blood stream. In contrast, systemic administration refers to oral, intravenous, intraperitoneal and intramuscular administration.

Pharmaceutical preparations suitable for topical administration include liquid or semi-liquid preparations suitable for penetration through the skin to the site of inflammation such as gels, liniments, lotions, creams, ointments or pastes, suspensions, powders, solutions, spray, aerosol, oil, and drops suitable for administration to the eye, ear or nose. Alternatively, a formulation can comprise a patch or a dressing such as a bandage or adhesive plaster impregnated with active ingredients and optionally one or more excipients or diluents. The amount of active ingredient present in the topical formulation can vary widely. The active ingredient can comprise, for topical administration, from 0.001% to 10% w/w, for instance from 1% to 2% by weight of the formulation. It can however comprise as much as 10% w/w but preferably will comprise less than 5% w/w, more preferably from 0.1% to 1% w/w of the formulation.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations suitable for topical administration to the eye also include eye drops wherein the active ingredient is dissolved or suspended in a suitable carrier, especially an aqueous solvent for the active ingredient.

The active agents can be utilized in aerosol formulation to be administered via inhalation.

The compounds of the present embodiments may be formulated into pressurized acceptable propellants such as dichlorodifluoromethane, propane, nitrogen and the like.

Furthermore, the active agents can be made into suppositories by mixing with a variety of bases such as emulsifying bases or water-soluble bases. The compounds of the present embodiments may be administered rectally via a suppository. The suppository can include vehicles such as cocoa butter, carbowaxes and polyethylene glycols, which melt at body temperature, yet are solidified at room temperature.

For oral preparations, the active agents can be used alone or in combination with appropriate additives to make tablets, powders, granules or capsules with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. For oral rinses, the preparations can be made in a manner conventional in the art.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

Some catecholic butane metabolites are water-soluble, hydrophilic compounds. Some embodiments include formulation of hydrophilic compounds in a pharmaceutically acceptable carrier or excipient and delivery of such as oral formulations, such as in the form of an aqueous liquid solution of the compound, or the compounds can be lyophilized and delivered as a powder, made into a tablet, or the compounds can be encapsulated.

The tablets herein can be enteric coated tablets. The formulations herein can be sustained release, either slow release or rapid release formulations.

The amount of the catecholic butane metabolites be included in the oral formulations can be adjusted depending on the desired dose to be administered to a subject. Such an adjustment is within the skill of persons conventional in the art.

Some catecholic butane metabolites are hydrophobic or lipophilic compounds. The absorption of lipophilic compounds in the gut can be improved by using pharmaceutically acceptable carriers that can enhance the rate or extent of solubilization of the compound into the aqueous intestinal fluid. Lipidic carriers are known in the art. The formulations herein can be delivered as oral liquids or can be encapsulated into various types of capsules.

The present embodiments include, in one example, a formulation containing lipophilic catecholic butane metabolites that are formulated for oral delivery by dissolution of such compounds in triacylglycerols, and the formulation is then encapsulated for oral delivery. Triacyglycerols are molecules with long chain and/or medium chain fatty acids linked to a glycerol molecule. The long chain fatty acids range from about $C_{14}$ to $C_{24}$, and can be found in common fat. The medium chain fatty acids range from about $C_6$ to $C_{12}$, and can be found in coconut oil or palm kernel oil. Triacylglycerols suitable for use herein include structured lipids that contain mixtures of either short-chain or medium chain fatty acids or both, esterified on the same glycerol molecule.

In another embodiment, one or more surfactants can be added to a mixture of catecholic butane metabolites and lipidic carrier such that the drug is present in fine droplets of oil/surfactant mix. The surfactants can act to disperse the oily formulation on dilution in the gastrointestinal fluid.

The present embodiments also include a formulation for oral delivery of the catecholic butane metabolites in the form of a micro-emulsion consisting of hydrophilic surfactant and oil. The micro-emulsion particles can be surfactant micelles containing solubilized oil and drug.

Formulations suitable for oral administration can be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient can also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients. Compressed tablets can be prepared by compressing in a suitable machine the active ingredient in a free-flowing form such as a powder or granules, optionally mixed with binders (e.g., povidone, gelatin, hydroxypropylmethyl cellulose), inert diluents, preservative, disintegrant (e.g., sodium starch glycolate, cross-linked povidone, cross-linked sodium carboxymethyl cellulose) or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. Tablets can optionally be provided with an enteric coating, to provide release in parts of the gut other than the stomach. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or Dragee coatings for identification or to characterize different combinations of active compound doses.

Also suitable for oral administration are formulations of the catecholic butane metabolites in a solid lipid nanoparticle preparation. Solid lipid nanoparticles can be prepared in any manner conventional in the art.

In one embodiment, the solid lipid nanoparticle can be prepared in a hot homogenization process by homogenization of melted lipids at elevated temperature. In this process, the solid lipid is melted and the catecholic butan, is dissolved in the melted lipid. A pre-heated dispersion medium is then mixed with the drug-loaded lipid melt, and the combination is mixed with a homogenisator to form a coarse pre-emulsion. High pressure homogenization is then performed at a temperature above the lipids melting point to produce a oil/water-nanoemulsion. The nanoemulsion is cooled down to room temperature to form solid lipid nanoparticles.

In another embodiment, the solid lipid nanoparticles can be prepared in a cold homogenization process. In this process, the lipid is melted and the catecholic butane metabolite is dissolved in the melted lipid. The drug-loaded lipid is then solidified in liquid nitrogen or dry ice. The solid drug-lipid is ground in a powder mill to form 50-100 μm particles. The lipid particles are then dispersed in cold aqueous dispersion medium and homogenized at room temperature or below to form solid lipid nanoparticles.

Also provided herein, in one example, is a formulation of the lipophilic catecholic butane metabolites in liposomes or micelles for oral delivery. These formulations can be made in any manner conventional in the art. Micelles are typically lipid monolayer vesicles in which the hydrophobic drug associates with the hydrophobic regions on the monolayer. Liposomes are typically phospholipids bilayer vesicles. A lipophilic catecholic butane metabolite will typically reside in the center of these vesicles.

Also provided herein, in another example, is a formulation of the catecholic butane metabolites for intravenous administration. Catecholic butanes may be formulated for injection into animals with a pharmaceutically acceptable carrier. Carriers include, but are not limited to one or more solubilizing agents and/or an excipient such as, for example: (a) a water-soluble organic solvent other than dimethyl sulfoxide; provided that when the water-soluble organic solvent is propylene glycol, the propylene glycol is in the absence of white petrolatum, in the absence of xanthan gum (also known as xantham gum and xantham gum) and in the absence of at least one of glycerine or glycine, when the water-soluble organic solvent is polyethylene glycol, the polyethylene glycol is present in the absence of ascorbic acid or butylated hydroxytoluene ("BHT"), and when the polyethylene glycol is polyethylene glycol 400, the polyethylene glycol 400 is present in the absence of polyethylene glycol 8000; (b) a cyclodextrin; (c) an ionic, non-ionic or amphipathic surfactant, provided that when the surfactant is a non-ionic surfactant, the non-ionic surfactant is present in the absence of xanthan gum; (d) a modified cellulose; (e) a water-insoluble lipid other than castor oil; or a combination of any of the carriers (a)-(e).

Pharmaceutical compositions can be in the form of a sterile injectable aqueous solution. Among the acceptable vehicles and solvents that can be employed are water, Ringer's solution and isotonic sodium chloride solution. The sterile injectable preparation can also be a sterile injectable oil-in-water microemulsion where the active ingredient is dissolved in the oily phase. For example, the active ingredient can be first dissolved in a mixture of soybean oil and lecithin. The oil solution then introduced into a water and glycerol mixture and processed to form a microemulsion. The injectable solutions or microemulsions can be introduced into a patient's blood-stream by local bolus injection. Alternatively, it can be advantageous to administer the solution or microemulsion in such a way as to maintain a constant circulating concentration of the instant compound. In order to maintain such a constant concentration, a continuous intravenous delivery device can be utilized. An example of such a device is the Deltec CADD-PLUS™ model 5400 intravenous pump. The pharmaceutical compositions can be in the form of a sterile injectable aqueous or oleaginous suspension for intramuscular and subcutaneous administration. This suspension can be formulated according to the known art using those suitable dispersing or wetting agents and suspending agents which have been mentioned above. The sterile injectable preparation can also be a sterile injectable solution or suspension in a non-toxic parenterally-acceptable diluent or solvent, for example as a solution in 1,3-butanediol. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Also provided herein is a formulation of the catecholic butane metabolites for intra-arterial administration, with or without accompanying blood brain barrier disruption ("BBBD"), and with or without occlusion, such as in hepatic artery chemoemobolization. Briefly, where catecholic butane metabolites are administered intra-arterially with occlusion, primary arteries leading to the target site are catheterized and the catecholic butane metabolites may be applied through a catheter. Embolization of the arteries, in order to retain the catecholic butane metabolites at the target site for a longer period, may be performed using polyvinyl alcohol particles alone or in combination with coils. Intra-arterial delivery of the catecholic butane metabolites may include water soluble compositions. The drugs or agents herein may be dissolved in saline prior to intra-arterial injection and such injection may be preceded by heparin treatment and sedation.

Osmotic disruption of the blood brain barrier ("BBB") as conventional in the art may accompany intra-arterial delivery of the agents herein. Such a procedure can be used to increase the transfer of drugs into the central nervous system ("CNS") preferably just prior to intra-arterial delivery. For such disruption, a catheter is placed into an artery, usually the superficial temporal artery, leading to the brain and the BBB is disrupted with a solution of mannitol. This invasive procedure is typically performed while the patient is under general anesthesia. Such treatment may require prior hydration and administration of anticonvulsants and/or atropine.

Also provided herein, in one example, is a formulation of catecholic butane metabolites for intranasal delivery and intranasal delivery thereof. Intranasal delivery may advantageously build up a higher concentration of the active agents in the brain than can be achieved by intravenous administration. Also, this mode of delivery avoids the problem of first pass metabolism in the liver and gut of the subject receiving the drug.

The amount of the active agents that can be absorbed partly depends on the solubility of the drug in the mucus, a composition that consists of about 95% water solution of serum proteins, glycoproteins, lipids and electrolytes. Generally, as lipophilicity of the active agents herein increases, the drug concentration in the CSF also increases.

Hydrophilic catecholic butane metabolites may be dissolved in a pharmaceutically acceptable carrier such as saline, phosphate buffer, or phosphate buffered saline. In one embodiment, a 0.05 M phosphate buffer at pH 7.4 can be used as the carrier.

Intranasal delivery of the present agents may be optimized by adjusting the position of the subject when administering the agents. For example, the head of the patient may be variously positioned upright-90°, supine-90°, supine-45°, or supine-70° to obtain maximal effect.

The carrier of the composition of catecholic butane metabolites may be any material that is pharmaceutically acceptable and compatible with the active agents of the composition. Where the carrier is a liquid, it can be hypotonic or isotonic with nasal fluids and within the pH of about 4.5 to about 7.5. Where the carrier is in powdered form it is also within an acceptable pH range.

The carrier composition for intranasal delivery may optionally contain lipophilic substances that may enhance absorption of the active agents across the nasal membrane and into the brain via the olfactory neural pathway. Examples of such lipophilic substances include, but are not limited to, gangliosides and phosphatidylserine. One or several lipophilic adjuvants may be included in the composition, such as, in the form of micelles.

The pharmaceutical composition of active agents for intranasal delivery to a subject for treatment of the diseases, disorders, or conditions herein can be formulated in the manner conventional in the art as described in, for example, U.S. Pat. No. 6,180,603 which is incorporated herein by reference. For example, the composition herein can be formulated as a powder, granules, solution, aerosol, drops, nanoparticles, or liposomes. In addition to the active agents, the composition may contain appropriate adjuvants, buffers, preservatives, salts. Solutions such as nose drops may contain anti-oxidants, buffers, and the like.

Catecholic butanes may be delivered to a subject for treatment by surgical implantation into a desired site, such as by implantation of a biodegradable polymer containing the catecholic butane metabolite.

Thus, the biodegradable polymer herein can be any polymer or copolymer that would dissolve in the interstitial fluid, without any toxicity or adverse effect on host tissues. Preferably, the polymer or monomers from which the polymer is synthesized is approved by the Food and Drug Administration for administration into humans. A copolymer having monomers of different dissolution properties is preferred so as to control the dynamics of degradation, such as increasing the proportion of one monomer over the other to control rate of dissolution.

In one embodiment, the polymer is a copolymer of 1,3-bis-(p-carboxyphenoxy)propane and sebacic acid [p(CPP:SA)], as described in Fleming A. B. and Saltzman, W. M., Pharmacokinetics of the Carmustine Implant, Clin. Pharmacokinet, 41: 403-419 (2002); and Brem, H. and Gabikian, P. (2001). In another embodiment, the polymer is a copolymer of polyethylene glycol ("PEG") and sebacic acid, as described in Fu, J. et al., (2002) Biomaterials, 23: 4425-4433.

Polymer delivery systems are applicable to delivery of both hydrophobic and hydrophilic catecholic butane metabolites described herein. The catecholic butane metabolites may be combined with the biodegradable polymers and surgically implanted at the desired or affected site. Some polymer compositions are also usable for intravenous or inhalation therapy herein.

Catecholic butanes may be delivered systemically and/or locally by administration to the lungs through inhalation Inhalation delivery of drugs has been well accepted as a method of achieving high drug concentration in the pulmonary tissues without triggering substantial systemic toxicity, as well as a method of accomplishing systemic circulation of the drug. The techniques for producing such formulations are conventional in the art. Efficacy against pulmonary diseases may be seen with either hydrophobic or hydrophilic catecholic butane metabolites delivered in this manner.

For pulmonary delivery via inhalation, catecholic butane metabolites may be formulated into dry powders, aqueous solutions, liposomes, nanoparticles, or polymers and administered, for example, as aerosols. Hydrophilic formulations may also be taken up through the alveolar surfaces and into the bloodstream for systemic applications.

In one embodiment, the polymers containing the active agents herein are made and used as described in Fu, J. et al. (2002) supra. For example, the polymers herein can be polymers of sebacic acid and polyethylene glycol ("PEG"), or can be poly(lactic-co-glycolic) acid ("PLGA"), or polymers of polyethyleneimine ("PEI") and poly-L-lysine ("PLL").

In another embodiment, catecholic butane metabolites for inhalation delivery may be dissolved in saline or ethanol before nebulization and administered.

In a further embodiment, the agents herein are also effective when delivered as a dry powder, prepared in the manner conventional in the art.

In one embodiment, delivery of the NDGA compounds may be accomplished with the aid of microprocessors embedded into drug delivery devices, such as, for example, SmartMist™ and AERx™.

The appropriate dose to be administered depends on the subject to be treated, such as the general health of the subject, the age of the subject, the state of the disease or condition, the weight of the subject, the size of the tumor, for example.

Pharmaceutical compositions may be formulated for a route of administration such as, for example, intranasal administration; oral administration; inhalation administration; subcutaneous administration; transdermal administration; intra-arterial administration, with or without occlusion; intracranial administration; intraventricular administration; intravenous administration; buccal administration; intraperitoneal administration; intraocular administration; intramuscular administration; implantation administration; and central venous administration. In one embodiment, the catecholic butane metabolite is formulated for oral administration. In another embodiment, the catecholic butane metabolite is formulated for intravenous administration.

An active agent may be administered in a single or, more typically, multiple doses. Preferred dosages for a given agent are readily determinable by those of skill in the art by a variety of means. Other effective dosages can be readily determined by one of ordinary skill in the art through routine trials establishing dose response curves. The amount of agent will, of course, vary depending upon the particular agent used.

The frequency of administration of the active agent, as with the doses, will be determined by the care giver based on age, weight, disease status, health status and patient responsiveness. Thus, the agents may be administered one or more times daily, weekly, monthly or as appropriate as conventionally determined. The agents may be administered intermittently, such as for a period of days, weeks or months, then not again until some time has passed, such as 3 or 6 months, and then administered again for a period of days, weeks, or months.

Unit dosage forms for injection or intravenous administration may comprise the API in a composition as a solution in sterile water, normal saline or another pharmaceutically acceptable carrier.

Methods of Treatment

The terms "effective amount" or "pharmaceutically effective amount" refer to a nontoxic but sufficient amount of the agent to provide the desired biological, therapeutic, and/or prophylactic result. That result can be reduction and/or alleviation of the signs, symptoms, or causes of a disease, or any other desired alteration of a biological system. For example, an "effective amount" for therapeutic uses is the amount of a catecholic butane metabolite as disclosed herein per se or a composition comprising the catecholic butane metabolite herein required to provide a therapeutically significant decrease in a disease. An appropriate effective amount in any individual case may be determined by one of ordinary skill in the art using routine experimentation.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

The term "treating" and its grammatical equivalents as used herein include achieving a therapeutic benefit and/or a prophylactic benefit. By therapeutic benefit is meant eradication or amelioration of the underlying disorder being treated. Treating also refers to obtaining a desired pharmacologic and/or physiologic effect. The effect may be prophylactic in terms of completely or partially preventing a condition or disease or symptom thereof and/or may be therapeutic in terms of a partial or complete cure for a condition or disease and/or adverse affect attributable to the condition or disease. "Treatment," thus, for example, covers any treatment of a condition or disease in a mammal, particularly in a human, and includes: (a) preventing the condition or disease from occurring in a subject which may be predisposed to the condition or disease but has not yet been diagnosed as having it; (b) inhibiting the condition or disease, such as, arresting its development; and (c) relieving, alleviating or ameliorating the condition or disease, such as, for example, causing regression of the condition or disease. By way of example only, in a cancer patient, therapeutic benefit may include eradication or amelioration of the underlying cancer. Also, a therapeutic benefit may be achieved with the eradication or amelioration of one or more of the physiological symptoms associated with the underlying disorder such that an improvement is observed in the patient, notwithstanding the fact that the patient may still be afflicted with the underlying disorder. For prophylactic benefit, a method may be performed on, or a composition administered to a patient at risk of developing cancer, or to a patient reporting one or more of the physiological symptoms of such conditions, even though a diagnosis of the condition may not have been made. In some instances, treating means stasis (i.e., that the disease does not get worse) and survival of the patient is prolonged. A dose to be administered depends on the subject to be treated, such as the general health of the subject, the age of the subject, the state of the disease or condition, the weight of the subject, the size of a tumor, for example.

The term "subject," "patient" or "individual" as used herein in reference to individuals suffering from a disorder, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the mammal is a human.

As used herein, the terms "co-administration," "administered in combination with" and their grammatical equivalents or the like are meant to encompass administration of the selected therapeutic agents to a single patient, and are intended to include treatment regimens in which the agents are administered by the same or different route of administration or at the same or different times. In some embodiments, an inhibitor will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, an inhibitor and the other agent(s) are administered in a single composition. In some embodiments, an inhibitor and the other agent(s) are admixed in the composition. In further embodiments, an inhibitor and the other agent(s) are administered at separate times in separate doses.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively nontoxic chemical compounds or agents that facilitate the incorporation of the compound into cells or tissues.

The term "pharmaceutically acceptable excipient," includes vehicles, adjuvants, or diluents or other auxiliary substances, such as those conventional in the art, which are readily available to the public. For example, pharmaceutically acceptable auxiliary substances include pH adjusting and buffering agents, tonicity adjusting agents, stabilizers, wetting agents and the like.

The term "metabolite," as used herein, refers to a derivative of the compound which is formed when the compound is metabolized. In one aspect, provided herein are multi-glucuronididated, methylated, and sulfated versions of metabolites of NDGA.

The term "active metabolite," as used herein, refers to a biologically active derivative of the compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to the compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from The Pharmacological Basis of Therapeutics, 9th Edition, McGraw-Hill (1996).

The term "unit dosage form," as used herein, refers to physically discrete units suitable as unitary dosages for human and animal subjects, each unit containing a predetermined quantity of API calculated in an amount sufficient to produce the desired effect in association with a pharmaceutically acceptable diluent, carrier or vehicle. The specifications for the novel unit dosage forms of the present compounds depend on the particular compound employed and the effect to be achieved, and the pharmacodynamics associated with each compound in the host.

As used herein, "percent," "percentage" or the symbol "%" means the percent of the component indicated in the composition based on the amount of the carrier present in the composition, on a weight/weight (w/w), weight/volume (w/v) or volume/volume (v/v), as indicated with respect to any particular component, all based on the amount of the carrier present in the composition. Thus, different types of carriers may be present in an amount of up to 100% as indicated, which does not preclude the presence of the API, the amount of which may be indicated as a % or as a certain number of mg present in the composition or a certain number of mg/mL present, where the % or mg/mL is based on the amount of the total carrier present in the composition. Certain types of carriers may be present in combination to make up 100% of the carrier.

A "substantially purified" compound in reference to the catecholic butane metabolite that is substantially free of materials that are not the catecholic butane metabolite. By way of example, substantially free is meant at least about 50% free of non-catecholic butane metabolite materials, at least about 70%, at least about 80%, at least about 90% free or at least about 95% free of non-catecholic butane metabolite materials.

Catecholic butane metabolites can sensitize cancers or other proliferative diseases to conventional therapies as well as re-sensitize cancers or other proliferative diseases after they have acquired resistance to such conventional therapies. The embodiments described herein provide a method of inhibiting both EGFR and IGF-1R in a cell, comprising contacting a cell in which inhibition of both EGFR and IGF-1R is desired with a catecholic butane metabolite as described herein. Because compounds described herein are dual kinase inhibitors, they are useful research tools for in vitro study of the role of EGFR and IGF-1R in biological processes.

Described herein are compounds, pharmaceutical compositions and methods for treating a patient suffering from a proliferative disease by administering an effective amount of a catecholic butane metabolite (i.e., a single compound that is a dual kinase inhibitor) as described herein, alone or in combination with one or more additional active ingredients (e.g., anticancer agents) and/or treatment regimens (e.g., surgery).

The present application relates generally to methods of treatment of diseases using a catecholic butane metabolite (or a derivative thereof) described herein. By way of example, the application relates to the use of a catecholic butane metabolite having a structure of any one of Formulas IV-LXVII, Formulas LXXII-CXXXV, or a phosphate ester thereof, where the formulas are provided in Tables 1 and 3 (R groups refer to those shown in the formula illustrated in FIG. 29.), in treating a proliferative disease by inhibiting IGF-1R and EGFR. By way of another example, the application relates to the use of a phosphate ester of a catecholic butane metabolite described herein has a structure of any one of Formulas LXVIII-LXXI or Formulas CXXXVI-CXXXVII, wherein the formulas are provided in Tables 2 and 4. R groups refer to those shown in the formula illustrated in FIG. 29.

Provided herein are methods for treating a disease comprising administering an effective amount of a pharmaceutical compound capable of inhibiting the tyrosine kinase activity of both IGF-1R and EGFR, wherein the pharmaceutical compound is a catecholic butane metabolite described herein (i.e., one compound that is a dual kinase inhibitor).

Also provided herein are methods for treating a disease in a subject that has developed resistance to one or more EGF-R inhibitors or IGF-1R inhibitors comprising administering an effective amount of a pharmaceutical compound capable of inhibiting the tyrosine kinase activity of both of IGF-1R and EGFR, wherein the pharmaceutical compound is a catecholic butane metabolite (i.e., a dual kinase inhibitor).

In one embodiment, the disease is a proliferative disease.

A proliferative disease includes, but is not limited to, a malignant, pre-malignant or benign cancer. Cancers to be treated using the disclosed methods include, for example, a solid tumor, a lymphoma or a leukemia. In one embodiment, a cancer can be, for example, a brain tumor (e.g., a malignant, pre-malignant or benign brain tumor such as, for example, a glioblastoma, an astrocytoma, a meningioma, a medulloblastoma or a peripheral neuroectodermal tumor), a carcinoma (e.g., gall bladder carcinoma, bronchial carcinoma, basal cell carcinoma, adenocarcinoma, squamous cell carcinoma, small cell carcinoma, large cell undifferentiated carcinoma, adenomas, cystadenoma, etc.), a basalioma, a teratoma, a retinoblastoma, a choroidea melanoma, a seminoma, a sarcoma (e.g., Ewing sarcoma, rhabdomyosarcoma, craniopharyngeoma, osteosarcoma, chondrosarcoma, myosarcoma, liposarcoma, fibrosarcoma, leimyosarcoma, Askin's tumor, lymphosarcoma, neurosarcoma, Kaposi's sarcoma, dermatofibrosarcoma, angiosarcoma, etc.), a plasmocytoma, a head and neck tumor (e.g., oral, laryngeal, nasopharyngeal, esophageal, etc.), a liver tumor, a kidney tumor, a renal cell tumor, a squamous cell carcinoma, a uterine tumor, a bone tumor, a prostate tumor, a breast tumor including, but not limited to a breast tumor that is Her2– and/or ER– and/or PR–, a bladder tumor, a pancreatic tumor, an endometrium tumor, a squamous cell carcinoma, a stomach tumor, gliomas, a colorectal tumor, a testicular tumor, a colon tumor, a rectal tumor, an ovarian tumor, a cervical tumor, an eye tumor, a central nervous system tumor (e.g., primary CNS lymphomas, spinal axis tumors, brain stem gliomas, pituitary adenomas, etc.), a thyroid tumor, a lung tumor (e.g., non-small cell lung cancer (NSCLC) or small cell lung cancer), a leukemia or a lymphoma (e.g., cutaneous T-cell lymphomas (CTCL), non-cutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma, etc.), a multiple myeloma, a skin tumor (e.g., basal cell carcinomas, squamous cell carcinomas, melanomas such as malignant melanomas, cutaneous melanomas or intraocular melanomas, Dermatofibrosarcoma protuberans, Merkel cell carcinoma or Kaposi's sarcoma), a gynecologic tumor (e.g., uterine sarcomas, carcinoma of the fallopian tubes, carcinoma of the endometrium, carcinoma of the cervix, carcinoma of the vagina, carcinoma of the vulva, etc.), Hodgkin's disease, a cancer of the small intestine, a cancer of the endocrine system (e.g., a cancer of the thyroid, parathyroid or adrenal glands, etc.), a mesothelioma, a cancer of the urethra, a cancer of the penis, tumors related to Gorlin's syndrome (e.g., medulloblastomas, meningioma, etc.), a tumor of unknown origin; or metastases of any thereto.

In another embodiment, the cancer is a lung tumor, a breast tumor, a colon tumor, a colorectal tumor, a head and neck tumor, a liver tumor, a prostate tumor, a glioma, glioblastoma multiforme, a ovarian tumor or a thyroid tumor; or metastases of any thereto.

In yet another embodiment, the cancer is an endometrial tumor, bladder tumor, multiple myeloma, melanoma, renal tumor, sarcoma, cervical tumor, leukemia, and neuroblastoma.

Tumors as provided herein may be primary tumors or metastases. Cancers may also be epithelial based cancers. In one embodiment, cells of tumors may express EGFR. In another embodiment, cells of tumors may express IGF-1R. In yet another embodiment, cells of tumors may express EGFR and IGF-1R.

Provided herein are methods for treating a malignant, pre-malignant or benign cancer, comprising administering an effective amount of a pharmaceutical compound capable of inhibiting the tyrosine kinase activity of IGF-1R and EGFR, wherein the pharmaceutical compound is a catecholic butane metabolite (i.e., a single compound that is a dual kinase inhibitor).

Provided herein are methods of selecting a subject for treatment with a catecholic butane metabolite capable of inhibiting the tyrosine kinase activity of both IGF-1R and EGF-R, wherein said subject is identified as having levels of IGF-1R, EGFR, or both at baseline levels or at 2× greater than baseline levels as compared to control levels.

In one aspect, a subject has been previously treated with an EGFR inhibitor or an IGF-1R inhibitor.

In another aspect, the subject may be resistant to treatment with an EGFR inhibitor alone or an IGF-1R inhibitor alone.

Provided herein are methods for degrading, inhibiting the growth of or killing cancer cells of epithelial origin comprising contacting the cells with an amount of a catecholic butane metabolite effective to degrade, inhibit the growth of or kill cancer cells.

Provided herein are methods of inhibiting tumor size increase, reducing the size of a tumor, reducing tumor proliferation or preventing tumor proliferation in an individual comprising administering to said individual an effective amount of a catecholic butane metabolite described herein to inhibit tumor size increase, reduce the size of a tumor, reduce tumor proliferation or prevent tumor proliferation. Treatment of tumors in some cases includes stasis of symptoms, that is, by treating the patient, the cancer does not worsen and survival of the patient is prolonged.

Patients may be assessed with respect to symptoms at one or more multiple time points including prior to, during, and after treatment regimens. Treatment can result in improving the subject's condition and can be assessed by determining if one or more of the following events has occurred: decreased tumor size, decreased tumor cell proliferation, decreased numbers of cells, decreased neovascularization and/or increased apoptosis. One or more of these occurrences may, in some cases, result in partial or total elimination of the cancer and prolongation of survival of the patient. Alternatively, for terminal stage cancers, treatment may result in stasis of disease, better quality of life and/or prolongation of survival. Other methods of assessing treatment are known in the art and contemplated herein.

One would understand that classification and staging systems described herein may be used to assess treatment of cancers described herein; additionally, other staging schemes are known in the art and may be used in connection with the methods described herein. By way of example only, the TNM classification of malignant tumors may be used as a cancer staging system to describe the extent of cancer in a patient's body. T describes the size of the tumor and whether it has invaded nearby tissue, N describes regional lymph nodes that are involved, and M describes distant metastasis. TNM is maintained by the International Union Against Cancer (UICC) and is used by the American Joint Committee on Cancer (AJCC) and the International Federation of Gynecology and Obstetrics (FIGO). One would understand that not all tumors have TNM classifications such as, for example, brain tumors. Generally, T (a,is,(0), 1-4) is measured as the size or direct extent of the primary tumor. N (0-3) refers to the degree of spread to regional lymph nodes: N0 means that tumor cells are absent from regional lymph nodes, N1 means that tumor cells spread to the closest or small numbers of regional lymph nodes, N2 means that tumor cells spread to an extent between N1 and N3; N3 means that tumor cells spread to most distant or numerous regional lymph nodes. M (0/1) refers to the presence of metastasis: M0 means that no distant metastasis are present; M1 means that metastasis has occurred to distant organs (beyond regional lymph nodes). Other parameters may also be assessed. G (1-4) refers to the grade of cancer cells (i.e., they are low grade if they appear similar to normal cells, and high grade if they appear poorly differentiated). R (0/1/2) refers to the completeness of an operation (i.e., resection-boundaries free of cancer cells or not). L (0/1) refers to invasion into lymphatic vessels. V (0/1) refers to invasion into vein. C (1-4) refers to a modifier of the certainty (quality) of V.

Breast Cancer

In one aspect, provided herein is a method of treating breast cancer, such as a ductal carcinoma in duct tissue in a mammary gland, a breast cancer that is Her2− and/or ER− and/or PR−.

Several types of breast cancer exist that may be treated by the methods described herein. A lobular carcinoma in situ and a ductal carcinoma in situ are breast cancers that have developed in the lobules and ducts, respectively, but have not spread to the fatty tissue surrounding the breast or to other areas of the body. Infiltrating (or invasive) lobular and ductal carcinoma are cancers that have developed in the lobules and ducts, respectively, and have spread to either the breast's fatty tissue and/or other parts of the body. Other cancers of the breast that would benefit from treatment by the methods are medullary carcinomas, colloid carcinomas, tubular carcinomas, and inflammatory breast cancer.

In one embodiment, breast cancer is staged according to the TNM system. Prognosis is closely linked to results of staging, and staging is also used to allocate patients to treatments both in clinical trials and clinical practice.

Briefly, the information for staging is as follows:

TX: Primary tumor cannot be assessed. T0: No evidence of tumor. Tis: Carcinoma in situ, no invasion; T1: Tumor is 2 cm or less; T2: Tumor is more than 2 cm but not more than 5 cm; T3: Tumor is more than 5 cm; T4: Tumor of any size growing into the chest wall or skin, or inflammatory breast cancer NX: Nearby lymph nodes cannot be assessed N0: cancer has not spread to regional lymph nodes. N1: cancer has spread to 1 to 3 axillary or one internal mammary lymph node N2: cancer has spread to 4 to 9 axillary lymph nodes or multiple internal mammary lymph nodes N3: One of the following applies: cancer has spread to 10 or more axillary lymph nodes, or cancer has spread to the lymph nodes under the clavicle (collar bone), or cancer has spread to the lymph nodes above the clavicle, or cancer involves axillary lymph nodes and has enlarged the internal mammary lymph nodes, or cancer involves 4 or more axillary lymph nodes, and tiny amounts of cancer are found in internal mammary lymph nodes on sentinel lymph node biopsy.

MX: presence of distant spread (metastasis) cannot be assessed. M0: no distant spread. M1: spread to distant organs (not including the supraclavicular lymph node) has occurred.

The methods provided herein may provide a beneficial effect for breast cancer patients, by administration of a catecholic butane metabolite or a combination of administration of a catecholic butane metabolite and one or more anticancer treatments.

Ovarian Cancer

In another aspect, provided herein is a method of treating ovarian cancer, including epithelial ovarian tumors. Preferably, the method treats an ovarian cancer selected from the following: an adenocarcinoma in the ovary and an adenocarcinoma that has migrated from the ovary into the abdominal cavity.

The methods provided herein may provide a beneficial effect for ovarian cancer patients, by administration of a catecholic butane metabolite or a combination of administration of a catecholic butane metabolite and one or more anticancer treatments.

Cervical Cancer

In another aspect, the method treats cervical cancer, preferably an adenocarcinoma in the cervix epithelial. Two main types of this cancer exist: squamous cell carcinoma and adenocarcinomas. The former constitutes about 80-90% of all cervical cancers and develops where the ectocervix (portion closest to the vagina) and the endocervix (portion closest to the uterus) join. The latter develop in the mucous-producing gland cells of the endocervix. Some cervical cancers have characteristics of both of these and are called adenosquamous carcinomas or mixed carcinomas.

The methods provided herein may provide a beneficial effect for cervical cancer patients, by administration of a catecholic butane metabolite or a combination of administration of a catecholic butane metabolite and one or more anticancer treatments.

Prostate Cancer

In one other aspect, provided herein is a method to treat prostate cancer, preferably a prostate cancer selected from the following: an adenocarcinoma or an adenocarinoma that has migrated to the bone. Prostate cancer develops in the prostate organ in men, which surrounds the first part of the urethra. The prostate has several cell types but 99% of tumors are adenocarcinomas that develop in the glandular cells responsible for generating seminal fluid.

There are two schemes commonly used to stage prostate cancer. The most common is the TNM system, which evaluates the size of the tumor, the extent of involved lymph nodes, and any metastasis (distant spread). As with many other cancers, these are often grouped into four stages (I-IV). Another scheme, used less commonly, is the Whitmore-Jewett stage.

Briefly, Stage I disease is cancer that is found incidentally in a small part of the sample when prostate tissue was removed for other reasons, such as benign prostatic hypertrophy, and the cells closely resemble normal cells and the gland feels normal to the examining finger. In Stage II more of the prostate is involved and a lump can be felt within the gland. In Stage III, the tumor has spread through the prostatic capsule and the lump can be felt on the surface of the gland. In Stage IV disease, the tumor has invaded nearby structures, or has spread to lymph nodes or other organs. Grading is based on cellular content and tissue architecture from biopsies (Gleason) which provides an estimate of the destructive potential and ultimate prognosis of the disease.

The methods provided herein may provide a beneficial effect for prostate cancer patients, by administration of a catecholic butane metabolite or a combination of administration of a cat catecholic butane metabolite and one or more anticancer treatments.

Pancreatic Cancer

In another aspect, provided herein is a method of treating pancreatic cancer, preferably a pancreatic cancer selected from the following: an epitheliod carcinoma in the pancreatic duct tissue and an adenocarcinoma in a pancreatic duct. The most common type of pancreatic cancer is an adenocarcinoma, which occurs in the lining of the pancreatic duct.

The methods provided herein may provide a beneficial effect for pancreatic cancer patients, by administration of a catecholic butane metabolite or a combination of administration of a catecholic butane metabolite and one or more anticancer treatments.

Bladder Cancer

In another aspect, provided herein is a method of treating bladder cancer, preferably a transitional cell carcinoma in urinary bladder. Bladder cancers are urothelial carcinomas (transitional cell carcinomas) or tumors in the urothelial cells that line the bladder. The remaining cases of bladder cancer are squamous cell carcinomas, adenocarcinomas, and small cell cancers. Several subtypes of urothelial carcinomas exist depending on whether they are noninvasive or invasive and whether they are papillary, or flat. Noninvasive tumors are in the urothelium, the innermost layer of the bladder, while invasive tumors have spread from the urothelium to deeper layers of the bladder's main muscle wall. Invasive papillary urothelial carcinomas are slender finger-like projections that branch into the hollow center of the bladder and also grow outward into the bladder wall. Non-invasive papillary urothelial tumors grow towards the center of the bladder. While a non-invasive, flat urothelial tumor (also called a flat carcinoma in situ) is confined to the layer of cells closest to the inside hollow part of the bladder, an invasive flat urothelial carcinoma invades the deeper layer of the bladder, particularly the muscle layer.

The methods provided herein may provide a beneficial effect for bladder cancer patients, by administration of a catecholic butane metabolite or a combination of administration of a catecholic butane metabolite and one or more anticancer treatments.

Acute Myeloid Leukemia

In another aspect, provided herein is a method of treating acute myeloid leukemia (AML), preferably acute promyleocytic leukemia in peripheral blood. AML begins in the bone marrow but can spread to other parts of the body including the lymph nodes, liver, spleen, central nervous system, and testes. It is acute meaning it develops quickly and may be fatal if not treated within a few months. AML is characterized by immature bone marrow cells usually granulocytes or monocytes, which continue to reproduce and accumulate.

There are other types of leukemia's that can also be treated by the methods provided herein including but not limited to, Acute Lymphocytic Leukemia, Acute Myeloid Leukemia, Chronic Lymphocytic Leukemia, Chronic Myeloid Leukemia, Hairy Cell Leukemia, Myelodysplasia, and Myeloproliferative Disorders.

The methods provided herein may provide a beneficial effect for leukemia patients, by administration of a catecholic butane metabolite or a combination of administration of a catecholic butane metabolite and one or more anticancer treatments.

Lung Cancer

In another aspect, provided herein is a method to treat lung cancer. The most common type of lung cancer is non-small cell lung cancer (NSCLC), which accounts for approximately 80-85% of lung cancers and is divided into squamous cell carcinomas, adenocarcinomas, and large cell undifferentiated carcinomas. Small cell lung cancer accounts for 15-20% of lung cancers.

Lung cancer staging is an assessment of the degree of spread of the cancer from its original source. It is an important factor affecting the prognosis and potential treatment of lung cancer. Non-small cell lung carcinoma is staged from IA ("one A"; best prognosis) to IV ("four"; worst prognosis). Small cell lung carcinoma is classified as limited stage if it is confined to one half of the chest and within the scope of a single radiotherapy field; otherwise, it is extensive stage.

Lung cancer may be staged using EUS (endoscopic ultrasound) or TNM. Staging a part of the assessment of patients with non-small cell lung carcinoma. These patients undergo staging as part of the process of considering prognosis and treatment. The AJCC recommends TNM staging followed by further grouping.

Primary tumor (T):

TX: The primary tumor cannot be assessed, or there are malignant cells in the sputum or bronchoalveolar lavage but not seen on imaging or bronchoscopy;

Tis: Carcinoma in situ.

T0: No evidence of primary tumor.

T1: Tumor less than 3 cm in its greatest dimension, surrounded by lung or visceral pleura and without bronchoscopic invasion into the main bronchus.

T2: A tumor with any of: more than 3 cm in greatest dimension; extending into the main bronchus (but more than 2 cm distal to the carina), and obstructive pneumonitis (but not involving the entire lung).

T3: A tumor with any of: invasion of the chest wall, diaphragm, mediastinal pleura, or parietal pericardium; extending into the main bronchus, within 2 cm of the carina, but not involving the carina; and obstructive pneumonitis of the entire lung.

T4: A tumor with any of: invasion of the mediastinum, heart, great vessels, trachea, esophagus, vertebra, or carina; separate tumor nodules in the same lobe; and malignant pleural effusion.

Lymph nodes (N): NX: Lymph nodes cannot be assessed; N0: No lymph nodes involved; N1: Metastasis to ipsilateral peribronchial or ipsilateral hilar lymph nodes; N2: Metastasis to ipsilateral mediastinal or subcarinal lymph nodes; and N3: Metastasis to any of: ipsilateral supraclavicular lymph nodes; ipsilateral scalene lymph nodes; and contralateral lymph nodes.

Distant metastasis (M): MX: Distant metastasis cannot be assessed; M0: No distant metastasis; and M1: Distant metastasis is present.

The methods provided herein may provide a beneficial effect for lung cancer patients, by administration of a catecholic butane metabolite or a combination of administration of a catecholic butane metabolite and one or more anticancer treatments.

Skin Cancer

In another aspect, provided herein is a method to treat skin cancer. There are several types of cancer that start in the skin. The most common types are basal cell carcinoma and squamous cell carcinoma, which are non-melanoma skin cancers. Actinic keratosis is a skin condition that sometimes develops into squamous cell carcinoma. Non-melanoma skin cancers rarely spread to other parts of the body. Melanoma, the rarest form of skin cancer, is more likely to invade nearby tissues and spread to other parts of the body.

The methods provided herein may provide a beneficial effect for skin cancer patients, by administration of a catecholic butane metabolite or a combination of administration of a catecholic butane metabolite and one or more anticancer treatments.

Eye Cancer, Retinoblastoma

In another aspect, provided herein is a method to treat eye retinoblastoma. Retinoblastoma is a malignant tumor of the retina. Although retinoblastoma may occur at any age, it most often occurs in younger children, usually before the age of 5 years. The tumor may be in one eye only or in both eyes. Retinoblastoma is usually confined to the eye and does not spread to nearby tissue or other parts of the body.

The methods provided herein may provide a beneficial effect for eye retinoblastoma patients, by administration of a catecholic butane metabolite or a combination of administration of a catecholic butane metabolite and one or more anticancer treatments.

Eye Cancer, Intraocular Melanoma

In another aspect, provided herein is a method to treat intraocular (eye) melanoma. Intraocular melanoma, a rare cancer, is a disease in which cancer cells are found in the part of the eye called the uvea. The uvea includes the iris, the ciliary body, and the choroid. Intraocular melanoma occurs most often in people who are middle aged.

The methods provided herein may provide a beneficial effect for intraocular melanoma patients, by administration of a catecholic butane metabolite or a combination of administration of a catecholic butane metabolite and one or more anticancer treatments.

Endometrium Cancer

In another aspect, provided herein is a method to treat endometrium cancer. Endometrial cancer is a cancer that starts in the endometrium, the inner lining of the uterus. Some of the examples of the cancer of uterus and endometrium include, but are not limited to, adenocarcinomas, adenoacanthomas, adenosquamous carcinomas, papillary serous adenocarcinomas, clear cell adenocarcinomas, uterine sarcomas, stromal sarcomas, malignant mixed mesodermal tumors, and leiomyosarcomas.

The methods provided herein may provide a beneficial effect for endometrium cancer patients, by administration of a catecholic butane metabolite or a combination of administration of a catecholic butane metabolite and one or more anticancer treatments.

Liver Cancer

In another aspect, provided herein is a method to treat primary liver cancer (cancer that begins in the liver). Primary liver cancer can occur in both adults and children.

The methods provided herein may provide a beneficial effect for liver cancer patients, by administration of a catecholic butane metabolite or a combination of administration of a catecholic butane metabolite and one or more anticancer treatments.

Kidney Cancer

In another aspect, provided herein is a method to treat kidney cancer. Kidney cancer (also called renal cell cancer or renal adenocarcinoma) is a disease in which malignant cells are found in the lining of tubules in the kidney.

The methods provided herein may provide a beneficial effect for kidney cancer patients, by administration of a catecholic butane metabolite or a combination of administration of a catecholic butane metabolite and one or more anticancer treatments.

Thyroid Cancer

In another aspect, provided herein is a method to treat thyroid cancer. Thyroid cancer is a disease in which cancer (malignant) cells are found in the tissues of the thyroid gland. The four main types of thyroid cancer are papillary, follicular, medullary and anaplastic.

The methods provided herein may provide a beneficial effect for thyroid cancer patients, by administration of a catecholic butane metabolite or a combination of administration of a catecholic butane metabolite and one or more anticancer treatments.

AIDS Related Cancers

Provided herein are methods to treat AIDS-related cancers including, but not limited to AIDS-related lymphoma and Kaposi's Sarcoma. The methods provided herein may provide a beneficial effect for AIDS-related cancers, by administration of a catecholic butane or a combination of administration of a catecholic butane metabolite or a combination of administration of a catecholic butane metabolite and one or more anticancer treatments.

AIDS-Related Lymphoma

In another aspect, provided herein is a method to treat AIDS-related lymphoma. AIDS-related lymphoma is a disease in which malignant cells form in the lymph system of patients who have acquired immunodeficiency syndrome (AIDS). AIDS is caused by the human immunodeficiency virus (HIV), which attacks and weakens the body's immune system. The immune system is then unable to fight infection and diseases that invade the body. People with HIV disease have an increased risk of developing infections, lymphoma, and other types of cancer. Lymphomas are cancers that affect the white blood cells of the lymph system. Lymphomas are divided into two general types: Hodgkin's lymphoma and non-Hodgkin's lymphoma. Both Hodgkin's lymphoma and non-Hodgkin's lymphoma may occur in AIDS patients, but non-Hodgkin's lymphoma is more common. When a person with AIDS has non-Hodgkin's lymphoma, it is called an AIDS-related lymphoma. Non-Hodgkin's lymphomas may be indolent (slow-growing) or aggressive (fast-growing). AIDS-related lymphoma is usually aggressive. The three main types of AIDS-related lymphoma are diffuse large B-cell lymphoma, B-cell immunoblastic lymphoma and small non-cleaved cell lymphoma.

Treatment of AIDS-related lymphoma combines treatment of the lymphoma with treatment for AIDS. Patients with AIDS have weakened immune systems and treatment can cause further damage. For this reason, patients who have AIDS-related lymphoma are usually treated with lower doses of drugs than lymphoma patients who do not have AIDS. Highly-active antiretroviral therapy (HAART) is used to slow progression of HIV. Medicine to prevent and treat infections, which can be serious, is also used.

Kaposi's Sarcoma

In another aspect, provided herein is a method to treat Kaposi's sarcoma. Kaposi's sarcoma is a disease in which cancer cells are found in the tissues under the skin or mucous membranes that line the mouth, nose, and anus. Classic Kaposi's sarcoma usually occurs in older men of Jewish, Italian, or Mediterranean heritage. This type of Kaposi's sarcoma progresses slowly, sometimes over 10 to 15 years. Kaposi's sarcoma may occur in people who are taking immunosuppressants. Kaposi's sarcoma in patients who have Acquired Immunodeficiency Syndrome (AIDS) is called epidemic Kaposi's sarcoma. Kaposi's sarcoma in people with AIDS usually spreads more quickly than other kinds of Kaposi's sarcoma and often is found in many parts of the body.

The methods provided herein may provide a beneficial effect for Kaposi's sarcoma, by administration of a catecholic butane metabolite or a combination of administration of a catecholic butane metabolite and one or more anticancer treatments.

Viral-Induced Cancers

In another aspect, provided herein is a method to treat viral-induced cancers. Several common viruses are clearly or probable causal factors in the etiology of specific malignancies. These viruses either normally establish latency or few can become persistent infections. Oncogenesis is probably linked to an enhanced level of viral activation in the infected host, reflecting heavy viral dose or compromised immune control. The major virus-malignancy systems include hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer. In general, these malignancies occur relatively early in life, typically peaking in middle-age or earlier.

Virus-Induced Hepatocellular Carcinoma

The causal relationship between both HBV and HCV and hepatocellular carcinoma or liver cancer is established through substantial epidemiologic evidence. Both appear to act via chronic replication in the liver by causing cell death and subsequent regeneration.

Viral-Induced Adult T cell leukemia/lymphoma

The association between HTLV-1 and Adult T cell leukemia (ATL) is firmly established. Unlike the other oncogenic viruses found throughout the world, HTLV-1 is highly geographically restricted, being found primarily in southern Japan, the Caribbean, west and central Africa, and the South Pacific islands. Evidence for causality includes the monoclonal integration of viral genome in almost all cases of ATL in carriers. The risk factors for HTLV-1-associated malignancy appear to be perinatal infection, high viral load, and being male sex. Adult T cell leukemia is a cancer of the blood and bone marrow.

Viral-Induced Cervical Cancer

Infection of the cervix with human papillomavirus (HPV) is the most common cause of cervical cancer. Not all women with HPV infection, however, will develop cervical cancer. Cervical cancer usually develops slowly over time. Before cancer appears in the cervix, the cells of the cervix go through changes known as dysplasia, in which cells that are not normal begin to appear in the cervical tissue. Later, cancer cells start to grow and spread more deeply into the cervix and to surrounding areas.

The methods provided herein may provide a beneficial effect for virally induced cancers, by administration of a catecholic butane metabolite or a combination of administration of a catecholic butane metabolite and one or more anticancer treatments.

Central Nervous System (CNS) Cancers

Brain and spinal cord tumors are abnormal growths of tissue found inside the skull or the bony spinal column, which are the primary components of the central nervous system (CNS). Benign tumors are non-cancerous, and malignant tumors are cancerous. The CNS is housed within rigid, bony quarters (i.e., the skull and spinal column), so any abnormal growth, whether benign or malignant, can place pressure on sensitive tissues and impair function. Tumors that originate in the brain or spinal cord are called primary tumors. Most primary tumors are caused by out-of-control growth among cells that surround and support neurons. In a small number of individuals, primary tumors may result from specific genetic disease (e.g., neurofibromatosis, tuberous sclerosis) or from exposure to radiation or cancer-causing chemicals. The cause of most primary tumors remains a mystery.

The first test to diagnose brain and spinal column tumors is a neurological examination. Special imaging techniques (computed tomography, and magnetic resonance imaging, positron emission tomography) are also employed. Laboratory tests include the EEG and the spinal tap. A biopsy, a surgical procedure in which a sample of tissue is taken from a suspected tumor, helps doctors diagnose the type of tumor.

Tumors are classified according to the kind of cell from which the tumor seems to originate. The most common primary brain tumor in adults comes from cells in the brain called astrocytes that make up the blood-brain barrier and contribute to the nutrition of the central nervous system. These tumors are called gliomas (astrocytoma, anaplastic astrocytoma, or glioblastoma multiforme) and account for 65% of all primary central nervous system tumors. Some of the tumors are, but not limited to, Oligodendroglioma, Ependymoma, Meningioma, Lymphoma, Schwannoma, and Medulloblastoma.

Neuroepithelial Tumors of the CNS

Astrocytic tumors, such as astrocytoma; anaplastic (malignant) astrocytoma, such as hemispheric, diencephalic, optic, brain stem, cerebellar; glioblastoma multiforme; pilocytic astrocytoma, such as hemispheric, diencephalic, optic, brain stem, cerebellar; subependymal giant cell astrocytoma; and pleomorphic xanthoastrocytoma. Oligodendroglial tumors, such as oligodendroglioma; and anaplastic (malignant) oligodendroglioma. Ependymal cell tumors, such as ependymoma; anaplastic ependymoma; myxopapillary ependymoma; and subependymoma. Mixed gliomas, such as mixed oligoastrocytoma; anaplastic (malignant) oligoastrocytoma; and others (e.g. ependymo-astrocytomas). Neuroepithelial tumors of uncertain origin, such as polar spongioblastoma; astroblastoma; and gliomatosis cerebri. Tumors of the choroid plexus, such as choroid plexus papilloma; and choroid plexus carcinoma (anaplastic choroid plexus papilloma). Neuronal and mixed neuronal-glial tumors, such as gangliocytoma; dysplastic gangliocytoma of cerebellum (Lhermitte-Duclos); ganglioglioma; anaplastic (malignant) ganglioglioma; desmoplastic infantile ganglioglioma, such as desmoplastic infantile astrocytoma; central neurocytoma; dysembryoplastic neuroepithelial tumor; olfactory neuroblastoma (esthesioneuroblastoma. Pineal Parenchyma Tumors, such as pineocytoma; pineoblastoma; and mixed pineocytoma/pineoblastoma. Tumors with neuroblastic or glioblastic elements (embryonal tumors), such as medulloepithelioma; primitive neuroectodermal tumors with multipotent differentiation, such as medulloblastoma; cerebral primitive neuroectodermal tumor; neuroblastoma; retinoblastoma; and ependymoblastoma.

Other CNS Neoplasms

Tumors of the Sellar Region, such as pituitary adenoma; pituitary carcinoma; and craniopharyngioma. Hematopoietic tumors, such as primary malignant lymphomas; plasmacytoma; and granulocytic sarcoma. Germ Cell Tumors, such as germinoma; embryonal carcinoma; yolk sac tumor (endodermal sinus tumor); choriocarcinoma; teratoma; and mixed germ cell tumors. Tumors of the Meninges, such as meningioma; atypical meningioma; and anaplastic (malignant) meningioma. Non-menigothelial tumors of the meninges, such as Benign Mesenchymal; Malignant Mesenchymal; Primary Melanocytic Lesions; Hemopoietic Neoplasms; and Tumors of Uncertain Histogenesis, such as hemangioblastoma (capillary hemangioblastoma). Tumors of Cranial and Spinal Nerves, such as schwannoma (neurinoma, neurilemoma); neurofibroma; malignant peripheral nerve sheath tumor (malignant schwannoma), such as epithelioid, divergent mesenchymal or epithelial differentiation, and melanotic. Local Extensions from Regional Tumors; such as paraganglioma (chemodectoma); chordoma; chodroma; chondrosarcoma; and carcinoma. Metastatic tumors, Unclassified Tumors and Cysts and Tumor-like Lesions, such as Rathke cleft cyst; Epidermoid; dermoid; colloid cyst of the third ventricle; enterogenous cyst; neuroglial cyst; granular cell tumor (choristoma, pituicytoma); hypothalamic neuronal hamartoma; nasal glial herterotopia; and plasma cell granuloma.

The methods provided herein may provide a beneficial effect for CNS neoplasms, by administration of a catecholic butane metabolite or a combination of administration of a catecholic butane metabolite and one or more anticancer treatments.

Peripheral Nervous System (PNS) Cancers

The peripheral nervous system consists of the nerves that branch out from the brain and spinal cord. These nerves form the communication network between the CNS and the body parts. The peripheral nervous system is further subdivided into the somatic nervous system and the autonomic nervous system. The somatic nervous system consists of nerves that go to the skin and muscles and is involved in conscious activities. The autonomic nervous system consists of nerves that connect the CNS to the visceral organs such as the heart, stomach, and intestines. It mediates unconscious activities.

Acoustic neuromas are benign fibrous growths that arise from the balance nerve, also called the eighth cranial nerve or vestibulocochlear nerve. These tumors are non-malignant, meaning that they do not spread or metastasize to other parts of the body. The location of these tumors is deep inside the skull, adjacent to vital brain centers in the brain stem. As the tumors enlarge, they involve surrounding structures which have to do with vital functions. In the majority of cases, these tumors grow slowly over a period of years.

The malignant peripheral nerve sheath tumor (MPNST) is the malignant counterpart to benign soft tissue tumors such as neurofibromas and schwannomas. It is most common in the deep soft tissue, usually in close proximity of a nerve trunk. The most common sites include the sciatic nerve, brachial plexus, and sarcal plexus. The most common symptom is pain which usually prompts a biopsy. It is a rare, aggressive, and lethal orbital neoplasm that usually arises from sensory branches of the trigeminal nerve in adults. Malignant PNS tumor spreads along nerves to involve the brain, and most patients die within 5 years of clinical diagnosis. The MPNST may be classified into three major categories with epithelioid, mesenchymal or glandular characteristics. Some of the MPNST include but not limited to, Subcutaneous malignant epithelioid schwannoma with cartilaginous differentiation, Glandular malignant schwannoma, Malignant peripheral nerve sheath tumor with perineurial differentiation, Cutaneous epithelioid malignant nerve sheath tumor with rhabdoid features, Superficial epithelioid MPNST, Triton Tumor (MPNST with rhabdomyoblastic differentiation), Schwannoma with rhabdomyoblastic differentiation. Rare MPNST cases contain multiple sarcomatous tissue types, especially osteosarcoma, chondrosarcoma and angiosarcoma. These have sometimes been indistinguishable from the malignant mesenchymoma of soft tissue.

Other types of PNS cancers include but not limited to, malignant fibrous cytoma, malignant fibrous histiocytoma, malignant meningioma, malignant mesothelioma, and malignant mixed Müllerian tumor.

The methods provided herein may provide a beneficial effect for PNS cancers, by administration of a catecholic butane metabolite or a combination of administration of a catecholic butane metabolite and one or more anticancer treatments.

Oral Cavity and Oropharyngeal Cancer

Management of patients with central nervous system (CNS) cancers remains a formidable task. Cancers such as, hypopharyngeal cancer, laryngeal cancer, nasopharyngeal cancer, oropharyngeal cancer, may be treated using the compounds described herein.

The methods provided herein may provide a beneficial effect for oral cavity and oropharyngeal cancer, by administration of a catecholic butane metabolite or a combination of administration of a catecholic butane metabolite and one or more anticancer treatments Stomach Cancer Stomach cancer is the result of cell changes in the lining of the stomach. There are three main types of stomach cancers: lymphomas, gastric stromal tumors, and carcinoid tumors. Lymphomas are cancers of the immune system tissue that are sometimes found in the wall of the stomach. Gastric stromal tumors develop from the tissue of the stomach wall. Carcinoid tumors are tumors of hormone-producing cells of the stomach. The causes of stomach cancer continue to be debated. A combination of heredity and environment (diet, smoking, etc) are all thought to play a part.

The methods provided herein may provide a beneficial effect for stomach cancer, by administration of a catecholic butane metabolite or a combination of administration of a catecholic butane metabolite and one or more anticancer treatments.

Testicular Cancer

Testicular cancer is cancer that typically develops in one or both testicles in young men. Cancers of the testicle develop in certain cells known as germ cells. The 2 main types of germ cell tumors (GCTs) that occur in men are seminomas (60%) and nonseminomas (40%). Tumors can also arise in the supportive and hormone-producing tissues, or stroma, of the testicles. Such tumors are known as gonadal stromal tumors. The 2 main types are Leydig cell tumors and Sertoli cell tumors. Secondary testicular tumors are those that start in another organ and then spread to the testicle. Lymphoma is the most common secondary testicular cancer.

The methods provided herein may provide a beneficial effect for testicular cancer, by administration of a catecholic butane metabolite or a combination of administration of a catecholic butane metabolite and one or more anticancer treatments.

Thymus Cancer

The thymus is a small organ located in the upper/front portion of your chest, extending from the base of the throat to the front of the heart. The thymus contains 2 main types of cells, thymic epithelial cells and lymphocytes. Thymic epithelial cells can give origin to thymomas and thymic carcinomas. Lymphocytes, whether in the thymus or in the lymph nodes, can become malignant and develop into cancers called Hodgkin disease and non-Hodgkin lymphomas. The thymus also contains another much less common type of cells called Kulchitsky cells, or neuroendocrine cells, which normally release certain hormones. These cells can give rise to cancers, called carcinoids or carcinoid tumors that often release the same type of hormones, and are similar to other tumors arising from neuroendocrine cells elsewhere in the body.

The methods provided herein may provide a beneficial effect for thymus cancer, by administration of a catecholic butane metabolite or a combination of administration of a catecholic butane metabolite and one or more anticancer treatments.

Provided herein are methods for treating a disorder of the skin, comprising administering an effective amount of a pharmaceutical compound capable of inhibiting the tyrosine kinase activity of IGF-1R and EGFR, wherein the pharmaceutical compound is a catecholic butane metabolite.

In one aspect, the disorder of the skin is for example, a tumor, actinic keratosis, acne, psoriasis, skin wounds, warts, bacterial infections, fungal infections or viral infections. Viral infections include, but are not limited to, an HIV infection, an HPV infection and an HSV infection. Tumors include, but are not limited to, basal cell carcinomas, squamous cell carcinomas, melanomas, Dermatofibrosarcoma protuberans, Merkel cell carcinoma and Kaposi's sarcoma.

Colon Cancer and Colorectal Cancer

Colorectal cancer, also called colon cancer or large bowel cancer, includes cancerous growths in the colon, rectum and appendix. With 655,000 deaths worldwide per year, it is the third most common form of cancer and the second leading cause of cancer-related death in the Western world. Many colorectal cancers are thought to arise from adenomatous polyps in the colon. These mushroom-like growths are usually benign, but some may develop into cancer over time.

In another embodiment, Dukes classification may be used to classify colorectal cancer based on stages A-D. Stage A refers to colorectal cancer that is limited to mucosa (i.e., has not invaded through the bowel wall). Stage B1 refers to extending into muscularis propria, but not penetrating through it (i.e., lymph nodes have not been invaded); whereas Stage B2 cancer has penetrated through the muscularis propria, but not penetrating through it (i.e., lymph nodes have not been invaded). Stage C1 refers to cancer that extends into the muscularis propria, but not penetrating through it (i.e., lymph nodes are involved); whereas Stage C2 refers to cancer that extends into the muscularis propria and penetrating through it (i.e., lymph nodes are involved).

Stage D refers to distant metastatic spread. The TNM system may also be used to stage colorectal cancer according to conventional means known in the art.

The methods provided herein may provide a beneficial effect for colorectal cancer, by administration of a catecholic butane metabolite or a combination of administration of a catecholic butane metabolite and one or more anticancer treatments.

Inflammatory Diseases

A composition described herein may also be used for treatment of an inflammatory disease, such as various types of arthritis and inflammatory bowel diseases.

Inflammatory diseases are intended to include all diseases in which leukotrienes are known to play a major role or have been implicated. Non-limiting examples of inflammatory diseases that may be treated effectively by a compound described herein include, but are not limited to, rheumatoid arthritis, osteoarthritis, psoriasis, sarcoidosis, systemic lupus erythematosis, Stills disease, cystic fibrosis, chronic obstructive pulmonary disease and inflammatory bowel diseases (such as ulcerative colitis and Crohns), asthma, allergic rhinitis, inflammatory pain, adult respiratory distress syndrome, glomerulonephritis, inflammation of the skin, and virally induced inflammation (caused by CMV and other members of the Herpesviridae) leading to atherosclerosis/arteriosclerosis and subsequent coronary artery disease, among others.

Dosing

A physician or veterinarian can readily determine and prescribe the "effective amount" (ED50) of a composition required to inhibit both EGFR and IGF-1R. For example, the physician or veterinarian could start doses of the compounds employed in the composition at levels lower than that required in order to achieve the desired therapeutic effect and gradually increase the dosage until the desired effect is achieved.

A "therapeutically effective amount" as used herein, is an amount that achieves at least partially a desired therapeutic or prophylactic effect in an organ or tissue. In one example, the amount of an inhibitor to bring about prevention and/or therapeutic treatment of the disease is not fixed per se. The amount of an inhibitor administered will vary with the type of disease, extent of the disease, and size of species of the mammal suffering from the disease.

One embodiment contemplates the use of the compositions described herein to make a medicament for treating a condition, disease or disorder described herein. Medicaments can be formulated based on the physical characteristics of the patient/subject needing treatment, and can be formulated in single or multiple formulations based on the stage of the condition, disease or disorder. Medicaments can be packaged in a suitable package with appropriate labels for the distribution to hospitals and clinics wherein the label is for the indication of treating a subject having a disease described herein. Medicaments can be packaged as a single or multiple units. Instructions for the dosage and administration of the compositions can be included with the packages as described elsewhere herein.

Pharmaceutical compositions of the present embodiments may be formulated for dosage by any route of administration such as, for example, intranasal administration; oral administration; inhalation administration; subcutaneous administration; transdermal administration; intra-arterial administration, with or without occlusion; intracranial administration; intraventricular administration; intravenous administration; buccal administration; intraperitoneal administration; intraocular administration; intramuscular administration; implantation administration; and central venous administration. In one embodiment, the catecholic butane metabolite is formulated for oral administration. In another embodiment, the catecholic butane metabolite is formulated for intravenous administration.

Catecholic butane metabolites may be administered in an amount of about 5 mg/kg to about 375 mg/kg per dose; about 5 mg/kg to about 250 mg/kg per dose; about 5 mg/kg to about 200 mg/kg per dose; about 5 mg/kg to about 150 mg/kg per dose; about 5 mg/kg to about 100 mg/kg per dose; about 5 mg/kg to about 75 mg/kg per dose; or about 5 mg/kg to about 50 mg/kg per dose. Alternatively, catecholic butane metabolites may be administered a flat dose of a catecholic butane metabolite in an amount of from about 1,500 mg per day to about 2,500 mg per day; from about 1,800 mg per day to about 2,300 mg per day; or about 2,000 mg per day. In one embodiment, a catecholic butane metabolite may be contacted with target cells in a concentration in a range of about 1 µM to about 30 µM. In another embodiment, a catecholic butane metabolite may be contacted with target cells in a concentration in a range of about 1 µM to about 10 µM.

In another embodiment, NDGA may be administered in different dosing and administration schedules such as, for example: (1) twice-daily oral administration on days 1-28. Treatment repeats every 28 days in the absence of disease progression or unacceptable toxicity; (2) 2000 mg once-daily oral administration; (3) IV on days 1-5, treatment repeats every 28 days in the absence of disease progression or unacceptable toxicity; (4) dose escalation with starting schedule to a target of 20 mg/cm3 tumor volume and then, new patient cohorts will have their schedule extended to weekly administration for 4 weeks. Dose escalation will continue, assuming tolerability, so that cohorts will be treated for 6 weeks, and finally, 8 weeks; (5) IV weekly over 24 hours, dose will commence with 100 mg/hour (2400 mg in a 24-hour period) with escalation in 5 cohorts of 3 to 6 patients with increments of 25 mg per hour to a maximum of 200 mg/hr (4800 mg in a 24-hour period) or until MTD is defined; (6) topical application to the cervix; and (7) dose escalation with IV infusion for 5 consecutive days every 28 days.

In one embodiment, a pharmaceutical composition may be administered more frequently than once every 6 days for a period of time, or more frequently than once every 2 days for a period of time. In one embodiment, a pharmaceutical composition is administered daily for four weeks. In another embodiment, a pharmaceutical composition is administered three times daily for three weeks with a one week hiatus prior to starting a new cycle. In another embodiment, a pharmaceutical composition is administered daily for one week followed by a one week hiatus. In another embodiment, a pharmaceutical composition is administered daily for two weeks followed by a two week hiatus. In another embodiment, a pharmaceutical composition is administered one time or two times daily continuously or with a one week hiatus prior to starting a new cycle. In yet another embodiment, a pharmaceutical composition is administered one time per week or two times per week. One would understand that, as needed, where cycles of treatment are considered, a patient may be assessed and the treatment repeated as needed.

In various embodiments, a catecholic butane metabolite may be prepared as a free base or a pharmaceutically acceptable salt, solvate, polymorph, ester, tautomer or pro-drug thereof. Also described, are pharmaceutical compositions comprising a catecholic butane metabolite or a pharmaceutically acceptable salt, solvate, polymorph, ester, tautomer or prodrug thereof. The compounds and compositions described herein may be administered either alone or in combination with pharmaceutically acceptable carriers, excipients or diluents, in a pharmaceutical composition, according to standard pharmaceutical practice.

In addition to the aforementioned examples and embodiments of dosages, cycles, and schedules of cycles, numerous permutations of the aforementioned dosages, cycles, and schedules of cycles for the co-administration of a compound with a second chemotherapeutic compound, radiotherapy, or surgery are contemplated herein and can be administered according to the patient, type of cancer, and/or appropriate treatment schedule as determined by qualified medical professionals.

In various embodiments, a therapeutically equivalent amount of a catecholic butane metabolite dose described herein is used.

In various embodiments, the catecholic butane metabolite is dosed in so as to minimize toxicity to the patient. In some embodiments, the catecholic butane metabolite is dosed in a manner adapted to provide particular pharmacokinetic (PK) parameters in a human patient. In some embodiments, the catecholic butane metabolite is dosed in a manner adapted to provide a particular maximum blood concentration ($C_{max}$) of the catecholic butane metabolite. In some embodiments, the catecholic butane metabolite is dosed in a manner adapted to provide a particular time ($T_{max}$) at which a maximum blood concentration of the catecholic butane metabolite is obtained. In some embodiments, the catecholic butane metabolite is dosed in a manner adapted to provide a particular area under the blood plasma concentration curve (AUC) for the catecholic butane metabolite. In some embodiments, the catecholic butane metabolite is dosed in a manner to provide a particular clearance rate (CL/F) or a particular half-life ($T_{1/2}$) for the catecholic butane metabolite. Unless otherwise specified herein, the PK parameters recited herein, including in the appended claims, refer to mean PK values for a cohort of at least 3 patients under the same dosing schedule. Thus, unless otherwise specified: AUC=mean AUC for a cohort of at least 3 patients; $C_{max}$=mean $C_{max}$ for a cohort of at least 3 patients; $T_{max}$=mean $T_{max}$ for a cohort of at least 3 patients; $T_{1/2}$=mean $T_{1/2}$ for a cohort of at least 3 patients; and CL/F=mean CL/F for a cohort of at least 3 patients. In some embodiments, the mean is a cohort of at least 6 patients, or at least 12 patients or at least 24 patients or at least 36 patients. Where other than mean PK values are intended, it will be indicated that the value pertains to individuals only. Also, unless otherwise indicated herein, AUC refers to the mean AUC for the cohort of at least 3 patients, extrapolated to infinity following a standard clearance model. If AUC for a time certain is intended, the start (x) and end (y) times will be indicated by suffix appellation to "AUC" (e.g., $AUC_{x,y}$). In one embodiment, the solubility of NDGA is about 8 μg/mL in intestinal fluids.

In one embodiment of the methods described herein, a patient exhibits an improvement in one or more symptoms of said proliferative disease or inflammatory disease of at least about a 2-fold, 5-fold, 10-fold, 15-fold, 20-fold, 25-fold, 30-fold, 35-fold, 40-fold, 45-fold, 50-fold or greater amount following administration of a metabolite of NDGA than a patient not receiving administration of a metabolite of NDGA.

In another embodiment of the methods described herein, a patient exhibits an improvement in one or more symptoms of said proliferative disease or inflammatory disease of at least about a 2-fold, 5-fold, 10-fold, 15-fold, 20-fold, 25-fold, 30-fold, 35-fold, 40-fold, 45-fold, 50-fold or greater amount following administration of a metabolite of NDGA than a patient administered a placebo.

In one embodiment of the methods described herein, a patient exhibits an improvement in one or more symptoms of said proliferative disease or inflammatory disease of about 2%, 5%, 10%, 15%, 20%, 25%, 30%, 35%, 40%, 45%, 50% or greater amount following administration of a metabolite of NDGA than a patient not receiving administration of a metabolite of NDGA.

In another embodiment of the methods described herein, a patient exhibits an improvement in one or more symptoms of said proliferative disease or inflammatory disease of at least about a 2%, 5%, 10%, 15%, 20%, 25%, 30%, 35%, 40%, 45%, 50% or greater amount following administration of a metabolite of NDGA than a patient administered a placebo.

Assessment and Diagnostics

Provided herein is a method of selecting a subject for treatment with a catecholic butane, comprising: (a) measuring the concentration of a catecholic butane metabolite in a sample obtained from said subject; and (b) administering to said subject a catecholic butane for treatment of a disease or disorder only if the concentration of the catecholic butane metabolite of (a) is above at least about 0.5 μg/mL.

Provided herein is a method of selecting a subject for treatment with a compound described herein, comprising: (a) measuring the concentration of a catecholic butane metabolite in a sample obtained from said subject; and (b) administering to said subject a catecholic butane metabolite, and/or a phosphate ester thereof, if the concentration of the catecholic butane metabolite of (a) is less than about 0.5 μg/mL.

In one embodiment, the sample to be tested is any fluid that may be extracted from a patient including, but not limited to, blood, plasma, serum, sputum, saliva, cerebrospinal fluid, sweat, urine, tears, and tissue extract, including tumor tissue, cell extract, tissue and organ extract.

Measuring may comprise any method by which one or more metabolites in the sample may be quantitatively or semi-quantitatively measured. In one embodiment, measuring comprises mass spectroscopy (MS), nuclear magnetic resonance (NMR), high phase liquid chromatography (HPLC), infrared (IR) UV/Vis spectroscopy, HPLC-MS, ELISA or any antibody-based assay.

Samples may be obtained from a patient one or more times prior to commencement of treatment, during one or more time points during treatment, or one or more times after treatment is stopped. Patients may be monitored for effectiveness of treatment using any of the methods described herein or in the examples below.

In one non-limiting example of such methods, measuring comprises: semi-quantitatively measuring the levels of one or more metabolites comprising mass spectrometry with high resolution accurate mass measurements; wherein said method comprises a pre-scan, an FT analyzer to perform a slow survey scan at high resolution (HRMS) and, in parallel, a LTQ ion trip to acquire MS(n) data using a data-dependent acquisition (DDA) event. The DDA comprises a decision event and two $MS^2$ product ion scans to select the two most intense ions detected in the pre-scan which are on the parent mass list. Data may be processed using Metworks™ software (v 1.3.0, Thermo) and data is processed using two steps: (1) subtraction of the chromatogram of a control sample (solvent control in blank matrix) from the analyzed sample, leading to creation of a "SUB" file. This file contains peaks of components unique to the analyzed sample and peaks of components with intensities in the analyzed sample at least two times higher (S/N ratio) than in the control sample. (2) A search for major unique peaks present in "SUB" ("chro" search) is conducted for comprehensive metabolite detection and, finally, the "SUB" file and the results of automatic detection are evaluated.

Following assessment of a subject using such methods, a subject may be administered one or more catecholic butane metabolites described herein or may be administered a one or more various anti-neoplastic chemotherapeutic agents, chemopreventative agents, side-effect limiting agents, and/or anti-neoplastic treatments (e.g., surgery) as described in more detail below.

Combination Therapy

One aspect of the embodiments described herein provides methods for treating cancer using different combinations of treatment regimens. For example, such catecholic butane metabolite compounds in conjunction with one or more various anti-neoplastic chemotherapeutic agents, chemopreventative agents, side-effect limiting agents, and/or anti-neoplastic treatments (e.g., surgery).

In any of such methods provided herein, a subject may be further administered one or more additional anti cancer agents. As described above, these additional cancer therapies can be, for example, surgery, radiation therapy, administration of chemotherapeutic agents and combinations of any two or all of these methods. Combination treatments may occur sequentially or concurrently and the combination therapies may be neoadjuvant therapies or adjuvant therapies. Anti-cancer agents include, but are not limited to, DNA damaging agents, topoisomerase inhibitors and mitotic inhibitors. Many chemotherapeutics are presently known in the art and can be used in combination with the compounds described herein. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

In one embodiment, the subject to be treated may be resistant to treatment with an EGFR inhibitor alone, an IGF-1R inhibitor alone, or an EGFR inhibitor and an IGF-1R inhibitor.

As used herein, the terms "cancer treatment," "cancer therapy" and the like encompasses treatments such as surgery such as cutting, abrading, ablating (by physical or chemical means, or a combination of physical or chemical means), suturing, lasering or otherwise physically changing body tissues and organs), radiation therapy, administration of chemotherapeutic agents and combinations of any two or all of these methods. Combination treatments may occur sequentially or concurrently. Treatments, such as radiation therapy and/or chemotherapy, that are administered prior to surgery, are referred to as neoadjuvant therapy. Treatments, such as radiation therapy and/or chemotherapy, administered after surgery is referred to herein as adjuvant therapy. Examples of surgeries that may be used for cancer treatment include, but are not limited to radical prostatectomy, cryotherapy, mastectomy, lumpectomy, transurethral resection of the prostate, and the like.

Many chemotherapeutic agents are known and operate via a wide variety of modes of action. In some non-limiting embodiments, the chemotherapeutic agent is a cytotoxic agent, an anti-proliferative, a targeting agent (such as kinase inhibitors and cell cycle regulators), a protease inhibitor, or a biologic agent (such as cytokines, vaccines, viral agents, and other immunostimulants such as BCG, hormones, monoclonal antibodies and siRNA). The nature of a combination therapy involving administration of a chemotherapeutic agent will depend upon the type of agent being used.

Where combination treatments are contemplated, it is not intended that an inhibitor be limited by the particular nature of the combination. For example, an inhibitor may be administered in combination as simple mixtures as well as chemical hybrids. An example of the latter is where the compound is covalently linked to a targeting carrier or to an active pharmaceutical. Covalent binding can be accomplished in many ways, such as, though not limited to, the use of a commercially available cross-linking compound.

As used herein, the terms "pharmaceutical combination," "administering an additional therapy," "administering an additional therapeutic agent" and the like refer to a pharmaceutical therapy resulting from the mixing or combining of more than one active ingredient and includes both fixed and non-fixed combinations of the active ingredients. The term "fixed combination" means that an inhibitor, and at least one co-agent, are both administered to a patient simultaneously in the form of a single entity or dosage. The term "non-fixed combination" means that an inhibitor, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g., the administration of three or more active ingredients.

As used herein, the terms "co-administration," "administered in combination with" and their grammatical equivalents or the like are meant to encompass administration of the selected therapeutic agents to a single patient, and are intended to include treatment regimens in which the agents are administered by the same or different route of administration or at the same or different times. In some embodiments, an inhibitor will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, an inhibitor and the other agent(s) are administered in a single composition. In some embodiments, an inhibitor and the other agent(s) are admixed in the composition.

As used herein, "anti-cancer agents or treatments" refer to, but are not limited to, a chemotherapeutic agent, a nucleic acid damaging agent, a nucleic acid damaging treatment, an anticancer antibody, an anti-proliferative agent, or an anti-proliferative treatment to the subject. One would understand that the listing of therapeutic regimens listed below represents conventional therapies, but the present embodiments encompass other known therapeutic regimens which are not specifically disclosed herein.

Suitable anti-neoplastic chemotherapeutic agents to be used in the present methods include, but are not limited to, alkylating agents, antimetabolites, natural anti-neoplastic agents, hormonal anti-neoplastic agents, angiogenesis inhibitors, differentiating reagents, RNA inhibitors, antibodies or immunotherapeutic agents, gene therapy agents, small molecule enzymatic inhibitors, biological response modifiers, and anti-metastatic agents.

Alkylating Agents

Alkylating agents are known to act through the alkylation of macromolecules such as the DNA of cancer cells, and are usually strong electrophiles. This activity can disrupt DNA synthesis and cell division. Examples of alkylating reagents suitable for use herein include nitrogen mustards and their analogues and derivatives including, cyclophosphamide, ifosfamide, chlorambucil, estramustine, mechlorethamine hydrochloride, melphalan, and uracil mustard. Other examples of alkylating agents include alkyl sulfonates (e.g. busulfan), nitrosoureas (e.g. carmustine, lomustine, and streptozocin), triazenes (e.g. dacarbazine and temozolomide), ethylenimines/methylmelamines (e.g. altretamine and thiotepa), and methylhydrazine derivatives (e.g. procarbazine). Included in the alkylating agent group are the alkylating-like platinum-containing drugs comprising carboplatin, cisplatin, and oxaliplatin.

Antimetabolites

Antimetabolic anti-neoplastic agents structurally resemble natural metabolites, and are involved in normal metabolic processes of cancer cells such as the synthesis of nucleic acids and proteins. They differ enough from the natural metabolites so that they interfere with the metabolic processes of cancer cells. Suitable antimetabolic anti-neoplastic agents to be used in the present methods can be classified according to the metabolic process they affect, and can include, but are not limited to, analogues and derivatives of folic acid, pyrimidines, purines, and cytidine. Members of the folic acid group of agents suitable for use herein include, but are not limited to, methotrexate (amethopterin), pemetrexed and their analogues and derivatives. Pyrimidine agents suitable for use herein include, but are not limited to, cytarabine, floxuridine, fluorouracil (5-fluorouracil), capecitabine, gemcitabine, and their analogues and derivatives. Purine agents suitable for use herein include, but are not limited to, mercaptopurine (6-mercaptopurine), pentostatin, thioguanine, cladribine, and their analogues and derivatives. Cytidine agents suitable for use herein include, but are not limited to, cytarabine (cytosine arabinodside), azacitidine (5-azacytidine) and their analogues and derivatives.

Natural Anti-Neoplastic Agents

Natural anti-neoplastic agents comprise antimitotic agents, antibiotic anti-neoplastic agents, camptothecin analogues, and enzymes. Antimitotic agents suitable for use herein include, but are not limited to, vinca alkaloids like vinblastine, vincristine, vindesine, vinorelbine, and their analogues and derivatives. They are derived from the Madagascar periwinkle plant and are usually cell cycle-specific for the M phase, binding to tubulin in the microtubules of cancer cells. Other antimitotic agents suitable for use herein are the podophyllotoxins, which include, but are not limited to etoposide, teniposide, and their analogues and derivatives. These reagents predominantly target the G2 and late S phase of the cell cycle.

Also included among the natural anti-neoplastic agents are the antibiotic anti-neoplastic agents. Antibiotic anti-neoplastic agents are antimicrobial drugs that have anti-tumor properties usually through interacting with cancer cell DNA. Antibiotic anti-neoplastic agents suitable for use herein include, but are not limited to, belomycin, dactinomycin, doxorubicin, idarubicin, epirubicin, mitomycin, mitoxantrone, pentostatin, plicamycin, and their analogues and derivatives.

The natural anti-neoplastic agent classification also includes camptothecin analogues and derivatives which are suitable for use herein and include camptothecin, topotecan, and irinotecan. These agents act primarily by targeting the nuclear enzyme topoisomerase I. Another subclass under the natural anti-neoplastic agents is the enzyme, L-asparaginase and its variants. L-asparaginase acts by depriving some cancer cells of L-asparagine by catalyzing the hydrolysis of circulating asparagine to aspartic acid and ammonia.

Hormonal Anti-Neoplastic Agents

Hormonal anti-neoplastic agents act predominantly on hormone-dependent cancer cells associated with prostate tissue, breast tissue, endometrial tissue, ovarian tissue, lymphoma, and leukemia. Such tissues may be responsive to and dependent upon such classes of agents as glucocorticoids, progestins, estrogens, and androgens. Both analogues and derivatives that are agonists or antagonists are suitable to treat tumors. Examples of glucocorticoid agonists/antagonists suitable for use herein are dexamethasone, cortisol, corticosterone, prednisone, mifepristone (RU486), their analogues and derivatives. The progestin agonist/antagonist subclass of agents suitable for use herein includes, but is not limited to, hydroxyprogesterone, medroxyprogesterone, megestrol acetate, mifepristone (RU486), ZK98299, their analogues and derivatives. Examples from the estrogen agonist/antagonist subclass of agents suitable for use herein include, but are not limited to, estrogen, tamoxifen, toremifene, RU58668, SR16234, ZD164384, ZK191703, fulvestrant, their analogues and derivatives. Examples of aromatase inhibitors suitable for use herein, which inhibit estrogen production, include, but are not limited to, androstenedione, formestane, exemestane, aminoglutethimide, anastrozole, letrozole, their analogues and derivatives. Examples from the androgen agonist/antagonist subclass of agents suitable for use herein include, but are not limited to, testosterone, dihydrotestosterone, fluoxymesterone, testolactone, testosterone enanthate, testosterone propionate, gonadotropin-releasing hormone agonists/antagonists (e.g. leuprolide, goserelin, triptorelin, buserelin), diethylstilbestrol, abarelix, cyproterone, flutamide, nilutamide, bicalutamide, their analogues and derivatives.

Angiogenesis Inhibitors

Angiogenesis inhibitors work by inhibiting the vascularization of tumors. Angiogenesis inhibitors encompass a wide variety of agents including small molecule agents, antibody agents, and agents that target RNA function. Examples of angiogenesis inhibitors suitable for use herein include, but are not limited to, ranibizumab, bevacizumab, SU11248, PTK787, ZK222584, CEP-7055, angiozyme, dalteparin, thalidomide, suramin, CC-5013, combretastatin A4 Phosphate, LY317615, soy isoflavones, AE-941, interferon alpha, PTK787/ZK 222584, ZD6474, EMD 121974, ZD6474, BAY 543-9006, celecoxib, halofuginone hydrobromide, bevacizumab, their analogues, variants, or derivatives.

Differentiating Reagents

Differentiating agents inhibit tumor growth through mechanisms that induce cancer cells to differentiate. One such subclass of these agents suitable for use herein includes, but is not limited to, vitamin A analogues or retinoids, and peroxisome proliferator-activated receptor agonists (PPARs). Retinoids suitable for use herein include, but are not limited to, vitamin A, vitamin A aldehyde (retinal), retinoic acid, fenretinide, 9-cis-retinoid acid, 13-cis-retinoid acid, all-trans-retinoic acid, isotretinoin, tretinoin, retinal palmitate, their analogues and derivatives. Agonists of PPARs suitable for use herein include, but are not limited to, troglitazone, ciglitazone, tesaglitazar, their analogues and derivatives.

RNA Inhibitors

Certain RNA inhibiting agents may be utilized to inhibit the expression or translation of messenger RNA ("mRNA") that is associated with a cancer phenotype. Examples of such agents suitable for use herein include, but are not limited to, short interfering RNA ("siRNA"), ribozymes, and antisense oligonucleotides. Specific examples of RNA inhibiting agents suitable for use herein include, but are not limited to, Candy, Sirna-027, fomivirsen, and angiozyme.

Antibodies/Immunotherapeutic Agents

Antibody agents bind targets selectively expressed in cancer cells and can either utilize a conjugate to kill the cell associated with the target, or elicit the body's immune response to destroy the cancer cells. Immunotherapeutic agents can either be comprised of polyclonal or monoclonal antibodies. The antibodies may be comprised of non-human animal (e.g. mouse) and human components, or be comprised of entirely human components ("humanized antibodies"). Examples of monoclonal immunotherapeutic agents suitable for use herein include, but are not limited to, rituximab, tosibtumomab, ibritumomab which target the CD-20 protein. Other examples suitable for use herein include trastuzumab, edrecolomab, bevacizumab, cetuximab, carcinoembryonic antigen antibodies, gemtuzumab, alemtuzumab, mapatumumab, panitumumab, EMD 72000, TheraCIM hR3, 2C4, HGS-TR2J, and HGS-ETR2.

Gene Therapy Agents

Gene therapy agents insert copies of genes into a specific set of a patient's cells, and can target both cancer and non-cancer cells. The goal of gene therapy can be to replace altered genes with functional genes, to stimulate a patient's immune response to cancer, to make cancer cells more sensitive to chemotherapy, to place "suicide" genes into cancer cells, or to inhibit angiogenesis. Genes may be delivered to target cells using viruses, liposomes, or other carriers or vectors. This may be done by injecting the gene-carrier composition into the patient directly, or ex vivo, with infected cells being introduced back into a patient. Such compositions are suitable for use in the present methods.

Small Molecule Enzymatic Inhibitors

Certain small molecule therapeutic agents are able to target the tyrosine kinase enzymatic activity or downstream signal transduction signals of certain cell receptors such as epidermal growth factor receptor ("EGFR") or vascular endothelial growth factor receptor ("VEGFR"). Such targeting by small molecule therapeutics can result in anti-cancer effects. Examples of such agents suitable for use herein include, but are not limited to, imatinib, gefitinib, erlotinib, lapatinib, canertinib, ZD6474, sorafenib (BAY 43-9006), ERB-569, and their analogues and derivatives.

Biological Response Modifiers

Certain protein or small molecule agents can be used in anti-cancer therapy through either direct anti-tumor effects or through indirect effects. Examples of direct-acting agents suitable for use herein include, but are not limited to, differentiating reagents such as retinoids and retinoid derivatives. Indirect-acting agents suitable for use herein include, but are not limited to, agents that modify or enhance the immune or other systems such as interferons, interleukins, hematopoietic growth factors (e.g. erythropoietin), and antibodies (monoclonal and polyclonal).

Protease Inhibitors

One or more protease inhibitors may be used in combination with a compound described herein. In one embodiment, the protease inhibitor is a low solubility compound (e.g., amprenavir) and a compound described herein (e.g., a phosphate prodrug) may be administered to improve absorption of low-solubility compounds (e.g., amprenavir). The phosphate in cleaved off at the surface of the enterocyte, creating a local supersaturated solution of free drug that is rapidly absorbed.

Anti-Metastatic Agents

The process whereby cancer cells spread from the site of the original tumor to other locations around the body is termed cancer metastasis. Certain agents have anti-metastatic properties, designed to inhibit the spread of cancer cells. Examples of such agents suitable for use herein include, but are not limited to, marimastat, bevacizumab, trastuzumab, rituximab, erlotinib, MMI-166, GRN163L, hunter-killer peptides, tissue inhibitors of metalloproteinases (TIMP5), their analogues, derivatives and variants.

Chemopreventative Agents

Certain pharmaceutical agents can be used to prevent initial occurrences of cancer, or to prevent recurrence or metastasis. Administration with such chemopreventative agents in combination with one or more other anticancer agents including the catecholic butane metabolites can act to both treat and prevent the recurrence of cancer. Examples of chemopreventative agents suitable for use herein include, but are not limited to, tamoxifen, raloxifene, tibolone, bisphosphonate, ibandronate, estrogen receptor modulators, aromatase inhibitors (letrozole, anastrozole), luteinizing hormone-releasing hormone agonists, goserelin, vitamin A, retinal, retinoic acid, fenretinide, 9-cis-retinoid acid, 13-cis-retinoid acid, all-trans-retinoic acid, isotretinoin, tretinoid, vitamin B6, vitamin B12, vitamin C, vitamin D, vitamin E, cyclooxygenase inhibitors, non-steroidal anti-inflammatory drugs (NSAIDs), aspirin, ibuprofen, celecoxib, polyphenols, polyphenol E, green tea extract, folic acid, glucaric acid, interferon-alpha, anethole dithiolethione, zinc, pyridoxine, finasteride, doxazosin, selenium, indole-3-carbinal, alpha-difluoromethylornithine, carotenoids, beta-carotene, lycopene, antioxidants, coenzyme Q10, flavonoids, quercetin, curcumin, catechins, epigallocatechin gallate, N-acetylcysteine, indole-3-carbinol, inositol hexaphosphate, isoflavones, glucanic acid, rosemary, soy, saw palmetto, and calcium.

Side-Effect Limiting Agents

Treatment of cancer with catecholic butane metabolite alone or in combination with other anti-neoplastic compounds may be accompanied by administration of pharmaceutical agents that can alleviate the side effects produced by the anti-neoplastic agents. Such agents suitable for use herein include, but are not limited to, anti-emetics, anti-mucositis agents, pain management agents, infection control agents, and anti-anemia/anti-thrombocytopenia agents. Examples of anti-emetics suitable for use herein include, but are not limited to, 5-hydroxytryptamine 3 receptor antagonists, metoclopramide, steroids, lorazepam, ondansetron, cannabinoids, their analogues and derivatives. Examples of anti-mucositis agents suitable for use herein include, but are not limited to, palifermin (keratinocyte growth factor), glucagon-like peptide-2, teduglutide, L-glutamine, amifostin, and fibroblast growth factor 20. Examples of pain management agents suitable for use herein include, but are not limited to, opioids, opiates, and non-steroidal anti-inflammatory compounds. Examples of agents used for control of infection suitable for use herein include, but are not limited to, antibacterials such as aminoglycosides, penicillins, cephalosporins, tetracyclines, clindamycin, lincomycin, macrolides, vancomycin, carbapenems, monobactams, fluoroquinolones, sulfonamides, nitrofurantoins, their analogues and derivatives. Examples of agents that can treat anemia or thrombocytopenia associated with chemotherapy suitable for use herein include, but are not limited to, erythropoietin, and thrombopoietin.

Several other suitable therapies for use in combination with a catecholic butane metabolite and other compounds described herein are also available. For example, see *Goodman & Gilman's The Pharmacological Basis of Therapeutics* 11th ed. Brunton L L, Lazo J S, and Parker K L, ed. McGraw-Hill, New York, 2006.

Ovarian Cancer

In one embodiment, the cancer is ovarian cancer and the one or more therapeutic treatments is surgery, chemotherapy (e.g., doxorubicin, doxil, gemcitabine, Rubitecan, and platinum-based chemotherapeutics such as cisplatin, carboplatin and oxaliplatin), melphalan, paclitaxel, topoisomerase I inhibitors such as topotecan and irinotecan, taxane-based therapy, hormones, radiation therapy, whole body hypothermia, isoflavone derivatives such as Phenoxodial, cytotoxic macrolides such as Epothilones, angiogenesis inhibitors such as bevacizumab, signal transduction inhibitors such as trastuzumab, gene therapy, RNAi therapy, immunotherapy, monoclonal antibodies, phosphatidylinositol-like kinase inhibitors such as rapamycin, or any combination thereof. In yet another embodiment the therapeutic treatment is a VEGF receptor inhibitor. Non-limiting examples of VEGF receptor inhibitors include bevacizumab (AVASTIN®), ranibizumab (LUCENTIS®), VEGF-Trap, sunitinib (SUTENT®), sorafenib (NEXAVAR®), axitinib, pegaptanib and pazopanib.

Liver Cancer

In one embodiment, the cancer is liver cancer and the one or more anticancer treatments is, for example, surgery, immunotherapy, radiation therapy, chemotherapy and percutaneous ethanol injection. The types of surgery that may be used are cryosurgery, partial hepatectomy, total hepatectomy and radiofrequency ablation. Radiation therapy may be external beam radiation therapy, brachytherapy, radiosensitizers or radiolabel antibodies. Other types of treatment include hyperthermia therapy and immunotherapy.

Skin Cancer

Different types of treatment are available for patients with non-melanoma and melanoma skin cancer and actinic keratosis including surgery, radiation therapy, chemotherapy and photodynamic therapy. Some possible surgical options for treatment of skin cancer are mohs micrographic surgery, simple excision, electrodesiccation and curettage, cryosurgery, laser surgery. Radiation therapy may be external beam radiation therapy or brachytherapy. Other types of treatments that are being tested in clinical trials are biologic therapy or immunotherapy, chemoimmunotherapy, topical chemotherapy with fluorouracil and photodynamic therapy.

Endometrium Cancer

In one embodiment, the cancer is endometrium cancer and the one or more anticancer treatments is, for example, surgery, radiation therapy, chemotherapy, gene therapy, photodynamic therapy, antiangiogenesis therapy, and immunotherapy, or a combination thereof.

Renal/Kidney Cancer

In one embodiment, the cancer is renal/kidney cancer and the one or more therapeutic treatments is surgery, chemotherapy, bevacizumab (AVASTIN®), ranibizumab (LUCENTIS®), VEGF-Trap, sunitinib (SUTENT®), sorafenib (NEXAVAR®), axitinib, pegaptanib, pazopanib, interferon-alpha, IL-2, or any combination thereof.

Testicular Cancer

In one embodiment, the cancer is testicular cancer and the one or more anticancer treatments is, for example, surgery, immunotherapy, chemotherapy, radiation therapy, combination of chemotherapy and radiation therapy or biological therapy. Several drugs are typically used to treat testicular cancer: Platinol (cisplatin), Vepesid or VP-16 (etoposide) and Blenoxane (bleomycin sulfate). Additionally, Ifex (ifosamide), Velban (vinblastine sulfate) and others may be used.

Stomach Cancer

In one embodiment, the cancer is testicular cancer and the one or more anticancer treatments is, for example, surgery, immunotherapy, chemotherapy, radiation therapy, combination of chemotherapy and radiation therapy or biological therapy.

Thymus Cancer

In one embodiment, the cancer is thymus cancer and the one or more anticancer treatments is, for example, surgery, immunotherapy, chemotherapy, radiation therapy, combination of chemotherapy and radiation therapy or biological therapy. Anticancer drugs that have been used in the treatment of thymomas and thymic carcinomas are doxorubicin (Adriamycin), cisplatin, ifosfamide, and corticosteroids (prednisone). Often, these drugs are given in combination to increase their effectiveness. Combinations used to treat thymic cancer include cisplatin, doxorubicin, etoposide and cyclophosphamide, and the combination of cisplatin, doxorubicin, cyclophosphamide, and vincristine.

Myeloma

In one embodiment, the cancer is myeloma and the one or more therapeutic treatments is surgery, radiotherapy, VELCADE®, lenalidomide, or thalidomide, or a combination thereof. In one embodiment, the therapeutic treatment is VELCADE®. The dosages for any of these therapies are known in the art and can be adjusted with combination therapy accordingly.

Prostate Cancer

In one embodiment, the cancer is prostate cancer and the one or more therapeutic treatments is surgery, radiotherapy (e.g., external beam or brachytherapy), hormonal deprivation (androgen suppression), heat shock protein 90 (HSP90) inhibitors, chemotherapy (e.g., docetaxel, platinum-based chemotherapy such as cisplatin, carboplatin, satraplatin and oxaliplatin, taxane, estramustine), prednisone or prednisolone, cholesterol-lowering drugs such as statins, leutinizing hormone-releasing hormone (LHRH) agonists, RNAi therapy, whole tumor cells genetically modified to secrete granulocyte macrophage-colony stimulating factor (GM-CSF) (also known as GVAX), or any combination thereof. In yet another embodiment, the one or more therapeutic treatments is a VEGF receptor inhibitor. Non-limiting examples of VEGF receptor inhibitors include bevacizumab (AVASTIN®), ranibizumab (LUCENTIS®), VEGF-Trap, sunitinib (SUTENT®), sorafenib (NEXAVAR®), axitinib, pegaptanib and pazopanib.

Lung Cancer

In one embodiment, the cancer is lung cancer and the one or more therapeutic treatments is surgery, radiotherapy (e.g., thoracic radiotherapy, radiation therapy with charged particles, Uracil-tegafur and Platinum-based chemotherapy (e.g., cisplatin, carboplatin, oxaliplatin, etc.) and vinorebline, Erlotinib (TARCEVA®), Gefitinib (IRESSA®), anti-epidermal growth factor receptor antibodies (e.g., Cetuximab), anti-vascular endothelial growth factor antibodies (e.g., Bevacizumab), small molecule inhibitors of tyrosine kinases, direct inhibitors of proteins involved in lung cancer cell proliferation, Aurora kinase inhibitors, laser-induced thermotherapy, RNAi therapy, whole tumor cells genetically modified to secrete granulocyte macrophage-colony stimulating factor (GM-CSF) (also known as GVAX), bevacizumab (AVASTIN®), ranibizumab (LUCENTIS®), VEGF- Trap, sunitinib (SUTENT®), sorafenib (NEXAVAR®), axitinib, pegaptanib and pazopanib, or any combination thereof. Additional therapeutic treatments include Taxol and pemetrexed. The dosages for any of these therapies are known in the art and can be adjusted with combination therapy accordingly.

Breast Cancer

In one embodiment, the cancer is breast cancer and the one or more therapeutic treatments is surgery, monoclonal antibodies (e.g., Her-2 antibodies, herceptin, bevacizumab (AVASTIN®), ranibizumab (LUCENTIS®), sunitinib (SUTENT®), sorafenib (NEXAVAR®), axitinib, pegaptanib and pazopanib), adjuvant chemotherapy such as single agent chemotherapy or combination chemotherapy (e.g., anthracycline- and taxane-based polychemotherapies, taxol, or target-specific trastuzumab with or without endocrine manipulation with or without PMRT, vinorelbine), VEGF-Trap, xeloda, taxotere, adriamycin, cyclophosphamide, xeloda, taxotere, selective estrogen receptor modulators such as Tamoxifen and Raloxifene, allosteric estrogen receptor modulators such as Trilostane, radiation (e.g., interstitial brachytherapy, Mammosite device, 3-dimensional conformal external radiation and intraoperative radiotherapy), Aromatase inhibitors that suppress total body synthesis (e.g., anastrozole, exemestane and letrozole), RNAi therapy, intravenous analogs of rapamycin that are immunosuppressive and anti-proliferative such as Temsirolimus (CCI779), or any combination thereof. The dosages for any of these therapies are known in the art and can be adjusted with combination therapy accordingly.

Colon Cancer

In one embodiment, the cancer is colon cancer and the one or more therapeutic treatments is surgery, radiation therapy, and chemotherapy (e.g., 5-fluorouracil, levamisole, leucovorin or semustine (methyl CCNU)), N[2-(dimethylamino) ethyl]acridine-4-carboxamide and other related carboxamide anticancer drugs; non-topoisomerase II inhibitors, irinotecan, liposomal topotecan, taxane class of anticancer agents (e.g., paclitaxel or docetaxel), a compound of the xanthenone acetic acid class (e.g., 5,6-dimethylanthenone-4-acetic acid PMAA), laminarin, site-selective cyclic AMP Analogs (e.g., 8-chloroadenosine 3',5'-cyclic phosphate), pyranoindole inhibitors of Cox-2, carbazole inhibitors of Cox-2, tetrahydrocarbazole inhibitors of Cox-2, indene inhibitors of Cox-2, localized inhibitors of NSAIDS (e.g., anthranilic acids, aspirin (5-acetylsalicylic acid), azodisal sodium, carboheterocyclic acids, carprofen, chlorambucil, diclophenac, fenbufen, fenclofenac, fenoprofen, flufenamic acid, flurbiprofen, fluprofen, furosemide, gold sodium thiomalate, ibuprofen, indomethacin, indoprofen, ketoprofen, lonazolac, loxoprofen, meclofenamic acid, mefanamic acid, melphalan, naproxen, penicillamine, phenylacetic acids, proprionic acids, salicylic acids, salazosulfapyridine, sulindac, tolmetin, a pyrazolone butazone propazone NSAID, meloxicam, oxicams, piroxicam, feldene, piroxicam beta cyclodextran, tenoxicam, etodolac, and oxaprozin), an inhibitor of HER-2/neu, RNAi therapy, GM-CSF, monoclonal antibodies (e.g., anti-Her-2/neu antibodies, anti-CEA antibodies, A33 (HB 8779), 100-210 (HB 11764) and 100-310 (HB 11028)), bevacizumab (AVASTIN®), ranibizumab (LUCENTIS®), VEGF-Trap, sunitinib (SUTENT®), sorafenib (NEXAVAR®), axitinib, pegaptanib pazopanib, and erbitux), vectibix, hormonal therapy, pyrimidineamines, camptothecin derivatives (e.g., CPT-11), folinic acid (FA), Gemcitabine, Ara-C, platinum-based chemotherapeutics such as cisplatin, carboplatin and oxaliplatin, a cGMP-specific phosphodiesterase inhibitor, or any combination thereof. The dosages for any of these therapies are known in the art and can be adjusted with combination therapy accordingly.

Pancreatic Cancer

In one embodiment, the cancer is pancreatic cancer and the one or more therapeutic treatments is surgery, radiation therapy (RT), Fluorouracil (5-FU) and RT, systemic therapy, stenting, Gemcitabine (GEMZAR®), Gemcitabine and RT, Cetuximab, erlotinib (TARCEVA®), chemoradiation, bevacizumab (AVASTIN®), or any combination thereof. The dosages for any of these therapies are known in the art and can be adjusted with combination therapy accordingly.

Cervical Cancer

In one embodiment, the cancer is cervical cancer and the one or more anticancer treatments include, but are not limited to, surgery, immunotherapy, radiation therapy and chemotherapy. Some possible surgical options are cryosurgery, a hysterectomy, and a radical hysterectomy. Radiation therapy for cervical cancer patients includes external beam radiation therapy or brachytherapy. Anti-cancer drugs that may be administered as part of chemotherapy to treat cervical cancer include cisplatin, carboplatin, hydroxyurea, irinotecan, bleomycin, vincristine, mitomycin, ifosfamide, fluorouracil, etoposide, methotrexate, and combinations thereof.

Thyroid Cancer

In one embodiment, the cancer is thyroid cancer and the one or more anticancer treatments include, but are not limited to, surgery, immunotherapy, radiation therapy, hormone therapy and chemotherapy. Surgery is the most common treatment of thyroid cancer. Some possible surgical options for treatment of thyroid cancer are lobectomy, near-total thyroidectomy, total thyroidectomy and lymph node dissection. Radiation therapy may be external radiation therapy or may required intake of a liquid that contains radioactive iodine. Hormone therapy uses hormones to stop cancer cells from growing. In treating thyroid cancer, hormones can be used to stop the body from making other hormones that might make cancer cells grow.

EGFR Inhibitor Resistance and EGFR Inhibitors

Over-expression of the epidermal growth factor receptor (EGFR), or its ligand TGFα, is frequently associated with, for example, breast, lung and head and neck cancer, and is believed to contribute to the malignant growth of these tumors. The development of compounds that inhibit the kinase activity of the EGFR, as well as antibodies that block EGFR activation, for use as anti-tumor agents is an area of intense research effort.

Epidermal growth factor (EGF), acting through its receptor EGFR, is a mitogen and survival factor for epithelial cells (Rheinwald, J. G. and Green, H., 1977, Nature 265, 421; Rodeck, U. et al., 1997, J. Cell Science 110, 113). Thus, there is the potential that use of EGFR inhibitors in chemotherapy would interfere with the normal renewal of skin and other epithelial tissues such as the cornea and the lining of the gastrointestinal tract: Toxicity to proliferating tissues such as skin and the GI tract is frequently a dose-limiting side effect of cytotoxic agents. Such toxicity may be manifested, among other symptoms, as a skin rash, diarrhea, corneal thinning, hair atrophy or loss, hair follicle dysplasia, degeneration, necrosis or inflammation, interfollicular epidermal hyperplasia, or a failure to heal or a delayed healing after injury.

As used herein, the term "EGFR inhibitor" refers to any EGFR inhibitor that is currently known in the art or that will be identified in the future, and includes any entity that, upon administration to a patient, results in inhibition of a biological activity associated with activation of the EGFRs in the patient, including any of the downstream biological effects otherwise resulting from the binding to an EGFR of its natural ligand. Such EGFR inhibitors include any agent that can block EGFR activation or any of the downstream biological effects of EGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the EGFR receptor or a portion thereof, thereby making the receptor inaccessible to its natural ligand so that its normal biological activity is prevented or reduced. EGFR inhibitors include but are not limited to low molecular weight inhibitors, antibodies or antibody fragments, antisense constructs and ribozymes. In a preferred embodiment, the EGFR inhibitor is a small organic molecule or an antibody that binds specifically to the human EGFR.

EGFR inhibitors that can be used according to the present methods include, but are not limited to, those classified in the art as quinazoline EGFR inhibitors, pyrido-pyrimidine EGFR inhibitors, pyrimido-pyrimidine EGFR inhibitors, pyrrolo-pyrimidine EGFR inhibitors, pyrazolo-pyrimidine EGFR inhibitors, phenylamino-pyrimidine EGFR inhibitors, oxindole EGFR inhibitors, indolocarbazole EGFR inhibitors, phthalazine EGFR inhibitors, isoflavone EGFR inhibitors, quinalone EGFR inhibitors, and tyrphostin EGFR inhibitors.

Non-limiting examples of low molecular weight EGFR inhibitors useful in practicing the present methods include any of the EGFR inhibitors described in the following patent publications, and all pharmaceutically acceptable salts and solvates of said EGFR inhibitors: European Patent Application EP 520722, published Dec. 30, 1992; European Patent Application EP 566226, published Oct. 20, 1993; PCT International Publication WO 96/33980, published Oct. 31, 1996; U.S. Pat. No. 5,747,498, issued May 5, 1998; PCT International Publication WO 96/30347, published Oct. 3, 1996; European Patent Application EP 787772, published Aug. 6, 1997; PCT International Publication WO 97/30034, published Aug. 21, 1997; PCT International Publication WO 97/30044, published Aug. 21, 1997; PCT International Publication WO 97/38994, published Oct. 23, 1997; PCT International Publication WO 97/49688, published Dec. 31, 1997; European Patent Application EP 837063, published Apr. 22, 1998; PCT International Publication WO 98/02434, published Jan. 22, 1998; PCT International Publication WO 97/38983, published Oct. 23, 1997; PCT International Publication WO 95/19774, published Jul. 27, 1995; PCT International Publication WO 95/19970, published Jul. 27, 1995; PCT International Publication WO 97/13771, published Apr. 17, 1997; PCT International Publication WO 98/02437, published Jan. 22, 1998; PCT International Publication WO 98/02438, published Jan. 22, 1998; PCT International Publication WO 97/32881, published Sep. 12, 1997; German Application DE 19629652, published Jan. 29, 1998; PCT International Publication WO 98/33798, published Aug. 6, 1998; PCT International Publication WO 97/32880, published Sep. 12, 1997; PCT International Publication WO 97/32880 published Sep. 12, 1997; European Patent Application EP 682027, published Nov. 15, 1995; PCT International Publication WO 97/02266, published January 23, 197; PCT International Publication WO 97/27199, published Jul. 31, 1997; PCT International Publication WO 98/07726, published Feb. 26, 1998; PCT International Publication WO 97/34895, published Sep. 25, 1997; PCT International Publication WO 96/31510, published Oct. 10, 1996; PCT International Publication WO 98/14449, published Apr. 9, 1998; PCT International Publication WO 98/14450, published Apr. 9, 1998; PCT International Publication WO 98/14451, published Apr. 9, 1998; PCT International Publication WO 95/09847, published Apr. 13, 1995; PCT International Publication WO 97/19065, published May 29, 1997; PCT International Publication WO 98/17662, published Apr. 30, 1998; U.S. Pat. No. 5,789,427, issued Aug. 4, 1998; U.S. Pat. No. 5,650,415, issued Jul. 22, 1997; U.S. Pat. No. 5,656,643, issued Aug. 12, 1997; PCT International Publication WO 99/35146, published Jul. 15, 1999; PCT International Publication WO 99/35132, published Jul. 15, 1999; PCT International Publication WO 99/07701, published Feb. 18, 1999; and PCT International Publication WO 92/20642 published Nov. 26, 1992. Additional non-limiting examples of low molecular weight EGFR inhibitors include any of the EGFR inhibitors described in Traxler, P., 1998, Exp. Opin. Ther. Patents 8(12):1599-1625.

Specific preferred examples of low molecular weight EGFR inhibitors that can be used according to the present methods include [6,7-bis(2-methoxyethoxy)-4-quinazolin-4-yl]-(3-ethynylphenyl)amine (U.S. Pat. No. 5,747,498 issued May 5, 1998 and Moyer et al., 1997, supra); C1-1033 and PD183805 (Sherwood et al., 1999, Proc. Am. Assoc. Cancer Res. 40:723); and ZD1839 (Woodburn et al., 1997, Proc. Am. Assoc. Cancer Res. 38:633).

Antibody-based EGFR inhibitors include any anti-EGFR antibody or antigen-binding fragment thereof that can partially or completely block EGFR activation by its natural ligand. Non-limiting examples of antibody-based EGFR inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR inhibitor can be monoclonal antibody Mab E7.6.3 (Yang, 1999 supra), or Mab C225 (ATCC Accession No. HB-8508), or an antibody or antigen-binding fragment thereof having the binding specificity thereof. Other examples of antibody-based EGFR inhibitors include, for example, TARCEVA® (Erlotinib), ERBITUX® (Cetuximab), and Iressa® (Gefitinib).

Additional antibody-based EGFR inhibitors can be raised according to known methods by administering the appropriate antigen or epitope to a host animal selected, e.g., from pigs, cows, horses, rabbits, goats, sheep, and mice, among others. Various adjuvants known in the art can be used to enhance antibody production (such as, for example, aluminum hydroxide, complete Freund's adjuvant, incomplete Freund's adjuvant, etc.).

Other inhibitors that are commercially available are contemplated for use herein.

Treatment of cancer with a compound described herein alone or in combination with other anti-neoplastic compounds may be accompanied by administration of pharmaceutical agents that can alleviate the side effects produced by the anti-neoplastic agents. Such agents suitable for use herein include, but are not limited to, anti-emetics, anti-mucositis agents, pain management agents, infection control agents, and anti-anemia/anti-thrombocytopenia agents. Examples of anti-emetics suitable for use herein include, but are not limited to, 5-hydroxytryptamine 3 receptor antagonists, metoclopramide, steroids, lorazepam, ondansetron, cannabinoids, their analogues and derivatives. Examples of anti-mucositis agents suitable for use herein include, but are not limited to, palifermin (keratinocyte growth factor), glucagon-like peptide-2, teduglutide, L-glutamine, amifostin, and fibroblast growth factor 20. Examples of pain management agents suitable for use herein include, but are not limited to, opioids, opiates, and non-steroidal anti-inflammatory compounds. Examples of agents used for control of infection suitable for use herein include, but are not limited to, antibacterials such as aminoglycosides, penicillins, cephalosporins, tetracyclines, clindamycin, lincomycin, macrolides, vancomycin, carbapenems, monobactams, fluoroquinolones, sulfonamides, nitrofurantoins, their analogues and derivatives. Examples of agents that can treat anemia or thrombocytopenia associated with chemotherapy suitable for use herein include, but are not limited to, erythropoietin, and thrombopoietin.

Several other suitable therapies for use in combination with a compound described herein and other compounds described herein are also available. For example, see *Goodman & Gilman's The Pharmacological Basis of Therapeutics* 11th ed. Brunton L L, Lazo J S, and Parker K L, ed. McGraw-Hill, New York, 2006.

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the embodiments; it should be understood that various alternatives to the embodiments described herein may be employed in practicing the methods described herein.

Example 1

Structure-Based Prediction of NDGA Kinase Allosteric Binding Site

Three X-ray crystal structures of IGF1-R, EGFR, and c-Met in the active form were selected from the Protein Data Bank (PDB) and converted to a full-atom models for structural analysis. Three allosteric pockets common to each of the three kinases were identified. The allosteric pockets are located next to the Alpha C in the N-terminal lobe, in the substrate binding cleft, and in the C-terminal lobe. Ligand docking and scoring was used to discriminate which of the three pockets is the NDGA binding pocket. The substrate binding pocket was determined to be the most likely NDGA binding pocket.

Results

X-Ray Crystal Structure Selection

The PDB was mined to find human kinase domain structures of IGF1R, EGFR, and c-Met for this work. For this study we chose to work with the following kinase structures: 3Q6W (c-Met)[1], 1M17 (EGFR)[2], and 1K3A (IGF1R)[3] (data not shown). The structures were selected based on their active conformation form, resolution, and sequence coverage. Each of the structures are co-crystallized with a ligand in the ATP pocket, the N-terminal lobe is closed due to the alpha C to beta3 salt bridge, and the activation loop is ordered. One of the structures (IGF1R-PDB 1K3A) has a peptide bound to the activation loop. A four residue segment of PDB 3Q6W (residues 1240-1243) which is disordered was remodeled using standard ICM protein modeling protocols[4-6].

Identification of Potential NDGA Allosteric Binding Pockets

NDGA binds to IGF1R, EGFR, and c-Met; therefore, it is reasonable to assume that there is a pocket common to each structure. Here the ligand binding pockets were identified and the likely binding site determined.

Pocket Finder Method

Hydrogen atoms were added to each of the three kinase structures and a determination of the correct orientation of Asn and Gln side-chains was made. Histidine residues were optimized to determine the best orientation and protonation state, the correct charges were added to Asp, Glu, Lys and Arg and all water molecules and Het atoms were removed.

MolSoft's ICMPocketFinder algorithm[7,8] was used to identify potential ligand binding pockets in the three kinase X-Ray crystal structures. The ICMPocketFinder method is based on a transformation of the Lennard-Jones potential and builds a grid map of a binding potential, and the position and size of the ligand binding pocket are determined based on the construction of equipotential surfaces along those maps. The pockets were assessed on their "druggability" properties and potential propensity to bind a small molecule.

Three Conserved Pockets Identified in the Target Kinases

Three allosteric pockets were found in the same location in c-Met, EGFR, and IGF1R data not shown).

The Alpha C Pocket is located in the N-terminal region of the kinase between Alpha C and the Beta 9 to Beta 10 loop.

The Substrate Pocket is located in the region of the activation loop and Beta 7 and Beta 10.

The C-terminal Pocket is formed by Alpha F to Alpha G and Alpha G to Alpha H loops. This pocket is distal to both the ATP pocket and activation loop.

Prediction of the NDGA Binding Pocket by Ligand Docking

Ligand docking and scoring were used to discriminate which of the three allosteric pockets (Alpha C, Substrate, and C-terminal) binds NDGA. This in silica approach provides a prediction about how well NDGA fits into each pocket.

Docking NDGA to the Allosteric Pockets

Five types of interaction potentials represented each of the three pockets in the three kinases. The potentials included (i) van der Waals potential for a hydrogen atom probe; (ii) van der Waals potential for a heavy-atom probe (generic carbon of 1.7 Å radius; (iii) optimized electrostatic term; (iv) hydrophobic terms; and (v) loan-pair-based potential, which reflects directional preferences in hydrogen bonding. The energy terms are based on the all-atom vacuum force field ECEPP/3 with appended terms to account for solvation free energy and entropic contribution. Conformational sampling was based on the biased probability Monte Carlo (BPMC) procedure[4], which randomly selects a conformation in the internal coordinate space and then makes a step to a new random position independent of the previous one but according to a predefined continuous probability distribution. It has also been shown that after each random step, full local minimization greatly improves the efficiency of the procedure. The ICM program relies on global optimization of the entire flexible ligand in the receptor field and combines large-scale random moves of several types with gradient local minimization and a search history mechanism.

NDGA Pocket Discrimination—Preference for Substrate Pocket

Once the ligand was docked to each pocket a score was then calculated to determine how well the ligand fits into each pocket. The scoring function gives a good approximation of the binding free energy between a ligand and a receptor and is a function of different energy terms based on a force-field. The ICM scoring function[9] is weighted according to the following parameters (i) internal force-field energy of the ligand, (ii) entropy loss of the ligand between bound and unbound states, (iii) ligand-receptor hydrogen bond interactions, (iv) polar and non-polar solvation energy differences between bound and unbound states, (v) electrostatic energy, (vi) hydrophobic energy, and (vii) hydrogen bond donor or acceptor desolvation. The lower the ICM score, the better the prediction that the NDGA ligand binds to that pocket.

Table 5 shows the ICM docking scores for each of the pockets in the three kinase structures. Although the differences in the scores are not dramatic the scores are consistently better for NDGA docked to the Substrate Binding Pocket.

TABLE 5

Docking scores for NDGA in each of the three conserved pockets: the lower the docking score, the better the prediction that NDGA binds. Based on the docking score NDGA prefers the substrate pocket compared to the other two pockets (Alpha C and C-terminal).

| Pocket | c-Met | EGFR | IGF1R |
| --- | --- | --- | --- |
| Alpha C Pocket | −17 | −15 | −17 |
| Substrate Pocket | −20 | −28 | −21 |
| C-terminal Pocket | −16 | −17 | −10 |

The poses of the ligand in IGF1R and c-Met match well to the substrate peptide binding pose seen in the crystal structure (data not shown). The docked pose matches well with the substrate peptide bound (data not shown) to the IGF1R crystal structure.

Docking NDGA Monoglucuronide and Monosulfate to the Substrate Binding Pocket

Table 6 shows a comparison of the binding scores for NDGA, NDGA monoglucuronide, and NDGA monosulfate in the substrate binding pocket.

The model suggests that the addition of a monoglucuronide or sulfate to the catechol ring will not improve or have a detrimental effect on binding, the binding scores were similar (but slightly lower) to those obtained with NDGA. The docking score is primarily designed to discriminate ligand binders from non-binders, therefore, unless significant detailed SAR is available, it will not be able to rank the ligands by experimentally determined binding affinity.

TABLE 6

Docking scores for NDGA, NDGA monoglucuronide, and NDGA to monosulfate to the three kinases.

| | c-Met | EGFR | IGF1R |
| --- | --- | --- | --- |
| NDGA | −20 | −28 | −21 |
| NDGA monoglucuronide | −18 | −25 | −12 |
| NDGA monosulfate | −17 | −28 | −18 |

Docking NDGA Metabolites to the Substrate Binding Pocket

Table 7 shows a comparison of the binding scores for NDGA, or metabolies thereof, in the substrate binding pocket where G=Gluc, M=Methyl and S=Sulfate.

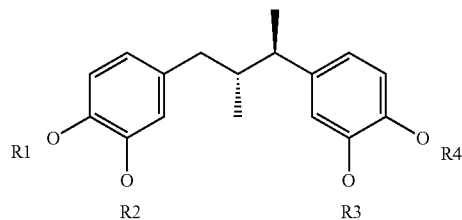

TABLE 7

| Metabolite | IGFR | EGFR | c-Met |
| --- | --- | --- | --- |
| NDGA (for reference) | −21 | −28 | −20 |
| R1 = G, R4 = G | −10 | −21 | −1 |
| R1 = G, R2 = M, R4 = G | −3 | −23 | −5 |
| R1 = M, R2 = G, R4 = G | −19 | −11 | −7 |
| R1 = G, R4 = S | −24 | −21 | −11 |

About MolSoft's ICM Technology Used in this Work

All pocket modeling was undertaken using MolSoft's ICM desktop modeling software package. ICM is based on the internal coordinates (IC) representation of molecular objects and naturally reflects the covalent bond geometry of molecules[4,5]. The method is supported by an accurate internal coordinate force field and a very efficient conformational state sampling algorithm BPMC[4]. ICM is one of the most advanced modeling tools available today for conformational analysis of flexible proteins and their interactions with ligands. The software is used worldwide in pharmaceutical and biotech companies as well as academic research laboratories.

Conclusions

The predicted binding pocket for NDGA is in the substrate binding region close to the activation loop (data not shown). Based on kinase biological and structural knowledge it is clear that out of the three common pockets found in this study the substrate binding site is the most likely and effective site for an allosteric inhibitor to bind. For example, it is uncertain how an inhibitor binding in the C-terminal pocket could disrupt substrate binding. The alpha C pocket could possibly be a good site because it may interfere with the N-terminal lobe movement, but in each case the docking scores were better for the substrate binding pocket. It is also encouraging how well the docked poses of NDGA in IGF1R and c-Met match the interactions seen with the substrate (data not shown).

Example 2

Metabolite Profiling of NDGA after Oral Administration in Male CD-1 Mice: Dosing, Sampling, and Analysis Objective The objectives of this study were to perform profiling of metabolites of test compound NDGA after oral dosing in male CD-1 mice and to determine in vitro whole blood stability.

Summary

Multiple metabolites were detected in plasma samples of the dosed animals. Based on the results of High Resolution Accurate Mass Measurements and acquired MS/MS data, the detected metabolites appear to be generated via complex Phase II metabolism (conjugation).

The results of semi-quantitative determination of plasma concentration of metabolites vs. time allows the metabolites to be divided into three groups—"first-formed," mirroring the concentration of the parent test compound; "later-formed," whose concentration increased over the investigated time interval; and plausible subjects of enterohepatic recycling, leading to a "saw-like" pattern. The results are summarized in Table 8.

TABLE 8

Summary of Pharmacokinetics of Test Compound and Metabolites in Mouse Plasma.

| Analyte Name (biotransformation) | m/z (R.T. min) | Ratio: Peak Area Analyte/Peak Area Internal Standard Time, minutes | | | | | | AUC (peak area ratio* min) |
|---|---|---|---|---|---|---|---|---|
| | | 5 | 10 | 40 | 60 | 120 | 240 | |
| NDGA (Parent) | 301.1445 (22.7) | 0.139 | 0.457 | 0.312 | 0.216 | 0.044 | 0.024 | 28.5 |
| M1 (Glucuronidation) | 477.1759 (21.3) | 0.493 | 2.549 | 6.649 | 7.379 | 2.620 | 2.467 | 739.7 |
| M2 (+Gluc + SO3) | 557.1338 (22.5-23.1) | 0.153 | 1.093 | 4.373 | 4.853 | 2.235 | 3.570 | 564.5 |
| M3i (+Gluc + SO3) | 557.1338 (23.1-32) | 0.461 | 2.949 | 14.027 | 16.000 | 7.879 | 13.946 | 1935.7 |
| M4 (bis-Gluc + bis-methylation) | 681.2390 (21.0) | 0.061 | 0.074 | 0.565 | 0.803 | 1.585 | 2.847 | 228.3 |
| M5 (bis-Gluc + bis-methylation) | 681.2390 (21.6) | 0.021 | 0.034 | 0.317 | 0.461 | 0.835 | 1.702 | 128.2 |
| M6 (+Gluc + methylation) | 491.1921 (21.9) | 0.033 | 0.228 | 0.801 | 1.018 | 0.374 | 0.520 | 102.9 |
| M7 (+Gluc + methylation) | 491.1921 (22.9) | 0.177 | 1.045 | 3.167 | 3.266 | 1.514 | 1.745 | 372.2 |
| M8 (+Gluc + methylation) | 491.1921 (23.4) | 0.187 | 0.964 | 3.120 | 3.621 | 1.135 | 1.222 | 345.4 |
| M9 (bis-Gluc + methylation) | 667.2227 (19.5-21) | 1.420 | 4.606 | 16.772 | 17.440 | 21.802 | 21.984 | 3172.2 |
| M10 (bis-Gluc + methylation) | 667.2227 (21-23) | 0.218 | 0.673 | 3.226 | 4.435 | 5.111 | 5.863 | 753.4 |
| M11 (bis-methylation + Gluc) | 505.2077 (23.4) | 0.006 | 0.032 | 0.117 | 0.126 | 0.167 | 0.092 | 21.3 |
| M12 (bis-methylation + Gluc) | 505.2077 (23.8) | 0.120 | 0.268 | 1.022 | 1.764 | 0.784 | 0.911 | 175.7 |
| M13i (bis-Glucuronidation) | 653.2087 (18-19.5) | 0.097 | 0.638 | 3.338 | 4.049 | 3.763 | 0.918 | 510.4 |
| M14i (bis-Glucuronidation) | 653.2087 (19.5-21) | 0.083 | 0.477 | 1.973 | 2.530 | 2.547 | 1.524 | 357.8 |

The results of determination of the stability of NDGA in freshly drawn whole blood of CD-1 mice (pooled from three animals) are summarized in Table 9.

TABLE 9

Stability of NDGA in whole blood.

| Analyte | Time (minutes) | | | |
| --- | --- | --- | --- | --- |
| | 0 | 15 | 30 | 60 |
| NDGA | 100 | 7.2 | NF | NF |

NF—peak not found

The MS signal of NDGA in samples prepared from whole blood appears to be very low, possibly indicating poor recovery (see Results). No putative metabolites were detected upon incubation in whole blood in vitro.

Experimental

The dosing solution was prepared at a nominal concentration of 20 mg/mL; detailed description is shown in Appendix I. The actual concentration, established using HPLC-MS, was 84.9% of nominal (+/−8.9%) and was within the acceptable range according to the study protocol. Animal dosing and blood collection were performed according to the study protocol; details are shown in Appendix II. No adverse effects were observed in the dosed animals. Plasma samples were prepared from blood according to the study protocol. Aliquots of the stabilized (with ascorbic acid) plasma samples were treated with MeCN (1:3 ratio) containing a mixture of internal standards (metoprolol, propranolol, and warfarin, each at 500 ng/mL) for protein precipitation. After centrifugation, clear supernatants were analyzed directly using LC-High Resolution Accurate Mass Spectrometry (HRAMS) as described below.

The incubation of test compound NDGA in pooled whole blood (n=3 animals) was carried out at +37° C. for 60 minutes, according to the study protocol. The aliquots were treated with MeCN (1:3 ratio) containing a mixture of internal standards (metoprolol, propranolol, and warfarin, each at 500 ng/mL) for protein precipitation. After centrifugation, supernatants were analyzed directly using LC-HRAMS as described below.

Metabolite Profiling: Introduction

The samples were separated using HPLC, and two stationary phases were evaluated: ACE pentaflurophenyl C18 (Phenomenex) and dC18 (Waters). Elution of the components was achieved using a linear gradient of MeCN/MeOH (1/1) in water at a constant level of AcOH (0.1%).

The eluted components were ionized (positive and negative mode; separate injections) and generated ions were surveyed using the LTQ Orbitrap hybrid instrument. The MS instrument combines a linear ion trap (LTQ) and high-resolution FT mass analyzer (Orbitrap).

The survey MS scans were performed on the Orbitrap FT analyzer operated at a resolution of Rs=30,000 (m/z range 150-900µ). The cycle starts with an FT pre-scan. In this pre-scan, the FT analyzer is operated at a high acquisition rate and a lower resolution (Rs=7500), and the results are used to calculate optimal parameters for the survey's high-resolution scan. The pre-scan also returns corresponding m/z values of all ions present in the HPLC eluate.

Following the pre-scan, the FT analyzer is set to perform a slow survey scan at high resolution (HRMS). In parallel, the LTQ ion trap is set to acquire MS(n) data using a data-dependent acquisition (DDA) event. The DDA consists of the decision event and two $MS^2$ product ion scans. The decision event selects the two most intense ions detected in the pre-scan which are on the parent mass list.

Automatically generated PDF files containing detailed method information are sent separately.

The data were processed using Metworks™ software (v 1.3.0, Thermo). The data processing is comprised of two steps:

1) Subtraction of the chromatogram of a control sample (solvent control in blank matrix) from the analyzed sample, leading to creation of a "SUB" file (Appendix II). This file contains peaks of components unique to the analyzed sample and peaks of components with intensities in the analyzed sample at least two times higher (S/N ratio) than in the control sample.

2) A search for major unique peaks present in "SUB" ("chro" search) for comprehensive metabolite detection.

Finally, the "SUB" file and the results of automatic detection were subjected to manual evaluation.

Results, Detection of Metabolites

Similar to the results obtained previously on a triple quad instrument, detection in negative mode on an LTQ-Orbitrap instrument led to much higher apparent sensitivity for both the parent compound and putative metabolites as compared to detection in the positive mode. Therefore, all results of metabolite detection were obtained in negative mode unless indicated otherwise.

Figure 1:
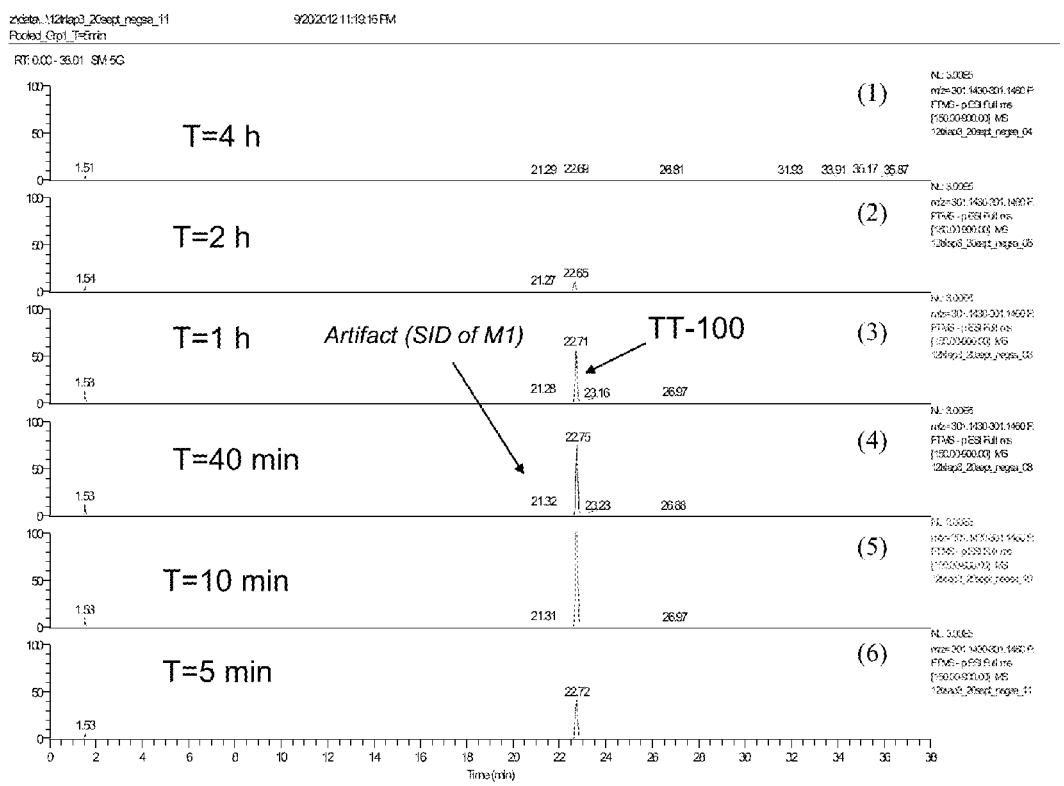
FIG. 1. XIC (m/z=301.1445) traces of the peak of the parent compound in plasma samples (normalized scale). The early eluting peak (RT~21.3 min) is an artifact due to in-source induced dissociation (SID) of putative metabolite M1 (glucuronidation).

Data processing for detection of putative metabolites was performed using all time points. The peak of the parent compound was detected in all samples. As an illustration, FIG. 1 shows the ion extraction chromatogram (XIC) of the peak of the parent compound across data points.

Determination of Relative Abundances of the Metabolites Using Area Under Curve Approach.

For semi-quantitative comparison of generated metabolites, a ratio of peak areas of the detected metabolites and the parent compound versus the internal standard was used to construct kinetics of metabolite formation and calculate corresponding AUCs using the trapezoidal approximation. Table 10 shows the results.

TABLE 10

Peak area ratios of parent compound and reported putative metabolites versus internal standard.

| Analyte Name (biotransformation) | m/z (R.T. min) | Ratio: Peak Area Analyte/Peak Area Internal Standard Time, minutes | | | | | | AUC (peak area ratio* min) |
| --- | --- | --- | --- | --- | --- | --- | --- | --- |
| | | 5 | 10 | 40 | 60 | 120 | 240 | |
| NDGA (Parent) | 301.1445 (22.7) | 0.139 | 0.457 | 0.312 | 0.216 | 0.044 | 0.024 | 28.5 |

TABLE 10-continued

Peak area ratios of parent compound and reported putative metabolites versus internal standard.

| Analyte Name (biotransformation) | m/z (R.T. min) | Ratio: Peak Area Analyte/Peak Area Internal Standard Time, minutes | | | | | | AUC (peak area ratio* min) |
|---|---|---|---|---|---|---|---|---|
| | | 5 | 10 | 40 | 60 | 120 | 240 | |
| M1 (Glucuronidation) | 477.1759 (21.3) | 0.493 | 2.549 | 6.649 | 7.379 | 2.620 | 2.467 | 739.7 |
| M2 (+Gluc + SO3) | 557.1338 (22.5-23.1) | 0.153 | 1.093 | 4.373 | 4.853 | 2.235 | 3.570 | 564.5 |
| M3i (+Gluc + SO3) | 557.1338 (23.1-32) | 0.461 | 2.949 | 14.027 | 16.000 | 7.879 | 13.946 | 1935.7 |
| M4 (bis-Gluc + bis-methylation) | 681.2390 (21.0) | 0.061 | 0.074 | 0.565 | 0.803 | 1.585 | 2.847 | 228.3 |
| M5 (bis-Gluc + bis-methylation) | 681.2390 (21.6) | 0.021 | 0.034 | 0.317 | 0.461 | 0.835 | 1.702 | 128.2 |
| M6 (+Gluc + methylation) | 491.1921 (21.9) | 0.033 | 0.228 | 0.801 | 1.018 | 0.374 | 0.520 | 102.9 |
| M7 (+Gluc + methylation) | 491.1921 (22.9) | 0.177 | 1.045 | 3.167 | 3.266 | 1.514 | 1.745 | 372.2 |
| M8 (+Gluc + methylation) | 491.1921 (23.4) | 0.187 | 0.964 | 3.120 | 3.621 | 1.135 | 1.222 | 345.4 |
| M9 (bis-Gluc + methylation) | 667.2227 (19.5-21) | 1.420 | 4.606 | 16.772 | 17.440 | 21.802 | 21.984 | 3172.2 |
| M10 (bis-Gluc + methylation) | 667.2227 (21-23) | 0.218 | 0.673 | 3.226 | 4.435 | 5.111 | 5.863 | 753.4 |
| M11 (bis-methylation + Gluc) | 505.2077 (23.4) | 0.006 | 0.032 | 0.117 | 0.126 | 0.167 | 0.092 | 21.3 |
| M12 (bis-methylation + Gluc) | 505.2077 (23.8) | 0.120 | 0.268 | 1.022 | 1.764 | 0.784 | 0.911 | 175.7 |
| M13i (bis-Glucuronidation) | 653.2087 (18-19.5) | 0.097 | 0.638 | 3.338 | 4.049 | 3.763 | 0.918 | 510.4 |
| M14i (bis-Glucuronidation) | 653.2087 (19.5-21) | 0.083 | 0.477 | 1.973 | 2.530 | 2.547 | 1.524 | 357.8 |

For visualization purposes, FIG. 19 shows normalized levels of the metabolites and test compound (each compound normalized to itself, such that the highest concentration of each analyte is 100%).

FIG. 30 shows normalized levels of the metabolites and parent compound (each compound normalized to itself, such that the highest concentration of each analyte is 100%). From a separate experiment from that described above.
Conclusion, Detection and Structure Elucidation of the Putative Metabolites Multiple metabolites were detected in plasma samples of the dosed animals. Based on the results of HRAMS measurements and acquired $MS^2$ data, all detected metabolites were assigned to be products of complex Phase II metabolism (conjugations). The results of semiquantitative determination of plasma concentration of metabolites allows the metabolites to be divided into three groups—"first-formed," mirroring the concentration of the parent test compound; "later formed," whose concentration increased over the investigated time interval; and plausible subjects of enterohepatic recycling, leading to a "saw-like" pattern.
Results, Determination of the Whole Blood Stability and Detection of Putative Metabolites The results of determination of the stability of NDGA in freshly drawn whole blood of CD-1 mice (pooled from three animals) are summarized in Table 11.

TABLE 11

Stability of NDGA in whole blood

| Analyte | Time (minutes) | | | |
|---|---|---|---|---|
| | 0 | 15 | 30 | 60 |
| NDGA | 100 | 7.2 | NF | NF |

NF—peak not found

The MS signal of NDGA in samples prepared from whole blood appears to be very low, possibly indicating poor recovery. For illustrative purposes, FIG. 20 shows the peak of TT100 in the T=0 minute sample and the peak of an internal standard (warfarin) alongside with the recorded HRAMS spectra.

Conclusion, Determination of the Whole Blood Stability and Detection of the Putative Metabolites The test compound NDGA appears to be unstable in whole blood sample. However, the obtained quantitative results (as well as results of the detection of the putative metabolites) could be negatively impacted by possible poor recovery of NDGA from whole blood. Optimization of the recovery from whole blood was beyond the scope of the current study protocol.

Dosing Solution Preparation and Analysis

The dosing solution was analyzed using an LC-targeted EPI method implemented on a QTRAP 4000 instrument. Two replicates were injected alongside two standard samples (100% of nominal). The measured concentration of dosing solution was 84.9+/−8.9% and standard 100+/−4.7%. The measured concentration is within the acceptable range.

Total Ion Current Chromatograms and Survey MS Spectra of Additional Putative Metabolites The Total Ion Current (TIC) trace of the "SUB" file (T=1 hour) is shown in the upper pane in each case; the lower pane shows the HRAMS spectrum for a different retention time interval (indicated by the blue line). The plausible peaks of additional putative metabolites are indicated by red arrows (See Figures. 21-23).

In Vivo Study Design:
Test Animal Description

| Species: | Mouse |
|---|---|
| Initial Age: | Commensurate with weight |
| Sex: | Male |
| Strain: | CD-1 |
| Initial Body Weight: | ~20-35 g |
| Source of Animals: | Hilltop Labs, Harlan Labs, or approved vendor |
| Identification Method: | Animals will be identified by tail mark and cage label. |
| Experimental Unit: | Individual animal |
| Replicates per Treatment: | N = 2 or 3 per timepoint; Total 22 mice |
| Inclusion Criteria: | Animals will be healthy at the start of the trial. |
| Exclusion Criteria: | Any of the above inclusion criteria out of specification. |
| Randomization: | Animals will be randomly assigned to dose groups. |
| Blinding of Study: | The study will not be blinded. |

Test System Management

| Acclimation/Conditioning: | Duration of acclimation will be approximately two days. |
|---|---|
| Anticipated Housing: | Animals will be housed up to three per cage. A single room will be used. |
| Species: | CD-1 Mouse (Male) |
| Feeding Schedule: | Food will be withheld from the animals for a minimum of twelve hours prior to test article administration through the duration of the study. Water will be supplied ad libitum. |
| Safety Precautions: | Routine |
| Dosing Solution: | Prepared fresh on the day of dosing |
| Storage of Dosing Solution After Dosing: | Refrigerated at 2 to 8° C. |
| Adverse Reactions: | None Expected |

Study Design:

| Dose Group | Test Compound | Dousing Route | Animals per Timepoint N = | Total Animals | Dose mg/kg | Dosing Solution Conc. mg/mL | Dosing Volume mL/kg | Vehicle | Sampling Time Points |
|---|---|---|---|---|---|---|---|---|---|
| 1 | NDGA | PO | 3 | 18 | 300 | 20 | 15 | 0.5% NaCMC in water | 5, 10, 40 min, 1, 2, and 4 hour |
| 2 | NA | PO | 2 | 4 | NA | NA | 15 | | 40 min and 2 hour |

NaCMC: sodium carboxy methyl cellulose, medium viscosity

| Blood Sample Site/Volume: | Cardiac puncture, ~0.4 ml |
|---|---|
| Type of Blood Tubes: | K$_2$EDTA |
| Type of Sample: | Acidified Plasma (ASLP analysis, see Section 6.2, protect from light) |
| Sample Storage and Shipment: | −60° C. to −80° C. |

Dosing

| Frequency: | Test compound will be administered to the animals at time 0 on the appropriate day on each day of dosing. |
|---|---|
| Dose Preparation: | The formulation will be prepared fresh on the day of dosing. |
| Procedure: | Test compound will be administered orally via gavage. |

Sampling

| Frequency: | See Section 5.3—Study Design |
|---|---|
| Blood Collection: | Blood samples will be collected via cardiac puncture, immediately placed into chilled tubes containing the appropriate anticoagulant, protected from light, and kept on ice until centrifugation within 30 minutes of sampling time. |
| Plasma Preparation and Storage: | The samples will be centrifuged at a temperature of 2 to 8° C., at 3,000 xg, for 5 minutes. Plasma will be |

| | |
|---|---|
| | collected after centrifugation of the blood samples into tubes already containing a 0.1M ascorbic acid solution following the instruction below: Pipette 150 μL of plasma from each sample supernatant and add to tubes containing 15 μL of 0.1M ascorbic acid solution in water (plasma will be mixed at 10:1 ratio yielding an acidic pH; this may be scaled for larger or smaller volumes). Samples will then be frozen immediately on dry ice. Acidified plasma samples will be stored frozen at −70° C. until transferred or shipped frozen on dry ice to the Absorption Systems Analytical Department for analysis. |

Analytical Method Evaluation:

| | |
|---|---|
| Method Development: | 1. LC-MS/MS analytical method for NDGA has previously been established at Absorption Systems in female Balb/c mouse plasma under study 11TRIAP2R2.<br>2. LC-HRAMS method set-up using system suitability samples.<br>3. Further method optimization for analysis of NDGA in male CD-1 mouse plasma and whole blood may be conducted per Absorption Systems' discretion. |
| In Vitro Whole Blood Stability: | 1. Single incubation (N = 1) of one concentration (1 μM) of test compound in fresh whole blood collected from untreated CD-1 mice and incubate for up to 1 hour at room temperature.<br>2. Sampling from the whole blood incubation at 0, 15, 30, and 60 min.<br>3. LC-HRAMS quantification of the test compound and metabolite ID/profiling in each whole blood sample. |
| Data Acquisition and Processing: | 1. From the in vivo experiment: Aliquots of plasma sample will be pooled across n = 3 animals at each sampling time point, i.e., n = 3 samples pooled for each time point resulting in a total 6 plasma samples (total 6 time points) for sample analysis.<br>2. From the in vitro experiment: All sample aliquots of whole blood sample (total 4 whole blood samples) analyzed.<br>3. Plasma and whole blood samples are typically extracted with organic solvent containing an appropriate internal standard.<br>4. Samples will be analyzed using a LTQ-ORBITRAP XL mass spectrometer.<br>5. Detection methodology: High Resolution Mass Scan (HRAMS)—Data Dependent acquisition (DDA)—MS(n).<br>6. HRAMS scan will be performed in an appropriate m/z range in order to detect the test compound and all plausible metabolites which could be formed in the particular matrix (i.e. Phase I and Phase II). The typical range for detection of both Phase I and II metabolites is~½ of MW or 150 amu (whichever is lower) to MW + 400 amu. The Orbitrap will be operated at resolution no less than 30,000.<br>7. The instrument method will trigger automatic MS/MS data acquisition on most intense ions observed in HRAMS using pre-defined criteria.<br>8. Data processing will be performed using Metworks and MS Frontier software packages. Typically, it involves combination of searches for the metabolites based on their exact mass (using built-in and/or customized list of biotransformation(s), as well as search for the major unique peaks (components) present in the in vivo sample but not in control sample at S/N > 3. In addition, multiple mass defect filters (MMDF) can be used to filter false positive peaks.<br>9. Optional:: If glucuronides for metabolites are detected, further experiments can be performed, per Customer's request, to differentiate between different types of glucuronides (O—, N—, or acyl glucuronides) based on the chemical properties of the glucuronides. |
| Determining AUC, Relative Abundance, and Kinetics of Metabolite Formation: | 1. On both incurred in vivo plasma and in vitro whole blood samples.<br>2. MS quantification of parent test compound and metabolites that meet the above defined criteria (S/N > 3) will be performed in all incurred plasma samples. |

| | |
|---|---|
| | 3. Up to 10 major metabolites with an AUC (based on PARR vs time) >5% of the parent test compound AUC will be reported.<br>4. Relative abundance/rank order is provided based on the AUC.<br>5. AUC profile is provided for each metabolite in order to determine the kinetics of metabolite formation. |
| Improved Quantification of Metabolites From In Vivo Samples (Optional): | 1. Reference metabolite mixture is generated using appropriate in vitro system and metabolite profile is compared to that in the in vivo sample.<br>2. If the match is satisfactory, the in vitro incubation sample is concentrated (10-50 fold) and analyzed using LC-UV-MS(n) method to record and compare UV spectra of parent drug and metabolites of interest.<br>3. If UV spectra are similar, correction factors based on peak area ratios in the extracted wavelengths chromatograms are established to calculate molar ratio of analytes in the concentrated sample.<br>4. The concentrated sample is diluted back to original level using post-extract supernatant from blank matrix and the obtained sample re-analyzed using quantitative (MS) bioanalytical method.<br>5. The correction factors for the MS responses of analytes is calculated based on the UV data and the level of metabolites are re-calculated to express it as molar percentage compared to the parent. |
| Structure Elucidation: | 1. The structure assignment of up to ten putative metabolites in plasma will be performed.<br>2. The structure assignment of the detected metabolites is based on:<br>a. Elaboration of recorded MS(n) data of metabolites via fragmentation of the proposed chemical structures.<br>b. Comparison with established fragmentation pathway(s) of the parent drug.<br>c. The elucidation process may also involve additional sample re-analysis using LC-MSn methods and/or acquiring MS/MS data using exact mass capabilities for additional confirmation of assigned structures. |

Report Generation:

| | |
|---|---|
| Materials and Methods | |
| Data Processing and Interpretation | The nominal concentration of the dosing solution will be used in all data analysis if the measured concentration is within 70% to 130% of nominal. Otherwise, the measured concentration of the dosing solution will be used for data analysis. |
| Results and Conclusions: | 1. A table summarizing results of the detection of metabolites in in vivo mouse plasma sample and in vitro whole blood sample.<br>2. Results of accurate mass measurements of up to 10 major (based on AUC comparison or relative abundance) detected putative metabolites.<br>3. Determination of biotransformation type based on mass shift.<br>4. Retention time<br>5. Peak area response ratio (PARR) of the detected metabolites and parent compound at each time point (for plasma samples only).<br>6. Relative abundance, based on comparison of PARR or AUC metabolite vs. AUC parent (e.g. for plasma samples).<br>7. Kinetics of metabolite formation in each matrix when multiple time points or collections periods are available. |
| Appendices: | 1. Study protocol<br>2. Dose vehicle preparation and animal data sheets<br>3. Print-outs of analytical method(s) electronically associated with raw data |
| Additional Deliverables for Structure Elucidation: | 1. Recorded MS ion tree and elaboration of MS(n) fragmentation pathway of the parent test compound.<br>2. Descriptions of the methodologies used for data acquisition and processing. |

-continued

| Materials and Methods | |
|---|---|
| Final Report: | 3. MS(n) data and representative extracted ion chromatograms for up to ten major putative detected metabolites per matrix.<br>4. Structure assignment of the major putative metabolites.<br>The final report will be issued in ASLP standard format. The report will include all materials and methods used, as well as any adverse reactions. |

Acceptable Time Range for Sampling

| Scheduled Collection Time | Acceptable Time Range |
|---|---|
| 0-2 min | ±10 sec |
| >2-5 min | ±20 sec |
| >5-15 min | ±45 sec |
| >15-60 min | ±2 min |
| >1-3 hrs | ±5 min |
| >3-24 hrs | ±15 min |

Example 3

Determination of the Exposure of NDGA after Oral Administration in Male CD-1 Mice Summary The plasma levels were determined by LC-MS/MS after oral dosing of NDGA in male CD-1 mice. Test compound was dosed at 100 mg/kg from 0.5% MC and 0.5% NaCMC in DI water in separate groups. Individual and average plasma concentrations are provided in Tables 8 and 10.

Analytical Methodology

Analytical Stock Solution Preparation

Analytical stock solutions (1 mg/mL of the free drug) were prepared in DMSO.

Standard and Quality Control Preparation

Standards were made from independently prepared stock solutions of the test compound. Standards and QCs were prepared in male CD-1 mouse plasma containing $K_2$EDTA as an anticoagulant with 10% of 0.1M ascorbic acid in water. Standards were prepared at concentrations of 1000, 500, 100, 50, 10, 5, 1, and 0.5 ng/mL by serial dilution. Standards were treated identically to the study samples.

Sample Extraction

Plasma samples were manually extracted using acetonitrile precipitation. All samples were thawed on ice, and kept on ice during preparation.

| Step | Procedure |
|---|---|
| 1 | Add 50 μL of samples, standards or QCs into 1.7 mL polypropylene centrifuge tube containing 150 μL of acetonitrile with internal standard (100 ng/mL warfarin). |
| 2 | Cap and vortex well. Centrifuge samples at 13000 rpm for ten minutes. |
| 3 | Combine 100 μL of the resulting supernatant with 100 μL of 0.1M ascorbic acid in a clean polypropylene 96-well plate. |
| 4 | Cap and vortex well prior to analysis. |

HPLC Conditions

| Instrument: | Perkin Elmer series 200 micropumps and Autosampler |
|---|---|
| Column: | Agilent Poroshell EC $C_{18}$, 30 × 2.1, 2.7 μm |
| Aqueous Reservoir (A): | 0.1% Formic Acid in water |
| Organic Reservoir (B): | 0.1% Formic Acid in acetonitrile |

Gradient Program:

| | Grad. | | | Diverter Valve | |
|---|---|---|---|---|---|
| Time (min) | Curve | % A | % B | Waste | MS |
| 0.0 | 1 | 100 | 0 | X | |
| 1.2 | 1 | 60 | 40 | | X |
| 3.0 | 1 | 0 | 100 | | X |
| 3.1 | 1 | 100 | 0 | | X |
| 4.0 | 1 | 100 | 0 | X | |

Flow Rate: 300 μL/min

Injection Volume: 10 μL

Run Time: 4.5 min

Temperature: ambient

Autosampler Wash: #1: 1:1:1 (v:v:v) water:acetonitrile:isopropanol with 0.2% formic acid

2: 50:50 (v:v) methanol:water

Mass Spectrometer Conditions

| Instrument: | PE Sciex API4000 |
|---|---|
| Interface: | TIS (Turbo ion spray) |
| Mode: | Multiple Reaction Monitoring (MRM) |
| Gases: | CUR 10, CAD 10, GS1 20, GS2 30 |
| Source Temperature: | 550° C. |

Voltages and Ions Monitored*:

| Analyte | Polarity | Precursor Ion | Product Ion | IS | DP | EP | CE | CXP |
|---|---|---|---|---|---|---|---|---|
| NDGA | Negative | 301.2 | 122.2 | −4500 | −94 | −11 | −39 | −9.7 |
| Warfarin (IS) | Negative | 307.1 | 250.0 | −4500 | −80 | −10 | −30 | −7 |

IS: Ion Spray Voltage; DP: Declustering Potential; FP: Focusing Potential; EP: Entrance Potential; CE: Collision Energy; CXP: Collision Cell Exit Potential;

Results

Observations and Adverse Reactions

Mouse #187 was died ~5 min after collection of 30 min sample, possibly due to stress during the study. No other adverse effects were observed after the oral administration of NDGA in male CD-1 mice in this study.

Dosing Solution Analysis

The dosing solution was analyzed by LC-MS/MS using the method outlined in below. The measured dosing solution concentration is shown in Table 12. The dosing solution was diluted in triplicate into mouse plasma and analyzed in parallel with the study samples. All concentrations are expressed as mg/mL of the free drug.

Plasma Sample Analysis

Individual and average plasma concentration for the test compound is shown in Tables 13 and 14. All data are expressed as ng/mL of the free drug. Samples that were below the limit of quantitation were not used in the calculation of averages. Plasma concentrations versus time data are plotted in FIGS. 24 and 25.

TABLE 12

Measured Dosing Solution Concentrations (mg/mL)

| Test Compound | Dose Route | Vehicle | Dosing Solution Observations | Nominal Dosing Conc. (mg/mL) | Measured Dosing Solution Conc. (mg/mL) | % of Nominal |
|---|---|---|---|---|---|---|
| NDGA | PO | 0.5% MC in DI water | Fine suspension | 20 | 21.4 | 107 |
|  |  | 0.5% NaCMC in DI water | Fine suspension | 20 | 25.5 | 128 |

MC: methyl cellulose, low viscosity; NaCMC: sodium carboxy methyl cellulose, medium viscosity.

TABLE 13

Individual and Average Plasma Concentrations (ng/mL) for NDGA after Oral Dosing in Male CD-1 Mice at 100 mg/kg PO; 0.5% MC in DI water

| Group# | Time point (hr) | Mouse # | Conc. (ng/mL) | Average (ng/mL) | SD |
|---|---|---|---|---|---|
| 1 | 0.167 | 168 | 102 | 43.4 | 33.1 |
|   |       | 169 | 28.3 |      |      |
|   |       | 170 | 24.9 |      |      |
|   |       | 171 | 25.5 |      |      |
|   |       | 172 | 36.3 |      |      |
| 2 | 0.50  | 173 | 14.8 | 44.2 | 35.6 |
|   |       | 174 | 42.7 |      |      |
|   |       | 175 | 105  |      |      |
|   |       | 176 | 34.6 |      |      |
|   |       | 177 | 23.9 |      |      |
| 1 | 2.0   | 168 | 2.00 | 3.08 | 2.74 |
|   |       | 169 | 7.94 |      |      |
|   |       | 170 | 2.25 |      |      |
|   |       | 171 | 1.31 |      |      |
|   |       | 172 | 1.90 |      |      |
| 2 | 4.0   | 173 | 1.97 | 3.19 | 1.92 |
|   |       | 174 | 2.51 |      |      |
|   |       | 175 | 2.59 |      |      |
|   |       | 176 | 6.61 |      |      |
|   |       | 177 | 2.29 |      |      |

MC: methyl cellulose, low viscosity

TABLE 14

Individual and Average Plasma Concentrations (ng/mL) for NDGA after Oral Dosing in Male CD-1 Mice at 100 mg/kg PO; 0.5% NaCMC in DI water

| Group# | Time point (hr) | Mouse # | Conc. (ng/mL) | Average (ng/mL) | SD |
|---|---|---|---|---|---|
| 1 | 0.167 | 178 | 60.1 | 70.8 | 50.8 |
|   |       | 179 | 83.2 |      |      |
|   |       | 180 | 24.9 |      |      |
|   |       | 181 | 152  |      |      |
|   |       | 182 | 34.0 |      |      |
| 2 | 0.50  | 183 | 40.9 | 49.6 | 13.3 |
|   |       | 184 | 68.3 |      |      |
|   |       | 185 | 56.5 |      |      |
|   |       | 186 | 34.5 |      |      |
|   |       | 187 | 47.7 |      |      |
| 1 | 2.0   | 178 | 4.34 | 1.83 | 1.51 |
|   |       | 179 | 2.08 |      |      |
|   |       | 180 | 0.78 |      |      |

TABLE 14-continued

Individual and Average Plasma Concentrations (ng/mL) for NDGA after Oral Dosing in Male CD-1 Mice at 100 mg/kg PO; 0.5% NaCMC in DI water

| Group# | Time point (hr) | Mouse # | Conc. (ng/mL) | Average (ng/mL) | SD |
|---|---|---|---|---|---|
| 2 | 4.0 | 181 | 1.27 | 2.75 | 0.52 |
|   |   | 182 | 0.683 |   |   |
|   |   | 183 | 3.24 |   |   |
|   |   | 184 | 2.53 |   |   |
|   |   | 185 | 2.12 |   |   |
|   |   | 186 | 3.11 |   |   |
|   |   | 187 | NA |   |   |

NaCMC: sodium carboxy methyl cellulose, medium viscosity;
BLOQ: Below the limit of quantitation (0.5 ng/mL);
NA: No sample available.

Example 4

In Vivo Treatment of Human Breast Adenocarcinoma

The in vivo antitumor effect of a catecholic butane metabolite is determined against MX-1 (human breast adenocarcinoma) cells.

Male or female athymic BALB/c mice, six to eight weeks of age and weighing 20 to 35 grams are used. MX-1 cells are cultured in the standard RPMI-1640 media and implanted subcutaneously in the flank of the nude mice in order to propagate the tumor line. Nude mice are implanted with 25 mg of the MX-1 solid tumor fragments. Tumors which reach the 25-100 $mm^2$ range are used for the experiment. Test compound (0.1 mL) is injected directly into the tumor.

The tumors are measured periodically to determine their weight calculated by using half the product of the length (L) times the width (W) times the height (H) of the tumor. The procedure is repeated at regular intervals until 60 days after the initial treatment or all mice have died. Mice which show no evidence of tumors are kept for 60 days to evaluate the potential for tumor recurrence at which time tumor characteristics, if any, are recorded.

Example 5

Anti-Cancer Therapy of Preformed Human Breast Cancer Tumors

The effect of a catecholic butane metabolite described herein can be assessed with respect to their anti-cancer effect on preformed human breast cancer tumors in human skin grafted into SCID mice.

Briefly, MCF-7 cells ($8 \times 10^6$ cells in 0.1 ml PBS) are transplanted intradermally into human full-thickness skin grafted into SCID mice when the grafts showed no signs of inflammation, contraction or rejection. The mice are left untreated until distinct palpable tumors (3 to 6 mm in diameter in most cases) appear. Mice with distinct tumors are divided into groups for the therapeutic studies. Control animals are administered sterile PBS intravenously (i.v.) via the tail vein. Groups of test animals (4 mice per group) are administered 5 mg/kg, 10 mg/kg, 25 mg/kg, or 50 mg/kg, of a catecholic butane metabolite intravenously (i.v.) via the tail vein. Administration is as follows: once per week; twice per week; three times daily for three weeks with one week hiatus; two times daily for three weeks with one week hiatus; or one time daily for three weeks with one week hiatus.

Additional groups of mice may be added to test for combination therapy of a catecholic butane metabolite with an EGFR inhibitor, an IGF-1R inhibitor, or both.

During the treatment, mice are monitored daily for tumor size and morbidity. Mice are weighed twice a week using an electronic balance (OHAUS™ Model GT210). Tumor size is measured three times a week using an electronic caliper (PRO-MAX 6 inch caliper; Fowler Co., Newton, Mass.) connected to a computer using OptoDemo™ software (Fowler Co.). The measured tumor diameters are converted to tumor volumes using the following formula: V=length×width×height×pi/6. Statistical analysis of the data for the comparison of different groups of mice is carried out using Student's t-test.

Example 6

SCID Mouse Model for Ovarian Cancer

To determine the ability of a catecholic butane metabolite to treat ovarian cancer, an ovarian cancer cell line may be used in SCID mice.

Briefly, ovarian cancer cells are implanted into SCID mice to generate ovarian tumors. Groups of mice bearing established tumors are treated by i.v. administration of escalating doses (starting at 5 mg/kg body weight) of a catecholic butane metabolite. Control animals are treated with sterile PBS. Additional groups of mice may be added to test for combination therapy of a catecholic butane metabolite with an EGFR inhibitor, an IGF-1R inhibitor, or both.

Mice are monitored and tumor growth is measured via sacrifice of animals on a weekly basis. Tumors are measured as described above.

Example 7

SCID Mouse Model for Kidney Cancer

To determine the ability of a catecholic butane metabolite to treat kidney cancer, a kidney cancer cell line is used in SCID mice.

Briefly, kidney cancer cells are implanted into SCID mice to generate kidney tumors. Groups of mice bearing established tumors are treated by i.v. administration of escalating doses (starting at 5 mg/kg body weight) of a catecholic butane metabolite. Control animals are treated with sterile PBS. Additional groups of mice may be added to test for combination therapy of a catecholic butane metabolite with an EGFR inhibitor, an IGF-1R inhibitor, or both.

Mice are monitored and tumor growth is measured via sacrifice of animals on a weekly basis. Tumors are measured as described above.

Example 8

Evaluation of the Anti-Proliferative Activity of NDGA in Cancer Cell Lines

In vitro studies may be used to evaluate the anti-proliferative activity of a single test compound, NDGA on lung cancer cell lines H1975, A427 and A549.

The first study measures the anti-proliferative activity of the compound in a cancer cell line. The second study will evaluate the anti-proliferative of the test agent in mouse plasma activity in a cancer cell line. MTT Cell Proliferation and/or CyQuant™ assays may be used for this purpose.

The MTT assay (Invitrogen) is a colorimetric assay for measuring the activity of cellular enzymes that reduce the tetrazolium dye, MTT, to its insoluble formazan, giving a purple color. This assay measures cellular metabolic activity via NAD(P)H-dependent cellular oxidoreductase enzymes and may, under defined conditions, reflects the number of viable cells (cell proliferation). Tetrazolium dye assays can also be used to measure cytotoxicity (loss of viable cells) or cytostatic activity (shift from proliferative to resting status) of potential medicinal agents and toxic materials The CyQuant™ assay (Invitrogen) may be used to differentiate antioxidant activity from anti-proliferative activity. Briefly, the assay is based on dye fluorescence enhancement upon binding to cellular nucleic acids. Cells are lysed by addition of a buffer containing the CyQUANT™-GR dye; there are no washing steps, growth medium changes or long incubations. The resulting fluorescence is proportional to the number of cells in the sample and is measured directly using the TD-700 fluorometer equipped with a fluorescein filter kit. The CyQUANT™ assay can detect much lower cell numbers than Neutral Red or methylene blue assays. (2, 3, 4) Unlike procedures that rely on the conversion of tetrazolium dyes to blue formazan (5) products or 3H thymidine incorporation assays, (6) the CyQUANT™ method is rapid and does not rely on cellular metabolic activity. Thus, cells can be frozen prior to assaying; time course assays are facile and data obtained from samples taken at widely different time intervals can be directly compared.

A. Anti-Proliferative Activity of Test Agent in Lung Cancer Cell Lines

A.1. Fresh H1975, A427 and A549 cells are thawed and expanded using standard procedures and medium recommended by the ATCC.

A.2. Approximately $1\times10^4$ cells are plated at a 200 µl volume in an appropriate number of wells in 96-well microtiter plates and placed in a tissue culture incubator (37° C./5% $CO_2$) overnight.

A.3. The following day, NDGA, or a metabolite thereof, is added to triplicate wells at concentrations of 0, 1, 3, 10, 30, 100 and 300 µM. Untreated wells are utilized as controls in addition to wells treated with camptothecin or another "standard" anti-proliferative agent.

A.4. Plates are incubated for 72 hours in a standard tissue culture incubator. At the completion of the incubation, relative cell number per well is determined using the CyQuant™ reagents as recommended by the vendor.

A.5. The results are compiled in an Excel spreadsheet. The IC50 value for all cell lines tested is determined (if possible) using GraphPad Prism® software.

B. Anti-Proliferative Activity of NDGA, or a Metabolite Thereof, Administered to Cells in Mouse Plasma/Serum B.1. Pooled mouse plasma is obtained by terminal bleed of five BALB/c mice. Blood is drawn by cardiac puncture without anticoagulant and allowed to clot. Plasma will is drawn off of the blood samples, pooled, stored on ice and clarified by centrifugation.

B.2. To determine the effect of mouse plasma on the growth of H1975, A427 and A549 cells, a pilot experiment is performed with all three cell lines. Mouse plasma is added to growth medium without FBS to final concentrations of 10%, 25%, 50% and 100% (no medium).

B.3. Cells are plated as in Step A.3 above and triplicate wells treated with mouse plasma. Cell growth is measured after 72 hours incubation with plasma using the CyQuant™ reagent.

B.4. The conditions determined in Step B.4 are used to test the anti-proliferative activity of NDGA, or a metabolite thereof, spiked into mouse plasma. For this experiment, plasma is collected from five mice, pooled and prepared as described above. Medium with the appropriate concentration of mouse plasma containing NDGA, or a metabolite thereof, at 0, 1, 3, 10, 30, 100 and 300 µM is added to triplicate wells containing each of the three cell lines. The plates are incubated for 72 hours and cell growth measured using the CyQuant™ reagent.

B.5. The IC50 value for all cell lines tested is determined (if possible) using GraphPad Prism® software.

C. Anti-Proliferative Activity of NDGA, or a Metabolite Thereof, Administered to Cells from Mice Treated with NDGA C.1. Following Part B, plasma from mice is treated with NDGA, or a metabolite thereof.

C.2. NDGA, or a metabolite thereof, is formulated as a 20 mg/mL suspension in 0.5% methylcellulose and administered orally to five BALB/c mice in a single dose of 300 mg/Kg.

C.3. All five mice from Step C.2 (as well as five mice not treated with NDGA, or a metabolite thereof) are sacrificed two hours post-dosing. Blood is drawn by cardiac puncture without anticoagulant and allowed to clot. Plasma is be drawn off of the blood samples, pooled, stored on ice and clarified by centrifugation.

C.4. H1975, A427 and A549 cells are plated as described in Part A and treated with plasma from mice treated with NDGA, or a metabolite thereof. The concentration of serum used is specified by TRIACT and based on Part B. The cells will be cultured for 72 hours and the CyQuant™ assay performed at that time.

C.5. The IC50 value for all cell lines tested is determined using GraphPad Prism® software.

Example 9

Effect of Metabolites on Cell Survival/Proliferation of NSCLC Cell Lines

The following experiments measured the effect of NDGA, or a metabolite thereof, on cell survival/proliferation in three NSCLC cell lines in the presence of mouse serum in two assay formats.

A: 10% Serum from Untreated Mice Spiked with Drug

The effect of NDGA, or a metabolite thereof, on cell proliferation/survival was measured in three NSCLC cell lines cultured in the presence of 10% mouse serum obtained from untreated mice.

Briefly, cells were cultured for 72 hours in medium from untreated mice spiked with NDGA, or a metabolite thereof, at concentrations of from 1-300 mM. Cell number differences were measured using the CyQuant® assay (Invitrogen).

H1975, A427, A549 cells were seeded at $1\times10^4$ cells/well in a 96 well plate and incubated overnight at 37° C.

24 hours later, triplicate wells were treated with 10% mouse serum each spiked in-vitro with NDGA, or a metabolite thereof, at 0, 1, 3, 10, 30, 100 and 300 mM concentration.

In parallel, a set of triplicate wells was treated with 10% pooled mouse serum obtained from five mice administered 300 mg/Kg NDGA, or a metabolite thereof, and sacrificed 2 hrs later.

The plates were incubated for 72 h at 37° C. and the relative cell number per well was determined using the CyQuant® reagent. Fluorescence was measured using a Molecular Devices plate reader.

The CyQuant® assay was performed 24 hours after cell plating ("Initial") and following 72 hour exposure to 10% mouse serum without NDGA, or a metabolite thereof, or 10% FBS (control).

Compared to cells cultured in 10% FBS, cell growth in the presence of 10% mouse serum was reduced in untreated cells 22%, 14% and 6% in A427, A549 and H9175 cells (data not shown).

Addition of 10% serum from untreated mice to growth medium induced a modest inhibition (14%, average) of cell proliferation when compared with medium containing 10% FBS (data not shown).

NDGA, or a metabolite thereof, induced a dose-related decrease in cell number in cells cultured in 10% mouse serum.

Reduced cell proliferation was observed at concentrations of NDGA, or a metabolite thereof, above of 10 mM and at the maximum concentration of NDGA, or a metabolite thereof, tested (300 mM); cell number was reduced by 33% when all cell lines were averaged (data not shown).

NDGA, or a metabolite thereof, was observed to inhibit cell proliferation and/or induce cytotoxicity in a dose-related manner in NSCLC lines when cultured in the presence of 10% mouse serum spiked with drug.

B: Pharmacodynamic Analysis of TT-100 in Mouse Serum

Mice were orally administered 300 mg/Kg NDGA, or a metabolite thereof, in 0.5% CMC and serum collected 2 hours following treatment.

Serum from five animals was pooled, mixed with culture medium at a concentration of 10% and cells incubated for 72 hours. Cell number was then determined using the CyQuant® assay.

Difference in cell number in NSCLC cells treated with serum from mice administered vehicle control (VC) and 300 mg/Kg NDGA, or a metabolite thereof, were determined (data not shown). Differences in cell number for cells cultured in 10% serum was compared by t-test. P values are: A427, p=0.009; A549, p=0.133; and H9175, p=0.744.

The number of cells after culture in the presence of 10% serum from treated mice was observed to decrease in two cell lines. In one, A427, the decrease was statistically significant (p=0.009) while in the other, A549 the p value was not significant at the 0.05 level (p=0.133).

Aspects of this application may be embodied in other forms or carried out in other ways without departing from the spirit or essential characteristics thereof. The present disclosure is therefore to be considered as in all aspects illustrated and not restrictive, and all changes which come within the meaning and range of equivalency are intended to be embraced therein.

REFERENCES

1. Rickert, K. W. et al. Structural basis for selective small molecule kinase inhibition of activated c-Met. *J. Biol. Chem.* 286, 11218-11225 (2011).
2. Stamos, J., Sliwkowski, M. X. & Eigenbrot, C. Structure of the epidermal growth factor receptor kinase domain alone and in complex with a 4-anilinoquinazoline inhibitor. *J. Biol. Chem.* 277, 46265-46272 (2002).
3. Favelyukis, S., Till, J. H., Hubbard, S. R. & Miller, W. T. Structure and autoregulation of the insulin-like growth factor 1 receptor kinase. *Nat. Struct. Biol.* 8, 1058-1063 (2001).
4. Abagyan, R. & Totrov, M. Biased probability Monte Carlo conformational searches and electrostatic calculations for peptides and proteins. *J. Mol. Biol.* 235, 983-1002 (1994).
5. Abagyan, R., Totrov, M. & Kuznetsov, D. ICM-A new method for protein modeling and design: Applications to docking and structure prediction from the distorted native conformation. *Journal of Computational Chemistry* 15, 488-506 (1994).
6. Arnautova, Y. A., Abagyan, R. A. & Totrov, M. Development of a new physics-based internal coordinate mechanics force field and its application to protein loop modeling. *Proteins* 79, 477-498 (2011).
7. An, J., Totrov, M. & Abagyan, R. Comprehensive identification of 'druggable' protein ligand binding sites. *Genome Inform* 15, 31-41 (2004).
8. Kufareva, I., Ilatovskiy, A. V. & Abagyan, R. Pocketome: an encyclopedia of small-molecule binding sites in 4D. *Nucleic Acids Res.* 40, D535-540 (2012).
9. Totrov, M. & Abagyan, R. Derivation of sensitive discrimination potential for virtual ligand screening. in Proceedings of the third annual international conference on Computational molecular biology 312-320 (ACM, 1999).doi:10.1145/299432.299509
10. Blecha, J. E. et al Inhibition of IGF-1R and lipoxygenase by nordihydroguaiaretic acid (NDGA) analogs. *Bioorg. Med. Chem. Lett.* 17, 4026-4029 (2007).

What is claimed is:

1. A composition comprising a therapeutically effective amount of a metabolite of nordihydroguaiaretic acid (NDGA) and one or more excipients, wherein the metabolite of nordihydroguaiaretic acid (NDGA) is a compound of formula II:

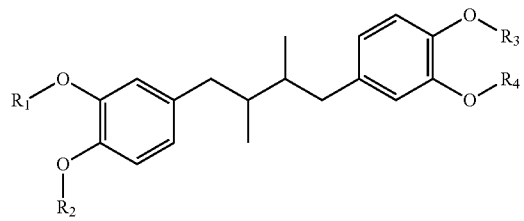

wherein $R_1$ is a glucuronide and $R_4$ is a sulfate; and
$R_2$ or $R_3$ are independently H, $CH_3$, a glucuronide, a sulfate, or a phosphate ester;
wherein the therapeutically effective amount is from about 50 mg per day to about 2,500 mg per day, and wherein the composition is formulated as a modified release composition.

2. The composition of claim 1, wherein said metabolite is a compound selected from the group consisting of:

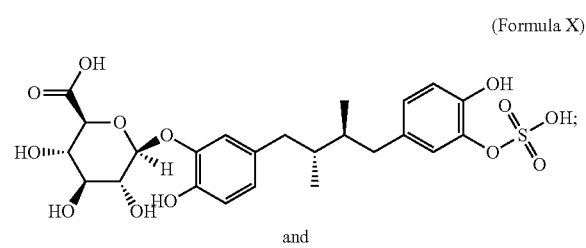

(Formula X)

and

-continued (Formula LXXVIII)

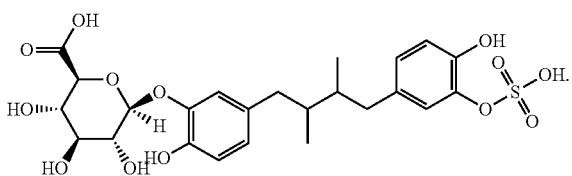

3. The composition of claim 1, wherein the modified release composition is formulated as a sustained or controlled release formulation.

4. A composition comprising:
a therapeutically effective amount of a phosphate ester of a compound of formula II:

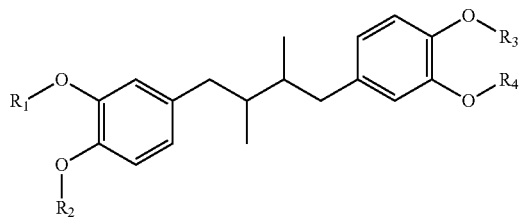

wherein,
$R_1$ is a glucuronide and $R_4$ is a sulfate;
$R_2$ or $R_3$ are independently H, $CH_3$, a glucuronide, a sulfate, or a phosphate ester; and
one or more excipients.

5. The composition of claim 4, wherein the phosphate ester of a compound of formula II is a phosphate prodrug of:

(Formula X)

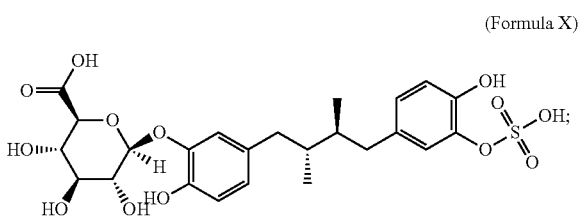

and (Formula LXXVIII)

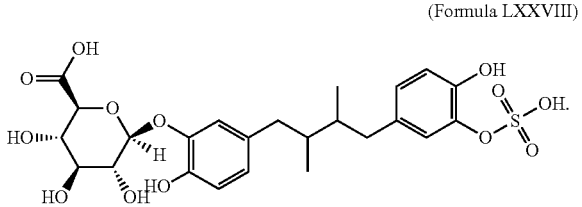

6. The composition of claim 4, wherein the composition is formulated as a modified release composition.

7. The composition of claim 6, wherein the modified release composition is a sustained or controlled release formulation.

8. The composition of claim 4, wherein the composition is administered to a patient in an amount of from about 50 mg per day to about 2,500 mg per day.

9. The composition of claim 4, wherein the composition is administered to a patient in an amount of from about 1,500 mg per day to about 2,500 mg per day.

10. A method of treating a patient with a proliferative disease in need thereof, comprising administering to the patient a therapeutically effective amount of a metabolite of NDGA, wherein said metabolite of NDGA inhibits the tyrosine kinase activity of both IGF-1R and EGFR, wherein the metabolite of NDGA is a compound of Formula II:

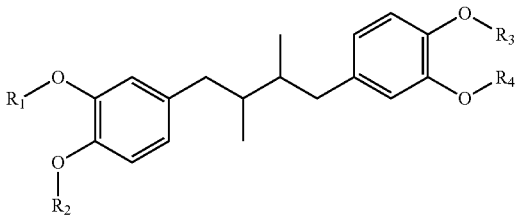

wherein $R_1$ is a glucuronide and $R_4$ is a sulfate; and $R_2$ or $R_3$ are independently H, $CH_3$, a glucuronide, a sulfate or a phosphate ester; and wherein the proliferative disease is malignant, pre-malignant or benign cancer.

11. The method of claim 10, wherein said metabolite is a compound selected from the group consisting of Formula X and Formula LXXVIII and a phosphate ester thereof:

(Formula X)

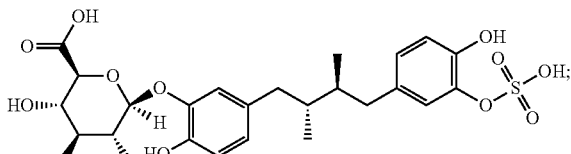

and (Formula LXXVIII)

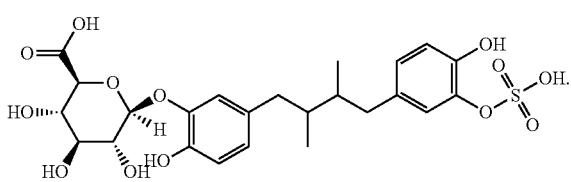

12. The method of claim 10, wherein the composition is administered to the patient in an amount of from about 5 mg/kg to about 375 mg/kg per dose of said metabolite of NDGA.

13. The method of claim 10, wherein the composition is administered to a patient in an amount of from about 1,500 mg per day to about 2,500 mg per day.

14. The method of claim 10, wherein the cancer is selected from the group consisting of small cell lung cancer, pancreatic cancer, breast cancer, breast cancer over-expressing Her-2, colon cancer, cervical cancer, neuroblastoma and non-small cell lung cancer (NSCLC).

15. The method of claim 10, wherein cancer cells contain an EGFR mutation that confers resistance to Erlotinib.

16. The method of claim 10, further comprising administering to the patient a therapeutically effective amount of Erlotinib or Gefitinib, wherein administration of said metabolite of NDGA and Erlotinib or Gefitinib provides a synergistic therapeutic effect compared to either compound alone.

17. The method of claim 10, wherein said metabolite of NDGA inhibits tyrosine kinase activity of IGF-1R, EGFR, cMet and/or KDR (VEGF2).

18. The method of claim 10, wherein said patient has a proliferative disease that is resistant to Erlotinib or Gefitinib, or who has relapsed after treatment with Erlotinib or Gefitinib.

19. The method of claim 18, wherein cancer cells contain a T790M mutation in an ATP binding domain of a receptor tyrosine kinase (RTK).

20. A method of treating a patient with a proliferative disease that is resistant to Erlotinib or Gefitinib, comprising administering to the patient a therapeutically effective amount of a metabolite of NDGA, wherein administration of said metabolite of NDGA restores the effectiveness of Erlotinib or Gefitinib, and wherein said metabolite of NDGA comprises a compound of formula II, pharmaceutically acceptable salts thereof, or pharmaceutically acceptable solvates thereof, wherein formula II comprises:

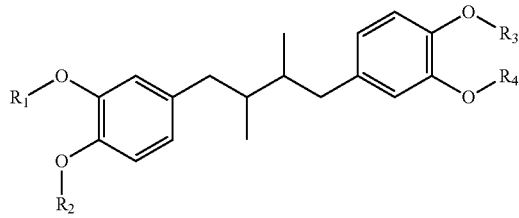

wherein $R_1$ is a glucuronide and $R_4$ is a sulfate; and $R_2$ or $R_3$ are independently H, $CH_3$, a glucuronide, a sulfate or a phosphate ester; and wherein the proliferative disease is malignant, pre-malignant or benign cancer.

21. The method of claim 20, wherein said metabolite of NDGA binds to a substrate-binding domain of a receptor tyrosine kinase (RTK) and induces a conformational change in the RTK.

22. The method of claim 20, further comprising administering to the patient a therapeutically effective amount of Erlotinib or Gefitinib.

23. The method of claim 20, wherein said metabolite is a compound selected from the group consisting of Formula X and Formula LXXVIII and a phosphate ester thereof:

(Formula X)

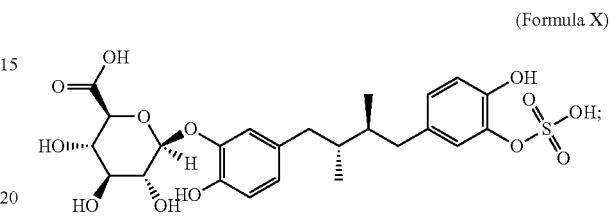

and (Formula LXXVIII)

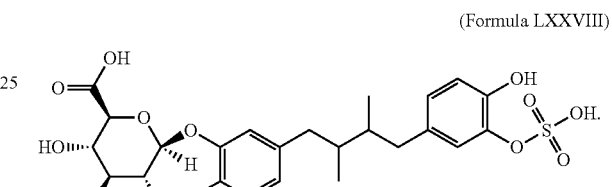

* * * * *